US008658637B2

(12) United States Patent
Kuzmich et al.

(10) Patent No.: US 8,658,637 B2
(45) Date of Patent: Feb. 25, 2014

(54) GLUCOCORTICOID MIMETICS, METHODS OF MAKING THEM, PHARMACEUTICAL COMPOSITIONS AND USES THEREOF

(75) Inventors: Daniel Kuzmich, Danbury, CT (US); Darren DiSalvo, New Milford, CT (US); Hossein Razavi, Danbury, CT (US); Michael Jason Burke, Chesire, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 564 days.

(21) Appl. No.: 12/517,874

(22) PCT Filed: Nov. 29, 2007

(86) PCT No.: PCT/US2007/085831
§ 371 (c)(1),
(2), (4) Date: Feb. 16, 2010

(87) PCT Pub. No.: WO2008/070507
PCT Pub. Date: Jun. 12, 2008

(65) Prior Publication Data
US 2010/0197678 A1    Aug. 5, 2010

Related U.S. Application Data

(60) Provisional application No. 60/868,844, filed on Dec. 6, 2006.

(51) Int. Cl.
A61K 31/5383    (2006.01)
A61K 31/437     (2006.01)
A61K 31/519     (2006.01)
C07D 471/04     (2006.01)
C07D 487/04     (2006.01)
C07D 498/04     (2006.01)

(52) U.S. Cl.
USPC ..... 514/230.5; 514/300; 514/303; 514/265.1; 544/280; 544/105; 546/113; 546/119; 546/118; 548/453

(58) Field of Classification Search
USPC ......... 514/230.5; 546/118, 119, 113; 548/453
See application file for complete search history.

(56) References Cited

U.S. PATENT DOCUMENTS

| | | | |
|---|---|---|---|
| 3,772,273 | A | 11/1973 | Gilbert, E. |
| 4,551,534 | A | 11/1985 | Sulkowski et al. |
| 4,774,240 | A | 9/1988 | Boshagen et al. |
| 4,880,839 | A | 11/1989 | Tucker |
| 5,039,691 | A | 8/1991 | Spagnuolo et al. |
| 5,206,377 | A | 4/1993 | McAfee |
| 5,688,810 | A | 11/1997 | Jones et al. |
| 5,948,820 | A | 9/1999 | Fujita et al. |
| 6,169,106 | B1 | 1/2001 | Heckel et al. |
| 6,187,918 | B1 | 2/2001 | Nugent |
| 6,323,199 | B1 | 11/2001 | Lehmann et al. |
| 6,329,534 | B1 | 12/2001 | Kym et al. |
| 6,362,344 | B1 | 3/2002 | Nugent |
| 6,380,223 | B1 | 4/2002 | Dow et al. |
| 6,436,986 | B1 | 8/2002 | Kym et al. |
| 6,506,766 | B1 | 1/2003 | Coghlan et al. |
| 6,583,180 | B2 | 6/2003 | Link et al. |
| 6,589,947 | B1 | 7/2003 | Hamanaka et al. |
| 6,699,893 | B2 | 3/2004 | Dow et al. |
| 6,777,404 | B2 | 8/2004 | Hamanaka et al. |

(Continued)

FOREIGN PATENT DOCUMENTS

| | | |
|---|---|---|
| BE | 900594 | 3/1985 |
| CA | 2305458 A1 | 12/1998 |

(Continued)

OTHER PUBLICATIONS

Hamann, Lawrence, et al ; Discovery of a potent, Orally active, Nonsteroidal Androgen Receptor Agonist: 4-Ethyl-1,2,3,4-tetrahydro-6-(trifluoromethyl)-8-pyridono[5,6-g]quinoline(LG121071), J. Med Chem, 1999, 42, 210-212.

Hamann, Lawrence, et al; Synthesis and Biological Activity of a Novel Series of Nonsteroidal, Peripherally Selective androgen Receptor Antagonists Derived from 1,2-Dihydropyridono[5,6-g] quinolines J. Med. Chem 1998, 41, 623-639.

Heck, S., et al "A distinct modulating domain in glucocorticoid receptor monomers in the repression of activity of the transcription factor AP-1" EMBO. J. 1994, 17, pp. 4087-4095.

Ho et al., Journal of Pharmaceutical Sciences (1971), 60(4), pp. 636-637.

Ho, Bt., et al; Central Nervous system Depressive Activity of some Amides of Tryptamine, J. Med. Chem., vol. 14, No. 6, 1971 pp. 553-554.

Hu,Hong, et al: "Synthesis and protein kinase C inhibitory activities of indane analogs of balanol" Bioorganic & Medicinal Chemistry Letters, Oxford, GB vol. 6, No. 8, Apr. 23, 1996, pp. 973-978.

(Continued)

Primary Examiner — Yong Chu
(74) Attorney, Agent, or Firm — Michael P. Morris; Timothy X. Witkowski; Usha R. Patel

(57) ABSTRACT

Compounds of Formula (IA)

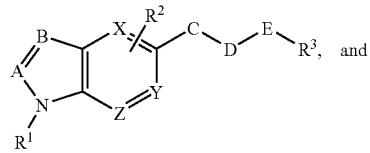

Formula (IB)

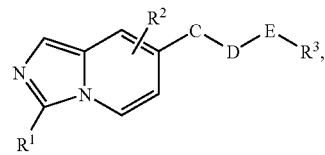

wherein $R^1$, $R^2$, $R^3$, A, B, C, D, E, G, X, Y, and Z are as defined herein, or a tautomer, prodrug, solvate, or salt thereof; pharmaceutical compositions containing such compounds, and methods of modulating the glucocorticoid receptor function and methods of treating disease-states or conditions mediated by the glucocorticoid receptor function or characterized by inflammatory, allergic, or proliferative processes in a patient using these compounds.

4 Claims, No Drawings

(56) References Cited

U.S. PATENT DOCUMENTS

| | | |
|---|---|---|
| 6,858,627 B2 | 2/2005 | Bekkali et al. |
| 6,903,215 B2 | 6/2005 | Betageri et al. |
| 6,960,581 B2 | 11/2005 | Betageri et al. |
| 7,074,806 B2 | 7/2006 | Kirrane, Jr. et al. |
| 7,125,996 B2 | 10/2006 | Prokopowicz, III et al. |
| 7,166,593 B2 | 1/2007 | Dow et al. |
| 7,179,919 B2 | 2/2007 | Song et al. |
| 7,186,864 B2 | 3/2007 | Kirrane, Jr. et al. |
| 7,189,758 B2 | 3/2007 | Betageri et al. |
| 7,256,300 B2 | 8/2007 | Lee et al. |
| 7,268,152 B2 | 9/2007 | Bekkali et al. |
| 7,425,629 B2 | 9/2008 | Song et al. |
| 7,507,843 B2 | 3/2009 | Song et al. |
| 7,553,966 B2 | 6/2009 | Betageri et al. |
| 7,579,469 B2 | 8/2009 | Kuzmich et al. |
| 7,622,594 B2 * | 11/2009 | Mugge et al. ............... 548/362.5 |
| 7,635,711 B2 | 12/2009 | Kuzmich et al. |
| 7,713,989 B2 | 5/2010 | Dow et al. |
| 7,741,361 B2 | 6/2010 | Kuzmich et al. |
| 7,888,381 B2 * | 2/2011 | Duan et al. .................. 514/406 |
| 7,932,392 B2 | 4/2011 | Betageri et al. |
| 2001/0014754 A1 | 8/2001 | Suzuki et al. |
| 2002/0077356 A1 | 6/2002 | Jaroch et al. |
| 2002/0156311 A1 | 10/2002 | Link et al. |
| 2003/0105099 A1 | 6/2003 | Graupe et al. |
| 2003/0108910 A1 | 6/2003 | Toland et al. |
| 2003/0171359 A1 | 9/2003 | Dahmann et al. |
| 2003/0232823 A1 | 12/2003 | Betageri et al. |
| 2004/0010020 A1 | 1/2004 | Kirrane et al. |
| 2004/0010148 A1 | 1/2004 | Kirrane et al. |
| 2004/0023999 A1 | 2/2004 | Bekkali et al. |
| 2004/0029932 A1 | 2/2004 | Bekkali et al. |
| 2004/0058978 A1 | 3/2004 | Walter et al. |
| 2004/0075864 A1 | 4/2004 | Kato et al. |
| 2004/0097574 A1 | 5/2004 | Marshall |
| 2004/0116455 A1 | 6/2004 | Bekkali et al. |
| 2004/0116694 A1 | 6/2004 | Jaroch et al. |
| 2004/0162321 A1 | 8/2004 | Kuzmich et al. |
| 2004/0209875 A1 | 10/2004 | Schmees et al. |
| 2004/0224992 A1 | 11/2004 | Cywin et al. |
| 2004/0242613 A1 | 12/2004 | Cardozo et al. |
| 2004/0254249 A1 | 12/2004 | Jaroch et al. |
| 2005/0043301 A1 | 2/2005 | Liu et al. |
| 2005/0059714 A1 | 3/2005 | Betageri et al. |
| 2005/0124640 A1 | 6/2005 | Cardozo et al. |
| 2005/0131241 A1 | 6/2005 | Song et al. |
| 2005/0176706 A1 | 8/2005 | Bekkali et al. |
| 2005/0203128 A1 | 9/2005 | Kirrane et al. |
| 2005/0209488 A1 | 9/2005 | Song et al. |
| 2005/0234091 A1 | 10/2005 | Regan et al. |
| 2005/0234250 A1 | 10/2005 | Lee et al. |
| 2005/0282881 A1 | 12/2005 | Bekkali et al. |
| 2006/0014787 A1 | 1/2006 | Kirrane et al. |
| 2006/0030561 A1 | 2/2006 | Betageri et al. |
| 2006/0030608 A1 | 2/2006 | Nelson et al. |
| 2006/0122189 A1 | 6/2006 | Feenstra et al. |
| 2006/0154925 A1 | 7/2006 | Kuzmich et al. |
| 2006/0189646 A1 | 8/2006 | Kuzmich et al. |
| 2006/0189647 A1 | 8/2006 | Bekkali et al. |
| 2006/0205712 A1 | 9/2006 | Calvani et al. |
| 2007/0060633 A1 | 3/2007 | Mugge et al. |
| 2007/0100142 A1 | 5/2007 | Song et al. |
| 2009/0176807 A1 | 7/2009 | Regan et al. |
| 2009/0325988 A1 | 12/2009 | Harcken et al. |

FOREIGN PATENT DOCUMENTS

| | | | |
|---|---|---|---|
| CA | 2323111 | A1 | 10/1999 |
| CA | 2342622 | A1 | 4/2000 |
| CA | 2411165 | A1 | 12/2002 |
| CA | 2463989 | A1 | 4/2003 |
| DE | 1017612 | B | 10/1957 |
| EP | 0154528 | | 9/1985 |
| EP | 0253500 | | 1/1988 |
| EP | 0253503 | | 1/1988 |
| EP | 0311447 | A1 | 4/1989 |
| GB | 2146987 | | 5/1985 |
| JP | 5194404 | A | 8/1993 |
| JP | 11080131 | A | 3/1999 |
| WO | 9315047 | A1 | 8/1993 |
| WO | 9619458 | | 6/1996 |
| WO | 9727852 | | 8/1997 |
| WO | 9854159 | | 12/1998 |
| WO | 9933786 | A1 | 7/1999 |
| WO | 9941256 | | 8/1999 |
| WO | 9952869 | A1 | 10/1999 |
| WO | 9963976 | A2 | 12/1999 |
| WO | 0018734 | A1 | 4/2000 |
| WO | 0032584 | A2 | 6/2000 |
| WO | 0066522 | | 11/2000 |
| WO | 0105784 | A1 | 1/2001 |
| WO | 0183471 | A1 | 11/2001 |
| WO | 0202565 | | 1/2002 |
| WO | 0209702 | A2 | 2/2002 |
| WO | 0210143 | A1 | 2/2002 |
| WO | 02051983 | | 7/2002 |
| WO | 02064550 | | 8/2002 |
| WO | 03031606 | A2 | 4/2003 |
| WO | 03032997 | A1 | 4/2003 |
| WO | 03059899 | A1 | 7/2003 |
| WO | 03082280 | A1 | 10/2003 |
| WO | 03082787 | A1 | 10/2003 |
| WO | 03082827 | A1 | 10/2003 |
| WO | 03104195 | A1 | 12/2003 |
| WO | 2004005278 | A1 | 1/2004 |
| WO | 2004018429 | A2 | 3/2004 |
| WO | 2004019935 | A1 | 3/2004 |
| WO | 2004063163 | A1 | 7/2004 |
| WO | 2004071389 | A2 | 8/2004 |
| WO | 2004075864 | A2 | 9/2004 |
| WO | 2004089415 | A2 | 10/2004 |
| WO | 2005019202 | A1 | 3/2005 |
| WO | 2005030213 | A1 | 4/2005 |
| WO | 2005090343 | A1 | 9/2005 |
| WO | 2006046916 | A1 | 5/2006 |
| WO | 2006071609 | A2 | 7/2006 |
| WO | 2006135826 | A1 | 12/2006 |
| WO | 2007040959 | A1 | 4/2007 |

OTHER PUBLICATIONS

International Search Report PCT/US07185831 mailed Jul. 4, 2008.
International Search Report PCT1US2007/085831 mailed Jul. 4, 2008.
Iseki, K. et al; "Asymmetric Trifluoromethylation of Aldehydes and Ketones with Trifluoromethyltrimethylsilane Catalysed by Chiral Quarternary Ammonium Fluorides"; Tetrahedron Letters, vol. 35, No. 19, 1994, pp. 3137-3138,.
Janoshazi, A. et al. "Rapid Vitro Conformational Changes of the Catalytic Site of PKCalpha Assessed by FIM-1 Fluorescence" Biochemistry 1999,38, p13316-13327.
Jordan V.C., Nature Reviews: Drug Discovery, 2, 2003, p. 205.
Krishnamurti, et al; Journal of Organic Chemistry 1991, 56, 984-989.
Kutney, J.P., et al; Total synthesis of Dregamine and Epidregamine, a General Routge to 2 Acylindole Alkaloids, J. Am., Chem. Soc. vol. 100 No. 3, 1978 pg. 938-943.
Lagidze et al., CA 102:184944, 1985.
Lagidze, D.R., et al: Synthesis of Some new analogs of melatonin and beta carboline from 4 phenylpentanoic acid; p. 637, 1981.
Maligres, P. et al: "Nosylaziridines: Activated Aziridine Electrophiles" Tetrhedron Letters, Elsevier, Amsterdam, vol. 38, No. 30, 28 Jul. 1997, p. 5253-5256.
Marshall, Daniel R; et al; Poster entitled: a-Methyltryptamine sulfonamide derivatives as novel glucocorticoid receptor ligands, presented at the 227th American Chemical Society National Meeting, Anaheim CA, Apr. 28-May 1, 2004.
Marshall, Daniel; et al; a-Methyltryptamine sulfonamide derivatives as novel glucocorticoid receptor ligands, Bioorganic and Medicinal Chemistry Letters 17, (2007) pg. 315-319.
Nenajdenko, Valetine G., et al; A new convenient approach to chiral -aryl(heteroaryl)alkylamines, Tetrahedron: Asymmetry 12(18) 2517-2527, Oct. 15, 2001.

(56) References Cited

OTHER PUBLICATIONS

Oakley, R.H., et al; The glucocorticoid receptor; expression, function and regulation of glucocorticoid responsiveness; Glucocorticoids, 2001, pgs. 55-80.
Onistschenko et al., CA 112:55520, 1990.
Osipov, Serge J.N. et al: a-Fluoromethyl Tryptophans via Imino Ene Reaction Synlett 2001, No. 8, 1287-1289, Letter.
Outinen et al., European Journal of Pharmaceutical Sciences (1998), 6(3), pp. 197-205.
Palmisano, G., et al; Synthetic Studies on Indole Alkaloids. A Stereocontrolled Entry to the Cuanzine Structural Unit, Tetrahedron, Elsevier Sccience Publisher, Amsterdam, NL. Vol. 45, No. 11, 1989, pp. 3583-3595.
Parente, L.; The development of synthetic glucocorticoids,; Glucocorticoids, 2001, pp. 35-54.
Pargellis et al. Inhibition of P38 Map Kinase by Utilizing a Novel Allosteric Binding Site; Nature Structural Biology, vol. 9, No. 4 (2002) pp. 268-272.
Patani, et al; Bioisosterism: A Rational Approach in Drug Design, 1996, Chem Rev, vol. 96, p. 3147-3150.
Peeters, B.W.M.M, et al; Glucocorticoid Receptor Antagonistis: New Tools to Investigate Disorders Characterized by Cortisol Hypersecretion; Stress, vol. 7(4), pp. 233-241, 2004.
Pelicano et al. Study of the Substrate-Binding Properties of Bovine Liver Adenosine Kinase and Inhibition by Fluorescent Nucleoside Analogues; European Journal of Biochemistry, vol. 248 (1997) pp. 930-937.
Plihal W., et al, Psychoneuroendocrinology 1996 vol. 21 No. 6, p. 515-523.
Pooley, Charlotte, et al; Discovery and Preliminary Sar Studies of a Novel Nonsteroidal Progesterone Receptor Antagonist Pharmacophore, J. Med. Chem 1998, 41, 3461-3466.
Prakash, et al; "Asymmetric Synthesis of Trifluoromethylated Allylic Amines Using alpha,beta-Unsaturated N-tert-Butanesulfinimines", Organic Letters, 2001, vol. 3, No. 18, pp. 2847-2850.
Prodrug [online], [retrieved on Mar. 26, 2007], Retrieved from the Internet, URL; http://en.wikipedia.org/wiki/Prodrug>.
Ramaiah, et al; "Direct Trifluoromethylation of alpha-Keto Esters to beta,beta,beta-Trifluorolactic Acid Derivatives Using Trifluoromethyltrimethylsilane"; Synlett, 1991, vol. 9, pp. 643-644.
Regan, John, et al; Advances Toward Dissociated Non-Steroidal Glucocorticoid Receptors Agonists, Annual reports in Medicinal Chemistry, vol. 43, pp. 141-151, 2008.
Reichartd, H.M., et al; DNA Binding of the Glucocorticoid Receptor is not Essential for Survival, Cell, 1998, 93, pp. 531-541.
Schisla et al; "Quaternary-Substituted Hydrocarbons. A General Method of Synthesis of Hydrocarbons Interspersed with Four gem-Dimethyl Unites" Journal of Organic Chemistry, vol. 35, No. 10, 19970, pg. 3224-3230.
Shono, Tatsuya, et al: Electroorganic Chimistry 81, Anodic Oxidation of Sulfonamides and Amidophosphates, J. Org. Chem; 1984, 49, 3711-3716.
Song et al. Journal of Organic Chemistry, 2007, 72, 292-294.
Souillac, et al., Characterization of Delivery Systems, Differential Scanning Calorimetry in Encyclopedia of Controlled Drug Delivery, 1999, John Wiley & Sons, pp. 212-227.
Takami et al.: synthesis of 4,4,4-trifluoro-3-indolylisocrotonamides: Medicinal Chemistry Research, vol. 9, No. 4, 1999, pp. 239-248.
Tegley, Christopher, et al; 5-Benzylidene 1,2-Dihydrochromeno[3,4-f]quinolines, a Novel Class of Nonsteroidal Human Progesterone Receptor Agonists; J. Med. Chem 1998, 41, 4354-4359.
Toogood, J.H.; Glucocorticoids and Asthma; Glucocorticoids, 2001, pgs. 161-174.
Tronche, F., et al; Genetic dissection of glucocorticoid receptor function in mice; Curr. Opin in Genetics and Dev., 1998, 8, pp. 532-538.
Vainshtein et al. A High-Throughput, Nonisotopic, Competitive Binding Assay for Kinases Using Nonselective Inhibitor Probes (ED-NSIP); Journal of Biomolecular Screening, vol. 7, No. 6 (2003) pp. 507-514. cited by examiner.
Vankayalapati, H. et al. "Targeting Auroral Kinase in Oncogenesis: A Structural Bioinformatics Approach to Target Validation and Rational Drug Design" Molecular Cancer Therapeutics 2003, 2, p. 283-294.
Vas et al. Antagonistic Binding of Substrates to 3-Phosphoglycerate Kinase Monitored by the Fluorescent Analogue 2'(3')-O-(2,4,6-Trinitrophenyl)Adenosine 5'-Triphosphate; Biochemical Journal, vol. 301 (1994) pp. 885-891.
Vippagunta, et al; "Crystalline solids" Advanced Drug Delivery Reviews, 48, 2001, p. 3-26.
Amat-M-et-al-Preparations-and-reactions-of-4-5-and-6-methoxy-substituted-3-lithioindoles-and-3-indolylzincderivatives-Synthesis-2001-pp. 267-275.
Berry-M-B-et-al-A-convenient-method-for-preparation-of-enantiomerically-pure-2-substituted-N-tosylaziridinesSynlett-1992-pp. 41-44.
Tochilkin-A-1-et-al-8-methoxy-5-quinolinesulfonyl-chloride-A-new-fluorogenic-reagent-for-the-cletection-of-amines-andamino-acids-Bioorganicheskaya-Khimiya-1990-vol.-16-pp. 956-962.
Misztal-S-et-al-New-synthesis-of-5-nitro-and-5-benzyloxytryptamine-and-theirN-acyl-derivatives-Polish-Journal-of-Pharmacology-and-Pharmacy-1984-vol. 36-pp. 345-349.
Abstract of DE 1017612 cited herein under foreign documents—1959-121889 caplus 53:121889;53:21820H-i21821a-c; Tertiary Amines and Derivatives Thereof, Thomae GmbH DE 1017612.
Abstract JP37004545, inventors Yoshida and Fukuda, assignee Nippon Shinyaku Co., Ltd, Jun. 14, 1962.
Abstract Mikhailitsyn, F.S, et al Search for New Antiparasitic Agents 10, Synthesis, Toxicity and Antimalarial Effect of Some Nitrogen Containing Heterocycles iwth 4-(4-alkylpiperazin-1yl)phenylamino-substituents-CAPLUS accession No. :1888, AN-1992:651317.
Abstract of JP 11080131A cited herein under Foreign documents—New ethynyl-pyrimidine derivatives have excellent tyrosine kinase inhibiting and cancer cell growth inhibiting activity Sep. 1, 1997 Mitsubishi Chemical Corporation.
Abstract of Japan vol. 010 No. 004(C322) Jan. 9, 1986 & JP 60 163814A, (Wataru Mori), Aug. 26, 1985 Abstract ,.
Ambrosi et al: "Stereoselective Ssynthesis of Trifluoro- and Monofluro-Analogues of Frontaliln and Evaluation of Their Biological Activity." J. Org. Chem. 2001, 66, p. 8336-8343.
Arnone et al: "Highly Diastereoselective Methylene Transfer from Diazomethane to the Carbonyl of b-Keto Sulfoxides. A General approach to Synthetically Versatile Fluorine-Containing Chiral Building Blocks." Tetrahedron 54 (1998) pp. 11841-11860.
Bailey et al., CA 80:3337,1974.
Bailey, A. Sydney, et al: Further Examination of the reactions of Simple Indoles with Arenosulphonyl Azides, PD 1973, pp. 1602-1606.
Bamberger, C.M, et al; Molecular mechanisms of dissociative glucocorticoid activity; Eur. J. Clin. Invest. 2000, 30, Suppl 3, pp. 6-9.
Barnes N.J. Allergy Clin. Immunol. Apr. 1998; 101 (4 Pt 2), S460-464 Abstract.
Barnes, P.J., Anti-inflammatory actions of glucocorticoids; molecular mechanisms; Clinical Science 1998 vol. 94, pp. 557-572.
Barnes, P.J., Anti-inflammatory actions of steroids; molecular mechanisms; Trends Pharm. Sci. 1993, 14, pp. 436-441.
Beilstein No. 7067440—J. Chem. Soc. Dalton, Trans. , vol. 22, 1994, pp. 3202-3210.
Beilstein Registry No. 318403 and 341608; Beilstein Institut zur Foerderung ger Chemischen Wissenschaffen, Frankfurt Am Main, DE, Entry date Jun. 27, 1998 update date May 13, 1992.
Bledsoe, K.R., Cell, 2002, vol. 110, p. 93-105.
Bravo, P., et al; Synthesis of (−)-(1S,5R) and (+)-1R,5S)-trifluoroanalogues of frontalin; Tetrahedron Letters 40 (1999)—6317-6320.
Bundgaard, Design of Prodrugs, 1985, Elsevier, p. 1-3.
CA Registry No. 288843-68-5—entry date into Registry file on STN is Sep. 13, 2000.
CA Registry No. 311781-49-4—entry date into Registry file on STN is Dec. 28, 2000.
CA Registry No. 442531-80-8—entry date into Registry file on STN is Aug. 5, 2002.

(56) References Cited

OTHER PUBLICATIONS

CA Registry No. 442531-85-3—entry date into Registry file on STN is Aug. 5, 2002.
CA Registry No. 442630-99-1—entry date into Registry file on STN is Aug. 6, 2002.
CA Registry No. 442632-92-0—entry date into Registry file on STN is Aug. 6, 2002.
CA Registry No. 442632-93-1—entry date into Registry file on STN is Aug. 6, 2002.
CA Registry No. 442633-42-3—entry date into Registry file on STN is Aug. 6, 2002.
CA Registry No. 442657-75-2—entry date into Registry file on STN is Aug. 6, 2006.
CA Registry No. 442657-79-6—entry date into Registry file on STN is Aug. 6, 2006.
CA Registry No. 442657-92-3—entry date into Registry file on STN is Aug. 6, 2006.
CA Registry No. 442658-57-3—entry date into Registry file on STN is Aug. 6, 2006.
CA Registry No. 442658-66-4—entry date into Registry file on STN is Aug. 6, 2006.
CA Registry No. 442658-95-9—entry date into Registry file on STN is Aug. 6, 2006.
CA Registry No. 442666-01-5—entry date into Registry file on STN is Aug. 6, 2006.
CA Registry No. 442666-02-6—entry date into Registry file on STN is Aug. 6, 2006.
Casella, Luigi, et al. "Cytochrome c Oxidase Models; Synthesis and Reactivity of Iron (III)-Copper (II) Complexes of Deuterohaemin-Polybenzimidazole Dinucleating Ligands " J. Chem. Soc. Dalton Trans, 1994, vol. 22, pp. 3202-3210.
Coghlan M.J. et al J. Med Chem. 2001, 44, 2879,-2885 (pp. 2880). Davis, CA 92:40803, 1980.
Doerwald, F.Z.: "Side Reactions in Organic Synthesis: A Guide o Successful Synthesis Design" 2005 Wiley & Co KGaA Weinheim.
Edwards, James, P. et al; 5-Aryl-1,2-dihydro-5H-chromeno[3,4-f]quinolines as Potent, Orally Active, Nonsteroidal Progstgerone Receptor Agonists; the Effect of D-Ring Substituents, J. Med. Chem 1998, 41, 303-310.
Edwards, James, P. et al; Preparation, Resolution and Biological Evaluation of 5-Aryl-1,2-dihydro-5H-chromeno[3,44] quinolines as Potent, Orally Active, Nonsteroidal Progesterone Receptor Agonists; J. Med. Chem, 1998,41, 2779-2785.
English Translation of WO/02/10143, Feb. 2002.
Epps et al. An Experimental Method for the Determination of Ensyme-Competitive Inhibitor Dissociation Constants from Displacement Curves: Application to Human Renin Using Fluorescence Energy Transfer to a Synthetic Dansylated Inhibitor Peptide; Analytical Biochemistry, vol. 181 (1989) pp. 172-181.
Evans, R.M., The Steroid and Thyroid Hormone Receptor Superfamily; Science 1988, 240, pgs. 889-895.
Friedman, J.E., et al; Phosphoenolpyruvate Carboxykinase (GTP) Gene Transcription and Hyperglycemia Are Regulated by Glucocorticoids in Genetically Obese db/db Transgenic Mice; J. Biol. Chem. 1997, 272, pp. 31475-31481.
Hagiwara, et al; "Lewis Base Catalyzed Trifluoromethylation of Carbonyl Compounds with Trialkyl(trifluoromethyl) silanes," Main Group Chem. 1997, vol. 2, p. 13.
Hall et al., Tetrahedron, 23, (1967), pp. 4131-4141.
Wolff, Manfred E., Ed. Burger's Medicinal Chemistry and Drug Discovery—Fifth Edition, New York: John Wiley & Sons, 1996 vol. 1, pp. 975-976.
Wu and Farrley, Toxicology 236: 1-6 2007.
Zembower, D.E. et al: "Enantiospecific Syntheses of Alpha-Fluoromethyl) Tryptophan Analogues: Interatctions with Tryptophan Hydroxylase and Aromatic L-Amino Acid Decarboxylase", Journal of Medicinal Chemistry, American Chemical Society, Washing, US vol. 36, No. 3 Feb. 5, 1993 p. 305-313.
Zhi, Lin, et al; 5-Aryl-1,2-dihydro-5H-chromeno[3,4-f]quinolines: A Novel Class of Nonsteroidal Human Progesterone Receptor Agonists, J. Med. Chem 1998, 41, 291-302.
Zhi, Lin; et al 5-Aryl-1,2,3,4-tetrahydrochromeno[3,4-f]quinolin-3-ones as a Novel Class of Nonsteroidal Progesterone Receptor Agonists: Effect of A-Ring Modification, J. Med. Chem 1999, 42, 1466-1472.
Abstract—Chemical Encylopaedic Dictionary, Moscow Soviet Encyclopeadia (1983) pp. 130-131.
Abstract—Mashkovsky M.D. Drugs, Moscow, Medicine (1993) vol. 1, pg. 8.
Banker G.S. et al.; editor "Modern Pharmaceutics, 3rd edition" Marcel Dekker, Inc. 1996, pp. 451 and 596.
Betageri, R.; U.S. Appl. No. 11/185,349, Office Action dated Jul. 14, 2009.
Biggadike, Keith et al. "Nonsteroidal Glucocorticoid Agonists: Tetrahydronaphthalens with Alternative Steroidal A-Ring Mimetics Possessing Dissociated (Transrepression/Transactivation) Efficacy Selectivity" J. Med. Chem. (2007) vol. 50, pp. 6519-6534.
Fahrenholtz, Kenneth E. et al. "3-Phenyl-5[2,2,2-trifluoro-1-hydroxy-1-(trifluoromethyl)ethyl]indole-2-carbonitrile, a Potent Inhibitor of Prostaglandin Synthetase and of Platelet Aggregation" (1979) Journal of Medicianl Chemistry vol. 22, No. 8, pp. 948-953.
Hoffmann, Reinhard W. et al. "Towards an Understanding of Cram/anti-Cram Selectivity on Addition of Crotylboronates to a-Methylbutyraldehyde" Chem. Ber. (1990) vol. 123, pgs. 2387-2394.
Response filed Sep. 18, 2009 to Office Action dated Jul. 14, 2009, U.S. Appl. No. 11/185,349.
Takami, Hitoshi et al. "Synthetic Studies on Trifluoroacetylindoles" Heterocycles (1999) vol. 51, No. 5 pp. 1119-1124.
West, Anthony R. "Solid state chemistry and its applications" Wiley & Sons, 1988 pp. 358 and 365.
WO02051983 (Part 1 of 2) International Publication Date: Jul. 4, 2002. Patentee: Celera, an Applera Corporation Business. Inventor: Frank Halley. Title: Novel Compounds and Compositions of Cathespin Inhibitors. Total pp. 724. Part 1 of 2. This foreign patent is too large for EFS submission via the Foreign patent section, therefore filing in two parts in the NPL section. pp. 1- 350.
W002051983 (Part 2 of 2) International Publication Date: Jul. 4, 2002. Patentee: Celera, an Applera Corporation Business. Inventor: Frank Halley. Title: Novel Compounds and Compositions of Cathespin Inhibitors. Total pp. 724. Part 2 of 2. This foreign patent is too large for EFS submission via the Foreign patent section, therefore filing in two parts in the NPL section. pp. 351-724.
Abstract—JP 59 053479A Mar. 28, 1984.
Abstract Karavan V.S., et al "Method of producing benzyl trifluoromethyl ketones by Grignard reaction" CAPLUS accession No. AN-1992:128371 (1992).
Abstract, Mikhailitsyn, F.S. et al, New Synthesis of Derivatives of 6,6' diquinoline from 4,4'-diaminodiphenykl-3,3'dicarboxylic acid; —XP002266777 (1974).
Bailey et al.; New asymmetric route to bridged indole alkaloids: formal enantiospecific syntheses of (-)-suaveoline, (-)-raumacline and (-)-Nb-methylraumacline; Journal of the Chemical Society; 1997; Perkin Trans. pp. 1209-1214.
Beilstein Registry No. 7178110 and 7178430, Online, Beilstein Institut zur Foerderung ger Chemischen Wissenschaffen, Frankfurt Am Main, DE, (1989).
Elliott et al.; Studies in the Indole Series. Part IV. Sulphonamides derived from Indole; Journal of Chemical Society; 1944; pp. 632-633.
Fleming et al.; CA 64:9697 f-g; 1966.
Hawley's Condensed Chemical Dictionary 14th Edition (2001).
Lee, Thomas W. et al. "A concise asymmetric route for the synthesis of a novel class of glucocorticoid mimetics containing a trifluoromethyl-substituted alcohol" (2006) Bioorganic & Medicinal Chemistry Letters pp. 654-657.
Otsuki et al.; Reaction of N-Haloamide. XXII. Reaction of N,N-dibromobenzenesulfonamide with safrole; Chemical Pharmaceutical Bulletin; 1975; vol. 23; No. 3; pp. 482-486.
Troschuetz et al.; Sensitive and Specific Determination of Serotonin in the Presence of Tryptamine and 5-Methoxytryptamine by High-Pressure Liquid-Chromatography; Fresenious Zeitschrift fuer Analytische Chemi; 1978; No. 289; pp. 202-205.

\* cited by examiner

GLUCOCORTICOID MIMETICS, METHODS OF MAKING THEM, PHARMACEUTICAL COMPOSITIONS AND USES THEREOF

This application is the national phase entry under 35 U.S.C. §371 of International Application No. PCT/US2007/85831, filed Nov. 29, 2007, which claims priority to U.S. Provisional Application No. 60/868,844, filed Dec. 6, 2006, each of which is hereby incorporated by reference in its entirety.

FIELD OF THE INVENTION

The present invention relates to glucocorticoid mimetics or ligands, methods of making such compounds, their use in pharmaceutical compositions, and their use in modulating the glucocorticoid receptor function, treating disease-states or conditions mediated by the glucocorticoid receptor function in a patient in need of such treatment, and other uses.

BACKGROUND OF THE INVENTION

Glucocorticoids, a class of corticosteroids, are endogenous hormones with profound effects on the immune system and multiple organ systems. They suppress a variety of immune and inflammatory functions by inhibition of inflammatory cytokines such as IL-1, IL-2, IL-6, and TNF, inhibition of arachidonic acid metabolites including prostaglandins and leukotrienes, depletion of T-lymphocytes, and reduction of the expression of adhesion molecules on endothelial cells (P. J. Barnes, Clin. Sci., 1998, 94, pp. 557-572; P. J. Barnes et al., Trends Pharmacol. Sci., 1993, 14, pp. 436-441). In addition to these effects, glucocorticoids stimulate glucose production in the liver and catabolism of proteins, play a role in electrolyte and water balance, reduce calcium absorption, and inhibit osteoblast function.

The anti-inflammatory and immune suppressive activities of endogenous glucocorticoids have stimulated the development of synthetic glucocorticoid derivatives including dexamethasone, prednisone, and prednisolone (L. Parente, *Glucocorticoids*, N. J. Goulding and R. J. Flowers (eds.), Boston: Birkhauser, 2001, pp. 35-54). These have found wide use in the treatment of inflammatory, immune, and allergic disorders including rheumatic diseases such as rheumatoid arthritis, juvenile arthritis, and ankylosing spondylitis, dermatological diseases including psoriasis and pemphigus, allergic disorders including allergic rhinitis, atopic dermatitis, and contact dermatitis, pulmonary conditions including asthma and chronic obstructive pulmonary disease (COPD), and other immune and inflammatory diseases including Crohn disease, ulcerative colitis, systemic lupus erythematosus, autoimmune chronic active hepatitis, osteoarthritis, tendonitis, and bursitis (J. Toogood, *Glucocorticoids*, N. J. Goulding and R. J. Flowers (eds.), Boston: Birkhauser, 2001, pp. 161-174). They have also been used to help prevent rejection in organ transplantation.

Unfortunately, in addition to the desired therapeutic effects of glucocorticoids, their use is associated with a number of adverse side effects, some of which can be severe and life-threatening. These include alterations in fluid and electrolyte balance, edema, weight gain, hypertension, muscle weakness, development or aggravation of diabetes mellitus, and osteoporosis. Therefore, a compound that exhibited a reduced side effect profile while maintaining the potent anti-inflammatory effects would be particularly desirable, especially when treating a chronic disease.

The effects of glucocorticoids are mediated at the cellular level by the glucocorticoid receptor (R. H. Oakley and J. Cidlowski, *Glucocorticoids*, N. J. Goulding and R. J. Flowers (eds.), Boston: Birkhauser, 2001, pp. 55-80). The glucocorticoid receptor is a member of a class of structurally related intracellular receptors that when coupled with a ligand can function as a transcription factor that affects gene expression (R. M. Evans, Science, 1988, 240, pp. 889-895). Other members of the family of steroid receptors include the mineralocorticoid, progesterone, estrogen, and androgen receptors. In addition to the effects mentioned above for glucocorticoids, hormones that act on this receptor family have a profound influence on body homeostasis, mineral metabolism, the stress response, and development of sexual characteristics. *Glucocorticoids*, N. J. Goulding and R. J. Flowers (eds.), Boston: Birkhauser, 2001, is hereby incorporated by reference in its entirety to better describe the state of the art.

A molecular mechanism which accounts for the beneficial anti-inflammatory effects and the undesired side effects has been proposed (e.g., S. Heck et al., EMBO J, 1994, 17, pp. 4087-4095; H. M. Reichardt et al., Cell, 1998, 93, pp. 531-541; F. Tronche et al., Curr. Opin. in Genetics and Dev., 1998, 8, pp. 532-538). Many of the metabolic and cardiovascular side effects are thought to be the result of a process called transactivation. In transactivation, the translocation of the ligand-bound glucocorticoid receptor to the nucleus is followed by binding to glucocorticoid response elements (GREs) in the promoter region of side effect-associated genes, for example, phosphoenolpyruvate carboxy kinase (PEPCK) in the case of increased glucose production. The result is an increased transcription rate of these genes which is believed to result, ultimately, in the observed side effects. The anti-inflammatory effects are thought to be due to a process called transrepression. In general, transrepression is a process independent of DNA binding that results from inhibition of NF-kB and AP-1-mediated pathways, leading to down regulation of many inflammatory and immune mediators. Additionally, it is believed that a number of the observed side effects may be due to the cross-reactivity of the currently available glucocorticoids with other steroid receptors, particularly the mineralocorticoid and progesterone receptors.

Thus, it may be possible to discover ligands for the glucocorticoid receptor that are highly selective and, upon binding, can dissociate the transactivation and transrepression pathways, providing therapeutic agents with a reduced side effect profile. Assay systems to determine effects on transactivation and transrepression have been described (e.g., C. M. Bamberger and H. M. Schulte, Eur. J. Clin. Invest., 2000, 30 (suppl. 3), pp. 6-9). Selectivity for the glucocorticoid receptor may be determined by comparing the binding affinity for this receptor with that of other steroid family receptors including those mentioned above.

Glucocorticoids also stimulate the production of glucose in the liver by a process called gluconeogenesis and it is believed that this process is mediated by transactivation events. Increased glucose production can exacerbate type II diabetes, therefore a compound that selectivity inhibited glucocorticoid mediated glucose production may have therapeutic utility in this indication (J. E. Freidman et al., J. Biol. Chem., 1997, 272, pp. 31475-31481).

Novel ligands for the glucocorticoid receptor have been described in the scientific and patent literature. For example, PCT International Publication No. WO 04/093805 discloses selective spirocyclic glucocorticoid receptor modulators potentially useful in treating many inflammatory diseases, including rheumatoid arthritis and Crohn's disease. PCT International Publication No. WO 04/026248 discloses octahydro-2H-naphtho[1,2-f]indole-4-carboxamide derivatives as selective glucocorticoid receptor modulators potentially useful in treating for the treatment of many inflammatory diseases, including rheumatoid arthritis and Crohn's disease. PCT International Publication No. WO 04/075840 discloses selective non-steroidal glucocorticoid receptor modulator with potential use as anti-inflammatory agents possessing advantages over the glucocorticoid ligands with respect to side-effects, efficacy, and toxicity. PCT International Publication No. WO 03/086294 discloses 1H-benzo[f] indazol-5-yl derivatives as selective glucocorticoid receptor modulators potentially useful in treating for the treatment of many inflammatory diseases, including rheumatoid arthritis and Crohn's disease. PCT International Publication No. WO 03/061651 and the corresponding U.S. Application Publication No. 2005/0054700 disclose non-steroidal ligands for the glucocorticoid receptor, potentially useful in treating metabolic and inflammatory diseases. PCT International Publication No. WO 99/33786 discloses triphenylpropanamide compounds with potential use in treating inflammatory diseases. PCT International Publication No. WO 00/66522 describes non-steroidal compounds as selective modulators of the glucocorticoid receptor potentially useful in treating metabolic and inflammatory diseases. PCT International Publication No. WO 99/41256 describes tetracyclic modulators of the glucocorticoid receptor potentially useful in treating immune, autoimmune, and inflammatory diseases. U.S. Pat. No. 5,688,810 describes various non-steroidal compounds as modulators of glucocorticoid and other steroid receptors. PCT International Publication No. WO 99/63976 describes a non-steroidal, liver-selective glucocorticoid antagonist potentially useful in the treatment of diabetes. PCT International Publication No. WO 00/32584 discloses non-steroidal compounds having anti-inflammatory activity with dissociation between anti-inflammatory and metabolic effects. PCT International Publication No. WO 98/54159 describes non-steroidal cyclically substituted acylanilides with mixed gestagen and androgen activity. U.S. Pat. No. 4,880,839 describes acylanilides having progestational activity and EP 253503 discloses acylanilides with antiandrogenic properties. PCT International Publication No. WO 97/27852 describes amides that are inhibitors of farnesylprotein transferase.

2,2,2-Trifluoro-1,1-bis-[1-(1-propylbutyl)-1H-indol-5-yl] ethanol has been reported as a byproduct of the condensation of 5-bromo-1-(1-propylbutyl)-1H-indole and trifluoroacetyl anhydride under metal halogen exchange conditions (H. Takami et al., Heterocycles, 1999, 51, pp. 1119-1124). The 4,4,4-trifluoro-3-hydroxy-3-[1-(1-propylbutyl)-1H-indol-5-yl]butyric acid ethyl ester has been disclosed as a product of a Reformatsky reaction between bromoacetic acid ethyl ester and 2,2,2-trifluoro-1-[1-(1-propylbutyl)-1H-indol-5-yl]ethanone (H. Takami et al., Med. Chem. Res. EN, 1999, 9(4), pp. 239-248).

A compound that is found to interact with the glucocorticoid receptor in a binding assay could be an agonist or an antagonist. The agonist properties of the compound could be evaluated in the transactivation or transrepression assays described above. Given the efficacy demonstrated by available glucocorticoid drugs in inflammatory and immune diseases and their adverse side effects, there remains a need for novel glucocorticoid receptor agonists with selectivity over other members of the steroid receptor family and a dissociation of the transactivation and transrepression activities. Alternatively, the compound may be found to have antagonist activity. As mentioned above, glucocorticoids stimulate glucose production in the liver. Increased glucose production induced by glucocorticoid excess can exacerbate existing diabetes or trigger latent diabetes. Thus, a ligand for the glucocorticoid receptor that is found to be an antagonist may be useful, inter alia, for treating or preventing diabetes.

SUMMARY OF THE INVENTION

The instant invention is directed to compounds of Formula (IA)

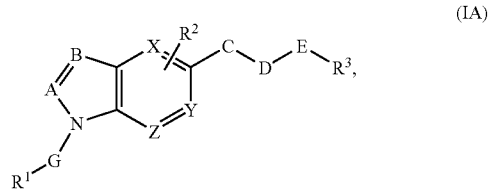

(IA)

wherein:
$R^1$ is hydrogen, aryl, heteroaryl, $C_3$-$C_7$ alkyl, or $C_3$-$C_7$ cycloalkyl, each optionally independently substituted with one to three substituent groups selected from $C_1$-$C_3$ alkyl, hydroxy, halogen, oxo, methoxy, amino wherein the nitrogen atom is optionally independently mono- or disubstituted with a methyl group, or thiomethyl wherein the sulfur atom is optionally oxidized to a sulfoxide or sulfone;
G is a bond or —C(O)—, —C(O)CH$_2$—, —CO$_2$—, —CO$_2$CH$_2$—, —SO$_2$—, —SO$_2$CH$_2$—, or —C(O)N (R$^7$)—, where $R^7$ is hydrogen or methyl;
$R^2$ is hydrogen or a halogen;
X, Y, and Z are each independently C or N;
A and B are each independently C or N, each optionally and independently substituted with a methyl, hydrogen, hydroxyl, or cyano group;
C is a bond or —NR$^4$— where $R^4$ is a hydrogen or $C_1$-$C_5$ alkyl group;
E is a bond —CH$_2$—, or —NR$^4$CH$_2$—, or —NR$^4$SO$_2$—, where $R^4$ is a hydrogen or $C_1$-$C_5$ alkyl group;
D is —CR$^5$R$^6$—, where $R^5$ is a trifluoromethyl group and $R^6$ is a hydroxy or a hydrogen; and
$R^3$ is $C_1$-$C_6$ alkyl, cycloalkyl, cycloalkenyl, aryl, heteroaryl, or heterocyclyl, each optionally independently substituted with one to three substituent groups, and each substituent group is connected to $R^3$ by a bond or $C_1$-$C_6$ alkyl group, wherein each substituent group of $R^3$ is independently aryl, heteroaryl, heterocyclyl, $C_1$-$C_5$ alkyl, $C_1$-$C_5$ alkenyl, cycloalkyl, cycloalkenyl, acyl, alkoxycarbonyl, $C_1$-$C_5$ alkanoyloxy, $C_1$-$C_5$ alkanoyl, aroyl, $C_1$-$C_5$ alkanoylamino, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, aryloxy, arylthio, halogen, hydroxy, oxo, cyano, trifluoromethyl, nitro, carboxyl, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone,
wherein each substituent group of $R^3$ is optionally independently substituted with one to three substituents selected from aryl, heteroaryl, heterocyclyl, acyl, $C_1$-$C_5$ alkyl, $C_1$-$C_5$ alkanoyloxy, $C_1$-$C_5$ alkanoyl, $C_1$-$C_5$ alkanoylamino, alkylaminocarbonyl, dialkylaminocarbonyl, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, $C_1$-$C_5$ cycloalkyl, aryloxy, halogen, hydroxy, oxo, cyano, trifluoromethyl, nitro, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, or a tautomer, prodrug, solvate, or salt thereof.

Another aspect of the invention includes compounds of Formula (IA), wherein:

$R^1$ is aryl, heteroaryl, $C_3$-$C_7$ alkyl, or $C_3$-$C_7$ cycloalkyl each optionally independently substituted with one to three substituent groups selected from $C_1$-$C_3$ alkyl, hydroxy, halogen, oxo, methoxy, amino wherein the nitrogen atom is optionally independently mono- or disubstituted with a methyl group, or thiomethyl wherein the sulfur atom is optionally oxidized to a sulfoxide or sulfone;

G is a bond;

$R^2$ is hydrogen or a halogen;

X, Y, and Z are each independently C or N;

A and B are each independently CH or N;

C is a —$NR^4$— where $R^4$ is a hydrogen or alkyl;

E is bond or a —$CH_2$—;

D is —$CR^5R^6$—, where $R^5$ is a trifluoromethyl group and $R^6$ is a hydrogen; and $R^3$ is $C_1$-$C_6$ alkyl, cycloalkyl, cycloalkenyl, aryl, heteroaryl, or heterocyclyl, each optionally independently substituted with one to three substituent groups, and each substituent group is connected to $R^3$ by a bond or $C_1$-$C_3$ alkyl group, wherein each substituent group of $R^3$ is independently aryl, heteroaryl, heterocyclyl, $C_1$-$C_5$ alkyl, $C_1$-$C_5$ alkenyl, cycloalkyl, cycloalkenyl, acyl, alkoxycarbonyl, $C_1$-$C_5$ alkanoyloxy, $C_1$-$C_5$ alkanoyl, aroyl, $C_1$-$C_5$ alkanoylamino, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, aryloxy, arylthio, halogen, hydroxy, oxo, cyano, trifluoromethyl, nitro, carboxyl, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, wherein each substituent group of $R^3$ is optionally independently substituted with one to three substituents selected from aryl, heteroaryl, heterocyclyl, acyl, $C_1$-$C_5$ alkyl, $C_1$-$C_5$ alkanoyloxy, $C_1$-$C_5$ alkanoyl, $C_1$-$C_5$ alkanoylamino, alkylaminocarbonyl, dialkylaminocarbonyl, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, $C_1$-$C_5$ cycloalkyl, aryloxy, halogen, hydroxy, oxo, cyano, trifluoromethyl, nitro, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, or a tautomer, prodrug, solvate, or salt thereof.

Another aspect of the invention includes compounds of Formula (IA), wherein:

$R^1$ is aryl or heteroaryl optionally independently substituted with one to three substituent groups selected from hydroxy, halogen, or oxo;

G is a bond;

$R^2$ is hydrogen;

X, Y, and Z are each independently C or N;

A and B are each independently CH or N;

C is a bond;

E is —$NR^4$—, —$NR^4CH_2$—, or —$NR^4SO_2$—, where $R^4$ is a hydrogen;

D is —$CR^5R^6$—, where $R^5$ is a trifluoromethyl group and $R^6$ is a hydrogen; and $R^3$ is $C_1$-$C_6$ alkyl, cycloalkyl, cycloalkenyl, aryl, heteroaryl, heterocyclyl, each optionally independently substituted with one to three substituent groups, and each substituent group is connected to $R^3$ by a bond or $C_1$-$C_3$ alkyl group, wherein each substituent group of $R^3$ is independently aryl, heteroaryl, heterocyclyl, $C_1$-$C_5$ alkyl, $C_1$-$C_5$ alkenyl, cycloalkyl, cycloalkenyl, acyl, alkoxycarbonyl, $C_1$-$C_5$ alkanoyloxy, $C_1$-$C_5$ alkanoyl, aroyl, $C_1$-$C_5$ alkanoylamino, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, aryloxy, arylthio, halogen, hydroxy, oxo, cyano, trifluoromethyl, nitro, carboxyl, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, wherein each substituent group of $R^3$ is optionally independently substituted with one to three substituents selected from aryl, heteroaryl, heterocyclyl, acyl, $C_1$-$C_5$ alkyl, $C_1$-$C_5$ alkanoyloxy, $C_1$-$C_5$ alkanoyl, $C_1$-$C_5$ alkanoylamino, alkylaminocarbonyl, dialkylaminocarbonyl, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, $C_1$-$C_5$ cycloalkyl, aryloxy, halogen, hydroxy, oxo, cyano, trifluoromethyl, nitro, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, or a tautomer, prodrug, solvate, or salt thereof.

Another aspect of the invention includes compounds of Formula (IA), wherein:

$R^1$ is aryl or heteroaryl optionally independently substituted with one to three substituent groups selected from hydroxy, halogen, or oxo;

G is a bond;

$R^2$ is hydrogen;

A and B are each independently CH or N;

C is a bond;

D is —$CR^5R^6$—, wherein $R^5$ is a trifluoromethyl group and $R^6$ is a hydroxy group;

E is a bond;

X, Y, and Z are each independently C or N; and $R^3$ is a phenyl, naphthyl, pyridyl, quinoline, isoquinoline, indole, azaindole, diazaindole, indazole, benzothiophene, benzofuran, pyrrolyl, pyrazolyl, thiazolyl, 2,3-dihydro-1,4-benzodioxin, 1,3-benzodioxole, 3,4-dihydro-2H-1,4-benzoxazine, 1,2,3,4-tetrahydroisoquinoline, N-ethyl-N'-methylbenzene-1,2-diamine, or 1,2,3,4-tetrahydroquinoline, each optionally independently substituted with one to three substituent groups, and each substituent group is connected to $R^3$ by a bond or $C_1$-$C_3$ alkyl group, wherein each substituent group of $R^3$ is independently heterocyclyl, $C_1$-$C_5$ alkyl, $C_1$-$C_5$ alkenyl, carboxyl, acyl, $C_1$-$C_5$ alkyloxy, halogen, hydroxy, oxo, cyano, trifluoromethyl, aminocarbonyl, alkylaminocarbonyl, dialkylaminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, wherein each substituent group of $R^3$ is optionally independently substituted with one to three substituents selected from $C_1$-$C_5$ alkyl, halogen, hydroxy, oxo, cyano, trifluoromethyl, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, or a tautomer, prodrug, solvate, or salt thereof.

Yet another aspect of the invention includes compounds of Formula (IA), wherein:

$R^1$ is aryl, heteroaryl, $C_3$-$C_7$ alkyl, or $C_3$-$C_7$ cycloalkyl optionally independently substituted with one to three substituent groups selected from hydroxy, halogen, or oxo;

G is —$CO_2CH_2$— or —$C(O)N(R^7)$ where $R^7$ is hydrogen;

$R^2$ is hydrogen;

A and B are each independently CH or N;

C is a bond;

D is —$CR^5R^6$—, wherein $R^5$ is a trifluoromethyl group and $R^6$ is a hydroxy group;

E is a bond;

X, Y, and Z are each independently C or N; and $R^3$ is a phenyl, naphthyl, pyridyl, quinoline, isoquinoline, indole, azaindole, diazaindole, indazole, benzothiophene, benzofuran, pyrrolyl, pyrazolyl, thiazolyl, 2,3-dihydro-1,4-benzodioxin, 1,3-benzodioxole, 3,4-dihydro-2H-1,4-benzoxazine, 1,2,3,4-tetrahydroisoquinoline, N-ethyl-N'-methylbenzene-1,2-diamine, or 1,2,3,4-tetrahydroquinoline, each optionally independently substituted with one to three substituent groups, and each substituent group is connected to $R^3$ by a bond or $C_1$-$C_3$ alkyl group, wherein each substituent group of $R^3$ is independently heterocyclyl, $C_1$-$C_5$ alkyl, $C_1$-$C_5$ alkenyl, carboxyl, acyl, $C_1$-$C_5$ alkyloxy, halogen, hydroxy, oxo, cyano, trifluoromethyl, aminocarbonyl, alkylaminocarbonyl, dialkylaminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, wherein each substituent group of $R^3$ is optionally independently substituted with one to three substituents selected from $C_1$-$C_5$ alkyl, halogen, hydroxy, oxo, cyano, trifluoromethyl, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, or a tautomer, prodrug, solvate, or salt thereof.

Representative compounds of Formula (IA) according to the invention are appended hereto as Table IA, where column A is the compound name according to standard nomenclature and column B is the corresponding chemical structure.

IA

| A | B |
|---|---|
| (3-{2,2,2-Trifluoro-1-[1-(4-fluorophenyl)-1H-indazol-5-yl]-1-hydroxyethyl}pyrrolo[2,3-b]pyridin-1-yl)acetonitrile | 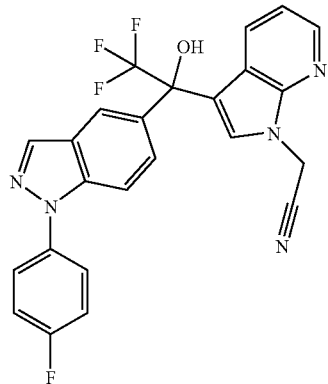 |
| 2,2,2-Trifluoro-1-(1-phenyl-1H-pyrazolo[3,4-b]pyridin-5-yl)-1-(1H-pyrrolo[2,3-b]pyridin-3-yl)ethanol | 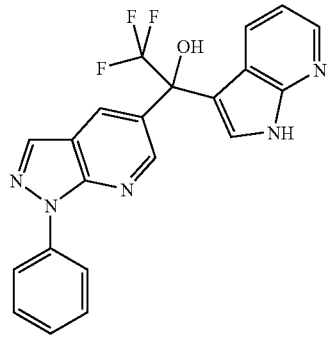 |

-continued

| IA | |
|---|---|
| A | B |
| 1-(4-Chloro-1-phenyl-1H-pyrazolo[3,4-b]pyridin-5-yl)-2,2,2-trifluoro-1-(1H-pyrrolo[2,3-b]pyridin-3-yl)ethanol | 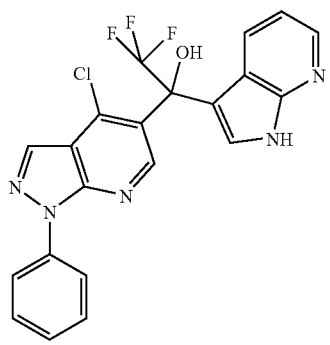 |
| 2-(7-Chloro-3-{2,2,2-trifluoro-1-[1-(4-fluorophenyl)-1H-indazol-5-yl]-1-hydroxyethyl}pyrrolo[2,3-c]pyridin-1-yl)acetamide | 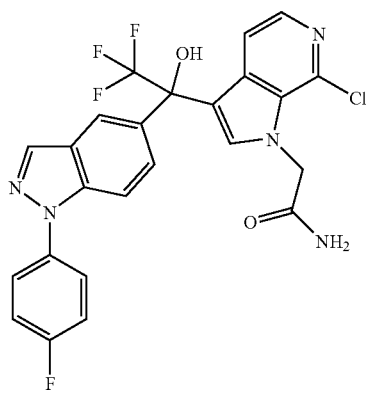 |
| N-[2-(3-{2,2,2-Trifluoro-1-[1-(4-fluorophenyl)-1H-indazol-5-yl]-1-hydroxyethyl}pyrrolo[2,3-b]pyridin-1-yl)acetyl]methanesulfonamide | 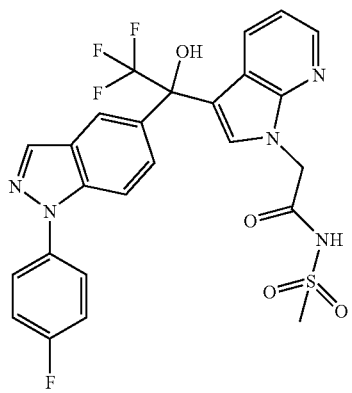 |
| 1-(7-Chloro-1H-pyrrolo[2,3-c]pyridin-3-yl)-2,2,2-trifluoro-1-[1-(4-fluorophenyl)-1H-indazol-5-yl]ethanol | 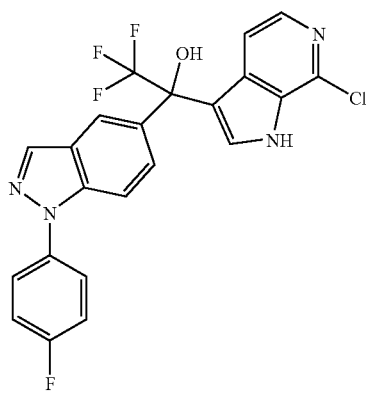 |

-continued
IA
| A | B |
|---|---|
| 2,2,2-Trifluoro-1-[1-(4-fluorophenyl)-1H-indazol-5-yl]-1-(7-oxy-1H-pyrrolo[2,3-b]pyridin-3-yl)ethanol | 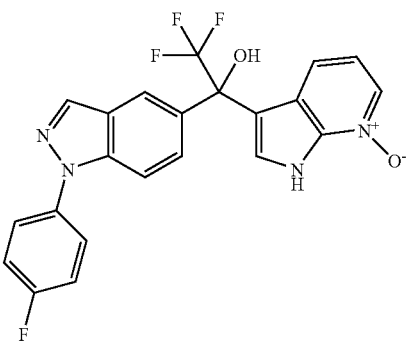 |
| 2,2,2-Trifluoro-1-(1H-pyrrolo[2,3-b]pyridin-3-yl)-1-(1-p-tolyl-1H-indazol-5-yl)ethanol | 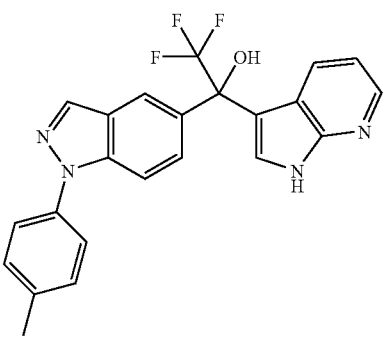 |
| 2,2,2-Trifluoro-1-[1-(4-fluorophenyl)-1H-indazol-5-yl]-1-(1H-pyrrolo[3,2-b]pyridin-3-yl)ethanol | 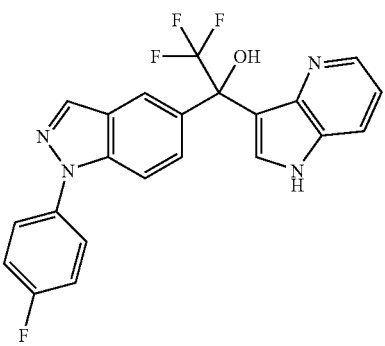 |
| 2,2,2-Trifluoro-1-[1-(4-fluorophenyl)-1H-indazol-5-yl]-1-(1H-pyrrolo[2,3-c]pyridin-3-yl)ethanol | 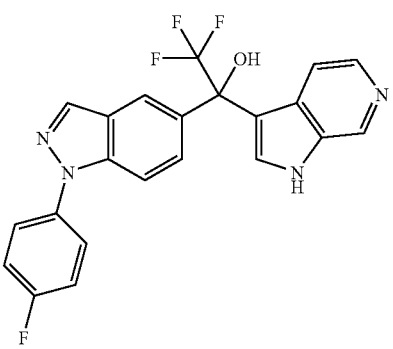 |

-continued
IA
| A | B |
|---|---|
| 2,2,2-Trifluoro-1-[1-(4-fluorophenyl)-1H-indazol-5-yl]-1-(1H-pyrrolo[3,2-c]pyridin-3-yl)ethanol | 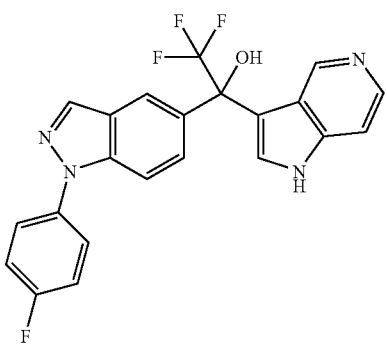 |
| 3-{2,2,2-Trifluoro-1-[1-(4-fluorophenyl)-1H-indazol-5-yl]-1-hydroxyethyl}pyrrolo[2,3-b]pyridine-1-sulfonic acid dimethylamide | 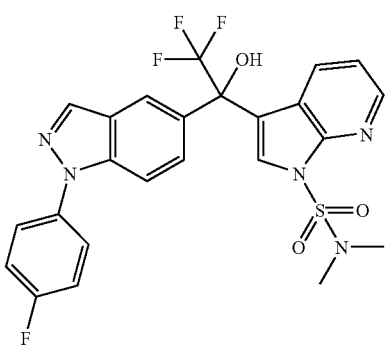 |
| 2-(3-{2,2,2-Trifluoro-1-[1-(4-fluorophenyl)-1H-indazol-5-yl]-1-hydroxyethyl}pyrrolo[2,3-b]pyridin-1-yl)acetamide | 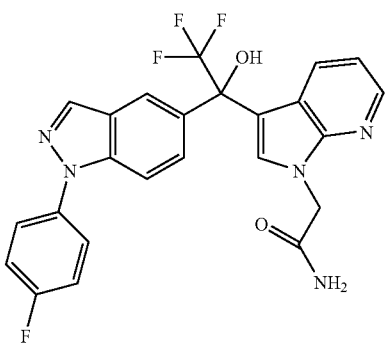 |
| 2,2,2-Trifluoro-1-[1-(4-fluorophenyl)-1H-indazol-5-yl]-1-(1H-pyrrolo[2,3-b]pyridin-3-yl)ethanol | 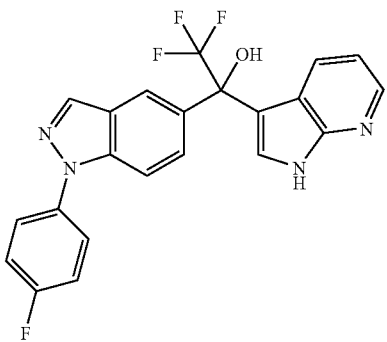 |

-continued
| IA | |
|---|---|
| A | B |
2,2,2-Trifluoro-1-[1-(4-fluorophenyl)-1H-indazol-5-yl]-1-(1H-indazol-3-yl)ethanol
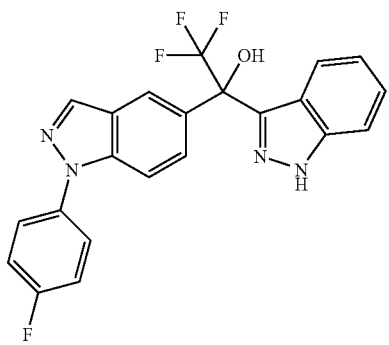
Phenyl-{2,2,2-trifluoro-1-[1-(4-fluorophenyl)-1H-indazol-5-yl]ethyl}amine
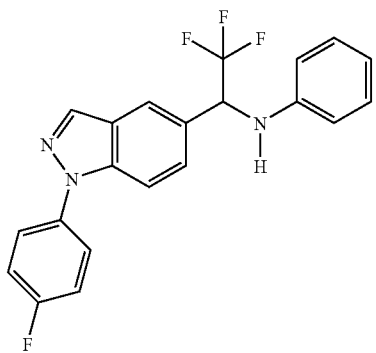 [SMILES: Fc1ccc(-n2ncc3cc(C(Nc4ccccc4)C(F)(F)F)ccc32)cc1]
(1H-Indol-5-yl)-{2,2,2-trifluoro-1-[1-(4-fluorophenyl)-1H-indazol-5-yl]ethyl}amine
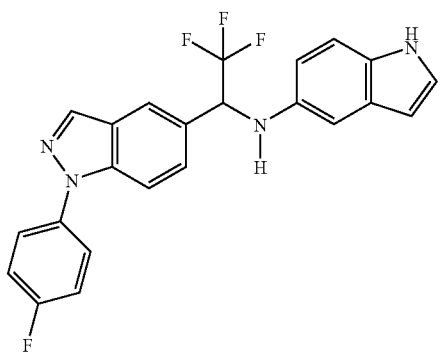 [SMILES: Fc1ccc(-n2ncc3cc(C(Nc4ccc5[nH]ccc5c4)C(F)(F)F)ccc32)cc1]
(1H-Indol-6-yl)-{2,2,2-trifluoro-1-[1-(4-fluorophenyl)-1H-indazol-5-yl]ethyl}amine
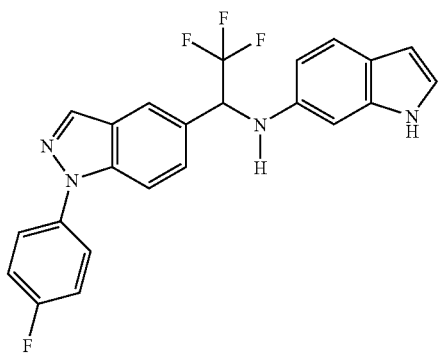 [SMILES: Fc1ccc(-n2ncc3cc(C(Nc4ccc5cc[nH]c5c4)C(F)(F)F)ccc32)cc1]

-continued
| IA | |
|---|---|
| A | B |
(1H-Indol-7-yl)-{2,2,2-trifluoro-1-[1-(4-fluorophenyl)-1H-indazol-5-yl]ethyl}amine
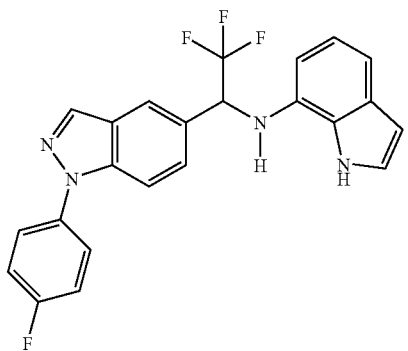 [SMILES: Fc1ccc(-n2ncc3cc(C(Nc4cccc5cc[nH]c45)C(F)(F)F)ccc32)cc1]
(1H-Indol-4-yl)-{2,2,2-trifluoro-1-[1-(4-fluorophenyl)-1H-indazol-5-yl]ethyl}amine
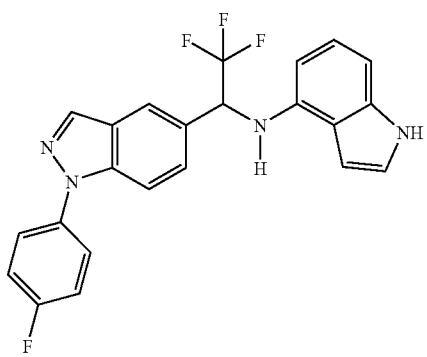 [SMILES: Fc1ccc(-n2ncc3cc(C(Nc4cccc5[nH]ccc45)C(F)(F)F)ccc32)cc1]
[1-(4-Fluorophenyl)-1H-indazol-5-yl]-(2,2,2-trifluoro-1-phenylethyl)amine
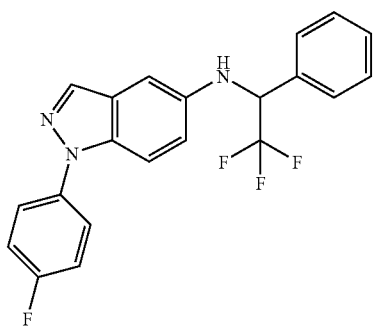 [SMILES: Fc1ccc(-n2ncc3cc(NC(c4ccccc4)C(F)(F)F)ccc32)cc1]
(1-Benzyl-2,2,2-trifluoroethyl)-[1-(4-fluorophenyl)-1H-indazol-5-yl]amine
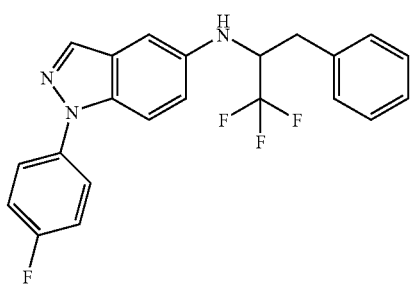 [SMILES: Fc1ccc(-n2ncc3cc(NC(Cc4ccccc4)C(F)(F)F)ccc32)cc1]

-continued
IA
| A | B |
|---|---|
| Benzyl-{2,2,2-trifluoro-1-[1-(4-fluorophenyl)-1H-indazol-5-yl]ethyl}amine | 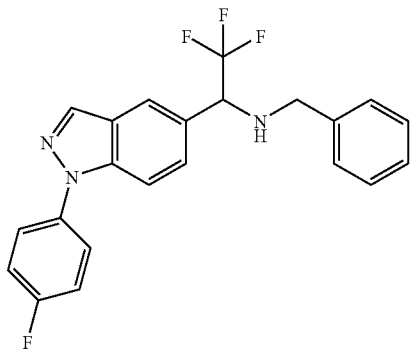 |
| (2-Nitrophenyl)-{2,2,2-trifluoro-1-[1-(4-fluorophenyl)-1H-indazol-5-yl]ethyl}amine | 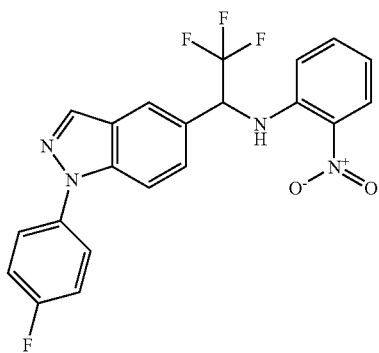 |
| N-{2,2,2-Trifluoro-1-[1-(4-fluorophenyl)-1H-indazol-5-yl]ethyl}benzene-1,2-diamine | 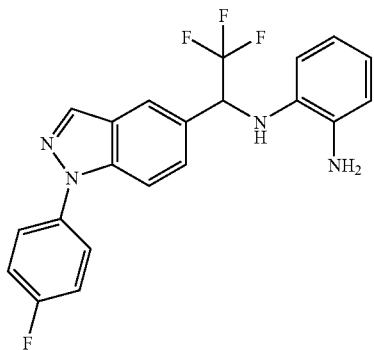 |
| 2-Amino-4,6-dichloro-N-{2,2,2-trifluoro-1-[1-(4-fluorophenyl)-1H-indazol-5-yl]ethyl}benzenesulfonamide | 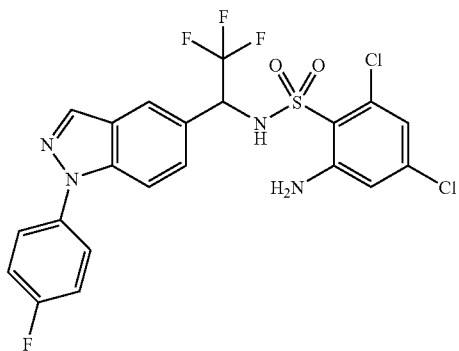 |

TABLE IA-continued
| A | B |
|---|---|
| 2-(7-{2,2,2-Trifluoro-1-[1-(4-fluorophenyl)-1H-indazol-5-yl]ethylamino}indol-1-yl)acetamide | 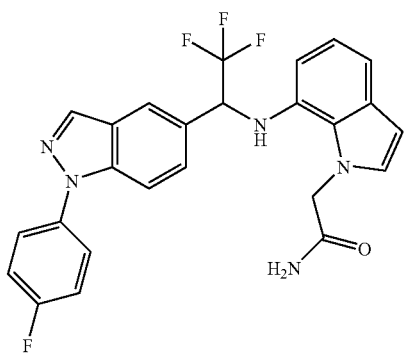 |
| 3-Methyl-N$^2$-{2,2,2-trifluoro-1-[1-(4-fluorophenyl)-1H-indazol-5-yl]ethyl}benzene-1,2-diamine | 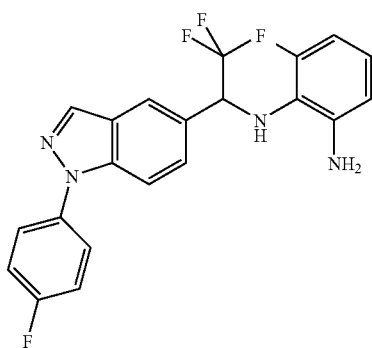 |
| 2-{3-[2,2,2-Trifluoro-1-hydroxy-1-(1-methoxymethyl-1H-indazol-5-yl)ethyl]indol-1-yl}acetamide | 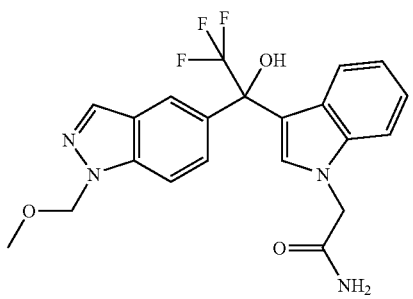 |
| 2-{3-[2,2,2-Trifluoro-1-hydroxy-1-(1H-indazol-5-yl)ethyl]indol-1-yl}acetamide | 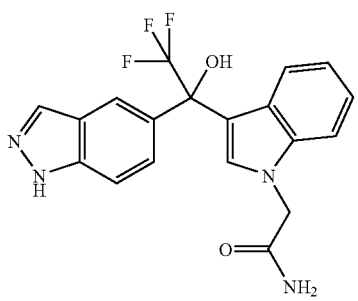 |

IA
| A | B |
|---|---|
| 2,2,2-Trifluoro-1-(1-methyl-1H-indol-3-yl)-1-(1-pyridin-3-yl-1H-indazol-5-yl)ethanol | 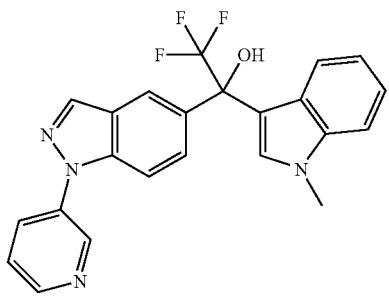 |
| 2,2,2-Trifluoro-1-(1-methyl-1H-indol-3-yl)-1-(1-pyridin-4-yl-1H-indazol-5-yl)ethanol | 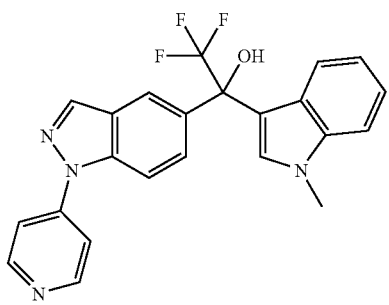 |
| 2,2,2-Trifluoro-1-(1-methyl-1H-indol-3-yl)-1-(1-pyrimidin-5-yl-1H-indazol-5-yl)ethanol | 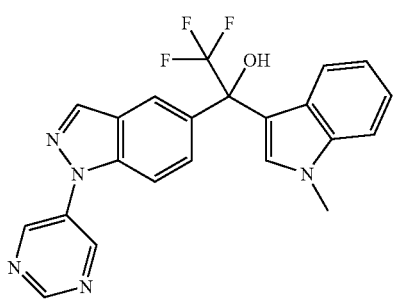 |
| 2,2,2-Trifluoro-1-(1-methyl-1H-indol-3-yl)-1-(1-thiophen-3-yl-1H-indazol-5-yl)ethanol | 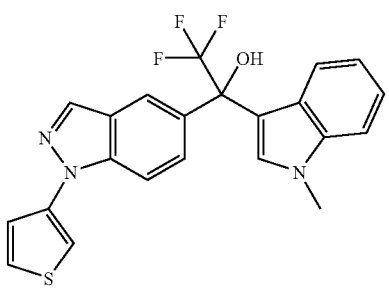 |
| 2,2,2-Trifluoro-1-(1H-indol-3-yl)-1-(1-pyridin-3-yl-1H-indazol-5-yl)ethanol | 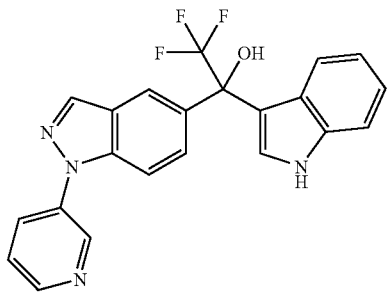 |

-continued
| A | B |
|---|---|
| 2-{3-[2,2,2-Trifluoro-1-hydroxy-1-(1-pyridin-3-yl-1H-indazol-5-yl)ethyl]indol-1-yl}acetamide | 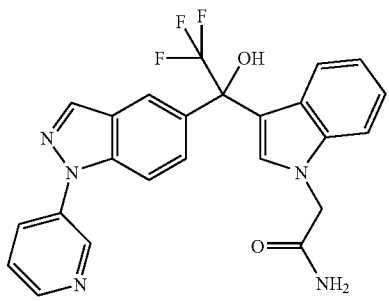 |
| 2,2,2-Trifluoro-1-(1-methyl-1H-indol-3-yl)-1-[1-(6-methylpyridin-3-yl)-1H-indazol-5-yl]ethanol | 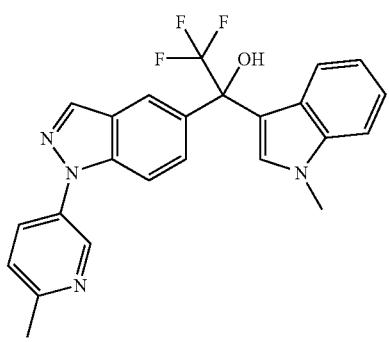 |
| 2,2,2-Trifluoro-1-(1-methyl-1H-indol-3-yl)-1-[1-(5-methylthiophen-2-yl)-1H-indazol-5-yl]ethanol | 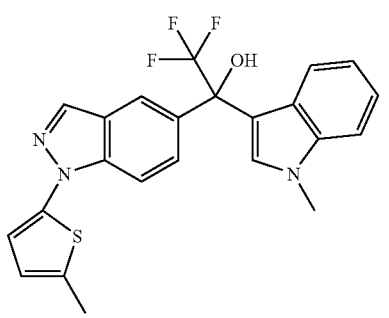 |
| 2,2,2-Trifluoro-1-[1-(1-methyl-1H-imidazol-4-yl)-1H-indazol-5-yl]-1-(1-methyl-1H-indol-3-yl)ethanol | 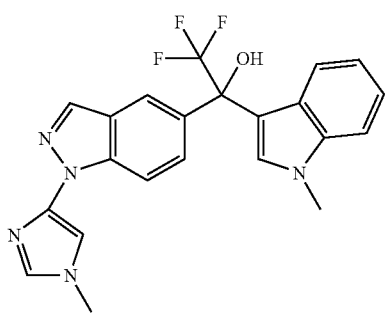 |
| 2,2,2-Trifluoro-1-(1-methyl-1H-indol-3-yl)-1-(1-pyridin-2-yl-1H-indazol-5-yl)ethanol | 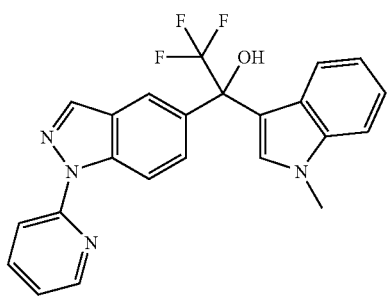 |

-continued
IA
| A | B |
|---|---|
| 2,2,2-Trifluoro-1-(1-methyl-1H-indol-3-yl)-1-[1-(1-methyl-1H-pyrazol-4-yl)-1H-indazol-5-yl]ethanol | 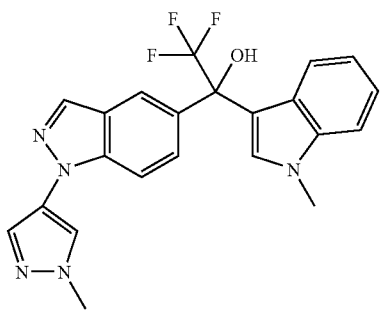 |
| 2,2,2-Trifluoro-1-[1-(6-fluoropyridin-3-yl)-1H-indazol-5-yl]-1-(1-methyl-1H-indol-3-yl)ethanol | 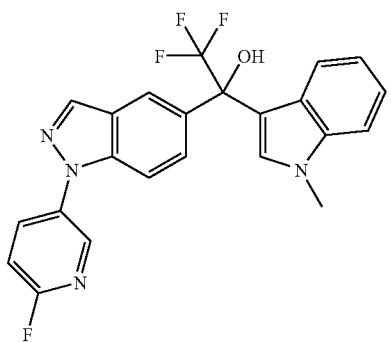 |
| (R)-1-(3-{2,2,2-Trifluoro-1-[1-(4-fluorophenyl)-1H-indazol-5-yl]-1-hydroxyethyl}indol-1-yl)propan-2-ol | 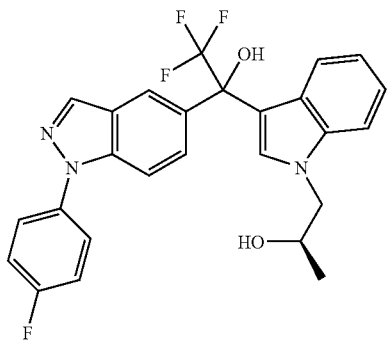 |
| (S)-1-(3-{2,2,2-Trifluoro-1-[1-(4-fluorophenyl)-1H-indazol-5-yl]-1-hydroxyethyl}indol-1-yl)propan-2-ol | 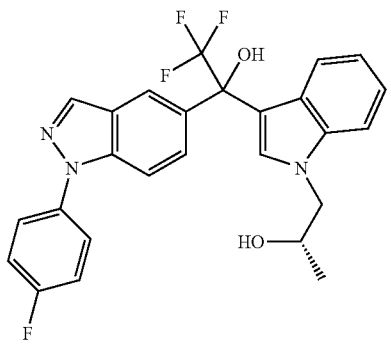 |

-continued
| IA | |
|---|---|
| A | B |
1-(5-Chloro-1,1-dioxo-1H-1λ⁶-thiophen-2-yl)-2,2,2-trifluoro-1-[1-(4-fluorophenyl)-1H-indazol-5-yl]ethanol
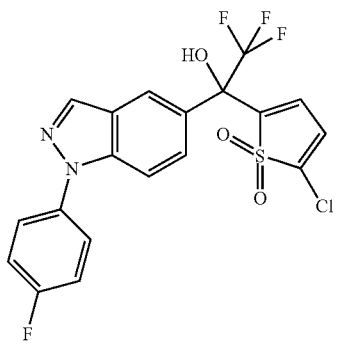 [SMILES: O=S1(=O)C(Cl)=CC=C1C(O)(c1ccc2c(cnn2-c2ccc(F)cc2)c1)C(F)(F)F]
2,2,2-Trifluoro-1-[1-(4-fluorophenyl)-1H-indazol-5-yl]-1-(5-methylthiophen-2-yl)ethanol
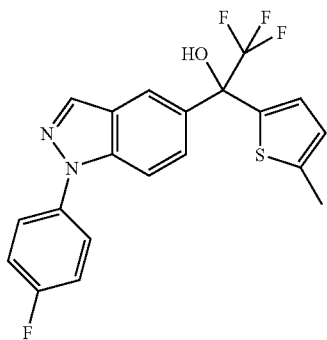 [SMILES: Cc1ccc(C(O)(c2ccc3c(cnn3-c3ccc(F)cc3)c2)C(F)(F)F)s1]
2,2,2-Trifluoro-1-[1-(4-fluorophenyl)-1H-indazol-5-yl]-1-[1-(tetrahydrofuran-2-ylmethyl)-1H-indol-3-yl]ethanol
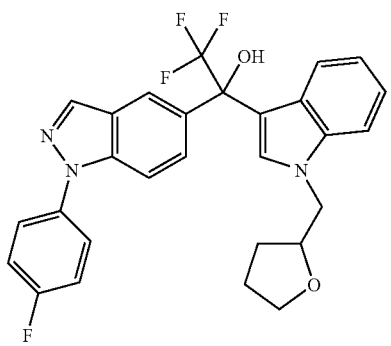 [SMILES: OC(c1ccc2c(cnn2-c2ccc(F)cc2)c1)(c1cn(CC2CCCO2)c2ccccc12)C(F)(F)F]
2,2,2-Trifluoro-1-[1-(4-fluorophenyl)-1H-indazol-5-yl]-1-[1-(2-morpholin-4-ylethyl)-1H-indol-3-yl]ethanol
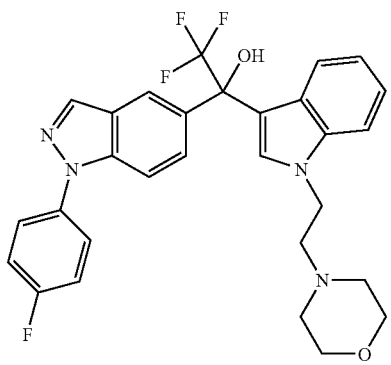 [SMILES: OC(c1ccc2c(cnn2-c2ccc(F)cc2)c1)(c1cn(CCN2CCOCC2)c2ccccc12)C(F)(F)F]

IA
| A | B |
|---|---|
| (3-{2,2,2-Trifluoro-1-[1-(4-fluorophenyl)-1H-indazol-5-yl]-1-hydroxyethyl}indol-1-yl)acetic acid | 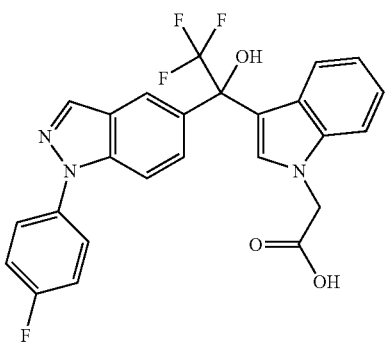 |
| 1-(1-Allyl-5-hydroxymethyl-1H-pyrrol-3-yl)-2,2,2-trifluoro-1-[1-(4-fluorophenyl)-1H-indazol-5-yl]ethanol | 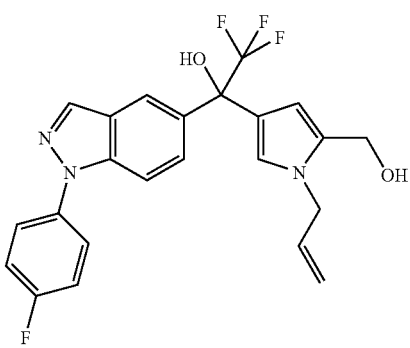 |
| 1-(5-1,3-Dioxolan-2-ylthiophen-2-yl)-2,2,2-trifluoro-1-[1-(4-fluorophenyl)-1H-indazol-5-yl]ethanol | 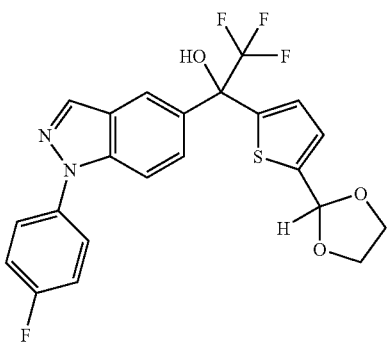 |
| (3-{2,2,2-Trifluoro-1-[1-(4-fluorophenyl)-1H-indazol-5-yl]-1-hydroxyethyl}indol-1-yl)acetic acid ethyl ester | 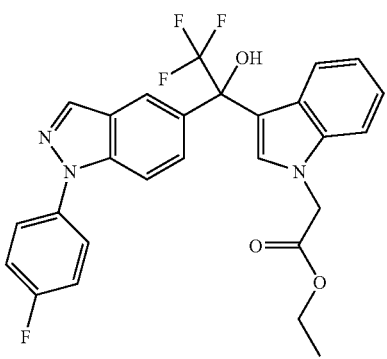 |

-continued
| IA | |
|---|---|
| A | B |
1-(5-Chlorothiophen-2-yl)-2,2,2-trifluoro-1-[1-(4-fluorophenyl)-1H-indazol-5-yl]ethanol
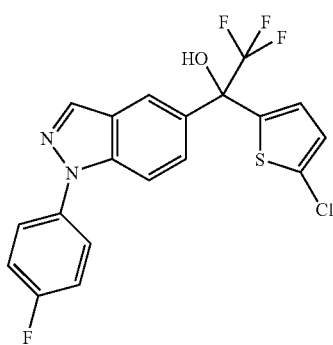 [SMILES: OC(c1ccc2c(cnn2-c2ccc(F)cc2)c1)(c1ccc(Cl)s1)C(F)(F)F]
2,2,2-Trifluoro-1-[1-(4-fluorophenyl)-1H-indazol-5-yl]-1-{1-[3-(4-hydroxymethylpiperidin-1-yl)propyl]-1H-indol-3-yl}ethanol
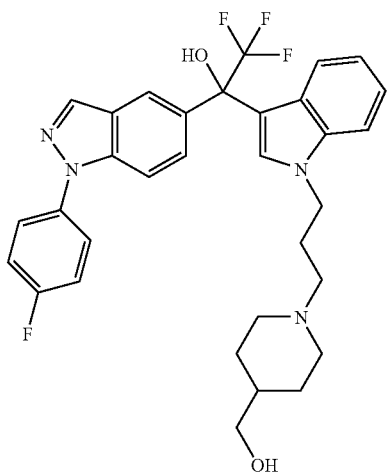 [SMILES: OCC1CCN(CCCn2cc(C(O)(c3ccc4c(cnn4-c4ccc(F)cc4)c3)C(F)(F)F)c3ccccc32)CC1]
1-{1-[3-((S)-3-Dimethylaminopyrrolidin-1-yl)propyl]-1H-indol-3-yl}-2,2,2-trifluoro-1-[1-(4-fluorophenyl)-1H-indazol-5-yl]ethanol
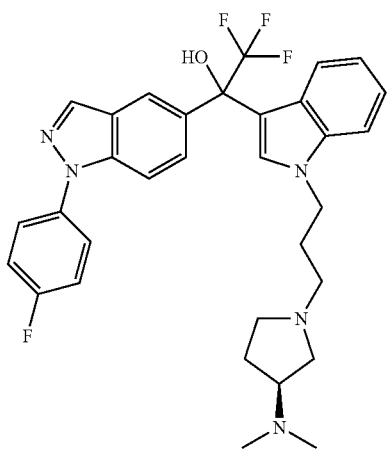 [SMILES: CN(C)[C@H]1CCN(CCCn2cc(C(O)(c3ccc4c(cnn4-c4ccc(F)cc4)c3)C(F)(F)F)c3ccccc32)C1]

-continued
| A | B |
|---|---|
| 1-{1-[3-((R)-3-Dimethylaminopyrrolidin-1-yl)propyl]-1H-indol-3-yl}-2,2,2-trifluoro-1-[1-(4-fluorophenyl)-1H-indazol-5-yl]ethanol | 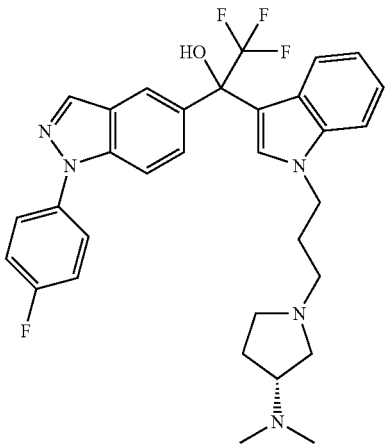 |
| 2,2,2-Trifluoro-1-[1-(4-fluorophenyl)-1H-indazol-5-yl]-1-[1-(3-pyrrolidin-1-ylpropyl)-1H-indol-3-yl]ethanol | 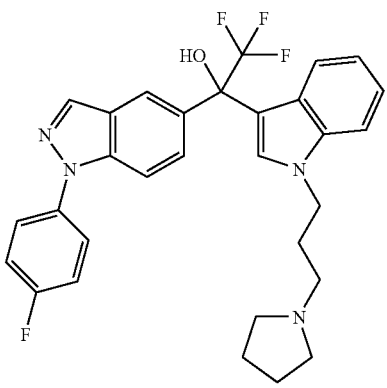 |
| 2,2,2-Trifluoro-1-[1-(4-fluorophenyl)-1H-indazol-5-yl]-1-{1-[3-(4-methylpiperazin-1-yl)propyl]-1H-indol-3-yl}ethanol | 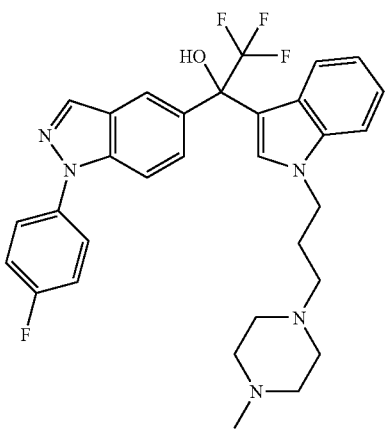 |

-continued
IA
| A | B |
|---|---|
| 2,2,2-Trifluoro-1-[1-(4-fluorophenyl)-1H-indazol-5-yl]-1-[1-(3-methylaminopropyl)-1H-indol-3-yl]ethanol | 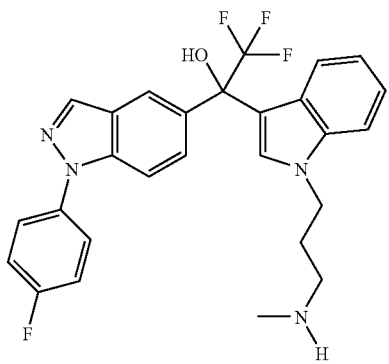 |
| 2,2,2-Trifluoro-1-[1-(4-fluorophenyl)-1H-indazol-5-yl]-1-[1-(3-morpholin-4-ylpropyl)-1H-indol-3-yl]ethanol | 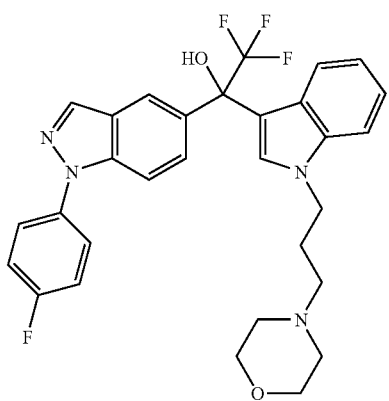 |
| 1-[1-(3-Dimethylaminopropyl)-1H-indol-3-yl]-2,2,2-trifluoro-1-[1-(4-fluorophenyl)-1H-indazol-5-yl]ethanol | 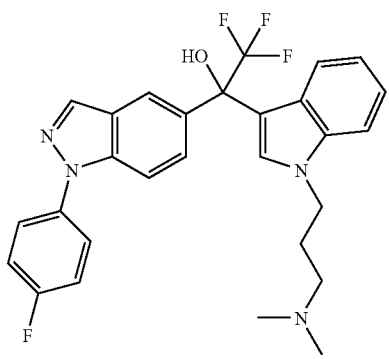 |
| 3-(6-(2H-Pyrazol-3-yl)-3-{2,2,2-trifluoro-1-[1-(4-fluorophenyl)-1H-indazol-5-yl]-1-hydroxyethyl}indol-1-yl)propane-1,2-diol | 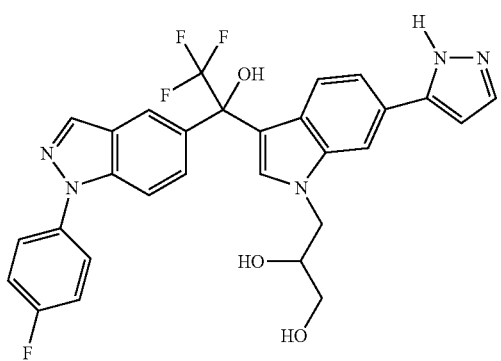 |

-continued
IA
| A | B |
|---|---|
| 1-[1-Allyl-6-(2H-pyrazol-3-yl)-1H-indol-3-yl]-2,2,2-trifluoro-1-[1-(4-fluorophenyl)-1H-indazol-5-yl]ethanol | 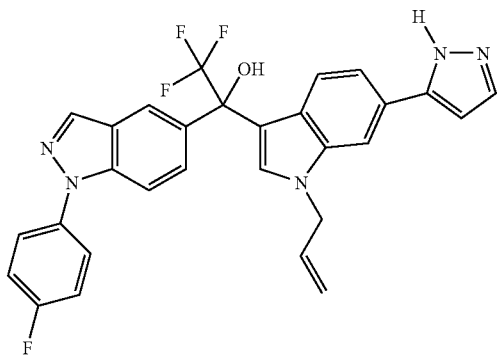 |
| 1-(6-Bromo-1-but-3-enyl-1H-indol-3-yl)-2,2,2-trifluoro-1-[1-(4-fluorophenyl)-1H-indazol-5-yl]ethanol | 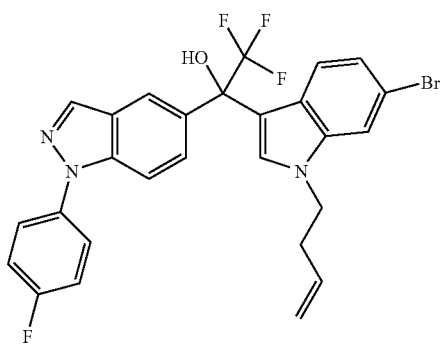 |
| 1-(1-Benzenesulfonyl-1H-indol-3-yl)-2,2,2-trifluoro-1-[1-(4-fluorophenyl)-1H-indazol-5-yl]ethanol | 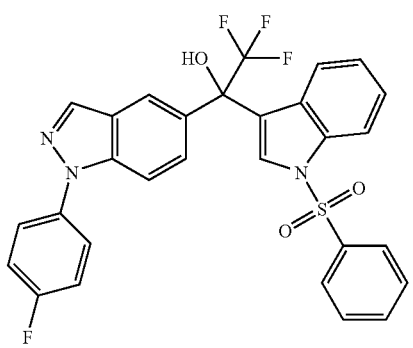 |
| 2,2,2-Trifluoro-1-[1-(4-fluorophenyl)-1H-indazol-5-yl]-1-[1-(propane-2-sulfonyl)-1H-indol-3-yl]ethanol | 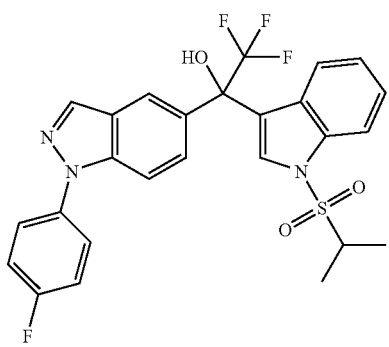 |

-continued
| IA | |
|---|---|
| A | B |
| 3-(3-{2,2,2-Trifluoro-1-[1-(4-fluorophenyl)-1H-indazol-5-yl]-1-hydroxyethyl}indol-1-yl)propionamide | 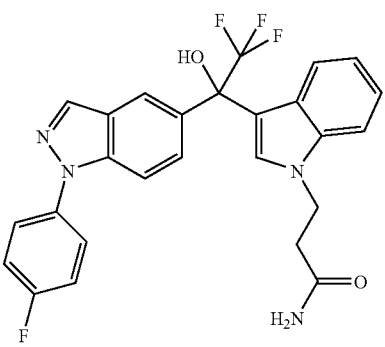 |
| N-Methyl-3-(3-{2,2,2-trifluoro-1-[1-(4-fluorophenyl)-1H-indazol-5-yl]-1-hydroxyethyl}indol-1-yl)propionamide | 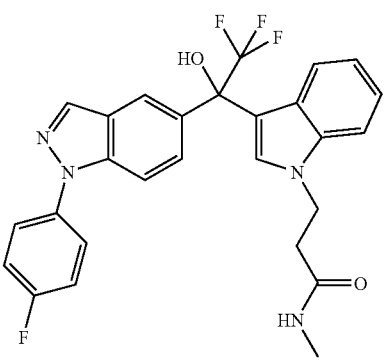 |
| 3-(6-Pyrrolidin-1-yl-3-{2,2,2-trifluoro-1-[1-(4-fluorophenyl)-1H-indazol-5-yl]-1-hydroxyethyl}indol-1-yl)propane-1,2-diol | 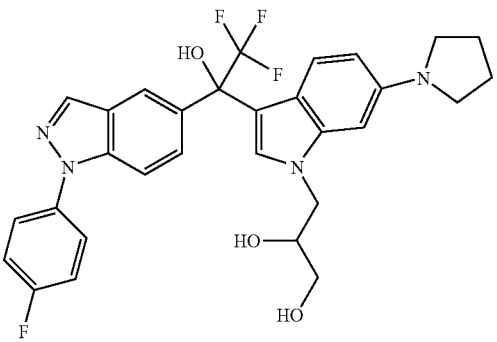 |
| 2-(6-Bromo-3-{2,2,2-trifluoro-1-[1-(4-fluorophenyl)-1H-indazol-5-yl]-1-hydroxyethyl}indol-1-yl)-N-methylacetamide | 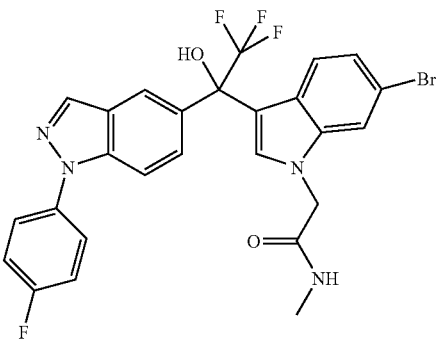 |

-continued
IA
| A | B |
|---|---|
| 4-(3-{2,2,2-Trifluoro-1-[1-(4-fluorophenyl)-1H-indazol-5-yl]-1-hydroxyethyl}indol-1-yl)-butane-1,2-diol | 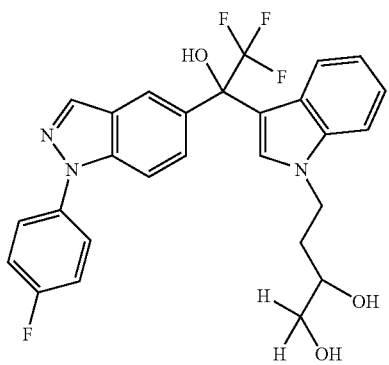 |
| 1-(1-But-3-enyl-1H-indol-3-yl)-2,2,2-trifluoro-1-[1-(4-fluorophenyl)-1H-indazol-5-yl]ethanol | 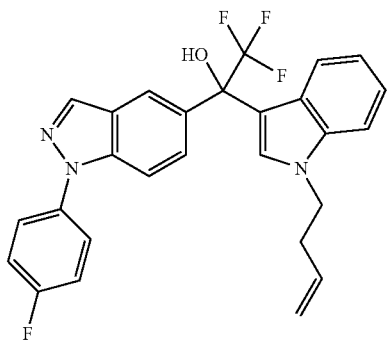 |
| 1-(1-Allyl-6-pyrrolidin-1-yl-1H-indol-3-yl)-2,2,2-trifluoro-1-[1-(4-fluorophenyl)-1H-indazol-5-yl]ethanol | 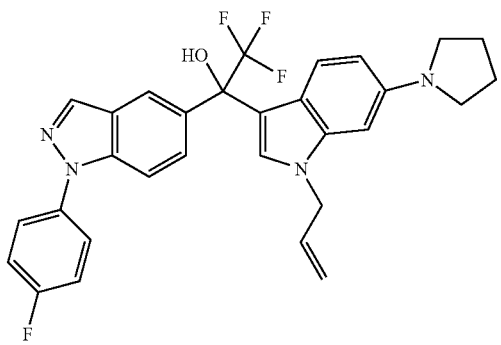 |
| 1-(1-Allyl-6-bromo-1H-indol-3-yl)-2,2,2-trifluoro-1-[1-(4-fluorophenyl)-1H-indazol-5-yl]ethanol | 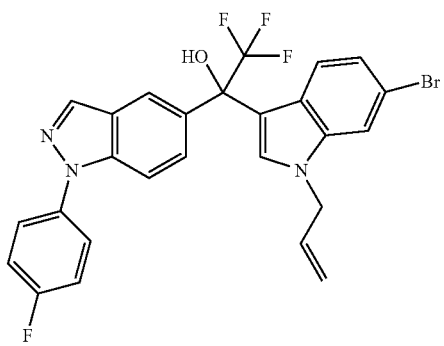 |

-continued
| A | B |
|---|---|
| 3-(6-Bromo-3-{2,2,2-trifluoro-1-[1-(4-fluorophenyl)-1H-indazol-5-yl]-1-hydroxyethyl}indol-1-yl)propane-1,2-diol | 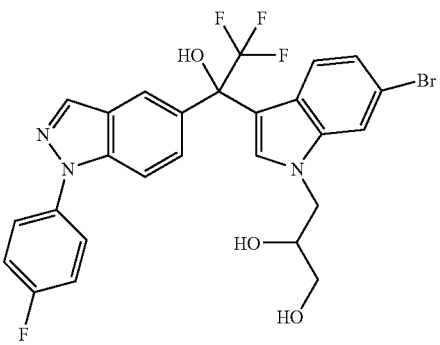 |
| 2,2,2-Trifluoro-1-[1-(4-fluorophenyl)-1H-indazol-5-yl]-1-[1-(4-methoxybenzyl)-6-vinyl-1H-indol-3-yl]ethanol | 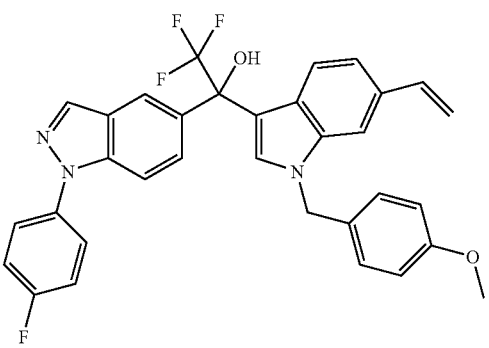 |
| 2,2,2-Trifluoro-1-[1-(4-fluorophenyl)-1H-indazol-5-yl]-1-[1-(4-methoxybenzyl)-6-pyrrolidin-1-yl-1H-indol-3-yl]ethanol | 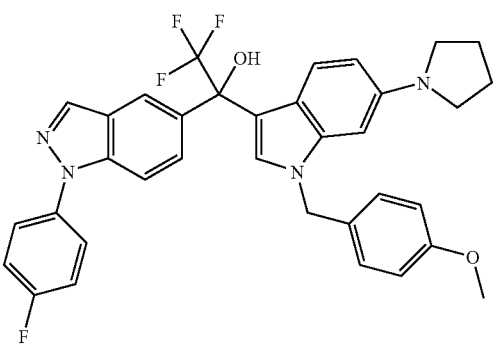 |
| 1-[4-Chloro-5-(2-hydroxyethyl)-5H-pyrrolo[3,2-d]pyrimidin-7-yl]-2,2,2-trifluoro-1-[1-(4-fluorophenyl)-1H-indazol-5-yl]ethanol | 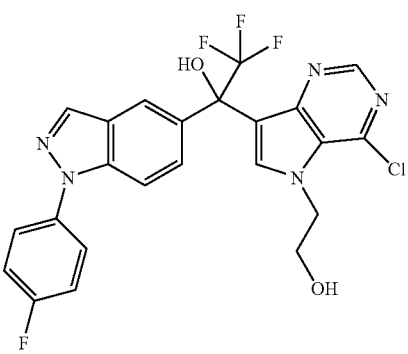 |

-continued

| IA | |
|---|---|
| A | B |

3-(4-Chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol

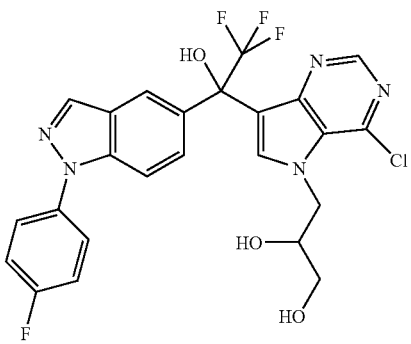 [SMILES: OCC(O)Cn1cc(C(O)(c2ccc3c(cnn3-c3ccc(F)cc3)c2)C(F)(F)F)c2ncnc(Cl)c21]

5-Allyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one

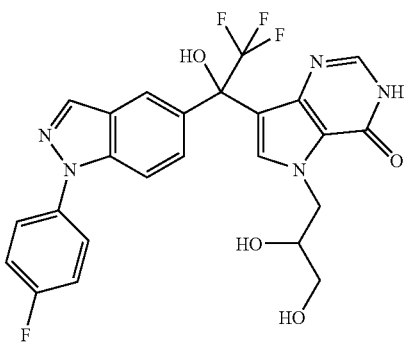 [SMILES: O=c1[nH]cnc2c(C(O)(c3ccc4c(cnn4-c4ccc(F)cc4)c3)C(F)(F)F)cn(CC(O)CO)c12]

5-Allyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one

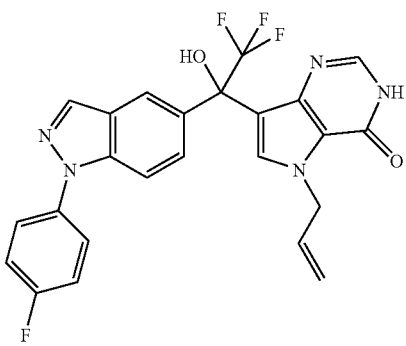 [SMILES: C=CCn1cc(C(O)(c2ccc3c(cnn3-c3ccc(F)cc3)c2)C(F)(F)F)c2nc[nH]c(=O)c21]

7-{2,2,2-Trifluoro-1-[1-(4-fluorophenyl)-1H-indazol-5-yl]-1-hydroxyethyl}-3,5-dihydropyrrolo[3,2-d]pyrimidin-4-one

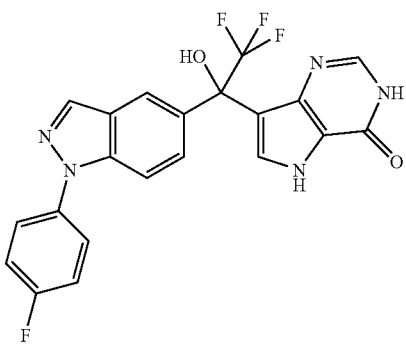 [SMILES: O=c1[nH]cnc2c(C(O)(c3ccc4c(cnn4-c4ccc(F)cc4)c3)C(F)(F)F)c[nH]c12]

-continued

IA

| A | B |
|---|---|
| 1-(4-Chloro-5H-pyrrolo[3,2-d]pyrimidin-7-yl)-2,2,2-trifluoro-1-[1-(4-fluorophenyl)-1H-indazol-5-yl]ethanol | 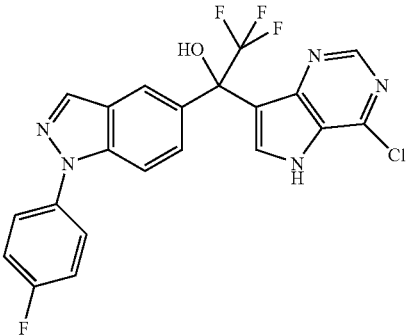 |
| 2-(3-Methyl-4-oxo-7-{2,2,2-trifluoro-1-[1-(4-fluorophenyl)-1H-indazol-5-yl]-1-hydroxyethyl}-3,4-dihydropyrrolo[3,2-d]pyrimidin-5-yl)acetamide | 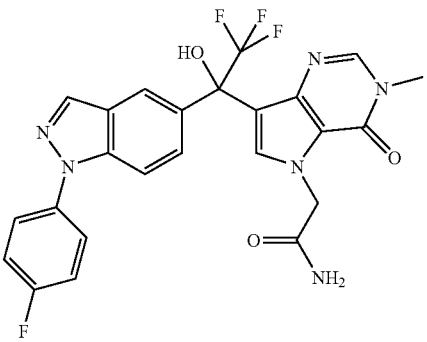 |
| 5-(2,3-Dihydroxypropyl)-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one | 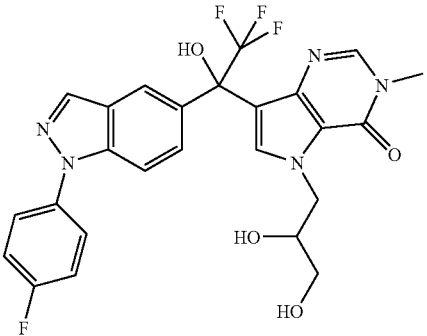 |
| 5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one | 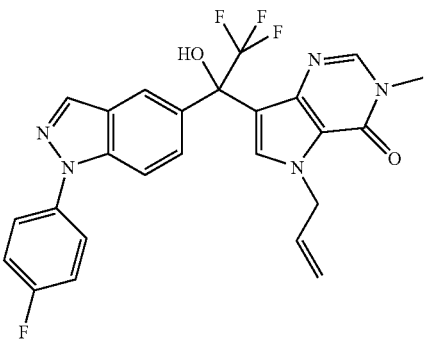 |

|   | IA |
|---|---|
| A | B |
| 1-Methylcarbamoylmethyl-4-{2,2,2-trifluoro-1-[1-(4-fluorophenyl)-1H-indazol-5-yl]-1-hydroxyethyl}-1H-pyrrole-2-carboxylic acid dimethylamide | 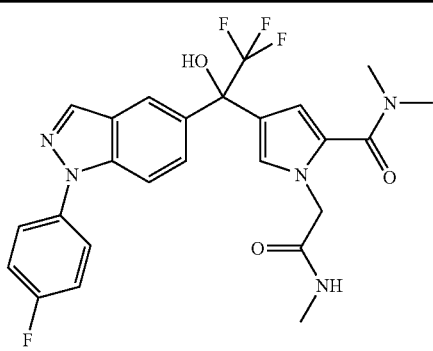 |
| 1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid dimethylamide | 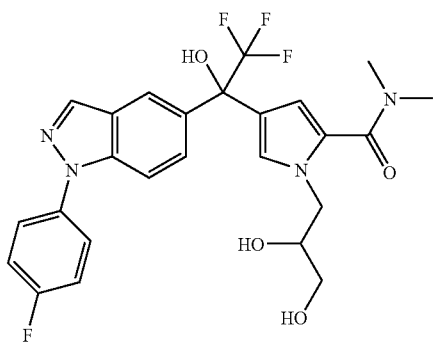 |
| 1-Allyl-4-{2,2,2-trifluoro-1-[1-(4-fluorophenyl)-1H-indazol-5-yl]-1-hydroxyethyl}-1H-pyrrole-2-carboxylic acid methylamide | 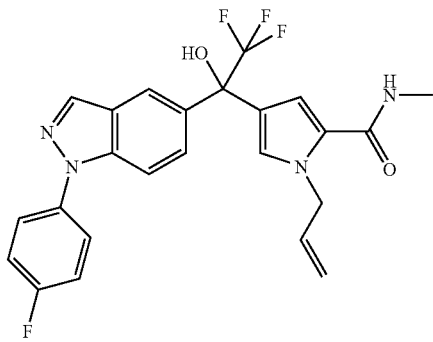 |
| 1-Allyl-4-{2,2,2-trifluoro-1-[1-(4-fluorophenyl)-1H-indazol-5-yl]-1-hydroxyethyl}-1H-pyrrole-2-carboxylic acid carbamoylmethylamide | 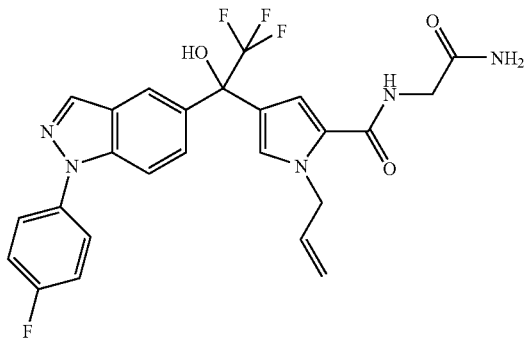 |

-continued

| A | B |
|---|---|
| 1-Allyl-4-{2,2,2-trifluoro-1-[1-(4-fluorophenyl)-1H-indazol-5-yl]-1-hydroxyethyl}-1H-pyrrole-2-carboxylic acid cyanomethylamide | 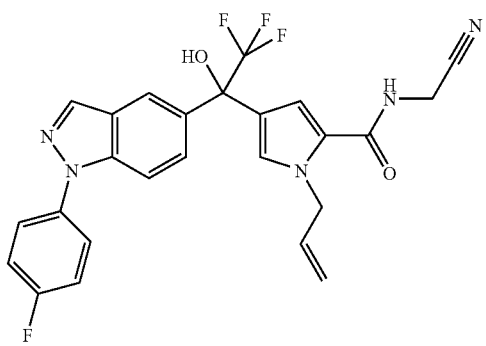 |
| 1-Allyl-4-{2,2,2-trifluoro-1-[1-(4-fluorophenyl)-1H-indazol-5-yl]-1-hydroxyethyl}-1H-pyrrole-2-carboxylic acid amide | 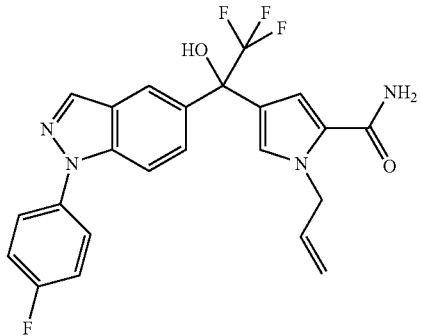 |
| 2-(2-Cyano-4-{2,2,2-trifluoro-1-[1-(4-fluorophenyl)-1H-indazol-5-yl]-1-hydroxyethyl}pyrrol-1-yl)acetamide | 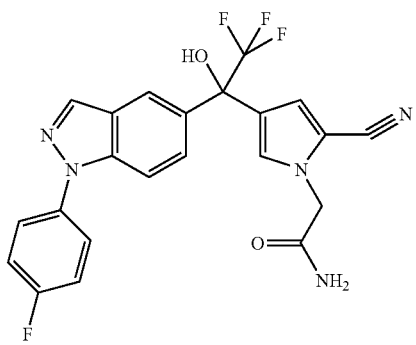 |
| 2-(2-Cyano-4-{2,2,2-trifluoro-1-[1-(4-fluorophenyl)-1H-indazol-5-yl]-1-hydroxyethyl}pyrrol-1-yl)-N-methylacetamide | 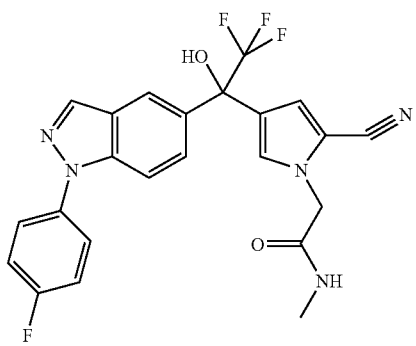 |

| A | B |
|---|---|
| 1-Allyl-4-{2,2,2-trifluoro-1-[1-(4-fluorophenyl)-1H-indazol-5-yl]-1-hydroxyethyl}-1H-pyrrole-2-carboxylic acid dimethylamide | 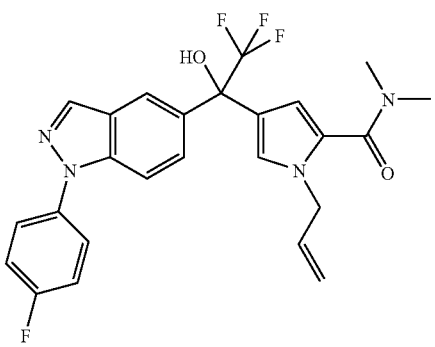 |
| 1-Allyl-4-{2,2,2-trifluoro-1-[1-(4-fluorophenyl)-1H-indazol-5-yl]-1-hydroxyethyl}-1H-pyrrole-2-carboxylic acid | 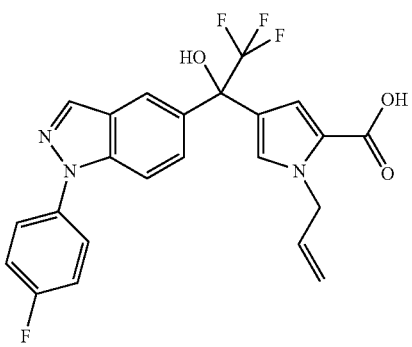 |
| 1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester | 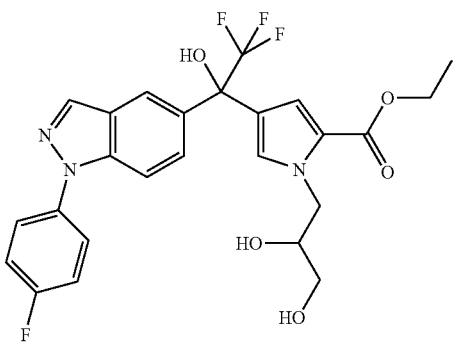 |
| 3-Hydroxymethyl-7-{2,2,2-trifluoro-1-[1-(4-fluorophenyl)-1H-indazol-5-yl]-1-hydroxyethyl}-3,4-dihydropyrrolo[2,1-c][1,4]oxazin-1-one | 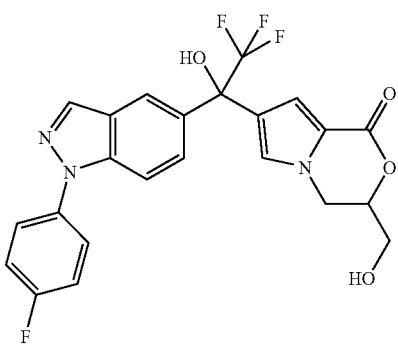 |

-continued

IA

| A | B |
|---|---|
| 1-Allyl-4-{2,2,2-trifluoro-1-[1-(4-fluorophenyl)-1H-indazol-5-yl]-1-hydroxyethyl}-1H-pyrrole-2-carboxylic acid ethyl ester | 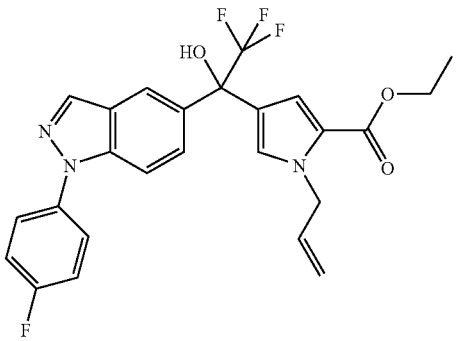 |
| 4-{2,2,2-Trifluoro-1-[1-(4-fluorophenyl)-1H-indazol-5-yl]-1-hydroxyethyl}-1H-pyrrole-2-carbonitrile | 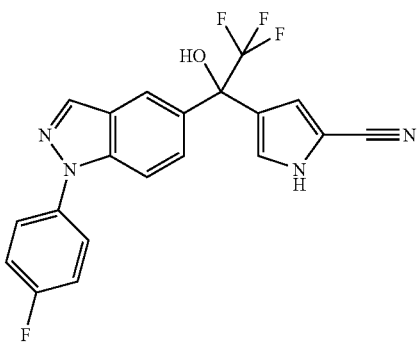 |
| 1-(2,3-Dihydroxypropyl)-4-{2,2,2-trifluoro-1-[1-(4-fluorophenyl)-1H-indazol-5-yl]-1-hydroxyethyl}-1H-pyrrole-2-carbonitrile | 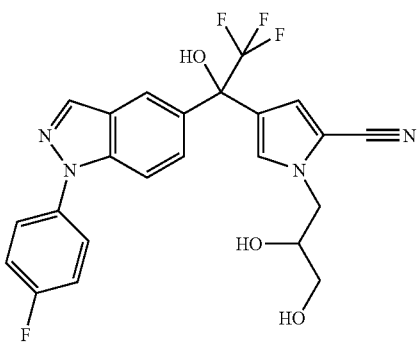 |
| 1-Allyl-4-{2,2,2-trifluoro-1-[1-(4-fluorophenyl)-1H-indazol-5-yl]-1-hydroxyethyl}-1H-pyrrole-2-carbonitrile | 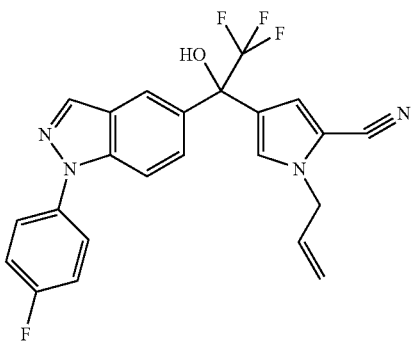 |

-continued

| IA | |
|---|---|
| A | B |

(1-(2,3-Dihydroxypropyl)-4-{2,2,2-trifluoro-1-[1-(4-fluorophenyl)-1H-indazol-5-yl]-1-hydroxyethyl}-1H-pyrrol-2-yl)morpholin-4-ylmethanone

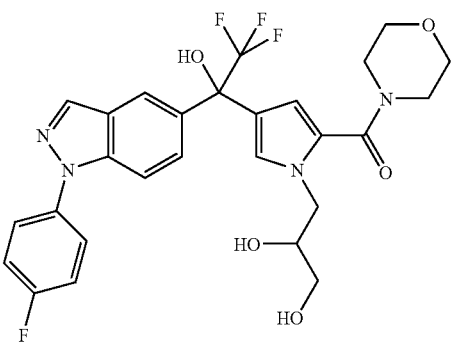 [SMILES: O=C(c1cc(C(O)(c2ccc3c(cnn3-c3ccc(F)cc3)c2)C(F)(F)F)cn1CC(O)CO)N1CCOCC1]

(1-Allyl-4-{2,2,2-trifluoro-1-[1-(4-fluorophenyl)-1H-indazol-5-yl]-1-hydroxyethyl}-1H-pyrrol-2-yl)-morpholin-4-ylmethanone

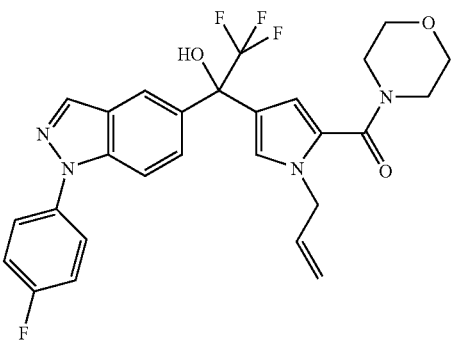 [SMILES: C=CCn1cc(C(O)(c2ccc3c(cnn3-c3ccc(F)cc3)c2)C(F)(F)F)cc1C(=O)N1CCOCC1]

2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide

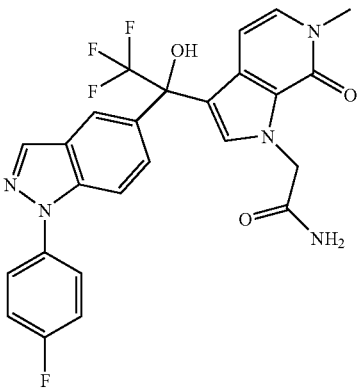 [SMILES: Cn1ccc2c(C(O)(c3ccc4c(cnn4-c4ccc(F)cc4)c3)C(F)(F)F)cn(CC(N)=O)c2c1=O]

3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol

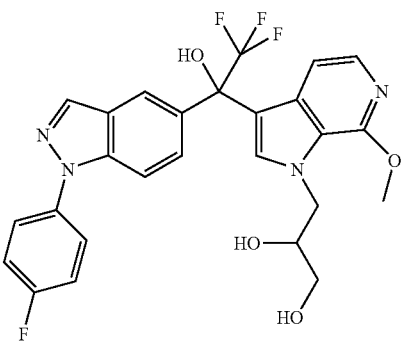 [SMILES: COc1nccc2c(C(O)(c3ccc4c(cnn4-c4ccc(F)cc4)c3)C(F)(F)F)cn(CC(O)CO)c12]

IA
| A | B |
|---|---|
| 2,2,2-Trifluoro-1-[1-(4-fluorophenyl)-1H-indazol-5-yl]-1-(7-methoxy-1H-pyrrolo[2,3-c]pyridin-3-yl)ethanol | 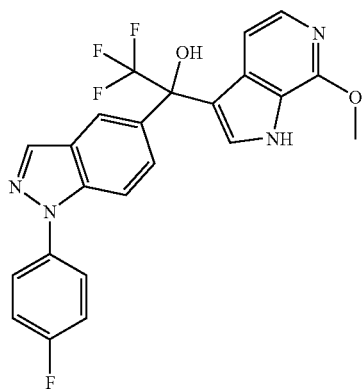 |
| 4-Bromo-1-(2,3-dihydroxypropyl)-5-{2,2,2-trifluoro-1-[1-(4-fluorophenyl)-1H-indazol-5-yl]-1-hydroxyethyl}-1H-pyrazole-3-carbonitrile | 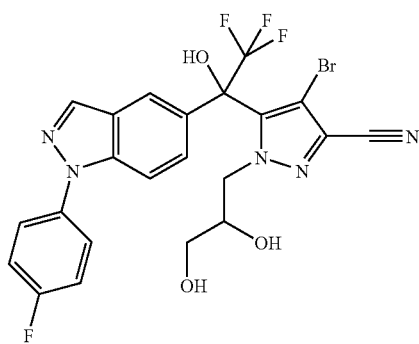 |
| 1-Allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one | 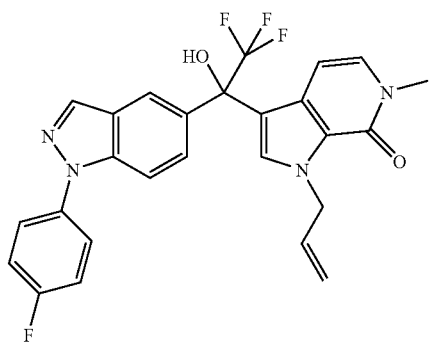 |
| 4-{2,2,2-Trifluoro-1-[1-(4-fluorophenyl)-1H-indazol-5-yl]-1-hydroxyethyl}-1H-pyrazole-3-carbonitrile | 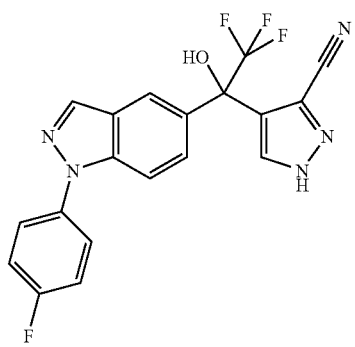 |

-continued
| IA | |
|---|---|
| A | B |
1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile
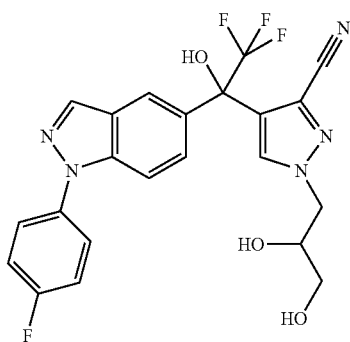 [SMILES: N#Cc1nn(CC(O)CO)cc1C(O)(c1ccc2c(cnn2-c2ccc(F)cc2)c1)C(F)(F)F]
2,2,2-Trifluoro-1-[1-(4-fluorophenyl)-1H-indazol-5-yl]-1-(2-hydroxymethylthiazol-5-yl)ethanol
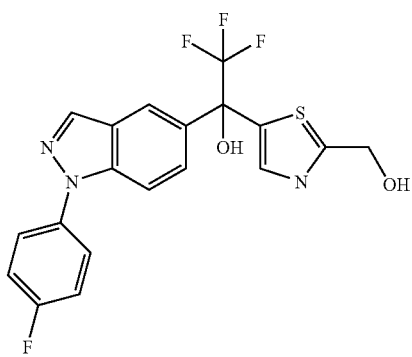
2,2,2-Trifluoro-1-[1-(4-fluorophenyl)-1H-indazol-5-yl]-1-(2-hydroxymethylthiazol-4-yl)ethanol
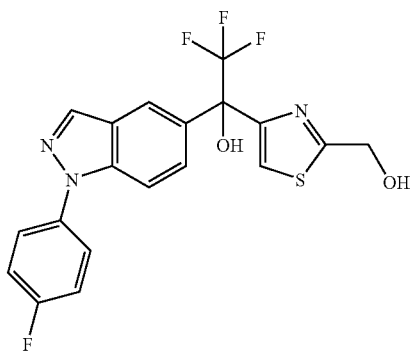
1-Allyl-4-bromo-5-{2,2,2-trifluoro-1-[1-(4-fluorophenyl)-1H-indazol-5-yl]-1-hydroxyethyl}-1H-pyrazole-3-carbonitrile
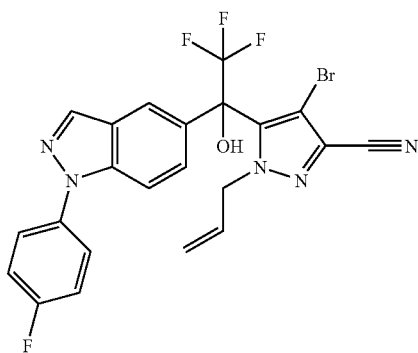 [SMILES: C=CCn1nc(C#N)c(Br)c1C(O)(c1ccc2c(cnn2-c2ccc(F)cc2)c1)C(F)(F)F]

-continued
IA
| A | B |
|---|---|
| 1-Allyl-4-{2,2,2-trifluoro-1-[1-(4-fluorophenyl)-1H-indazol-5-yl]-1-hydroxyethyl}-1H-pyrazole-3-carbonitrile | 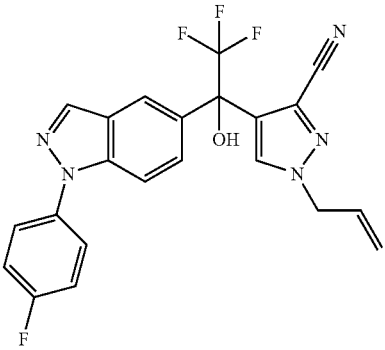 |
| 2,2,2-Trifluoro-1-[1-(4-fluorophenyl)-1H-indazol-5-yl]-1-(2-morpholin-4-yl-thiazol-4-yl)ethanol | 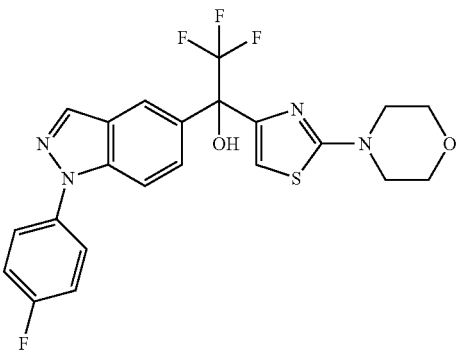 |
| 2,2,2-Trifluoro-1-[1-(4-fluorophenyl)-1H-indazol-5-yl]-1-thiazol-5-ylethanol | 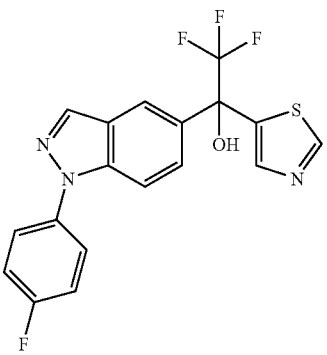 |
| N-(5-{2,2,2-Trifluoro-1-[1-(4-fluorophenyl)-1H-indazol-5-yl]-1-hydroxyethyl}thiazol-2-yl)acetamide | 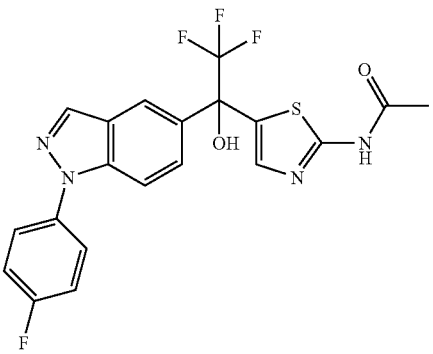 |

-continued
| IA | |
|---|---|
| A | B |
1-(2-Aminothiazol-5-yl)-2,2,2-trifluoro-1-[1-(4-fluorophenyl)-1H-indazol-5-yl]ethanol
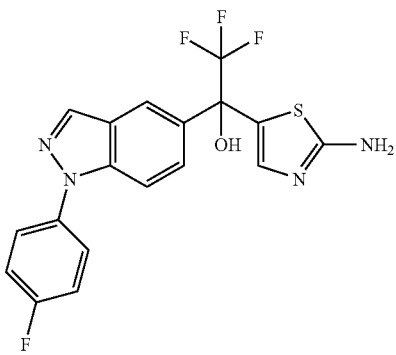 [SMILES: Nc1ncc(C(O)(c2ccc3c(cnn3-c3ccc(F)cc3)c2)C(F)(F)F)s1]
2,2,2-Trifluoro-1-[1-(4-fluorophenyl)-1H-indazol-5-yl]-1-(2-morpholin-4-ylthiazol-5-yl)ethanol
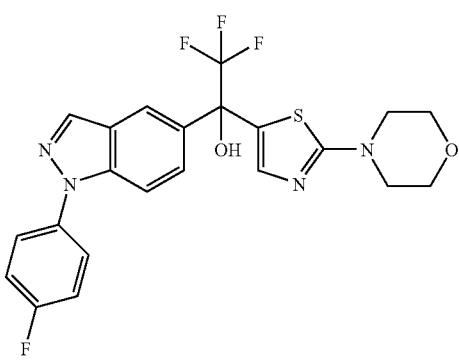 [SMILES: OC(c1ccc2c(cnn2-c2ccc(F)cc2)c1)(c1cnc(N2CCOCC2)s1)C(F)(F)F]
3-(3-{2,2,2-Trifluoro-1-[1-(4-fluorophenyl)-1H-benzotriazol-5-yl]-1-hydroxyethyl}indol-1-yl)propane-1,2-diol
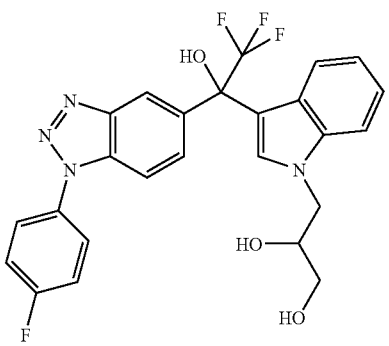 [SMILES: OCC(O)Cn1cc(C(O)(c2ccc3c(c2)nnn3-c2ccc(F)cc2)C(F)(F)F)c2ccccc21]
1-[1-(2,2-Dimethyl-1,3-dioxolan-4-ylmethyl)-1H-indol-3-yl]-2,2,2-trifluoro-1-[1-(4-fluorophenyl)-1H-benzotriazol-5-yl]ethanol
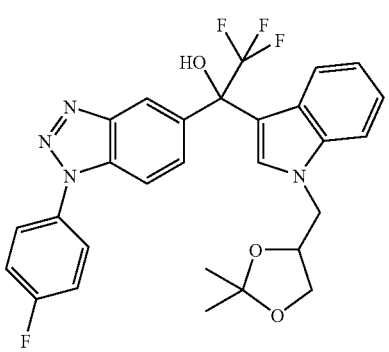 [SMILES: CC1(C)OCC(Cn2cc(C(O)(c3ccc4c(c3)nnn4-c3ccc(F)cc3)C(F)(F)F)c3ccccc32)O1]

-continued
| IA | |
|---|---|
| A | B |
2,2,2-Trifluoro-1-[1-(4-fluorophenyl)-1H-benzotriazol-5-yl]-1-(1-methyl-1H-indol-3-yl)ethanol
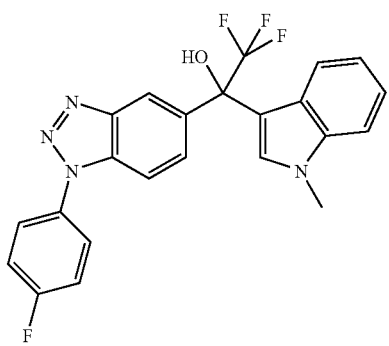 [SMILES: Cn1cc(C(O)(c2ccc3c(c2)nnn3-c2ccc(F)cc2)C(F)(F)F)c2ccccc21]
2,2,2-Trifluoro-1-[1-(4-fluorophenyl)-2-methyl-1H-benzimidazol-5-yl]-1-(1-methyl-1H-indol-3-yl)ethanol
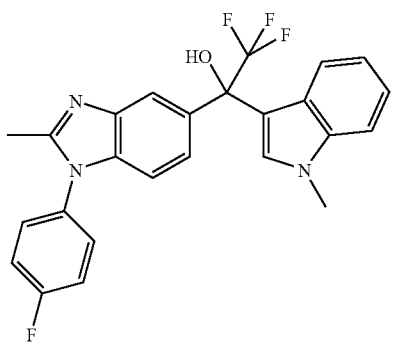 [SMILES: Cc1nc2cc(C(O)(c3cn(C)c4ccccc34)C(F)(F)F)ccc2n1-c1ccc(F)cc1]
1-(4-Fluorophenyl)-3-methyl-5-[2,2,2-trifluoro-1-hydroxy-1-(1-methyl-1H-indol-3-yl)ethyl]-1,3-dihydrobenzimidazol-2-one
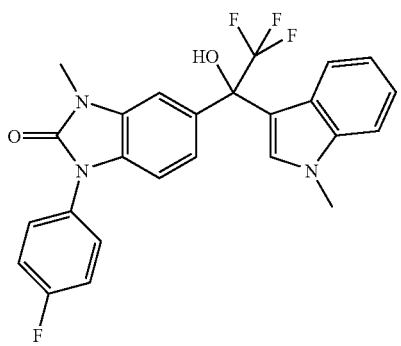 [SMILES: Cn1cc(C(O)(c2ccc3c(c2)n(C)c(=O)n3-c2ccc(F)cc2)C(F)(F)F)c2ccccc21]
(3-Methyl-2-oxo-5-{2,2,2-trifluoro-1-[1-(4-fluorophenyl)-1H-indazol-5-yl]-1-hydroxyethyl}-2H-pyridin-1-yl)acetamide
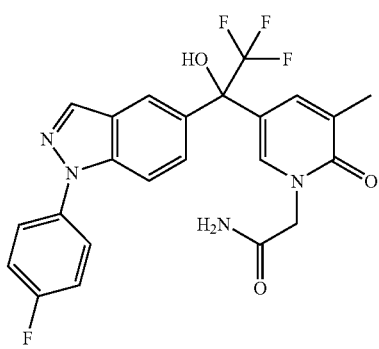 [SMILES: Cc1cc(C(O)(c2ccc3c(cnn3-c3ccc(F)cc3)c2)C(F)(F)F)cn(CC(N)=O)c1=O]

-continued
| A | B |
|---|---|
| 1,3-Dimethyl-5-{2,2,2-trifluoro-1-[1-(4-fluorophenyl)-1H-indazol-5-yl]-1-hydroxyethyl}-1H-pyridin-2-one | 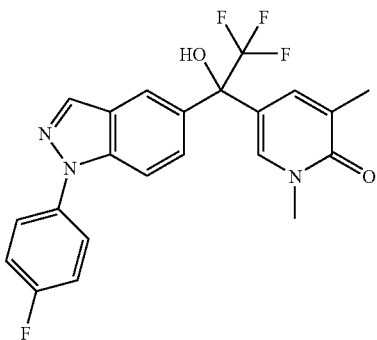 |
| (2-Oxo-5-{2,2,2-trifluoro-1-[1-(4-fluorophenyl)-1H-indazol-5-yl]-1-hydroxyethyl}-2H-pyridin-1-yl)acetamide | 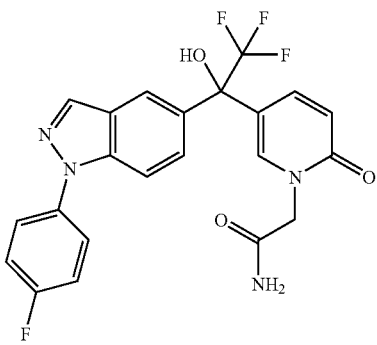 |
| 3-Methyl-5-{2,2,2-trifluoro-1-[1-(4-fluorophenyl)-1H-indazol-5-yl]-1-hydroxyethyl}-1H-pyridin-2-one | 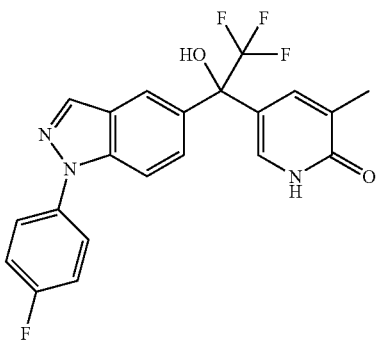 |
| 5-{2,2,2-trifluoro-1-[1-(4-fluorophenyl)-1H-indazol-5-yl]-1-hydroxyethyl}-1H-pyridin-2-one | 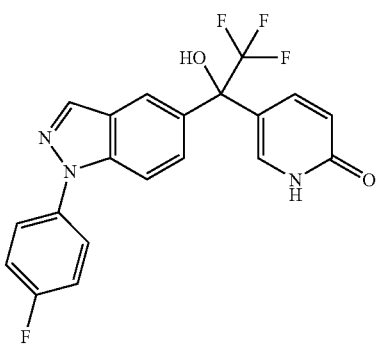 |

-continued
IA
| A | B |
|---|---|
| 2,2,2-Trifluoro-1-[1-(4-fluorophenyl)-1H-indazol-5-yl]-1-(6-methoxypyridin-3-yl)ethanol | 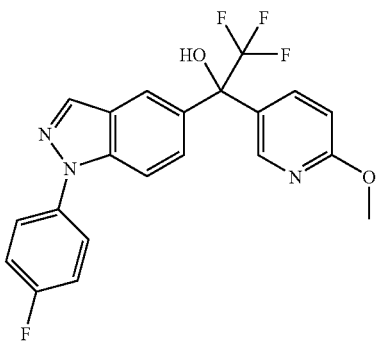 |
| 5-[1-(1-Allyl-1H-indol-3-yl)-2,2,2-trifluoro-1-hydroxyethyl]indazole-1-carboxylic acid ethylamide | 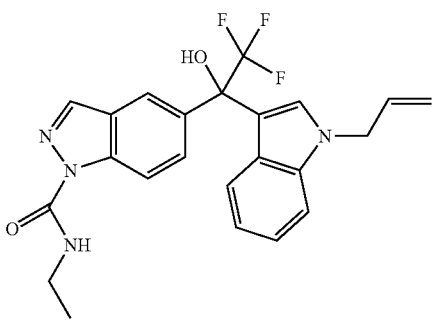 |
| 5-[1-(1-Allyl-1H-indol-3-yl)-2,2,2-trifluoro-1-hydroxyethyl]indazole-1-carboxylic acid (1-ethylpropyl)amide | 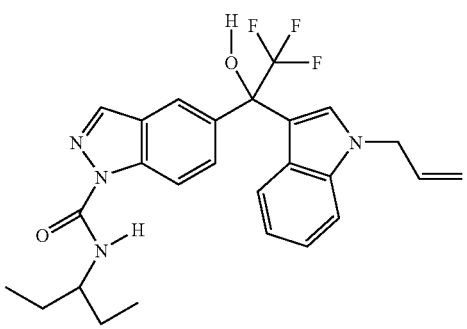 |
| 5-[1-(1-Allyl-1H-indol-3-yl)-2,2,2-trifluoro-1-hydroxyethyl]indazole-1-carboxylic acid (1,2-dimethylpropyl)amide | 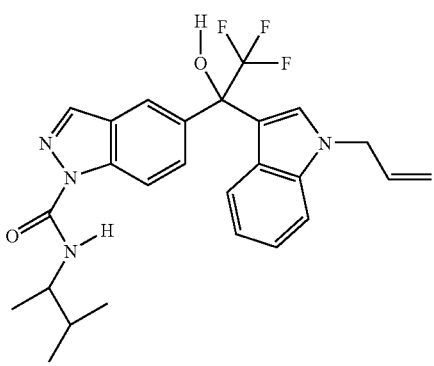 |

| A | B |
|---|---|
| 5-[1-(1-Allyl-1H-indol-3-yl)-2,2,2-trifluoro-1-hydroxyethyl]indazole-1-carboxylic acid (1,1-dimethylethyl)amide | 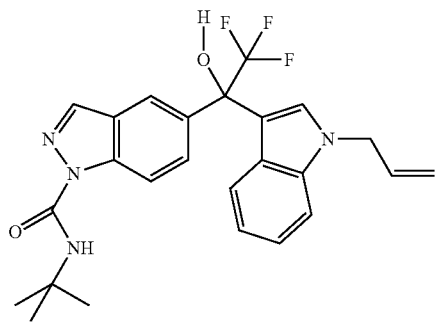 |
| 5-[1-(1-Allyl-1H-indol-3-yl)-2,2,2-trifluoro-1-hydroxyethyl]indazole-1-carboxylic acid (1-methylpropyl)amide | 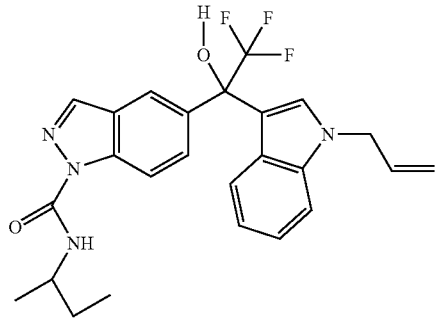 |
| 5-[1-(1-Allyl-1H-indol-3-yl)-2,2,2-trifluoro-1-hydroxyethyl]indazole-1-carboxylic acid propylamide | 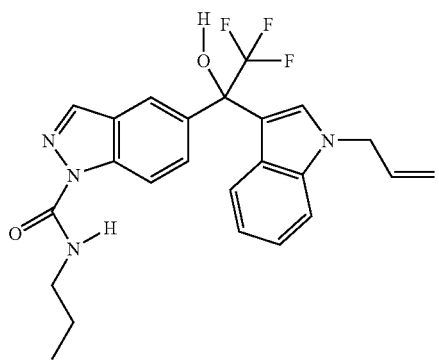 |
| 5-[1-(1-Allyl-1H-indol-3-yl)-2,2,2-trifluoro-1-hydroxyethyl]indazole-1-carboxylic acid (1-methylethyl)amide | 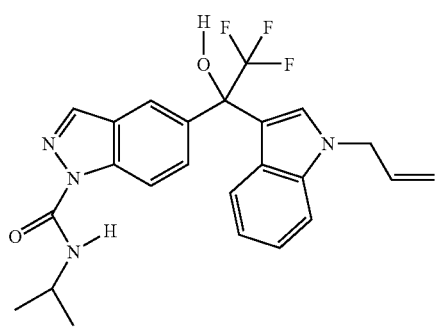 |

-continued
IA
| A | B |
|---|---|
| 5-[1-(1-Methyl-1H-indol-3-yl)-2,2,2-trifluoro-1-hydroxyethyl]indazole-1-carboxylic acid cyclobutyl ester | 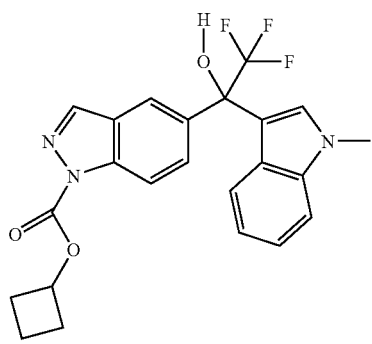 |
| Cyclopentyl-{5-[2,2,2-trifluoro-1-hydroxy-1-(1-methyl-1H-indol-3-yl)ethyl]indazol-1-yl}methanone | 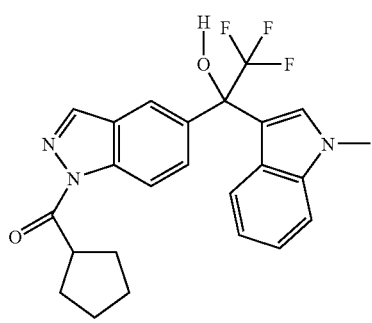 |
| Cyclobutyl-{5-[2,2,2-trifluoro-1-hydroxy-1-(1-methyl-1H-indol-3-yl)ethyl]indazol-1-yl}methanone | 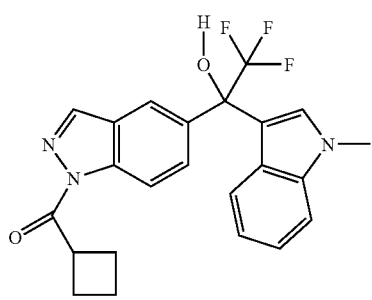 |
| Cyclopropyl-{5-[2,2,2-trifluoro-1-hydroxy-1-(1-methyl-1H-indol-3-yl)ethyl]indazol-1-yl}methanone | 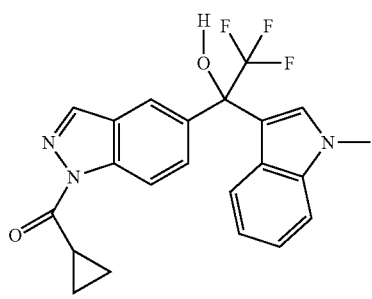 |

-continued

IA

| A | B |
|---|---|
| 5-[2,2,2-Trifluoro-1-hydroxy-1-(1-methyl-1H-indol-3-yl)ethyl]indazole-1-carboxylic acid cyclopentylmethylamide | 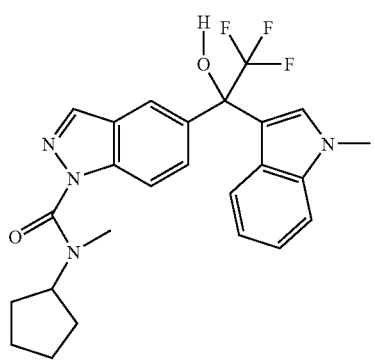 |
| 5-[2,2,2-Trifluoro-1-hydroxy-1-(1-methyl-1H-indol-3-yl)ethyl]indazole-1-carboxylic acid isopropylmethylamide | 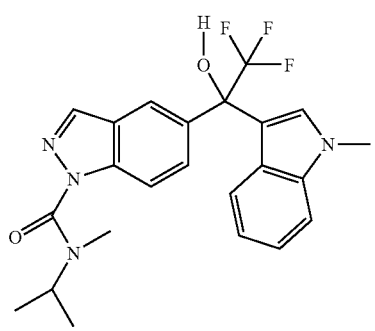 |
| 5-[2,2,2-Trifluoro-1-hydroxy-1-(1-methyl-1H-indol-3-yl)ethyl]indazole-1-carboxylic acid cyclopropylamide | 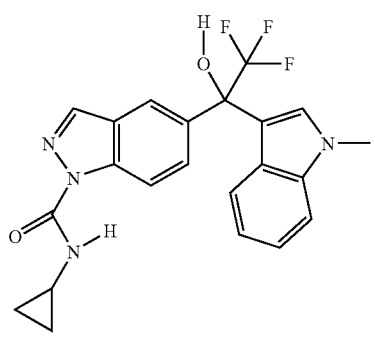 |
| 5-[2,2,2-Trifluoro-1-hydroxy-1-(1-methyl-1H-indol-3-yl)ethyl]indazole-1-carboxylic acid cyclopentylamide | 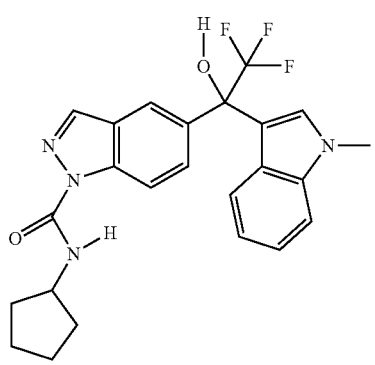 |

| IA | |
|---|---|
| A | B |
5-[2,2,2-Trifluoro-1-hydroxy-1-(1-methyl-1H-indol-3-yl)ethyl]indazole-1-carboxylic acid cyclopropylmethylamide
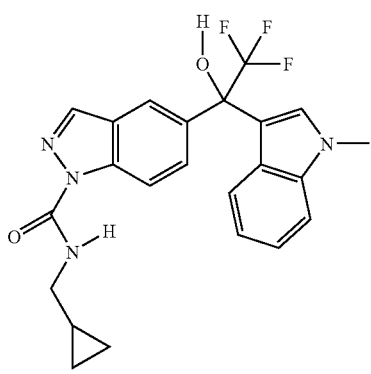 [SMILES: Cn1cc(C(O)(c2ccc3c(cnn3C(=O)NCC3CC3)c2)C(F)(F)F)c2ccccc21]
5-[2,2,2-Trifluoro-1-hydroxy-1-(1-methyl-1H-indol-3-yl)ethyl]indazole-1-carboxylic acid isopropylamide
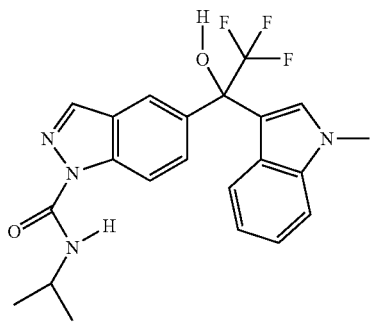 [SMILES: CC(C)NC(=O)n1ncc2cc(C(O)(c3cn(C)c4ccccc34)C(F)(F)F)ccc21]
5-[1-(1-Methyl-1H-indol-3-yl)-2,2,2-trifluoro-1-hydroxyethyl]indazole-1-carboxylic acid cyclopentyl ester
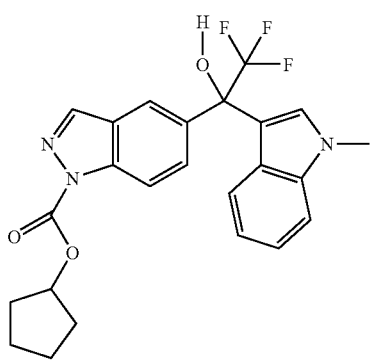 [SMILES: Cn1cc(C(O)(c2ccc3c(cnn3C(=O)OC3CCCC3)c2)C(F)(F)F)c2ccccc21]
5-[1-(1-Methyl-1H-indol-3-yl)-2,2,2-trifluoro-1-hydroxyethyl]indazole-1-carboxylic acid ethyl ester
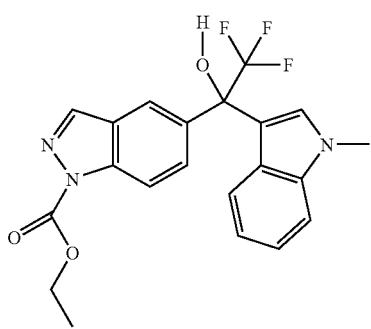 [SMILES: CCOC(=O)n1ncc2cc(C(O)(c3cn(C)c4ccccc34)C(F)(F)F)ccc21]

-continued
IA
| A | B |
|---|---|
| 5-[1-(1-Methyl-1H-indol-3-yl)-2,2,2-trifluoro-1-hydroxyethyl]indazole-1-carboxylic acid cyclopropylmethyl ester | 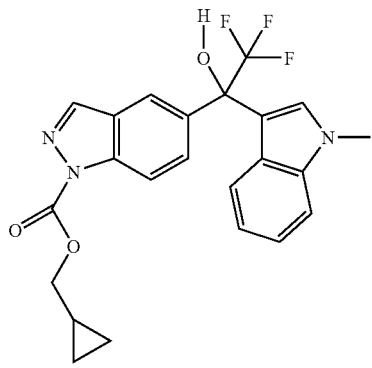 |
| 5-[2,2,2-Trifluoro-1-hydroxy-1-(1-methyl-1H-indol-3-yl)ethyl]indazole-1-carboxylic acid phenyl ester | 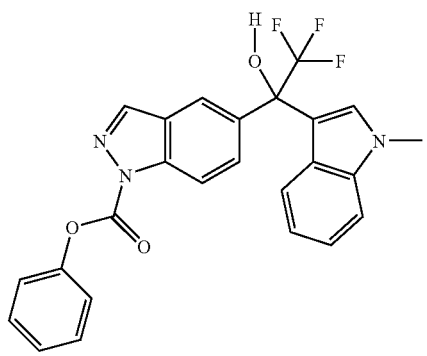 |
| 5-[1-(1-Methyl-1H-indol-3-yl)-2,2,2-trifluoro-1-hydroxyethyl]indazole-1-carboxylic acid isopropyl ester | 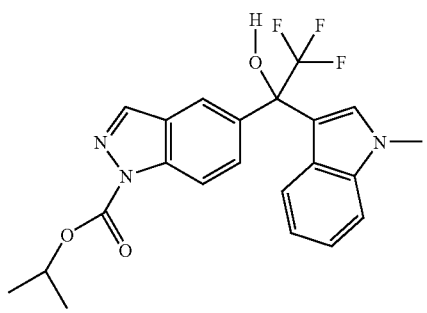 |
| 2,2,2-Trifluoro-1-(1-methyl-1H-indol-3-yl)-1-(1-phenylmethanesulfonyl-1H-indazol-5-yl)ethanol | 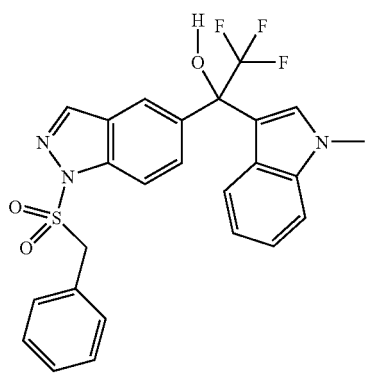 |

-continued

| A | B |
|---|---|
| 2-Phenyl-1-{5-[2,2,2-trifluoro-1-hydroxy-1-(1-methyl-1H-indol-3-yl)ethyl]indazol-1-yl}ethanone | 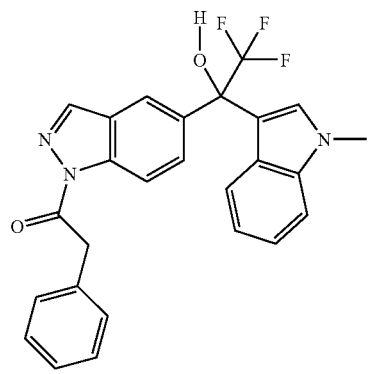 |
| 2-Thiophen-2-yl-1-{5-[2,2,2-trifluoro-1-hydroxy-1-(1-methyl-1H-indol-3-yl)ethyl]indazol-1-yl}ethanone | 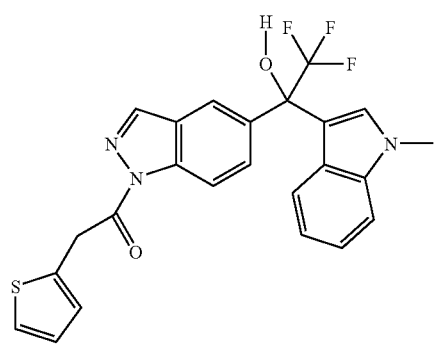 |
| Phenyl-{5-[2,2,2-trifluoro-1-hydroxy-1-(1-methyl-1H-indol-3-yl)ethyl]indazol-1-yl}-methanone | 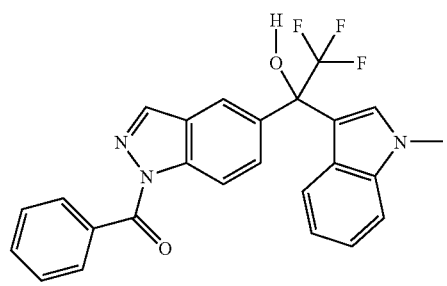 |
| 3-Methyl-1-{5-[2,2,2-trifluoro-1-hydroxy-1-(1-methyl-1H-indol-3-yl)ethyl]indazol-1-yl}butan-1-one | 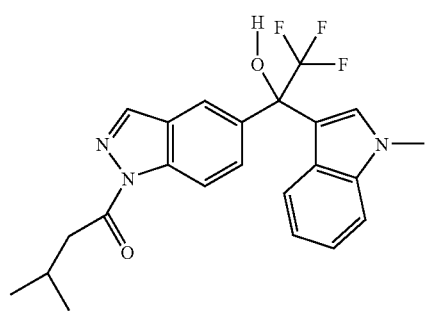 |
| 1-(1-Benzenesulfonyl-1H-indazol-5-yl)-2,2,2-trifluoro-1-(1-methyl-1H-indol-3-yl)ethanol | 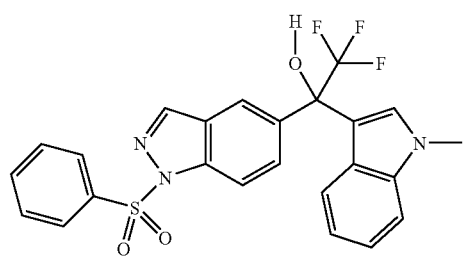 |

-continued

IA

| A | B |
|---|---|
| 2,2,2-Trifluoro-1-(1-methyl-1H-indol-3-yl)-1-[1-(propane-2-sulfonyl)-1H-indazol-5-yl]ethanol | 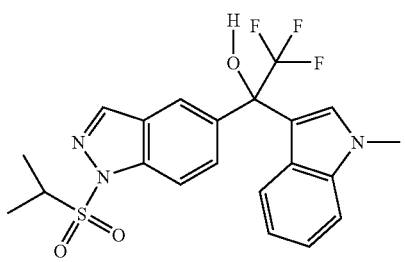 |
| 2,2,2-Trifluoro-1-(1-methanesulfonyl-1H-indazol-5-yl)-1-(1-methyl-1H-indol-3-yl)ethanol | 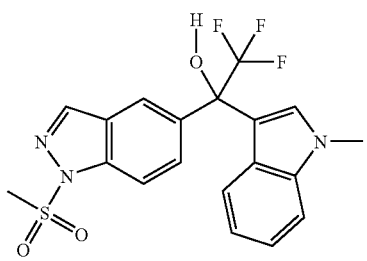 |
| 2,2,2-Trifluoro-1-(1H-indazol-5-yl)-1-(1-methyl-1H-indol-3-yl)ethanol | 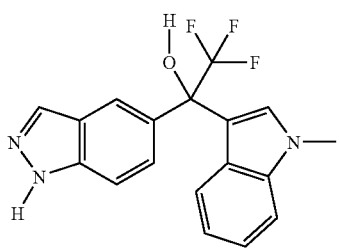 |
| 2-Phenyl-1-[5-(2,2,2-trifluoro-1-hydroxy-1-phenylethyl)indazol-1-yl]ethanone | 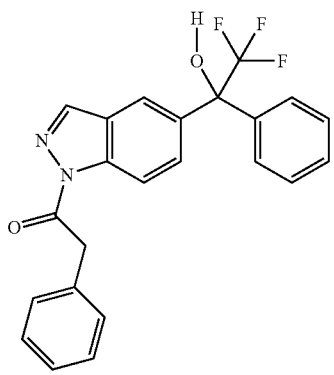 |
| 1-(1-Allyl-6-dimethylamino-1H-indol-3-yl)-2,2,2-trifluoro-1-[1-(4-fluorophenyl)-1H-indazol-5-yl]ethanol | 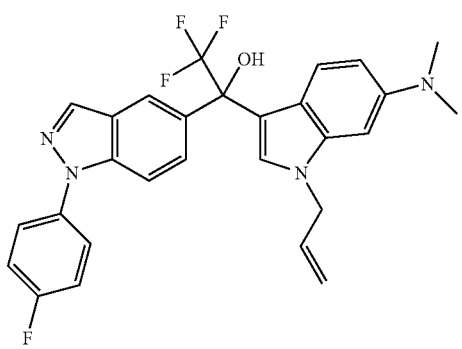 | or a tautomer, prodrug, solvate, or salt thereof.

Preferred compounds of Formula (IA) include the following:

(3-{2,2,2-Trifluoro-1-[1-(4-fluorophenyl)-1H-indazol-5-yl]-1-hydroxyethyl}pyrrolo[2,3-b]pyridin-1-yl)acetonitrile;
2,2,2-Trifluoro-1-(1-phenyl-1H-pyrazolo[3,4-b]pyridin-5-yl)-1-(1H-pyrrolo[2,3-b]pyridin-3-yl)ethanol;
1-(4-Chloro-1-phenyl-1H-pyrazolo[3,4-b]pyridin-5-yl)-2,2,2-trifluoro-1-(1H-pyrrolo[2,3-b]pyridin-3-yl)ethanol;
2-(7-Chloro-3-{2,2,2-trifluoro-1-[1-(4-fluorophenyl)-1H-indazol-5-yl]-1-hydroxyethyl}pyrrolo[2,3-c]pyridin-1-yl)acetamide;
N-[2-(3-{2,2,2-Trifluoro-1-[1-(4-fluorophenyl)-1H-indazol-5-yl]-1-hydroxyethyl}pyrrolo[2,3-b]pyridin-1-yl)acetyl]methanesulfonamide;
1-(7-Chloro-1H-pyrrolo[2,3-c]pyridin-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-(7-oxy-1H-pyrrolo[2,3-b]pyridin-3-yl)ethanol;
2,2,2-Trifluoro-1-(1H-pyrrolo[2,3-b]pyridin-3-yl)-1-(1-p-tolyl-1H-indazol-5-yl)ethanol;
2,2,2-Trifluoro-1-[1-(4-fluorophenyl)-1H-indazol-5-yl]-1-(1H-pyrrolo[3,2-b]pyridin-3-yl)ethanol;
2,2,2-Trifluoro-1-[1-(4-fluorophenyl)-1H-indazol-5-yl]-1-(1H-pyrrolo[2,3-c]pyridin-3-yl)ethanol;
2,2,2-Trifluoro-1-[1-(4-fluorophenyl)-1H-indazol-5-yl]-1-(1H-pyrrolo[3,2-c]pyridin-3-yl)ethanol;
3-{2,2,2-Trifluoro-1-[1-(4-fluorophenyl)-1H-indazol-5-yl]-1-hydroxyethyl}pyrrolo[2,3-b]pyridine-1-sulfonic acid dimethylamide;
2-(3-{2,2,2-Trifluoro-1-[1-(4-fluorophenyl)-1H-indazol-5-yl]-1-hydroxyethyl}pyrrolo[2,3-b]pyridin-1-yl)acetamide;
2,2,2-Trifluoro-1-[1-(4-fluorophenyl)-1H-indazol-5-yl]-1-(1H-pyrrolo[2,3-b]pyridin-3-yl)ethanol;
2,2,2-Trifluoro-1-[1-(4-fluorophenyl)-1H-indazol-5-yl]-1-(1H-indazol-3-yl)ethanol;
Phenyl-{2,2,2-trifluoro-1-[1-(4-fluorophenyl)-1H-indazol-5-yl]ethyl}amine;
(1H-Indol-5-yl)-{2,2,2-trifluoro-1-[1-(4-fluorophenyl)-1H-indazol-5-yl]ethyl}amine;
(1H-Indol-6-yl)-{2,2,2-trifluoro-1-[1-(4-fluorophenyl)-1H-indazol-5-yl]ethyl}amine;
(1H-Indol-7-yl)-{2,2,2-trifluoro-1-[1-(4-fluorophenyl)-1H-indazol-5-yl]ethyl}amine;
(1H-Indol-4-yl)-{2,2,2-trifluoro-1-[1-(4-fluorophenyl)-1H-indazol-5-yl]ethyl}amine;
(1-Benzyl-2,2,2-trifluoroethyl)-[1-(4-fluorophenyl)-1H-indazol-5-yl]amine;
Benzyl-{2,2,2-trifluoro-1-[1-(4-fluorophenyl)-1H-indazol-5-yl]ethyl}amine;
(2-Nitrophenyl)-{2,2,2-trifluoro-1-[1-(4-fluorophenyl)-1H-indazol-5-yl]ethyl}amine;
N-{2,2,2-Trifluoro-1-[1-(4-fluorophenyl)-1H-indazol-5-yl]ethyl}-benzene-1,2-diamine;
2-Amino-4,6-dichloro-N-{2,2,2-trifluoro-1-[1-(4-fluorophenyl)-1H-indazol-5-yl]ethyl}-benzenesulfonamide;
2-(7-{2,2,2-Trifluoro-1-[1-(4-fluorophenyl)-1H-indazol-5-yl]ethylamino}indol-1-yl)acetamide;
3-Methyl-N$^2$-{2,2,2-trifluoro-1-[1-(4-fluorophenyl)-1H-indazol-5-yl]ethyl}-benzene-1,2-diamine;
2,2,2-Trifluoro-1-(1-methyl-1H-indol-3-yl)-1-(1-pyridin-3-yl-1H-indazol-5-yl)ethanol;
2,2,2-Trifluoro-1-(1-methyl-1H-indol-3-yl)-1-(1-pyridin-4-yl-1H-indazol-5-yl)ethanol;
2,2,2-Trifluoro-1-(1-methyl-1H-indol-3-yl)-1-(1-pyrimidin-5-yl-1H-indazol-5-yl)ethanol;
2,2,2-Trifluoro-1-(1-methyl-1H-indol-3-yl)-1-(1-thiophen-3-yl-1H-indazol-5-yl)ethanol;
2,2,2-Trifluoro-1-(1H-indol-3-yl)-1-(1-pyridin-3-yl-1H-indazol-5-yl)ethanol;
2-{3-[2,2,2-Trifluoro-1-hydroxy-1-(1-pyridin-3-yl-1H-indazol-5-yl)ethyl]indol-1-yl}acetamide;
2,2,2-Trifluoro-1-(1-methyl-1H-indol-3-yl)-1-[1-(6-methylpyridin-3-yl)-1H-indazol-5-yl]ethanol;
2,2,2-Trifluoro-1-(1-methyl-1H-indol-3-yl)-1-[1-(5-methylthiophen-2-yl)-1H-indazol-5-yl]ethanol;
2,2,2-Trifluoro-1-[1-(1-methyl-1H-imidazol-4-yl)-1H-indazol-5-yl]-1-(1-methyl-1H-indol-3-yl)ethanol;
2,2,2-Trifluoro-1-(1-methyl-1H-indol-3-yl)-1-(1-pyridin-2-yl-1H-indazol-5-yl)ethanol;
2,2,2-Trifluoro-1-(1-methyl-1H-indol-3-yl)-1-[1-(1-methyl-1H-pyrazol-4-yl)-1H-indazol-5-yl]ethanol;
2,2,2-Trifluoro-1-[1-(6-fluoropyridin-3-yl)-1H-indazol-5-yl]-1-(1-methyl-1H-indol-3-yl)ethanol;
(R)-1-(3-{2,2,2-Trifluoro-1-[1-(4-fluorophenyl)-1H-indazol-5-yl]-1-hydroxyethyl} indol-1-yl)propan-2-ol;
(S)-1-(3-{2,2,2-Trifluoro-1-[1-(4-fluorophenyl)-1H-indazol-5-yl]-1-hydroxyethyl} indol-1-yl)propan-2-ol;
1-(5-Chloro-1,1-dioxo-1H-1$\lambda^6$-thiophen-2-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(tetrahydro-furan-2-ylmethyl)-1H-indol-3-yl]ethanol;
2,2,2-Trifluoro-1-[1-(4-fluorophenyl)-1H-indazol-5-yl]-1-[1-(2-morpholin-4-ylethyl)-1H-indol-3-yl]ethanol;
(3-{2,2,2-Trifluoro-1-[1-(4-fluorophenyl)-1H-indazol-5-yl]-1-hydroxyethyl} indol-1-yl)acetic acid;
1-(1-Allyl-5-hydroxymethyl-1H-pyrrol-3-yl)-2,2,2-trifluoro-1-[1-(4-fluorophenyl)-1H-indazol-5-yl]ethanol;
1-(5-1,3-Dioxolan-2-ylthiophen-2-yl)-2,2,2-trifluoro-1-[1-(4-fluorophenyl)-1H-indazol-5-yl]ethanol;
(3-{2,2,2-Trifluoro-1-[1-(4-fluorophenyl)-1H-indazol-5-yl]-1-hydroxyethyl}indol-1-yl)acetic acid ethyl ester;
1-(5-Chlorothiophen-2-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-{1-[3-(4-hydroxymethylpiperidin-1-yl)propyl]-1H-indol-3-yl}ethanol;
1-{1-[3-((S)-3-Dimethylaminopyrrolidin-1-yl)propyl]-1H-indol-3-yl}-2,2,2-trifluoro-1-[1-(4-fluorophenyl)-1H-indazol-5-yl]ethanol;
1-{1-[3-((R)-3-Dimethylaminopyrrolidin-1-yl)propyl]-1H-indol-3-yl}-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(3-pyrrolidin-1-ylpropyl)-1H-indol-3-yl]ethanol;
2,2,2-Trifluoro-1-[1-(4-fluorophenyl)-1H-indazol-5-yl]-1-{1-[3-(4-methylpiperazin-1-yl)-propyl]-1H-indol-3-yl}ethanol;
2,2,2-Trifluoro-1-[1-(4-fluorophenyl)-1H-indazol-5-yl]-1-[1-(3-methylaminopropyl)-1H-indol-3-yl]ethanol;
2,2,2-Trifluoro-1-[1-(4-fluorophenyl)-1H-indazol-5-yl]-1-[1-(3-morpholin-4-ylpropyl)-1H-indol-3-yl]ethanol;
1-[1-(3-Dimethylaminopropyl)-1H-indol-3-yl]-2,2,2-trifluoro-1-[1-(4-fluorophenyl)-1H-indazol-5-yl]ethanol;
3-(6-(2H-Pyrazol-3-yl)-3-{2,2,2-trifluoro-1-[1-(4-fluorophenyl)-1H-indazol-5-yl]-1-hydroxyethyl}indol-1-yl)propane-1,2-diol;
1-[1-Allyl-6-(2H-pyrazol-3-yl)-1H-indol-3-yl]-2,2,2-trifluoro-1-[1-(4-fluorophenyl)-1H-indazol-5-yl]ethanol;
1-(6-Bromo-1-but-3-enyl-1H-indol-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(propane-2-sulfonyl)-1H-indol-3-yl]ethanol;

3-(3-{2,2,2-Trifluoro-1-[1-(4-fluorophenyl)-1H-indazol-5-yl]-1-hydroxyethyl}indol-1-yl)propionamide;

N-Methyl-3-(3-{2,2,2-trifluoro-1-[1-(4-fluorophenyl)-1H-indazol-5-yl]-1-hydroxyethyl}indol-1-yl)propionamide;

3-(6-Pyrrolidin-1-yl-3-{2,2,2-trifluoro-1-[1-(4-fluorophenyl)-1H-indazol-5-yl]-1-hydroxyethyl}indol-1-yl)propane-1,2-diol;

2-(6-Bromo-3-{2,2,2-trifluoro-1-[1-(4-fluorophenyl)-1H-indazol-5-yl]-1-hydroxyethyl}indol-1-yl)-N-methylacetamide;

4-(3-{2,2,2-Trifluoro-1-[1-(4-fluorophenyl)-1H-indazol-5-yl]-1-hydroxyethyl}indol-1-yl)-butane-1,2-diol;

1-(1-But-3-enyl-1H-indol-3-yl)-2,2,2-trifluoro-1-[1-(4-fluorophenyl)-1H-indazol-5-yl]ethanol;

1-(1-Allyl-6-pyrrolidin-1-yl-1H-indol-3-yl)-2,2,2-trifluoro-1-[1-(4-fluorophenyl)-1H-indazol-5-yl]ethanol;

1-(1-Allyl-6-bromo-1H-indol-3-yl)-2,2,2-trifluoro-1-[1-(4-fluorophenyl)-1H-indazol-5-yl]ethanol;

3-(6-Bromo-3-{2,2,2-trifluoro-1-[1-(4-fluorophenyl)-1H-indazol-5-yl]-1-hydroxyethyl}indol-1-yl)propane-1,2-diol;

2,2,2-Trifluoro-1-[1-(4-fluorophenyl)-1H-indazol-5-yl]-1-[1-(4-methoxybenzyl)-6-vinyl-1H-indol-3-yl]ethanol;

2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide;

3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol;

2,2,2-Trifluoro-1-[1-(4-fluorophenyl)-1H-indazol-5-yl]-1-(7-methoxy-1H-pyrrolo[2,3-c]pyridin-3-yl)ethanol;

4-Bromo-1-(2,3-dihydroxypropyl)-5-{2,2,2-trifluoro-1-[1-(4-fluorophenyl)-1H-indazol-5-yl]-1-hydroxyethyl}-1H-pyrazole-3-carbonitrile;

1-Allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one;

4-{2,2,2-Trifluoro-1-[1-(4-fluorophenyl)-1H-indazol-5-yl]-1-hydroxyethyl}-1H-pyrazole-3-carbonitrile;

1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile;

2,2,2-Trifluoro-1-[1-(4-fluorophenyl)-1H-indazol-5-yl]-1-(2-hydroxymethyl-thiazol-5-yl)ethanol;

2,2,2-Trifluoro-1-[1-(4-fluorophenyl)-1H-indazol-5-yl]-1-(2-hydroxymethyl-thiazol-4-yl)ethanol;

1-Allyl-4-bromo-5-{2,2,2-trifluoro-1-[1-(4-fluorophenyl)-1H-indazol-5-yl]-1-hydroxyethyl}-1H-pyrazole-3-carbonitrile;

1-Allyl-4-{2,2,2-trifluoro-1-[1-(4-fluorophenyl)-1H-indazol-5-yl]-1-hydroxyethyl}-1H-pyrazole-3-carbonitrile;

2,2,2-Trifluoro-1-[1-(4-fluorophenyl)-1H-indazol-5-yl]-1-(2-morpholin-4-yl-thiazol-4-yl)ethanol;

2,2,2-Trifluoro-1-[1-(4-fluorophenyl)-1H-indazol-5-yl]-1-thiazol-5-ylethanol;

N-(5-{2,2,2-Trifluoro-1-[1-(4-fluorophenyl)-1H-indazol-5-yl]-1-hydroxyethyl}thiazol-2-yl)acetamide;

2,2,2-Trifluoro-1-[1-(4-fluorophenyl)-1H-indazol-5-yl]-1-(2-morpholin-4-yl-thiazol-5-yl)ethanol;

1-[4-Chloro-5-(2-hydroxyethyl)-5H-pyrrolo[3,2-c]pyrimidin-7-yl]-2,2,2-trifluoro-1-[1-(4-fluorophenyl)-1H-indazol-5-yl]ethanol;

3-(4-Chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol;

5-(2,3-Dihydroxypropyl)-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

5-Allyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

7-{2,2,2-Trifluoro-1-[1-(4-fluorophenyl)-1H-indazol-5-yl]-1-hydroxyethyl}-3,5-dihydropyrrolo[3,2-d]pyrimidin-4-one;

1-(4-Chloro-5H-pyrrolo[3,2-d]pyrimidin-7-yl)-2,2,2-trifluoro-1-[1-(4-fluorophenyl)-1H-indazol-5-yl]ethanol;

2-(3-Methyl-4-oxo-7-{2,2,2-trifluoro-1-[1-(4-fluorophenyl)-1H-indazol-5-yl]-1-hydroxyethyl}-3,4-dihydropyrrolo[3,2-d]pyrimidin-5-yl)acetamide;

5-(2,3-Dihydroxypropyl)-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid dimethylamide;

1-Allyl-4-{2,2,2-trifluoro-1-[1-(4-fluorophenyl)-1H-indazol-5-yl]-1-hydroxyethyl}-1H-pyrrole-2-carboxylic acid methylamide;

1-Allyl-4-{2,2,2-trifluoro-1-[1-(4-fluorophenyl)-1H-indazol-5-yl]-1-hydroxyethyl}-1H-pyrrole-2-carboxylic acid carbamoylmethylamide;

1-Allyl-4-{2,2,2-trifluoro-1-[1-(4-fluorophenyl)-1H-indazol-5-yl]-1-hydroxyethyl}-1H-pyrrole-2-carboxylic acid cyanomethylamide;

1-Allyl-4-{2,2,2-trifluoro-1-[1-(4-fluorophenyl)-1H-indazol-5-yl]-1-hydroxyethyl}-1H-pyrrole-2-carboxylic acid amide;

2-(2-Cyano-4-{2,2,2-trifluoro-1-[1-(4-fluorophenyl)-1H-indazol-5-yl]-1-hydroxyethyl}pyrrol-1-yl)acetamide;

2-(2-Cyano-4-{2,2,2-trifluoro-1-[1-(4-fluorophenyl)-1H-indazol-5-yl]-1-hydroxyethyl}pyrrol-1-yl)-N-methylacetamide;

1-Allyl-4-{2,2,2-trifluoro-1-[1-(4-fluorophenyl)-1H-indazol-5-yl]-1-hydroxyethyl}-1H-pyrrole-2-carboxylic acid dimethylamide;

1-Allyl-4-{2,2,2-trifluoro-1-[1-(4-fluorophenyl)-1H-indazol-5-yl]-1-hydroxyethyl}-1H-pyrrole-2-carboxylic acid;

1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester;

3-Hydroxymethyl-7-{2,2,2-trifluoro-1-[1-(4-fluorophenyl)-1H-indazol-5-yl]-1-hydroxyethyl}-3,4-dihydropyrrolo[2,1-c][1,4]oxazin-1-one;

1-Allyl-4-{2,2,2-trifluoro-1-[1-(4-fluorophenyl)-1H-indazol-5-yl]-1-hydroxyethyl}-1H-pyrrole-2-carboxylic acid ethyl ester;

4-{2,2,2-Trifluoro-1-[1-(4-fluorophenyl)-1H-indazol-5-yl]-1-hydroxyethyl}-1H-pyrrole-2-carbonitrile;

1-(2,3-Dihydroxypropyl)-4-{2,2,2-trifluoro-1-[1-(4-fluorophenyl)-1H-indazol-5-yl]-1-hydroxyethyl}-1H-pyrrole-2-carbonitrile;

1-Allyl-4-{2,2,2-trifluoro-1-[1-(4-fluorophenyl)-1H-indazol-5-yl]-1-hydroxyethyl}-1H-pyrrole-2-carbonitrile;

(1-(2,3-Dihydroxypropyl)-4-{2,2,2-trifluoro-1-[1-(4-fluorophenyl)-1H-indazol-5-yl]-1-hydroxyethyl}-1H-pyrrol-2-yl)-morpholin-4-yl-methanone;

(1-Allyl-4-{2,2,2-trifluoro-1-[1-(4-fluorophenyl)-1H-indazol-5-yl]-1-hydroxyethyl}-1H-pyrrol-2-yl)-morpholin-4-yl-methanone;

3-(3-{2,2,2-Trifluoro-1-[1-(4-fluorophenyl)-1H-benzotriazol-5-yl]-1-hydroxyethyl}indol-1-yl)propane-1,2-diol;
2,2,2-Trifluoro-1-[1-(4-fluorophenyl)-1H-benzotriazol-5-yl]-1-(1-methyl-1H-indol-3-yl)ethanol;
1-[1-(2,2-Dimethyl-1,3-dioxolan-4-ylmethyl)-1H-indol-3-yl]-2,2,2-trifluoro-1-[1-(4-fluorophenyl)-1H-benzotriazol-5-yl]ethanol;
(2-Oxo-5-{2,2,2-trifluoro-1-[1-(4-fluorophenyl)-1H-indazol-5-yl]-1-hydroxyethyl}-2H-pyridin-1-yl)acetamide;
5-[1-(1-Allyl-1H-indol-3-yl)-2,2,2-trifluoro-1-hydroxyethyl]indazole-1-carboxylic acid (1,1-dimethylethyl)amide;
5-[1-(1-Methyl-1H-indol-3-yl)-2,2,2-trifluoro-1-hydroxyethyl]indazole-1-carboxylic acid cyclobutyl ester;
Cyclopentyl-{5-[2,2,2-trifluoro-1-hydroxy-1-(1-methyl-1H-indol-3-yl)ethyl]indazol-1-yl}-methanone
5-[2,2,2-Trifluoro-1-hydroxy-1-(1-methyl-1H-indol-3-yl)ethyl]indazole-1-carboxylic acid cyclopentyl-methylamide
5-[2,2,2-Trifluoro-1-hydroxy-1-(1-methyl-1H-indol-3-yl)ethyl]indazole-1-carboxylic acid isopropyl-methylamide;
5-[1-(1-Methyl-1H-indol-3-yl)-2,2,2-trifluoro-1-hydroxyethyl]indazole-1-carboxylic acid ethyl ester;
2,2,2-Trifluoro-1-(1-methyl-1H-indol-3-yl)-1-(1-phenylmethanesulfonyl-1H-indazol-5-yl)ethanol;
2-Phenyl-1-{5-[2,2,2-trifluoro-1-hydroxy-1-(1-methyl-1H-indol-3-yl)ethyl]indazol-1-yl}ethanone;
1-(1-Benzenesulfonyl-1H-indazol-5-yl)-2,2,2-trifluoro-1-(1-methyl-1H-indol-3-yl)ethanol;
2,2,2-Trifluoro-1-(1-methyl-1H-indol-3-yl)-1-[1-(propane-2-sulfonyl)-1H-indazol-5-yl]ethanol;
2,2,2-Trifluoro-1-(1-methanesulfonyl-1H-indazol-5-yl)-1-(1-methyl-1H-indol-3-yl)ethanol;
2-Phenyl-1-[5-(2,2,2-trifluoro-1-hydroxy-1-phenylethyl)indazol-1-yl]ethanone;
1-Methylcarbamoylmethyl-4-{2,2,2-trifluoro-1-[1-(4-fluorophenyl)-1H-indazol-5-yl]-1-hydroxyethyl}-1H-pyrrole-2-carboxylic acid dimethylamide;
1-(1-Allyl-6-dimethylamino-1H-indol-3-yl)-2,2,2-trifluoro-1-[1-(4-fluorophenyl)-1H-indazol-5-yl]ethanol
or a tautomer, prodrug, solvate, or salt thereof.

More preferred compounds of Formula (I) include the following:
(3-{2,2,2-Trifluoro-1-[1-(4-fluorophenyl)-1H-indazol-5-yl]-1-hydroxyethyl}pyrrolo[2,3-b]pyridin-1-yl)acetonitrile;
2,2,2-Trifluoro-1-(1-phenyl-1H-pyrazolo[3,4-b]pyridin-5-yl)-1-(1H-pyrrolo[2,3-b]pyridin-3-yl)ethanol;
2-(7-Chloro-3-{2,2,2-trifluoro-1-[1-(4-fluorophenyl)-1H-indazol-5-yl]-1-hydroxyethyl}pyrrolo[2,3-c]pyridin-1-yl)acetamide;
N-[2-(3-{2,2,2-Trifluoro-1-[1-(4-fluorophenyl)-1H-indazol-5-yl]-1-hydroxyethyl}pyrrolo[2,3-b]pyridin-1-yl)acetyl]-methanesulfonamide;
1-(7-Chloro-1H-pyrrolo[2,3-c]pyridin-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-(7-oxy-1H-pyrrolo[2,3-b]pyridin-3-yl)ethanol;
2,2,2-Trifluoro-1-(1H-pyrrolo[2,3-b]pyridin-3-yl)-1-(1-p-tolyl-1H-indazol-5-yl)ethanol;
2,2,2-Trifluoro-1-[1-(4-fluorophenyl)-1H-indazol-5-yl]-1-(1H-pyrrolo[3,2-b]pyridin-3-yl)ethanol;
2,2,2-Trifluoro-1-[1-(4-fluorophenyl)-1H-indazol-5-yl]-1-(1H-pyrrolo[2,3-c]pyridin-3-yl)ethanol;
2,2,2-Trifluoro-1-[1-(4-fluorophenyl)-1H-indazol-5-yl]-1-(1H-pyrrolo[3,2-c]pyridin-3-yl)ethanol;
3-{2,2,2-Trifluoro-1-[1-(4-fluorophenyl)-1H-indazol-5-yl]-1-hydroxyethyl}pyrrolo[2,3-b]pyridine-1-sulfonic acid dimethylamide;
2-(3-{2,2,2-Trifluoro-1-[1-(4-fluorophenyl)-1H-indazol-5-yl]-1-hydroxyethyl}pyrrolo[2,3-b]pyridin-1-yl)acetamide;
2,2,2-Trifluoro-1-[1-(4-fluorophenyl)-1H-indazol-5-yl]-1-(1H-pyrrolo[2,3-b]pyridin-3-yl)ethanol;
2,2,2-Trifluoro-1-[1-(4-fluorophenyl)-1H-indazol-5-yl]-1-(1H-indazol-3-yl)ethanol;
Phenyl-{2,2,2-trifluoro-1-[1-(4-fluorophenyl)-1H-indazol-5-yl]ethyl}amine;
(1H-Indol-5-yl)-{2,2,2-trifluoro-1-[1-(4-fluorophenyl)-1H-indazol-5-yl]ethyl}amine;
(1H-Indol-6-yl)-{2,2,2-trifluoro-1-[1-(4-fluorophenyl)-1H-indazol-5-yl]ethyl}amine;
(1H-Indol-7-yl)-{2,2,2-trifluoro-1-[1-(4-fluorophenyl)-1H-indazol-5-yl]ethyl}amine;
(1H-Indol-4-yl)-{2,2,2-trifluoro-1-[1-(4-fluorophenyl)-1H-indazol-5-yl]ethyl}amine;
(1-Benzyl-2,2,2-trifluoroethyl)-[1-(4-fluorophenyl)-1H-indazol-5-yl]-amine;
Benzyl-{2,2,2-trifluoro-1-[1-(4-fluorophenyl)-1H-indazol-5-yl]ethyl}amine;
(2-Nitrophenyl)-{2,2,2-trifluoro-1-[1-(4-fluorophenyl)-1H-indazol-5-yl]ethyl}amine;
N-{2,2,2-Trifluoro-1-[1-(4-fluorophenyl)-1H-indazol-5-yl]ethyl}-benzene-1,2-diamine;
2-Amino-4,6-dichloro-N-{2,2,2-trifluoro-1-[1-(4-fluorophenyl)-1H-indazol-5-yl]ethyl}-benzenesulfonamide;
2-(7-{2,2,2-Trifluoro-1-[1-(4-fluorophenyl)-1H-indazol-5-yl]ethylamino}indol-1-yl)acetamide;
3-Methyl-$N^2$-{2,2,2-trifluoro-1-[1-(4-fluorophenyl)-1H-indazol-5-yl]ethyl}-benzene-1,2-diamine;
2,2,2-Trifluoro-1-(1-methyl-1H-indol-3-yl)-1-(1-pyridin-3-yl-1H-indazol-5-yl)ethanol;
2,2,2-Trifluoro-1-(1-methyl-1H-indol-3-yl)-1-(1-pyridin-4-yl-1H-indazol-5-yl)ethanol;
2,2,2-Trifluoro-1-(1-methyl-1H-indol-3-yl)-1-(1-pyrimidin-5-yl-1H-indazol-5-yl)ethanol;
2,2,2-Trifluoro-1-(1-methyl-1H-indol-3-yl)-1-(1-thiophen-3-yl-1H-indazol-5-yl)ethanol;
2,2,2-Trifluoro-1-(1H-indol-3-yl)-1-(1-pyridin-3-yl-1H-indazol-5-yl)ethanol;
2-{3-[2,2,2-Trifluoro-1-hydroxy-1-(1-pyridin-3-yl-1H-indazol-5-yl)ethyl]indol-1-yl}acetamide;
2,2,2-Trifluoro-1-(1-methyl-1H-indol-3-yl)-1-[1-(6-methylpyridin-3-yl)-1H-indazol-5-yl]ethanol;
2,2,2-Trifluoro-1-(1-methyl-1H-indol-3-yl)-1-[1-(5-methylthiophen-2-yl)-1H-indazol-5-yl]ethanol;
2,2,2-Trifluoro-1-[1-(1-methyl-1H-imidazol-4-yl)-1H-indazol-5-yl]-1-(1-methyl-1H-indol-3-yl)ethanol;
2,2,2-Trifluoro-1-(1-methyl-1H-indol-3-yl)-1-(1-pyridin-2-yl-1H-indazol-5-yl)ethanol;
2,2,2-Trifluoro-1-(1-methyl-1H-indol-3-yl)-1-[1-(1-methyl-1H-pyrazol-4-yl)-1H-indazol-5-yl]ethanol;
2,2,2-Trifluoro-1-[1-(6-fluoropyridin-3-yl)-1H-indazol-5-yl]-1-(1-methyl-1H-indol-3-yl)ethanol;
(R)-1-(3-{2,2,2-Trifluoro-1-[1-(4-fluorophenyl)-1H-indazol-5-yl]-1-hydroxyethyl}indol-1-yl)propan-2-ol;
(S)-1-(3-{2,2,2-Trifluoro-1-[1-(4-fluorophenyl)-1H-indazol-5-yl]-1-hydroxyethyl}indol-1-yl)propan-2-ol;
2,2,2-Trifluoro-1-[1-(4-fluorophenyl)-1H-indazol-5-yl]-1-[1-(tetrahydro-furan-2-ylmethyl)-1H-indol-3-yl]ethanol;
2,2,2-Trifluoro-1-[1-(4-fluorophenyl)-1H-indazol-5-yl]-1-[1-(2-morpholin-4-ylethyl)-1H-indol-3-yl]ethanol;

(3-{2,2,2-Trifluoro-1-[1-(4-fluorophenyl)-1H-indazol-5-yl]-1-hydroxyethyl}indol-1-yl)acetic acid;

1-(1-Allyl-5-hydroxymethyl-1H-pyrrol-3-yl)-2,2,2-trifluoro-1-[1-(4-fluorophenyl)-1H-indazol-5-yl]ethanol;

1-(5-1,3-Dioxolan-2-ylthiophen-2-yl)-2,2,2-trifluoro-1-[1-(4-fluorophenyl)-1H-indazol-5-yl]ethanol;

(3-{2,2,2-Trifluoro-1-[1-(4-fluorophenyl)-1H-indazol-5-yl]-1-hydroxyethyl}indol-1-yl)acetic acid ethyl ester;

1-(5-Chlorothiophen-2-yl)-2,2,2-trifluoro-1-[1-(4-fluorophenyl)-1H-indazol-5-yl]ethanol;

2,2,2-Trifluoro-1-[1-(4-fluorophenyl)-1H-indazol-5-yl]-1-{1-[3-(4-hydroxymethylpiperidin-1-yl)propyl]-1H-indol-3-yl}ethanol;

1-{1-[3-((S)-3-Dimethylaminopyrrolidin-1-yl)propyl]-1H-indol-3-yl}-2,2,2-trifluoro-1-[1-(4-fluorophenyl)-1H-indazol-5-yl]ethanol;

1-{1-[3-((R)-3-Dimethylaminopyrrolidin-1-yl)propyl]-1H-indol-3-yl}-2,2,2-trifluoro-1-[1-(4-fluorophenyl)-1H-indazol-5-yl]ethanol;

2,2,2-Trifluoro-1-[1-(4-fluorophenyl)-1H-indazol-5-yl]-1-[1-(3-pyrrolidin-1-ylpropyl)-1H-indol-3-yl]ethanol;

2,2,2-Trifluoro-1-[1-(4-fluorophenyl)-1H-indazol-5-yl]-1-{1-[3-(4-methylpiperazin-1-yl)-propyl]-1H-indol-3-yl}ethanol;

2,2,2-Trifluoro-1-[1-(4-fluorophenyl)-1H-indazol-5-yl]-1-[1-(3-methylaminopropyl)-1H-indol-3-yl]ethanol;

2,2,2-Trifluoro-1-[1-(4-fluorophenyl)-1H-indazol-5-yl]-1-[1-(3-morpholin-4-ylpropyl)-1H-indol-3-yl]ethanol;

1-[1-(3-Dimethylaminopropyl)-1H-indol-3-yl]-2,2,2-trifluoro-1-[1-(4-fluorophenyl)-1H-indazol-5-yl]ethanol;

3-(6-(2H-Pyrazol-3-yl)-3-{2,2,2-trifluoro-1-[1-(4-fluorophenyl)-1H-indazol-5-yl]-1-hydroxyethyl}indol-1-yl)propane-1,2-diol;

1-[1-Allyl-6-(2H-pyrazol-3-yl)-1H-indol-3-yl]-2,2,2-trifluoro-1-[1-(4-fluorophenyl)-1H-indazol-5-yl]ethanol;

1-(6-Bromo-1-but-3-enyl-1H-indol-3-yl)-2,2,2-trifluoro-1-[1-(4-fluorophenyl)-1H-indazol-5-yl]ethanol;

2,2,2-Trifluoro-1-[1-(4-fluorophenyl)-1H-indazol-5-yl]-1-[1-(propane-2-sulfonyl)-1H-indol-3-yl]ethanol;

3-(3-{2,2,2-Trifluoro-1-[1-(4-fluorophenyl)-1H-indazol-5-yl]-1-hydroxyethyl}indol-1-yl)propionamide;

N-Methyl-3-(3-{2,2,2-trifluoro-1-[1-(4-fluorophenyl)-1H-indazol-5-yl]-1-hydroxyethyl}indol-1-yl)propionamide;

3-(6-Pyrrolidin-1-yl-3-{2,2,2-trifluoro-1-[1-(4-fluorophenyl)-1H-indazol-5-yl]-1-hydroxyethyl}indol-1-yl)propane-1,2-diol;

2-(6-Bromo-3-{2,2,2-trifluoro-1-[1-(4-fluorophenyl)-1H-indazol-5-yl]-1-hydroxyethyl}indol-1-yl)-N-methylacetamide;

4-(3-{2,2,2-Trifluoro-1-[1-(4-fluorophenyl)-1H-indazol-5-yl]-1-hydroxyethyl}indol-1-yl)-butane-1,2-diol;

1-(1-But-3-enyl-1H-indol-3-yl)-2,2,2-trifluoro-1-[1-(4-fluorophenyl)-1H-indazol-5-yl]ethanol;

1-(1-Allyl-6-pyrrolidin-1-yl-1H-indol-3-yl)-2,2,2-trifluoro-1-[1-(4-fluorophenyl)-1H-indazol-5-yl]ethanol;

1-(1-Allyl-6-bromo-1H-indol-3-yl)-2,2,2-trifluoro-1-[1-(4-fluorophenyl)-1H-indazol-5-yl]ethanol;

3-(6-Bromo-3-{2,2,2-trifluoro-1-[1-(4-fluorophenyl)-1H-indazol-5-yl]-1-hydroxyethyl}indol-1-yl)propane-1,2-diol;

2,2,2-Trifluoro-1-[1-(4-fluorophenyl)-1H-indazol-5-yl]-1-[1-(4-methoxy-benzyl)-6-vinyl-1H-indol-3-yl]ethanol;

2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide;

3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol;

2,2,2-Trifluoro-1-[1-(4-fluorophenyl)-1H-indazol-5-yl]-1-(7-methoxy-1H-pyrrolo[2,3-c]pyridin-3-yl)ethanol;

1-Allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one;

4-{2,2,2-Trifluoro-1-[1-(4-fluorophenyl)-1H-indazol-5-yl]-1-hydroxyethyl}-1H-pyrazole-3-carbonitrile;

1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile;

2,2,2-Trifluoro-1-[1-(4-fluorophenyl)-1H-indazol-5-yl]-1-(2-hydroxymethyl-thiazol-5-yl)ethanol;

1-Allyl-4-bromo-5-{2,2,2-trifluoro-1-[1-(4-fluorophenyl)-1H-indazol-5-yl]-1-hydroxyethyl}-1H-pyrazole-3-carbonitrile;

1-Allyl-4-{2,2,2-trifluoro-1-[1-(4-fluorophenyl)-1H-indazol-5-yl]-1-hydroxyethyl}-1H-pyrazole-3-carbonitrile;

2,2,2-Trifluoro-1-[1-(4-fluorophenyl)-1H-indazol-5-yl]-1-(2-morpholin-4-yl-thiazol-4-yl)ethanol;

2,2,2-Trifluoro-1-[1-(4-fluorophenyl)-1H-indazol-5-yl]-1-thiazol-5-ylethanol;

2,2,2-Trifluoro-1-[1-(4-fluorophenyl)-1H-indazol-5-yl]-1-(2-morpholin-4-yl-thiazol-5-yl)ethanol;

1-[4-Chloro-5-(2-hydroxyethyl)-5H-pyrrolo[3,2-d]pyrimidin-7-yl]-2,2,2-trifluoro-1-[1-(4-fluorophenyl)-1H-indazol-5-yl]ethanol;

3-(4-Chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol;

5-Allyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

7-{2,2,2-Trifluoro-1-[1-(4-fluorophenyl)-1H-indazol-5-yl]-1-hydroxyethyl}-3,5-dihydropyrrolo[3,2-d]pyrimidin-4-one;

1-(4-Chloro-5H-pyrrolo[3,2-d]pyrimidin-7-yl)-2,2,2-trifluoro-1-[1-(4-fluorophenyl)-1H-indazol-5-yl]ethanol;

2-(3-Methyl-4-oxo-7-{2,2,2-trifluoro-1-[1-(4-fluorophenyl)-1H-indazol-5-yl]-1-hydroxyethyl}-3,4-dihydropyrrolo[3,2-d]pyrimidin-5-yl)acetamide;

5-(2,3-Dihydroxypropyl)-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid dimethylamide;

1-Allyl-4-{2,2,2-trifluoro-1-[1-(4-fluorophenyl)-1H-indazol-5-yl]-1-hydroxyethyl}-1H-pyrrole-2-carboxylic acid methylamide;

1-Allyl-4-{2,2,2-trifluoro-1-[1-(4-fluorophenyl)-1H-indazol-5-yl]-1-hydroxyethyl}-1H-pyrrole-2-carboxylic acid cyanomethylamide;

1-Allyl-4-{2,2,2-trifluoro-1-[1-(4-fluorophenyl)-1H-indazol-5-yl]-1-hydroxyethyl}-1H-pyrrole-2-carboxylic acid amide;

2-(2-Cyano-4-{2,2,2-trifluoro-1-[1-(4-fluorophenyl)-1H-indazol-5-yl]-1-hydroxyethyl}pyrrol-1-yl)acetamide;

2-(2-Cyano-4-{2,2,2-trifluoro-1-[1-(4-fluorophenyl)-1H-indazol-5-yl]-1-hydroxyethyl}pyrrol-1-yl)-N-methylacetamide;

1-Allyl-4-{2,2,2-trifluoro-1-[1-(4-fluorophenyl)-1H-indazol-5-yl]-1-hydroxyethyl}-1H-pyrrole-2-carboxylic acid dimethylamide;
1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester;
1-Allyl-4-{2,2,2-trifluoro-1-[1-(4-fluorophenyl)-1H-indazol-5-yl]-1-hydroxyethyl}-1H-pyrrole-2-carboxylic acid ethyl ester;
4-{2,2,2-Trifluoro-1-[1-(4-fluorophenyl)-1H-indazol-5-yl]-1-hydroxyethyl}-1H-pyrrole-2-carbonitrile;
1-(2,3-Dihydroxypropyl)-4-{2,2,2-trifluoro-1-[1-(4-fluorophenyl)-1H-indazol-5-yl]-1-hydroxyethyl}-1H-pyrrole-2-carbonitrile;
1-Allyl-4-{2,2,2-trifluoro-1-[1-(4-fluorophenyl)-1H-indazol-5-yl]-1-hydroxyethyl}-1H-pyrrole-2-carbonitrile;
(1-Allyl-4-{2,2,2-trifluoro-1-[1-(4-fluorophenyl)-1H-indazol-5-yl]-1-hydroxyethyl}-1H-pyrrol-2-yl)-morpholin-4-yl-methanone;
3-(3-{2,2,2-Trifluoro-1-[1-(4-fluorophenyl)-1H-benzotriazol-5-yl]-1-hydroxyethyl}indol-1-yl)propane-1,2-diol;
2,2,2-Trifluoro-1-[1-(4-fluorophenyl)-1H-benzotriazol-5-yl]-1-(1-methyl-1H-indol-3-yl)ethanol;
5-{2,2,2-trifluoro-1-[1-(4-fluorophenyl)-1H-indazol-5-yl]-1-hydroxyethyl}-1H-pyridin-2-one;
5-[1-(1-Allyl-1H-indol-3-yl)-2,2,2-trifluoro-1-hydroxyethyl]indazole-1-carboxylic acid (1-ethylpropyl)amide;
5-[1-(1-Allyl-1H-indol-3-yl)-2,2,2-trifluoro-1-hydroxyethyl]indazole-1-carboxylic acid (1,2-dimethylpropyl)amide;
5-[1-(1-Allyl-1H-indol-3-yl)-2,2,2-trifluoro-1-hydroxyethyl]indazole-1-carboxylic acid (1-methylethyl)amide;
Cyclobutyl-{5-[2,2,2-trifluoro-1-hydroxy-1-(1-methyl-1H-indol-3-yl)ethyl]indazol-1-yl}-methanone;
Cyclopropyl-{5-[2,2,2-trifluoro-1-hydroxy-1-(1-methyl-1H-indol-3-yl)ethyl]indazol-1-yl}-methanone;
5-[2,2,2-Trifluoro-1-hydroxy-1-(1-methyl-1H-indol-3-yl)ethyl]indazole-1-carboxylic acid cyclopropylamide;
5-[2,2,2-Trifluoro-1-hydroxy-1-(1-methyl-1H-indol-3-yl)ethyl]indazole-1-carboxylic acid cyclopentylamide;
5-[1-(1-Methyl-1H-indol-3-yl)-2,2,2-trifluoro-1-hydroxyethyl]indazole-1-carboxylic acid cyclopentyl ester;
5-[1-(1-Methyl-1H-indol-3-yl)-2,2,2-trifluoro-1-hydroxyethyl]indazole-1-carboxylic acid cyclopropylmethyl ester;
5-[2,2,2-Trifluoro-1-hydroxy-1-(1-methyl-1H-indol-3-yl)ethyl]indazole-1-carboxylic acid phenyl ester;
2-Thiophen-2-yl-1-{5-[2,2,2-trifluoro-1-hydroxy-1-(1-methyl-1H-indol-3-yl)ethyl]indazol-1-yl}ethanone;
Phenyl-{5-[2,2,2-trifluoro-1-hydroxy-1-(1-methyl-1H-indol-3-yl)ethyl]indazol-1-yl}-methanone;
3-Methyl-1-{5-[2,2,2-trifluoro-1-hydroxy-1-(1-methyl-1H-indol-3-yl)ethyl]indazol-1-yl}-butan-1-one;
2,2,2-Trifluoro-1-(1H-indazol-5-yl)-1-(1-methyl-1H-indol-3-yl)ethanol;
1-Methylcarbamoylmethyl-4-{2,2,2-trifluoro-1-[1-(4-fluorophenyl)-1H-indazol-5-yl]-1-hydroxyethyl}-1H-pyrrole-2-carboxylic acid dimethylamide;
1-(1-Allyl-6-dimethylamino-1H-indol-3-yl)-2,2,2-trifluoro-1-[1-(4-fluorophenyl)-1H-indazol-5-yl]ethanol;
or a tautomer, prodrug, solvate, or salt thereof.

Most preferred compounds of Formula (I) include the following:
(3-{2,2,2-Trifluoro-1-[1-(4-fluorophenyl)-1H-indazol-5-yl]-1-hydroxyethyl}pyrrolo[2,3-b]pyridin-1-yl)acetonitrile;
2-(7-Chloro-3-{2,2,2-trifluoro-1-[1-(4-fluorophenyl)-1H-indazol-5-yl]-1-hydroxyethyl}pyrrolo[2,3-c]pyridin-1-yl)acetamide;
1-(7-Chloro-1H-pyrrolo[2,3-c]pyridin-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-(7-oxy-1H-pyrrolo[2,3-b]pyridin-3-yl)ethanol;
2,2,2-Trifluoro-1-[1-(4-fluorophenyl)-1H-indazol-5-yl]-1-(1H-pyrrolo[3,2-b]pyridin-3-yl)ethanol;
2,2,2-Trifluoro-1-[1-(4-fluorophenyl)-1H-indazol-5-yl]-1-(1H-pyrrolo[2,3-c]pyridin-3-yl)ethanol;
3-{2,2,2-Trifluoro-1-[1-(4-fluorophenyl)-1H-indazol-5-yl]-1-hydroxyethyl}pyrrolo[2,3-b]pyridine-1-sulfonic acid dimethylamide;
2-(3-{2,2,2-Trifluoro-1-[1-(4-fluorophenyl)-1H-indazol-5-yl]-1-hydroxyethyl}pyrrolo[2,3-b]pyridin-1-yl)acetamide;
2,2,2-Trifluoro-1-[1-(4-fluorophenyl)-1H-indazol-5-yl]-1-(1H-pyrrolo[2,3-b]pyridin-3-yl)ethanol;
2,2,2-Trifluoro-1-[1-(4-fluorophenyl)-1H-indazol-5-yl]-1-(1H-indazol-3-yl)ethanol;
(1H-Indol-6-yl)-{2,2,2-trifluoro-1-[1-(4-fluorophenyl)-1H-indazol-5-yl]ethyl}amine;
(1H-Indol-7-yl)-{2,2,2-trifluoro-1-[1-(4-fluorophenyl)-1H-indazol-5-yl]ethyl}amine;
(1H-Indol-4-yl)-{2,2,2-trifluoro-1-[1-(4-fluorophenyl)-1H-indazol-5-yl]ethyl}amine;
N-{2,2,2-Trifluoro-1-[1-(4-fluorophenyl)-1H-indazol-5-yl]ethyl}-benzene-1,2-diamine;
2-Amino-4,6-dichloro-N-{2,2,2-trifluoro-1-[1-(4-fluorophenyl)-1H-indazol-5-yl]ethyl}-benzenesulfonamide;
2-(7-{2,2,2-Trifluoro-1-[1-(4-fluorophenyl)-1H-indazol-5-yl]ethylamino}indol-1-yl)acetamide;
2,2,2-Trifluoro-1-(1-methyl-1H-indol-3-yl)-1-(1-pyridin-3-yl-1H-indazol-5-yl)ethanol;
2,2,2-Trifluoro-1-(1-methyl-1H-indol-3-yl)-1-(1-pyridin-4-yl-1H-indazol-5-yl)ethanol
2,2,2-Trifluoro-1-(1-methyl-1H-indol-3-yl)-1-(1-thiophen-3-yl-1H-indazol-5-yl)ethanol;
2,2,2-Trifluoro-1-(1H-indol-3-yl)-1-(1-pyridin-3-yl-1H-indazol-5-yl)ethanol;
2-{3-[2,2,2-Trifluoro-1-hydroxy-1-(1-pyridin-3-yl-1H-indazol-5-yl)ethyl]indol-1-yl}acetamide;
2,2,2-Trifluoro-1-(1-methyl-1H-indol-3-yl)-1-[1-(5-methylthiophen-2-yl)-1H-indazol-5-yl]ethanol;
2,2,2-Trifluoro-1-(1-methyl-1H-indol-3-yl)-1-(1-pyridin-2-yl-1H-indazol-5-yl)ethanol;
2,2,2-Trifluoro-1-(1-methyl-1H-indol-3-yl)-1-[1-(1-methyl-1H-pyrazol-4-yl)-1H-indazol-5-yl]ethanol;
2,2,2-Trifluoro-1-[1-(6-fluoropyridin-3-yl)-1H-indazol-5-yl]-1-(1-methyl-1H-indol-3-yl)ethanol;
(R)-1-(3-{2,2,2-Trifluoro-1-[1-(4-fluorophenyl)-1H-indazol-5-yl]-1-hydroxyethyl}indol-1-yl)propan-2-ol;
(S)-1-(3-{2,2,2-Trifluoro-1-[1-(4-fluorophenyl)-1H-indazol-5-yl]-1-hydroxyethyl}indol-1-yl)propan-2-ol;
2,2,2-Trifluoro-1-[1-(4-fluorophenyl)-1H-indazol-5-yl]-1-[1-(tetrahydro-furan-2-ylmethyl)-1H-indol-3-yl]ethanol;
2,2,2-Trifluoro-1-[1-(4-fluorophenyl)-1H-indazol-5-yl]-1-[1-(2-morpholin-4-ylethyl)-1H-indol-3-yl]ethanol;
(3-{2,2,2-Trifluoro-1-[1-(4-fluorophenyl)-1H-indazol-5-yl]-1-hydroxyethyl}indol-1-yl)acetic acid;
1-(5-1,3-Dioxolan-2-ylthiophen-2-yl)-2,2,2-trifluoro-1-[1-(4-fluorophenyl)-1H-indazol-5-yl]ethanol;
(3-{2,2,2-Trifluoro-1-[1-(4-fluorophenyl)-1H-indazol-5-yl]-1-hydroxyethyl}indol-1-yl)acetic acid ethyl ester;
1-(5-Chlorothiophen-2-yl)-2,2,2-trifluoro-1-[1-(4-fluorophenyl)-1H-indazol-5-yl]ethanol;

1-{1-[3-((S)-3-Dimethylaminopyrrolidin-1-yl)propyl]-1H-indol-3-yl}-2,2,2-trifluoro-1-[1-(4-fluorophenyl)-1H-indazol-5-yl]ethanol;
1-{1-[3-((R)-3-Dimethylaminopyrrolidin-1-yl)propyl]-1H-indol-3-yl}-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(3-pyrrolidin-1-ylpropyl)-1H-indol-3-yl]ethanol;
2,2,2-Trifluoro-1-[1-(4-fluorophenyl)-1H-indazol-5-yl]-1-[1-(3-methylaminopropyl)-1H-indol-3-yl]ethanol;
2,2,2-Trifluoro-1-[1-(4-fluorophenyl)-1H-indazol-5-yl]-1-[1-(3-morpholin-4-ylpropyl)-1H-indol-3-yl]ethanol;
1-[1-(3-Dimethylaminopropyl)-1H-indol-3-yl]-2,2,2-trifluoro-1-[1-(4-fluorophenyl)-1H-indazol-5-yl]ethanol;
3-(6-(2H-Pyrazol-3-yl)-3-{2,2,2-trifluoro-1-[1-(4-fluorophenyl)-1H-indazol-5-yl]-1-hydroxyethyl}indol-1-yl)propane-1,2-diol;
1-[1-Allyl-6-(2H-pyrazol-3-yl)-1H-indol-3-yl]-2,2,2-trifluoro-1-[1-(4-fluorophenyl)-1H-indazol-5-yl]ethanol;
1-(6-Bromo-1-but-3-enyl-1H-indol-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(propane-2-sulfonyl)-1H-indol-3-yl]ethanol;
3-(3-{2,2,2-Trifluoro-1-[1-(4-fluorophenyl)-1H-indazol-5-yl]-1-hydroxyethyl}indol-1-yl)propionamide;
N-Methyl-3-(3-{2,2,2-trifluoro-1-[1-(4-fluorophenyl)-1H-indazol-5-yl]-1-hydroxyethyl}indol-1-yl)propionamide;
3-(6-Pyrrolidin-1-yl-3-{2,2,2-trifluoro-1-[1-(4-fluorophenyl)-1H-indazol-5-yl]-1-hydroxyethyl}indol-1-yl)propane-1,2-diol;
2-(6-Bromo-3-{2,2,2-trifluoro-1-[1-(4-fluorophenyl)-1H-indazol-5-yl]-1-hydroxyethyl}indol-1-yl)-N-methylacetamide;
4-(3-{2,2,2-Trifluoro-1-[1-(4-fluorophenyl)-1H-indazol-5-yl]-1-hydroxyethyl}indol-1-yl)-butane-1,2-diol;
1-(1-But-3-enyl-1H-indol-3-yl)-2,2,2-trifluoro-1-[1-(4-fluorophenyl)-1H-indazol-5-yl]ethanol;
1-(1-Allyl-6-bromo-1H-indol-3-yl)-2,2,2-trifluoro-1-[1-(4-fluorophenyl)-1H-indazol-5-yl]ethanol;
3-(6-Bromo-3-{2,2,2-trifluoro-1-[1-(4-fluorophenyl)-1H-indazol-5-yl]-1-hydroxyethyl}indol-1-yl)propane-1,2-diol;
2,2,2-Trifluoro-1-[1-(4-fluorophenyl)-1H-indazol-5-yl]-1-[1-(4-methoxy-benzyl)-6-vinyl-1H-indol-3-yl]ethanol;
2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide;
3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol;
2,2,2-Trifluoro-1-[1-(4-fluorophenyl)-1H-indazol-5-yl]-1-(7-methoxy-1H-pyrrolo[2,3-c]pyridin-3-yl)ethanol;
1-Allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one;
4-{2,2,2-Trifluoro-1-[1-(4-fluorophenyl)-1H-indazol-5-yl]-1-hydroxyethyl}-1H-pyrazole-3-carbonitrile;
1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile;
1-Allyl-4-bromo-5-{2,2,2-trifluoro-1-[1-(4-fluorophenyl)-1H-indazol-5-yl]-1-hydroxyethyl}-1H-pyrazole-3-carbonitrile;
1-Allyl-4-{2,2,2-trifluoro-1-[1-(4-fluorophenyl)-1H-indazol-5-yl]-1-hydroxyethyl}-1H-pyrazole-3-carbonitrile;
2,2,2-Trifluoro-1-[1-(4-fluorophenyl)-1H-indazol-5-yl]-1-(2-morpholin-4-yl-thiazol-4-yl)ethanol;
1-[4-Chloro-5-(2-hydroxyethyl)-5H-pyrrolo[3,2-d]pyrimidin-7-yl]-2,2,2-trifluoro-1-[1-(4-fluorophenyl)-1H-indazol-5-yl]ethanol;
3-(4-Chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol;
1-(4-Chloro-5H-pyrrolo[3,2-d]pyrimidin-7-yl)-2,2,2-trifluoro-1-[1-(4-fluorophenyl)-1H-indazol-5-yl]ethanol;
5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;
1-Allyl-4-{2,2,2-trifluoro-1-[1-(4-fluorophenyl)-1H-indazol-5-yl]-1-hydroxyethyl}-1H-pyrrole-2-carboxylic acid dimethylamide;
1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester;
1-Allyl-4-{2,2,2-trifluoro-1-[1-(4-fluorophenyl)-1H-indazol-5-yl]-1-hydroxyethyl}-1H-pyrrole-2-carboxylic acid ethyl ester;
4-{2,2,2-Trifluoro-1-[1-(4-fluorophenyl)-1H-indazol-5-yl]-1-hydroxyethyl}-1H-pyrrole-2-carbonitrile;
1-Allyl-4-{2,2,2-trifluoro-1-[1-(4-fluorophenyl)-1H-indazol-5-yl]-1-hydroxyethyl}-1H-pyrrole-2-carbonitrile;
(3-Methyl-2-oxo-5-{2,2,2-trifluoro-1-[1-(4-fluorophenyl)-1H-indazol-5-yl]-1-hydroxyethyl}-2H-pyridin-1-yl)acetamide;
1,3-Dimethyl-5-{2,2,2-trifluoro-1-[1-(4-fluorophenyl)-1H-indazol-5-yl]-1-hydroxyethyl}-1H-pyridin-2-one;
3-Methyl-5-{2,2,2-trifluoro-1-[1-(4-fluorophenyl)-1H-indazol-5-yl]-1-hydroxyethyl}-1H-pyridin-2-one;
2,2,2-Trifluoro-1-[1-(4-fluorophenyl)-1H-indazol-5-yl]-1-(6-methoxypyridin-3-yl)ethanol;
5-[1-(1-Allyl-1H-indol-3-yl)-2,2,2-trifluoro-1-hydroxyethyl]indazole-1-carboxylic acid ethylamide;
5-[1-(1-Allyl-1H-indol-3-yl)-2,2,2-trifluoro-1-hydroxyethyl]indazole-1-carboxylic acid (1-methylpropyl)amide
5-[1-(1-Allyl-1H-indol-3-yl)-2,2,2-trifluoro-1-hydroxyethyl]indazole-1-carboxylic acid propylamide;
5-[2,2,2-Trifluoro-1-hydroxy-1-(1-methyl-1H-indol-3-yl)ethyl]indazole-1-carboxylic acid cyclopropylmethylamide;
5-[2,2,2-Trifluoro-1-hydroxy-1-(1-methyl-1H-indol-3-yl)ethyl]indazole-1-carboxylic acid isopropylamide;
Phenyl-{5-[2,2,2-trifluoro-1-hydroxy-1-(1-methyl-1H-indol-3-yl)ethyl]indazol-1-yl}-methanone;
5-[1-(1-Methyl-1H-indol-3-yl)-2,2,2-trifluoro-1-hydroxyethyl]indazole-1-carboxylic acid isopropyl ester; and
1-(1-Allyl-6-dimethylamino-1H-indol-3-yl)-2,2,2-trifluoro-1-[1-(4-fluorophenyl)-1H-indazol-5-yl]ethanol,
or a tautomer, prodrug, solvate, or salt thereof.

The invention also provides a method of making a compound of Formula (IA)

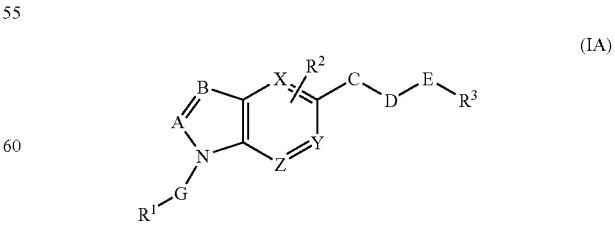

wherein: C, E, and G are each a bond, D is CR$^4$R$^5$ (where R$^4$ is CF$_3$ and R$^5$ is OH), and A, B, X, Y, Z, R$^1$, R$^2$, and R$^3$ are as defined above, the method comprising: reacting the trifluoromethyl ketone of Formula (III) with an organometallic reagent of Formula (II), such as an organolithium reagent where M is Li or a Grignard reagent where M is MgBr, MgCl, or MgI, in a suitable solvent, such as ether or THF, to form the compound of Formula (IA)

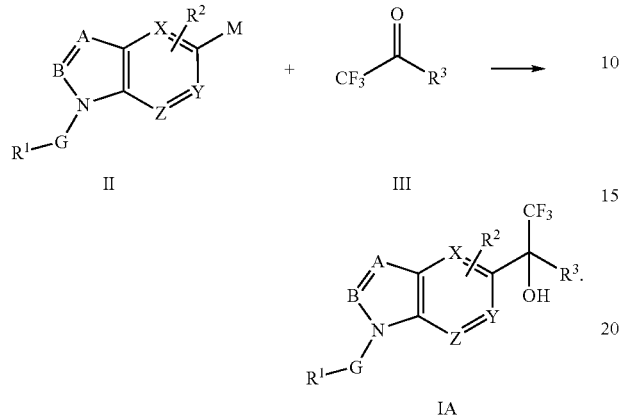

A second method for making a compound of Formula (IA) wherein C and G are each a bond, D is $CR^4R^5$ (where $R^4$ is $CF_3$ and $R^5$ is OH), E is a bond, and A, B, X, Y, Z, $R^1$, $R^2$, and $R^3$ are as defined above, the method comprising: reacting the trifluoromethyl ketone of Formula (IV) with an organometallic reagent of Formula (V), such as an organolithium reagent where M is Li or a Grignard reagent where M is MgBr, MgCl, or MgI, in a suitable solvent, such as ether or THF, to form the compound of Formula (IA)

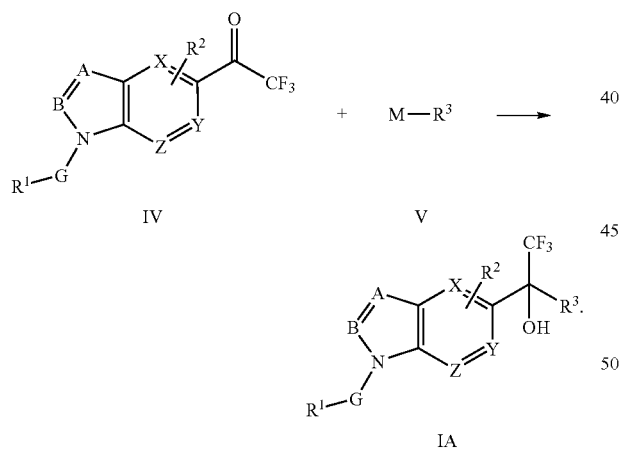

Alternatively, a compound of Formula (IA), wherein G and C are each a bond, D is $CR^5R^6$ (where $R^5$ is $CF_3$ and $R^6$ is H), E is a —$NR^4$—, where $R^4$ is hydrogen, and A, B, X, Y, Z, $R^1$, $R^2$, and $R^3$ are as defined above, the method comprising: reacting the trifluoromethyl ketone of Formula (IV) with an aryl amine of Formula (VI), in the presence of a dehydrating agent, such as titanium tetrachloride, and a suitable base, such as triethylamine, in a suitable solvent, such as dichloromethane, followed by addition of a reducing agent, such as sodium borohydride in methanol or borane, to form the compound of Formula (IA)

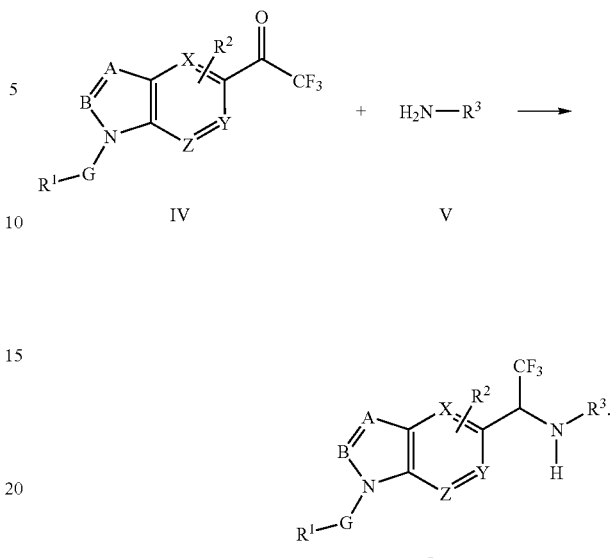

Yet another method of making a compound of Formula (IA), wherein: C is a —$NR^4$—; where $R^4$ is hydrogen, D is $CR^5R^6$ (where $R^5$ is $CF_3$ and $R^6$ is H), G is a bond, and E is a bond or, for this example, a —$CH_2$—, and A, B, X, Y, Z, $R^1$, $R^2$, and $R^3$ are as defined above, the method comprising: reacting the trifluoromethyl ketone of Formula (VII) with an aryl amine of Formula (VI), in the presence of a dehydrating agent, such as titanium tetrachloride, and a suitable base, such as triethylamine, in a suitable solvent, such as dichloromethane, followed by addition of a reducing agent, such as lithium aluminum hydride in THF or sodium borohydride in methanol or borane, to form the compound of Formula (IA)

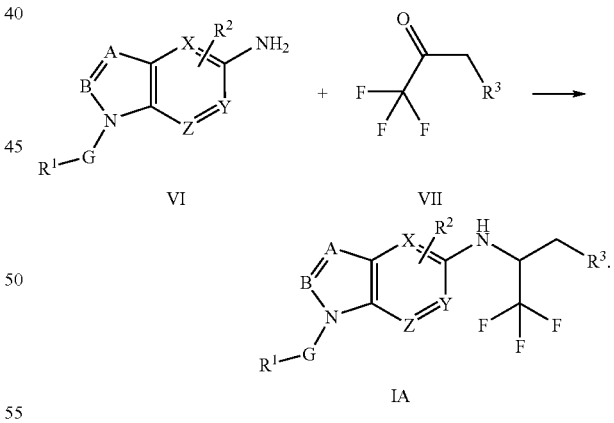

Yet another method of making a compound of Formula (IA), wherein C and G is a bond, D is $CR^5R^6$ (where $R^5$ is $CF_3$ and $R^6$ is H), E is a —$NR^4SO_2$—; where $R^4$ is hydrogen, and A, B, X, Y, Z, $R^1$, $R^2$, and $R^3$ are as defined above, the method comprising:

(a) reacting the trifluoromethyl ketone of Formula (IV) with lithium bis(trimethylsilylamide) of Formula (VIII) in a suitable solvent, such as tetrahydrofuran, followed by addition of a reducing agent, such as borane dimethylsulfide, to form the compound of Formula (IX)

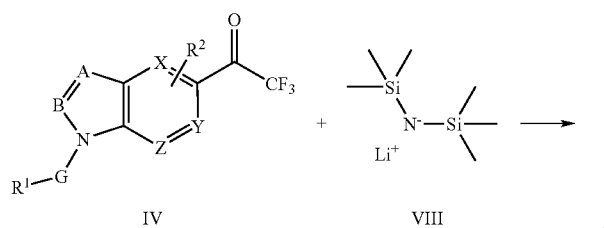

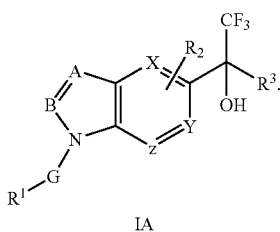

and
(b) reacting the amino compound of Formula (IX) with a sulfonyl halide of Formula (X) in the presence of a suitable base, such as triethylamine or pyridine, in a suitable solvent, such as dichloromethane or pyridine, to form the compound of Formula (IA) where E is a —NR⁴SO₂—, and R⁴ is hydrogen

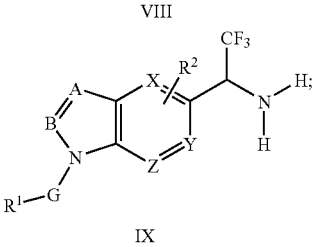

Yet another for making a compound of Formula (IA) with various $R^1$, wherein C is a bond, D is $CR^4R^5$ (where $R^4$ is $CF_3$ and $R^5$ is OH), E is a bond, G is —C(O)— or —CO₂— or —SO₂—, and A, B, X, Y, Z, $R^3$, and $R^2$ are as defined above, the method comprising: reacting a heterocycle of Formula (XI) with an chloride reagent of Formula (XIII) in a suitable solvent, such as pyridine, to form the compound of Formula (IA)

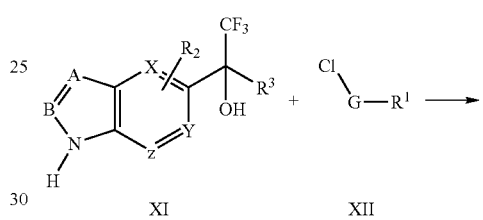

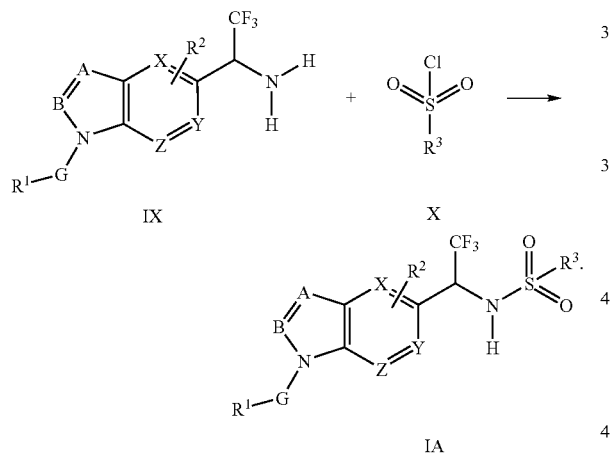

Yet another for making a compound of Formula (IA) with various $R^1$, wherein C is a bond, D is $CR^4R^5$ (where $R^4$ is $CF_3$ and $R^5$ is OH), G and E is a bond, and A, B, X, Y, Z, $R^3$, and $R^2$ are as defined above, the method comprising: reacting a heterocycle of Formula (XI) with an aryl boronic acid reagent of Formula (XII) or its ester with a copper reagent, such as copper acetate, and a suitable base, such as pyridine, in a suitable solvent, such as dichloromethane, to form the compound of Formula (IA)

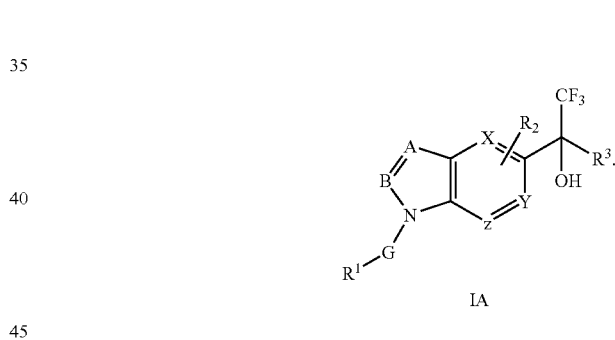

Yet another for making a compound of Formula (IA) with various $R^1$,
wherein C is a bond, D is $CR^4R^5$ (where $R^4$ is $CF_3$ and $R^5$ is OH), E is a bond, G is —C(O)NR⁷— where $R^7$, and A, B, X, Y, Z, $R^3$, and $R^2$ are as defined above, the method comprising: reacting a heterocycle of Formula (XI) with N,N-carbonyldiimidazole (XIII) followed by an amine of Formula (IVX) in a suitable solvent such as pyridine to form the compound of Formula (IA)

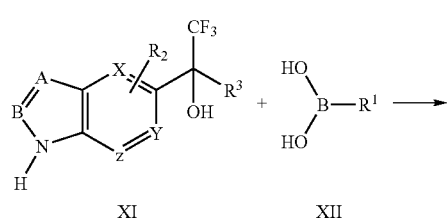

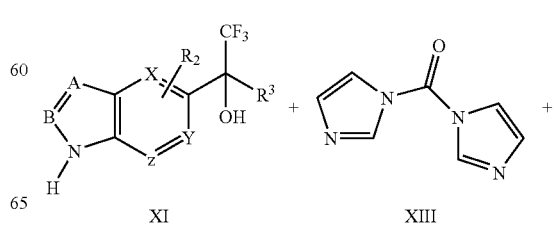

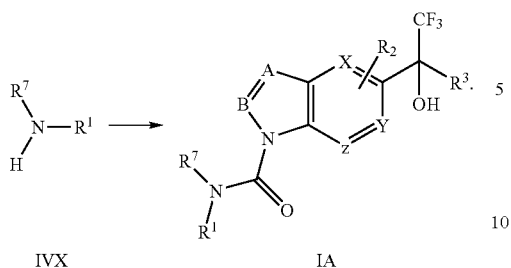

IVX  →  IA

Yet another for making a compound of Formula (IA) with various R¹, wherein C is a bond, D is CR⁴R⁵ (where R⁴ is CF₃ and R⁵ is OH), E is a bond, G is —CO₂— where R⁷, and A, B, X, Y, Z, R³, and R² are as defined above, the method comprising: reacting a heterocycle of Formula (XI) with N,N-carbonyldiimidazole (XIII) followed by an alcohol of Formula (XV) in a suitable solvent such as cyclobutanol to form the compound of Formula (IA)

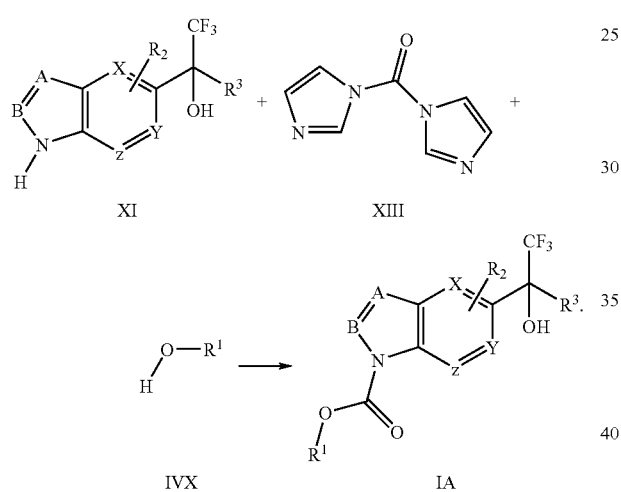

XI + XIII

IVX → IA

A method for making a compound of Formula (IA) with various substituted R¹, where in this example, R³ is an indole, C and G is a bond, D is CR⁴R⁵ (where R⁴ is CF₃ and R⁵ is OH), E is a bond, and A, B, X, Y, Z, R¹, and R² are as defined above, the method comprising:

(a) oxidizing an olefin of Formula (XVI) with a suitable oxidant, such as potassium permanganate, in a suitable solvent, such as acetone and water, to form an alcohol of Formula (IA)

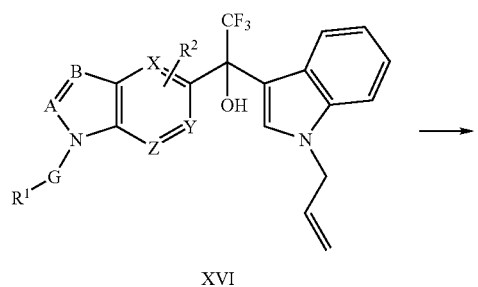

XVI

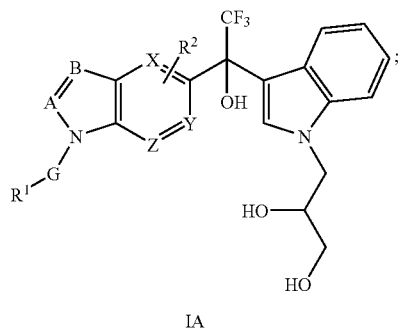

IA (b) oxidizing a diol of Formula (IA) with a suitable oxidant, such as sodium periodate, in a suitable solvent, such as acetone and water, to form an aldehyde of Formula (IA)

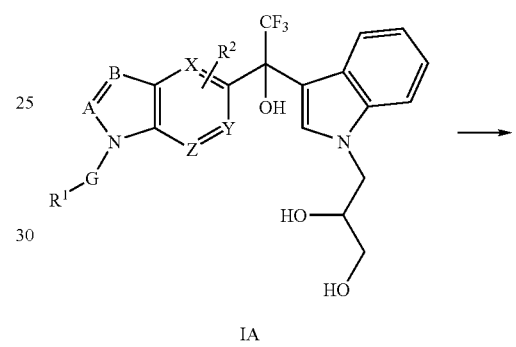

IA

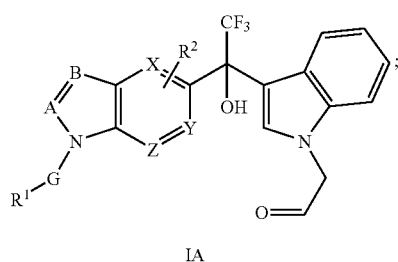

IA (c) oxidizing an aldehyde of Formula (IA) with a suitable oxidant, such as potassium permanganate, in a suitable solvent, such as acetone and water, to form a carboxylic acid of Formula (IA)

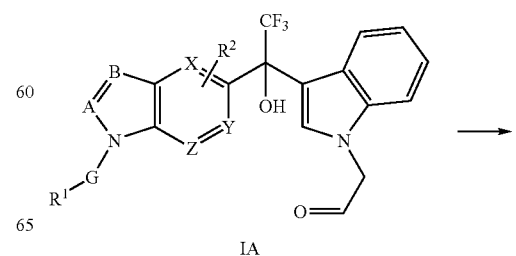

IA

-continued

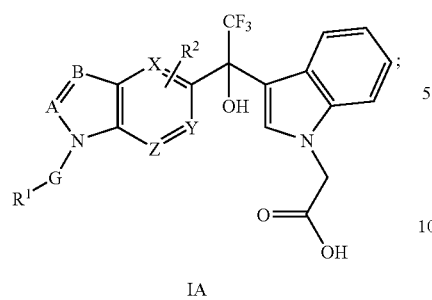

IA

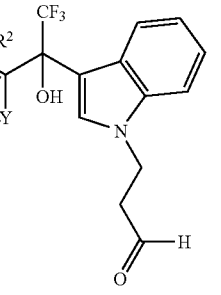

XVII (d) oxidizing a carboxylic acid with a coupling reagent, such as benzotriazolelyloxytris(pyrrolidino)phosphonium hexafluorophosphate, in the presence of a suitable base, such as triethylamine, followed by the addition of an amine, such as methyl amine, in a suitable solvent, such as dimethylformamide, to form an amide of Formula (IA)

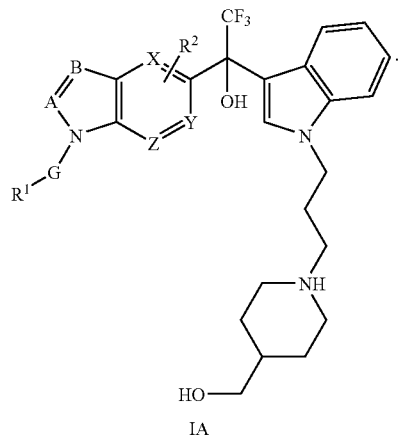

IA

The instant invention is directed to compounds of Formula (IB)

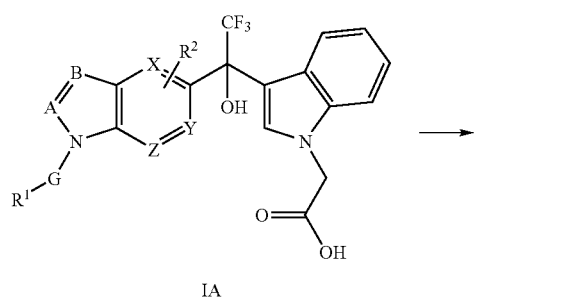

IA

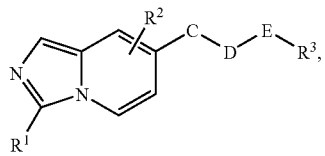
(IB)

wherein:
$R^1$ is aryl, heteroaryl, $C_3$-$C_7$ alkyl, or $C_3$-$C_7$ cycloalkyl each optionally independently substituted with one to three substituent groups selected from $C_1$-$C_3$ alkyl, hydroxy, halogen, oxo, methoxy, amino wherein the nitrogen atom is optionally independently mono- or disubstituted with a methyl group, or thiomethyl wherein the sulfur atom is optionally oxidized to a sulfoxide or sulfone;
$R^2$ is hydrogen or halogen;
C is a bond or a —$NR^4$—, wherein $R^4$ is hydrogen or $C_1$-$C_5$ alkyl group;
E is a bond, —$CH_2$—, —$NR^4CH_2$—, or —$NR^4SO_2$—, where $R^4$ is a hydrogen or $C_1$-$C_5$ alkyl group;
D is —$CR^5R^6$—, where $R^5$ is a trifluoromethyl group and $R^6$ is a hydroxy or a hydrogen; and
$R^3$ is $C_1$-$C_6$ alkyl, cycloalkyl, cycloalkenyl, aryl, heteroaryl, or heterocyclyl, each optionally independently substituted with one to three substituent groups, and each substituent group is connected to $R^3$ by a bond or $C_1$-$C_6$ alkyl group, wherein each substituent group of $R^3$ is independently aryl, heteroaryl, heterocyclyl, $C_1$-$C_5$ alkyl, $C_1$-$C_5$ alkenyl, cycloalkyl, cycloalkenyl, acyl, alkoxycarbonyl, $C_1$-$C_5$ alkanoyloxy, $C_1$-$C_5$ alkanoyl, aroyl, $C_1$-$C_5$ alkanoylamino, alkylaminocarbonyl, dialkylaminocarbonyl,

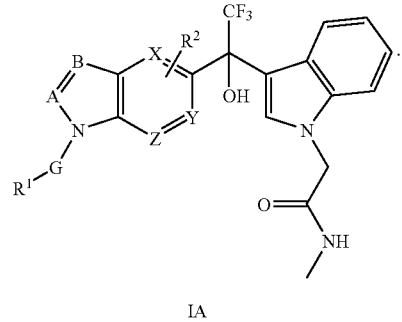

IA

Yet another method for making a compound of Formula (IA) with various substituted $R^3$ where in this example $R^3$ is an indole, C and G is a bond, D is $CR^4R^5$ (where $R^4$ is $CF_3$ and $R^5$ is OH), E is a bond, and A, B, X, Y, Z, $R^1$, $R^2$, and $R^3$, are as defined above, the method comprising: condensation of an amine (for this example, 4-piperidinemethanol) with an aldehyde of Formula (XVII) in the presence of acetic acid in a suitable solvent, such as dichloroethane followed by the addition of a reducing agent, such as sodium triacetoxyborohydride, to form a amide of Formula (IA)

aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkyl sulfonyl amino, aminosulfonyl, $C_1$-$C_5$ alkylaminosulfonyl, $C_1$-$C_5$ dialkylaminosulfonyl, $C_1$-$C_5$ alkyloxy, aryloxy, arylthio, halogen, hydroxy, oxo, cyano, trifluoromethyl, nitro, carboxyl, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, wherein each substituent group of $R^3$ is optionally independently substituted with one to three substituents selected from aryl, heteroaryl, heterocyclyl, acyl, $C_1$-$C_5$ alkyl, $C_1$-$C_5$ alkanoyloxy, $C_1$-$C_5$ alkanoyl, $C_1$-$C_5$ alkanoylamino, alkylaminocarbonyl, dialkylaminocarbonyl, $C_1$-$C_5$ alkyl sulfonylamino, aminosulfonyl, $C_1$-$C_5$ alkylaminosulfonyl, $C_1$-$C_5$ dialkylaminosulfonyl, $C_1$-$C_5$ alkyloxy, $C_1$-$C_5$ cycloalkyl, aryloxy, halogen, hydroxy, oxo, cyano, trifluoromethyl, nitro, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, or a tautomer, prodrug, solvate, or salt thereof.

Another aspect of the invention includes compounds of Formula (IB), wherein:

$R^1$ is aryl, heteroaryl, $C_3$-$C_7$ alkyl, or $C_3$-$C_7$ cycloalkyl, each optionally independently substituted with one to three substituent groups selected from $C_1$-$C_3$ alkyl, hydroxy, halogen, oxo, methoxy, amino wherein the nitrogen atom is optionally independently mono- or disubstituted with a methyl group, or thiomethyl wherein the sulfur atom is optionally oxidized to a sulfoxide or sulfone;

$R^2$ is hydrogen or a halogen;

C is a bond;

E is a bond;

D is —$CR^5R^6$—, where $R^5$ is a trifluoromethyl group and $R^6$ is a hydroxy; and $R^3$ is $C_1$-$C_6$ alkyl, cycloalkyl, cycloalkenyl, aryl, heteroaryl, or heterocyclyl, each optionally independently substituted with one to three substituent groups, and each substituent group is connected to $R^3$ by a bond or $C_1$-$C_6$ alkyl group, wherein each substituent group of $R^3$ is independently aryl, heteroaryl, heterocyclyl, $C_1$-$C_5$ alkyl, $C_1$-$C_5$ alkenyl, cycloalkyl, cycloalkenyl, acyl, alkoxycarbonyl, $C_1$-$C_5$ alkanoyloxy, $C_1$-$C_5$ alkanoyl, aroyl, $C_1$-$C_5$ alkanoylamino, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, aryloxy, arylthio, halogen, hydroxy, oxo, cyano, trifluoromethyl, nitro, carboxyl, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, wherein each substituent group of $R^3$ is optionally independently substituted with one to three substituents selected from aryl, heteroaryl, heterocyclyl, acyl, $C_1$-$C_5$ alkyl, $C_1$-$C_5$ alkanoyloxy, $C_1$-$C_5$ alkanoyl, $C_1$-$C_5$ alkanoylamino, alkylaminocarbonyl, dialkylaminocarbonyl, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, $C_1$-$C_5$ cycloalkyl, aryloxy, halogen, hydroxy, oxo, cyano, trifluoromethyl, nitro, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, or a tautomer, prodrug, solvate, or salt thereof.

Representative compounds of Formula (IB) according to the invention are appended hereto as Table IB, where column A is the compound name according to standard nomenclature and column B is the corresponding chemical structure.

| A | B |
|---|---|
| 3-(3-{2,2,2-Trifluoro-1-[3-(4-fluorophenyl)imidazo[1,5-a]pyridin-7-yl]-1-hydroxyethyl}indol-1-yl)propane-1,2-diol | 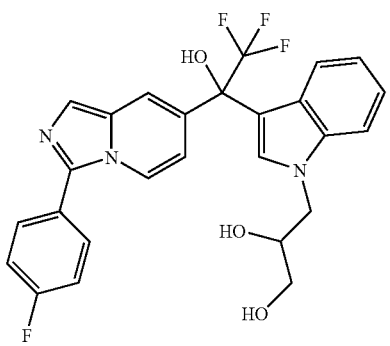 |

IB

-continued

| IB | |
|---|---|
| A | B |
| 1-[1-(2,2-Dimethyl-1,3-dioxolan-4-ylmethyl)-1H-indol-3-yl]-2,2,2-trifluoro-1-[3-(4-fluorophenyl)imidazo[1,5-a]pyridin-7-yl]ethanol | 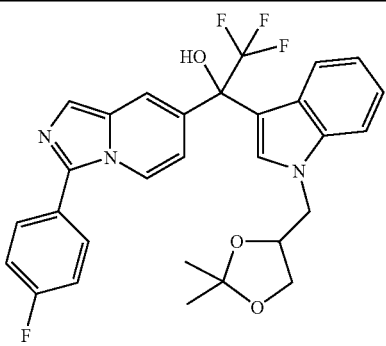 |
| 2,2,2-Trifluoro-1-[3-(4-fluorophenyl)imidazo[1,5-a]pyridin-7-yl]-1-(1-methyl-1H-indol-3-yl)ethanol | 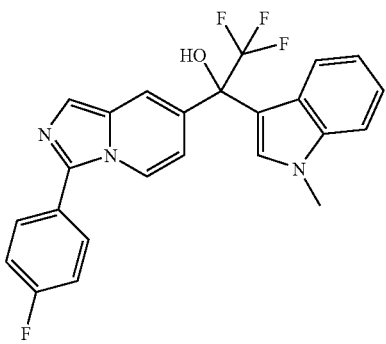 | or a tautomer, prodrug, solvate, or salt thereof.

The invention also provides a method of making a compound of Formula (IB)

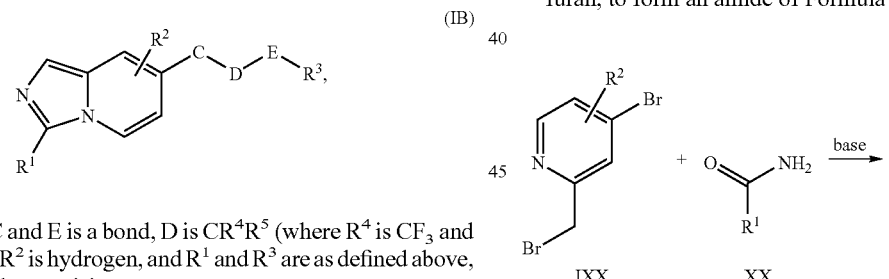

(IB)

wherein: C and E is a bond, D is $CR^4R^5$ (where $R^4$ is $CF_3$ and $R^5$ is OH), $R^2$ is hydrogen, and $R^1$ and $R^3$ are as defined above, the method comprising:

(a) reacting a methylpyridine of Formula (XVIII) with an brominating reagent, such as N-bromosuccinimide, in a suitable solvent, such as carbon tetrachloride, in the presence of a peroxide, such as benzoyl peroxide, to form a benzyl bromide of Formula (IXX)

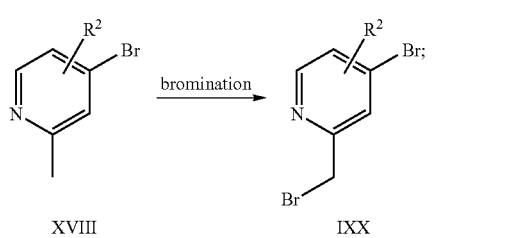

(b) reacting the benzyl bromide of Formula MOO with an amide of Formula (XX) in the presence of a base, such as sodium hydride, in a suitable solvent, such as tetrahydrofuran, to form an amide of Formula (XXI)

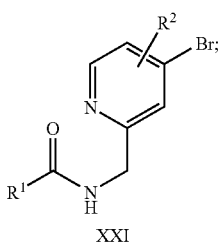

(c) reacting an amide of Formula (XXI) with a dehydrating agent, such as phosphorus oxychloride, to form an imidazo[1,5-a]pyridine of Formula (XXII)

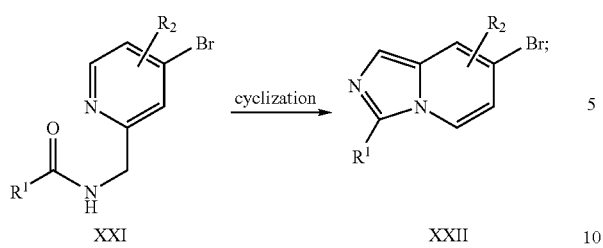

(d) reacting the trifluoromethyl ketone of Formula (III) with an organometallic reagent of Formula (XXIII), such as a organolithium reagent where M is Li or a Grignard reagent where M is MgBr, MgCl, or MgI, in a suitable solvent, such as ether or THF, to form the compound of Formula (IB)

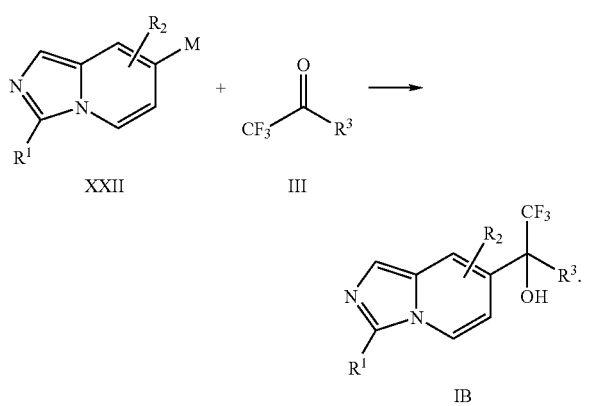

The instant invention is directed to compounds of Formula (IC)

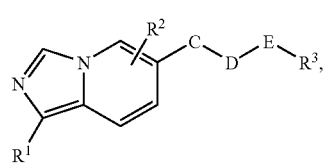

wherein:

$R^1$ is aryl, heteroaryl, $C_3$-$C_7$ alkyl, or $C_3$-$C_7$ cycloalkyl each optionally independently substituted with one to three substituent groups selected from $C_1$-$C_3$ alkyl, hydroxy, halogen, oxo, methoxy, amino wherein the nitrogen atom is optionally independently mono- or disubstituted with a methyl group, or thiomethyl wherein the sulfur atom is optionally oxidized to a sulfoxide or sulfone;

$R^2$ is hydrogen or a halogen;

C is a bond or a —$NR^4$— wherein $R^4$ is a hydrogen or $C_1$-$C_5$ alkyl group;

E is a bond, —$CH_2$—, —$NR^4$—$CH_2$—, or —$NR^4SO_2$—, where $R^4$ is a hydrogen or $C_1$-$C_5$ alkyl group;

D is —$CR^5R^6$—, where $R^5$ is a trifluoromethyl group and $R^6$ is a hydroxy or a hydrogen; and $R^3$ is $C_1$-$C_6$ alkyl, cycloalkyl, cycloalkenyl, aryl, heteroaryl, or heterocyclyl, each optionally independently substituted with one to three substituent groups, and each substituent group is connected to $R^3$ by a bond or $C_1$-$C_6$ alkyl group, wherein each substituent group of $R^3$ is independently aryl, heteroaryl, heterocyclyl, $C_1$-$C_5$ alkyl, $C_1$-$C_5$ alkenyl, cycloalkyl, cycloalkenyl, acyl, alkoxycarbonyl, $C_1$-$C_5$ alkanoyloxy, $C_1$-$C_5$ alkanoyl, aroyl, $C_1$-$C_5$ alkanoylamino, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, aryloxy, arylthio, halogen, hydroxy, oxo, cyano, trifluoromethyl, nitro, carboxyl, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, wherein each substituent group of $R^3$ is optionally independently substituted with one to three substituents selected from aryl, heteroaryl, heterocyclyl, acyl, $C_1$-$C_5$ alkyl, $C_1$-$C_5$ alkanoyloxy, $C_1$-$C_5$ alkanoyl, $C_1$-$C_5$ alkanoylamino, alkylaminocarbonyl, dialkylaminocarbonyl, $C_1$-$C_5$ alkyl sulfonylamino, aminosulfonyl, $C_1$-$C_5$ alkylaminosulfonyl, $C_1$-$C_5$ dialkylaminosulfonyl, $C_1$-$C_5$ alkyloxy, $C_1$-$C_5$ cycloalkyl, aryloxy, halogen, hydroxy, oxo, cyano, trifluoromethyl, nitro, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, or a tautomer, prodrug, solvate, or salt thereof.

Another aspect of the invention includes compounds of Formula (IC), wherein:

$R^1$ is aryl, heteroaryl, $C_3$-$C_7$ alkyl, or $C_3$-$C_7$ cycloalkyl, each optionally independently substituted with one to three substituent groups selected from $C_1$-$C_3$ alkyl, hydroxy, halogen, oxo, methoxy, amino wherein the nitrogen atom is optionally independently mono- or disubstituted with a methyl group; or thiomethyl wherein the sulfur atom is optionally oxidized to a sulfoxide or sulfone;

$R^2$ is hydrogen or a halogen;

C is a bond;

E is a bond;

D is —$CR^5R^6$—, where $R^5$ is a trifluoromethyl group and $R^6$ is a hydroxy; and $R^3$ is $C_1$-$C_6$ alkyl, cycloalkyl, cycloalkenyl, aryl, heteroaryl, or heterocyclyl, each optionally independently substituted with one to three substituent groups, and each substituent group is connected to $R^3$ by a bond or $C_1$-$C_6$ alkyl group, wherein each substituent group of $R^3$ is independently aryl, heteroaryl, heterocyclyl, $C_1$-$C_5$ alkyl, $C_1$-$C_5$ alkenyl, cycloalkyl, cycloalkenyl, acyl, alkoxycarbonyl, $C_1$-$C_5$ alkanoyloxy, $C_1$-$C_5$ alkanoyl, aroyl, $C_1$-$C_5$ alkanoylamino, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, aryloxy, arylthio, halogen, hydroxy, oxo, cyano, trifluoromethyl, nitro, carboxyl, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, wherein each substituent group of $R^3$ is optionally independently substituted with one to three substituents selected from aryl, heteroaryl, heterocyclyl, acyl, $C_1$-$C_5$ alkyl, $C_1$-$C_5$ alkanoyloxy, $C_1$-$C_5$ alkanoyl, $C_1$-$C_5$ alkanoylamino, alkylaminocarbonyl, dialkylaminocarbonyl, $C_1$-$C_5$ alkylsulfonylamino, aminosulfonyl, $C_1$-$C_5$ alkylaminosulfonyl, $C_1$-$C_5$ dialkylaminosulfonyl, $C_1$-$C_5$ alkyloxy, $C_1$-$C_5$ cycloalkyl, aryloxy, halogen, hydroxy, oxo, cyano, trifluoromethyl, nitro, aminocarbonyl, amino wherein the nitrogen atom is optionally independently mono- or disubstituted with a $C_1$-$C_5$ alkyl, or $C_1$-$C_5$ alkylthio wherein the sulfur atom is optionally oxidized to a sulfoxide or sulfone, or a tautomer, prodrug, solvate, or salt thereof.

In another aspect of the invention, the compounds according to the invention are formulated into pharmaceutical compositions comprising an effective amount, preferably a pharmaceutically effective amount, of a compound according to the invention or a tautomer, prodrug, solvate, or salt thereof, and a pharmaceutically acceptable excipient or carrier.

The invention also provides a method of modulating the glucocorticoid receptor function in a patient, the method comprising administering to the patient an effective amount of a compound according to the invention or a tautomer, prodrug, solvate, or salt thereof.

The invention further provides a method of treating a disease-state or condition mediated by the glucocorticoid receptor function in a patient in need of such treatment, the method comprising administering to the patient an effective amount of a pharmaceutically acceptable compound according to the invention or a tautomer, prodrug, solvate, or salt thereof.

In addition, the invention also provides a method of treating a disease-state or condition selected from: type II diabetes, obesity, cardiovascular diseases, hypertension, arteriosclerosis, neurological diseases, adrenal and pituitary tumors, and glaucoma, in a patient in need of such treatment, the method comprising administering to the patient an effective amount of a pharmaceutically acceptable compound according to the invention or a tautomer, prodrug, solvate, or salt thereof.

The invention provides a method of treating a disease characterized by inflammatory, allergic, or proliferative processes, in a patient in need of such treatment, the method comprising administering to the patient an effective amount of a pharmaceutically acceptable compound according to the invention or a tautomer, prodrug, solvate, or salt thereof. In a preferred embodiment of the invention, the disease characterized by inflammatory, allergic, or proliferative processes is selected from: (i) lung diseases (ii) rheumatic diseases or autoimmune diseases or joint diseases (iii) allergic diseases (iv) vasculitis diseases (v) dermatological diseases (vi) renal diseases (vii) hepatic diseases (viii) gastrointestinal diseases (ix) proctological diseases (x) eye diseases (xi) diseases of the ear, nose, and throat (ENT) area (xii) neurological diseases (xiii) blood diseases (xiv) tumor diseases (xv) endocrine diseases (xvi) organ and tissue transplantations and graft-versus-host diseases (xvii) severe states of shock (xviii) substitution therapy; and (xix) pain of inflammatory genesis. In another preferred embodiment of the invention, the disease characterized by inflammatory, allergic, or proliferative processes is selected from: type I diabetes, osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis, and syndromes associated with hemodialysis, leukopheresis, and granulocyte transfusion.

The invention further provides methods of treating the disease-states or conditions mentioned above, in a patient in need of such treatment, the methods comprising sequentially or simultaneously administering to the patient: (a) an effective amount of a pharmaceutically acceptable compound according to the invention or a tautomer, prodrug, solvate, or salt thereof; and (b) a pharmaceutically acceptable glucocorticoid.

The invention further provides a method of assaying the glucocorticoid receptor function in a sample, comprising: (a) contacting the sample with a selected amount of a compound according to the invention or a tautomer, prodrug, solvate, or salt thereof; and (b) detecting the amount of the compound according to the invention or a tautomer, prodrug, solvate, or salt thereof bound to glucocorticoid receptors in the sample. In a preferred embodiment of the invention, the compound according to the invention or a tautomer, prodrug, solvate, or salt thereof is labeled with a detectable marker selected from: a radiolabel, fluorescent tag, a chemiluminescent tag, a chromophore, and a spin label.

The invention also provides a method of imaging the glucocorticoid receptor distribution in a sample or patient, the method comprising: (a) contacting the sample or administering to a patient a compound according to the invention or a tautomer, prodrug, solvate, or salt thereof having a detectable marker (b) detecting the spatial distribution and amount of the compound according to the invention or a tautomer, prodrug, solvate, or salt thereof having a detectable marker bound to glucocorticoid receptors in the sample or patient using an imaging means to obtain an image; and (c) displaying an image of the spatial distribution and amount of the compound according to the invention or a tautomer, prodrug, solvate, or salt thereof having a detectable marker bound to glucocorticoid receptors in the sample. In a preferred embodiment of the invention, the imaging means is selected from: radioscintigraphy, nuclear magnetic resonance imaging (MRI), computed tomography (CT scan), or positron emission tomography (PET).

The invention also provides a kit for the in vitro diagnostic determination of the glucocorticoid receptor function in a sample, comprising: (a) a diagnostically effective amount of a compound according to the invention or a tautomer, prodrug, solvate, or salt thereof; and (b) instructions for use of the diagnostic kit.

Definition Of Terms And Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $C_1$-$C_{10}$ alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar—, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk".

The terms "alkenyl" or "alkenyl group" mean a branched or straight-chain aliphatic hydrocarbon monovalent radical containing at least one carbon-carbon double bond. This term is exemplified by groups such as ethenyl, propenyl, n-butenyl, isobutenyl, 3-methylbut-2-enyl, n-pentenyl, heptenyl, octenyl, decenyl, and the like.

The terms "alkynyl" or "alkynyl group" mean a branched or straight-chain aliphatic hydrocarbon monovalent radical containing at least one carbon-carbon triple bond. This term is exemplified by groups such as ethynyl, propynyl, n-butynyl, 2-butynyl, 3-methylbutynyl, n-pentynyl, heptynyl, octynyl, decynyl, and the like.

The terms "alkylene" or "alkylene group" mean a branched or straight-chain saturated aliphatic hydrocarbon divalent radical having the specified number of carbon atoms. This term is exemplified by groups such as methylene, ethylene, propylene, n-butylene, and the like, and may alternatively and equivalently be denoted herein as -(alkyl)-.

The terms "alkenylene" or "alkenylene group" mean a branched or straight-chain aliphatic hydrocarbon divalent radical having the specified number of carbon atoms and at least one carbon-carbon double bond. This term is exemplified by groups such as ethenylene, propenylene, n-butenylene, and the like, and may alternatively and equivalently be denoted herein as -(alkylenyl)-.

The terms "alkynylene" or "alkynylene group" mean a branched or straight-chain aliphatic hydrocarbon divalent radical containing at least one carbon-carbon triple bond. This term is exemplified by groups such as ethynylene, propynylene, n-butynylene, 2-butynylene, 3-methylbutynylene, n-pentynylene, heptynylene, octynylene, decynylene, and the like, and may alternatively and equivalently be denoted herein as -(alkynyl)-.

The terms "alkoxy" or "alkoxy group" mean a monovalent radical of the formula AlkO—, where Alk is an alkyl group. This term is exemplified by groups such as methoxy, ethoxy, propoxy, isopropoxy, butoxy, sec-butoxy, tert-butoxy, pentoxy, and the like.

The terms "aryloxy", "aryloxy group", mean a monovalent radical of the formula ArO—, where Ar is aryl. This term is exemplified by groups such as phenoxy, naphthoxy, and the like.

The terms "alkylcarbonyl", "alkylcarbonyl group", "alkanoyl", or "alkanoyl group" mean a monovalent radical of the formula AlkC(O)—, where Alk is alkyl or hydrogen.

The terms "arylcarbonyl", "arylcarbonyl group", "aroyl" or "aroyl group" mean a monovalent radical of the formula ArC(O)—, where Ar is aryl.

The terms "acyl" or "acyl group" mean a monovalent radical of the formula RC(O)—, where R is a substituent selected from hydrogen or an organic substituent. Exemplary substituents include alkyl, aryl, arylalkyl, cycloalkyl, heterocyclyl, heteroaryl, heteroarylalkyl, and the like. As such, the terms comprise alkylcarbonyl groups and arylcarbonyl groups.

The terms "acylamino" or "acylamino group" mean a monovalent radical of the formula RC(O)N(R)—, where each R is a substituent selected from hydrogen or a substituent group.

The terms "alkoxycarbonyl" or "alkoxycarbonyl group" mean a monovalent radical of the formula AlkO—C(O)—, where Alk is alkyl. Exemplary alkoxycarbonyl groups include methoxycarbonyl, ethoxycarbonyl, tert-butyloxycarbonyl, and the like.

The terms "aryloxycarbonyl" or "aryloxycarbonyl group" mean a monovalent radical of the formula ArO—C(O)—, where Ar is aryl.

The terms "alkylcarbonyloxy" or "alkylcarbonyloxy group" or "alkanoyloxy" or "alkanoyloxy group" mean a monovalent radical of the formula AlkC(O)O—, where Alk is alkyl.

The terms "arylcarbonyloxy" or "arylcarbonyloxy group" or "aroyloxy" or "aroyloxy group" mean a monovalent radical of the formula ArC(O)O—, where Ar is aryl.

The terms "alkylaminocarbonyloxy" or "alkylaminocarbonyloxy group" mean a monovalent radical of the formula $R_2NC(O)O$—, where each R is independently hydrogen or lower alkyl.

The term "alkoxycarbonylamino" or "alkoxycarbonylamino group" mean a monovalent radical of the formula ROC(O)NH—, where R is lower alkyl.

The terms "alkylcarbonylamino" or "alkylcarbonylamino group" or "alkanoylamino" or "alkanoylamino groups" mean a monovalent radical of the formula AlkC(O)NH—, where Alk is alkyl. Exemplary alkylcarbonylamino groups include acetamido ($CH_3C(O)NH$—).

The terms "alkylaminocarbonyloxy" or "alkylaminocarbonyloxy group" mean a monovalent radical of the formula AlkNHC(O)O—, where Alk is alkyl.

The terms "amino" or "amino group" mean an $—NH_2$ group.

The terms "alkylamino" or "alkylamino group" mean a monovalent radical of the formula (Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "substituted amino" or "substituted amino group" mean a monovalent radical of the formula $—NR_2$, where each R is independently a substituent selected from hydrogen or the specified substituents (but where both Rs cannot be hydrogen). Exemplary substituents include alkyl, alkanoyl, aryl, arylalkyl, cycloalkyl, heterocyclyl, heteroaryl, heteroarylalkyl, and the like.

The terms "alkoxycarbonylamino" or "alkoxycarbonylamino group" mean a monovalent radical of the formula AlkOC(O)NH—, where Alk is alkyl.

The terms "ureido" or "ureido group" mean a monovalent radical of the formula $R_2NC(O)NH$—, where each R is independently hydrogen or alkyl.

The terms "halogen" or "halogen group" mean a fluoro, chloro, bromo, or iodo group.

The term "halo" means one or more hydrogen atoms of the group are replaced by halogen groups.

The terms "haloalkyl" or "haloalkyl group" mean a branched or straight-chain saturated aliphatic hydrocarbon monovalent radical, wherein one or more hydrogen atoms thereof are each independently replaced with halogen atoms. This term is exemplified by groups such as chloromethyl, 1,2-dibromoethyl, 1,1,1-trifluoropropyl, 2-iodobutyl, 1-chloro-2-bromo-3-fluoropentyl, and the like.

The terms "sulfanyl", "sulfanyl group", "thioether", or "thioether group" mean a divalent radical of the formula —S—.

The terms "alkylthio" or "alkylthio group" mean a monovalent radical of the formula AlkS—, where Alk is alkyl. Exemplary groups include methylthio, ethylthio, n-propylthio, isopropylthio, n-butylthio, and the like.

The terms "arylthio" or "arylthio group" mean a monovalent radical of the formula ArS—, where Ar is aryl.

The terms "sulfinyl", "sulfinyl group", "thionyl", or "thionyl group" mean a divalent radical of the formula —SO—.

The terms "sulfonyl" or "sulfonyl group" mean a divalent radical of the formula —SO$_2$—.

The terms "sulfonylamino" or "sulfonylamino group" mean a divalent radical of the formula —SO$_2$NR—, where R is a hydrogen or a substituent group.

The terms "aminosulfonyl" or "aminosulfonyl group" mean a monovalent radical of the formula NR$_2$SO$_2$—, where R is each independently a hydrogen or a substituent group.

The terms "carbocycle" or "carbocyclic group" mean a stable aliphatic 3- to 15-membered monocyclic or polycyclic monovalent or divalent radical consisting solely of carbon and hydrogen atoms which may comprise one or more fused or bridged ring(s), preferably a 5- to 7-membered monocyclic or 7- to 10-membered bicyclic ring. Unless otherwise specified, the carbocycle may be attached at any carbon atom which results in a stable structure and, if substituted, may be substituted at any suitable carbon atom which results in a stable structure. The term comprises cycloalkyl (including spiro cycloalkyl), cycloalkylene, cycloalkenyl, cycloalkenylene, cycloalkynyl, and cycloalkynylene, and the like.

The terms "cycloalkyl" or "cycloalkyl group" mean a stable aliphatic saturated 3- to 15-membered monocyclic or polycyclic monovalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornane, adamantyl, tetrahydronaphthyl (tetralin), 1-decalinyl, bicyclo[2.2.2]octanyl, 1-methylcyclopropyl, 2-methylcyclopentyl, 2-methylcyclooctyl, and the like.

The terms "cycloalkenyl" or "cycloalkenyl group" mean a stable aliphatic 5- to 15-membered monocyclic or polycyclic monovalent radical having at least one carbon-carbon double bond and consisting solely of carbon and hydrogen atoms which may comprise one or more fused or bridged ring(s), preferably a 5- to 7-membered monocyclic or 7- to 10-membered bicyclic ring. Unless otherwise specified, the cycloalkenyl ring may be attached at any carbon atom which results in a stable structure and, if substituted, may be substituted at any suitable carbon atom which results in a stable structure. Exemplary cycloalkenyl groups include cyclopentenyl, cyclohexenyl, cycloheptenyl, cyclooctenyl, cyclononenyl, cyclodecenyl, norbornenyl, 2-methylcyclopentenyl, 2-methylcyclooctenyl, and the like.

The terms "cycloalkynyl" or "cycloalkynyl group" mean a stable aliphatic 8- to 15-membered monocyclic or polycyclic monovalent radical having at least one carbon-carbon triple bond and consisting solely of carbon and hydrogen atoms which may comprise one or more fused or bridged ring(s), preferably a 8- to 10-membered monocyclic or 12- to 15-membered bicyclic ring. Unless otherwise specified, the cycloalkynyl ring may be attached at any carbon atom which results in a stable structure and, if substituted, may be substituted at any suitable carbon atom which results in a stable structure. Exemplary cycloalkynyl groups include, cyclooctynyl, cyclononynyl, cyclodecynyl, 2-methylcyclooctynyl, and the like.

The terms "cycloalkylene" or "cycloalkylene group" mean a stable saturated aliphatic 3- to 15-membered monocyclic or polycyclic divalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkylene groups include cyclopentylene, and the like.

The terms "cycloalkenylene" or "cycloalkenylene group" mean a stable aliphatic 5- to 15-membered monocyclic or polycyclic divalent radical having at least one carbon-carbon double bond and consisting solely of carbon and hydrogen atoms which may comprise one or more fused or bridged ring(s), preferably a 5- to 7-membered monocyclic or 7- to 10-membered bicyclic ring. Unless otherwise specified, the cycloalkenylene ring may be attached at any carbon atom which results in a stable structure and, if substituted, may be substituted at any suitable carbon atom which results in a stable structure. Exemplary cycloalkenylene groups include cyclopentenylene, cyclohexenylene, cycloheptenylene, cyclooctenylene, cyclononenylene, cyclodecenylene, norbornenylene, 2-methylcyclopentenylene, 2-methylcyclooctenylene, and the like.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). Unless otherwise specified, the aryl ring may be attached at any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, azaindolyl, diazaindolyl, dihydroindolyl, isoindolyl, benzofuranyl, dihydrobenzofuranyl, benzothienyl, dihydrobenzothienyl, indazolyl, benzimidazolyl, benzthiazolyl, benzoxazolyl, benzisoxazolyl, benzpyrazolyl, benzopyranone, purinyl, quinolizinyl, quinolinyl, dihydroquinolinyl, tetrahydroquinolinyl, tetrahydroquinoxalinyl, isoquinolinyl, dihydroisoquinolinyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl, acridine, dihydropyrrolooxazineyl, and the like.

The terms "heterocycle", "heterocycle group", "heterocyclyl", or "heterocyclyl group" mean a stable non-aromatic 5- to 14-membered monocyclic or polycyclic, monovalent or divalent, ring which may comprise one or more fused or bridged ring(s), preferably a 5- to 7-membered monocyclic or 7- to 10-membered bicyclic ring, having from one to three heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heterocyclyl ring may be attached at any suitable heteroatom or carbon atom which results in a stable structure and, if substituted, may be substituted at any suitable heteroatom or carbon atom which results in a stable structure. Exemplary and preferred heterocycles include pyrrolinyl, pyrrolidinyl, pyrazolinyl, pyrazolidinyl, piperidinyl, morpholinyl, thiomorpholinyl, piperazinyl, tetrahydropyranyl, tetrahydrothiopyranyl, tetrahydrofuranyl, hexahydropyrimidinyl, hexahydropyridazinyl, 2,3-dihydro-1,4-benzodioxin, 1,3-benzodioxole, 3,4-dihydro-2H-1,4-benzoxazine-1,2,3,4-tetrahydroisoquinoline, N-ethyl-N'-methylbenzene-1,2-diamine, 1,2,3,4-tetrahydroquinoline and the like.

The term "compounds of the invention" and equivalent expressions are meant to embrace compounds of Formula (I) as herein described, including the tautomers, the prodrugs, the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 $R^5$, then such group is optionally substituted with up to two $R^5$ groups and $R^5$ at each occurrence is selected independently from the defined list of possible $R^5$. Such combinations of substituents and/or variables, however, are permissible only if such combinations result in stable compounds.

In a specific embodiment, the term "about" or "approximately" means within 20%, preferably within 10%, and more preferably within 5% of a given value or range.

The yield of each of the reactions described herein is expressed as a percentage of the theoretical yield.

B. Salt, Prodrug, Derivative, and Solvate Terms and Conventions

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309-396; *Burger's Medicinal Chemistry and Drug Discovery*, 5th Ed., M. Wolff (ed.), John Wiley & Sons, 1995, particularly Vol. 1 and pp. 172-178 and pp. 949-982; *Pro-Drugs as Novel Delivery Systems*, T. Higuchi and V. Stella (eds.), Am. Chem. Soc., 1975; and *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "salt" means an ionic form of the parent compound or the product of the reaction between the parent compound with a suitable acid or base to make the acid salt or base salt of the parent compound. Salts of the compounds of the present invention can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzyl amine, N,N-dibenzylphenethyl amine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "solvate" means a physical association of a compound with one or more solvent molecules or a complex of variable stoichiometry formed by a solute (for example, a compound of Formula (I)) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

The term "hydrate" means a solvate wherein the solvent molecule(s) is/are $H_2O$.

The compounds of the present invention as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

The term "isomers" means compounds having the same number and kind of atoms, and hence the same molecular weight, but differing with respect to the arrangement or configuration of their atoms in space. The term includes stereoisomers and geometric isomers.

The terms "stereoisomer" or "optical isomer" means a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the invention which may give rise to stereoisomerism, the invention contemplates stereoisomers and mixtures thereof. The compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of stereoisomers that are non-superimposable mirror images of each other.

The terms "diastereoisomers" or "diastereomers" mean stereoisomers which are not mirror images of each other.

The terms "racemic mixture" or "racemate" mean a mixture containing equal parts of individual enantiomers.

The term "non-racemic mixture" means a mixture containing unequal parts of individual enantiomers.

The term "geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the invention, the invention contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, *Advanced Organic Chemistry: Reactions, Mechanisms, and Structure,* 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as X-ray crystallography, $^1$H NMR, and $^{13}$C NMR.

Some of the compounds of the invention can exist in more than one tautomeric form. As mentioned above, the compounds of the invention include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the invention from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of Pure Enantiomers or Mixtures of Desired Enantiomeric Excess (Ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in *Chiral Separation Techniques: A Practical Approach* (2nd Ed.), G. Subramanian (ed.), Wiley-VCH, 2000; T. E. Beesley and R. P. W. Scott, *Chiral Chromatography,* John Wiley & Sons, 1999; and Satinder Ahuja, *Chiral Separations by Chromatography,* Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

D. Pharmaceutical Administration and Diagnostic and Treatment Terms and Conventions The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The term "modulate" means the ability of a compound to alter the function of the glucocorticoid receptor by, for example, binding to and stimulating or inhibiting the glucocorticoid receptor functional responses.

The term "modulator" in the context of describing compounds according to the invention means a compound that modulates the glucocorticoid receptor function. As such, modulators include, but are not limited to, agonists, partial agonists, antagonists, and partial antagonists.

The term "agonist" in the context of describing compounds according to the invention means a compound that, when bound to the glucocorticoid receptor, enhances or increases the glucocorticoid receptor function. As such, agonists include partial agonists and full agonists.

The term "full agonist" in the context of describing compounds according to the invention means a compound that evokes the maximal stimulatory response from the glucocorticoid receptor, even when there are spare (unoccupied) glucocorticoid receptors present.

The term "partial agonist" in the context of describing compounds according to the invention means a compound that is unable to evoke the maximal stimulatory response from the glucocorticoid receptor, even at concentrations sufficient to saturate the glucocorticoid receptors present.

The term "antagonist" in the context of describing compounds according to the invention means a compound that directly or indirectly inhibits or suppresses the glucocorticoid receptor function. As such, antagonists include partial antagonists and full antagonists.

The term "full antagonist" in the context of describing compounds according to the invention means a compound that evokes the maximal inhibitory response from the glucocorticoid receptor, even when there are spare (unoccupied) glucocorticoid receptors present.

The term "partial antagonist" in the context of describing compounds according to the invention means a compound that is unable to evoke the maximal inhibitory response from the glucocorticoid receptor, even at concentrations sufficient to saturate the glucocorticoid receptors present.

The terms "treating" or "treatment" mean the treatment of a disease-state in a patient, and include:

(i) preventing the disease-state from occurring in a patient, in particular, when such patient is genetically or otherwise predisposed to the disease-state but has not yet been diagnosed as having it;

(ii) inhibiting or ameliorating the disease-state in a patient, i.e., arresting or slowing its development; or (iii) relieving the disease-state in a patient, i.e., causing regression or cure of the disease-state.

General Synthetic Methods for Making Compounds of Formula (IA) and (IB)

The invention also provides processes for making compounds of Formula (IA) and (IB). In all schemes, unless specified otherwise, A, B, C, D, E, G, X, Y, Z, $R^1$, $R^2$, and $R^3$ in the formulas below shall have the meaning of A, B, C, D, E, G, X, Y, Z, $R^1$, $R^2$, and $R^3$ in the Formula (IA) and (IB) of the invention described hereinabove. Intermediates used in the preparation of compounds of the invention are either commercially available or readily prepared by methods known to those skilled in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by crystallization.

Compounds of Formula (IA) may be prepared by the method outlined in Scheme I.

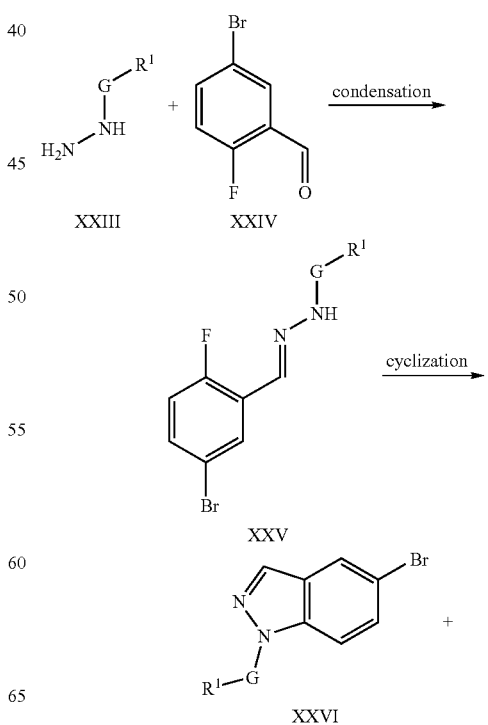

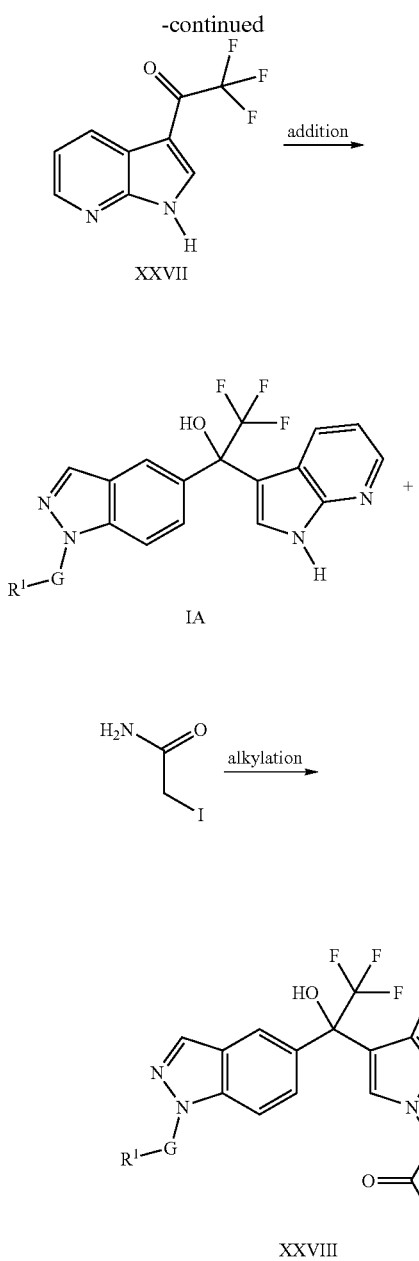

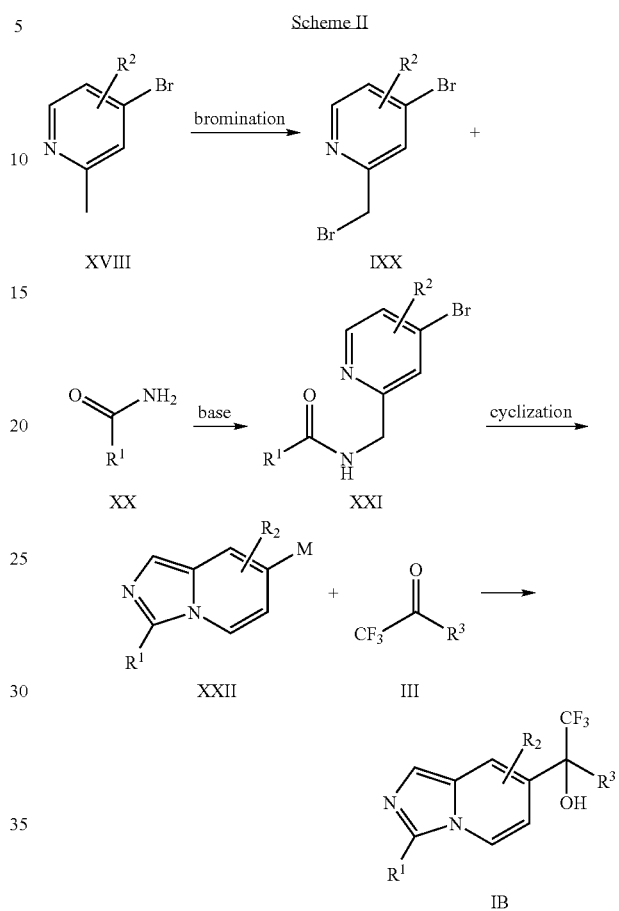

Compounds of Formula (IB) may be prepared by the method outlined in Scheme II.

As illustrated in Scheme I, a hydrazine (XXIII) (with various R[1]'s where G is a bond) is condensed with 5-bromo-2-benzaldehyde (XXIV) in suitable solvent such as ethanol to produce a hydrazone (XXV). Cyclization of hydrazone (XXV) using a suitable base, such as cesium carbonate, in a suitable solvent, such as DMF, to product indazole (XXVI). Reacting the trifluoromethyl ketone of Formula (XXVII), in this example R[3] is 7-azaindole, with an organometallic reagent such as an organolithium reagent where M is Li or a Grignard reagent where M is MgBr, MgCl, or MgI, prepared from the aryl bromide (XXVI) in a suitable solvent, such as ether or THF, to form the compound of Formula (IA) where R[3] is an azaindole. Additional analogs of Formula (IA) may be prepared by alkylation of azaindole (IA) with an alkyl halide, such as iodoacetamide, in the presence of a suitable base, such as KOH or sodium hydride, in a suitable solvent, such as DMF or DMSO.

As shown in Scheme II, reaction of a methylpyridine of Formula (XVIII) with an brominating reagent, such as N-bromosuccinimide, in a suitable solvent, such as carbon tetrachloride, in the presence of a peroxide, such as benzoyl peroxide, to form a benzyl bromide of Formula (IXX). Reaction of a benzyl bromide of Formula (IXX) with an amide of Formula (XX) in the presence of a base, such as sodium hydride, in a suitable solvent, such as tetrahydrofuran, to form an amide of Formula (XXI). Cyclization of an amide of Formula (XXI) using a dehydrating agent such as phosphorus oxychloride to form an imidazo[1,5-a]pyridine of Formula (XXII). Reacting the trifluoromethyl ketone of Formula (III) with an organometallic reagent, prepared from the corresponding bromide (M is Br) of Formula (XXIII), such as an organolithium reagent where M is Li or a Grignard reagent where M is MgBr, MgCl, or MgI, in a suitable solvent, such as ether or THF, to form the compound of Formula (IB).

In order that this invention is more fully understood, the following examples are set forth. These examples are for the purpose of illustrating embodiments of this invention, and are not to be construed as limiting the scope of the invention in any way since, as recognized by one skilled in the art, particular reagents or conditions could be modified as needed for individual compounds. Starting materials used are either commercially available or easily prepared from commercially available materials by those skilled in the art.

Resolution to the (+)- and (−)enantiomers was accomplished by chiral HPLC on a CHIRALCEL™ AD-H column, eluting with 20% isopropanol-hexanes.

EXPERIMENTAL EXAMPLES

Example 1

2,2,2-Trifluoro-1-[1-(4-fluorophenyl)-1H-indazol-5-yl]-1-(1H-pyrrolo[2,3-b]pyridin-3-yl)ethanol

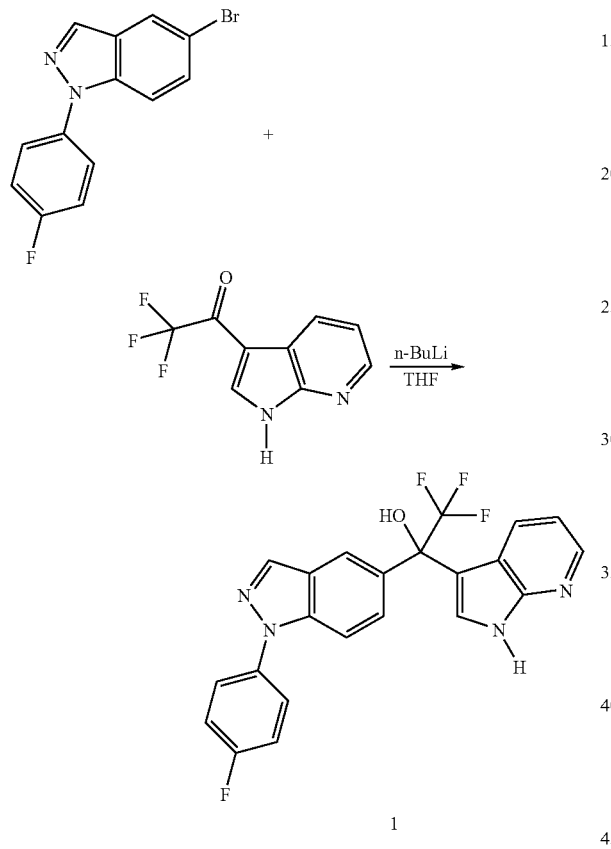

1

To a chilled (−78° C.) (dry ice-acetone) solution of 291 mg (1.0 mmol) of 5-bromo-1-(4-fluorophenyl)-1H-indazole in 5 mL of anhydrous THF was added rapidly 0.4 mL (1.0 mmol) of a 2.5 M solution of n-butyllithium (n-BuLi) in hexanes. Immediately after, a chilled (dry ice-acetone bath) solution of 2,2,2-trifluoro-1-(1H-pyrrolo[2,3-b]pyridin-3-yl)ethanone (prepared according to the procedure described in J. Org. Chem. 2002, 76, 6226) in 3 mL of THF was added rapidly. The mixture stirred for 1 hour, TLC [ethyl acetate-hexanes (1:1)] indicated a new more polar product than both starting materials. The mixture was diluted with 10 mL of saturated aqueous ammonium chloride and extracted with three 10 mL portions of ethyl acetate. The combined organic layers were washed with three 10 mL portions of brine, dried over magnesium sulfate, filtered, and concentrated in vacuo. The crude residue was chromatographed on silica gel using dichloromethane to load the sample and then eluting with ethyl acetate-CH$_2$Cl$_2$ (0-30% gradient). The material from the column was solidified from ether-hexanes (1:1), dried under house vacuum at 90° C. for 3 hours, to afford 91 mg (42%) of the title compound. MS m/z 427.18 (MH$^+$).

Additional indoles prepared according to the procedure described in J. Org. Chem. 2002, 76, 6226: 2,2,2-Trifluoro-1-(1H-pyrrolo[3,2-b]pyridin-3-yl)ethanone, 2,2,2-Trifluoro-1-(1H-pyrrolo[3,2-c]pyridin-3-yl)ethanone, and 2,2,2-Trifluoro-1-(1H-pyrrolo[2,3-c]pyridin-3-yl)ethanone.

Example 2

1-(7-Chloro-1H-pyrrolo[2,3-c]pyridin-3-yl)-2,2,2-trifluoro-1-[1-(4-fluorophenyl)-1H-indazol-5-yl]ethanol

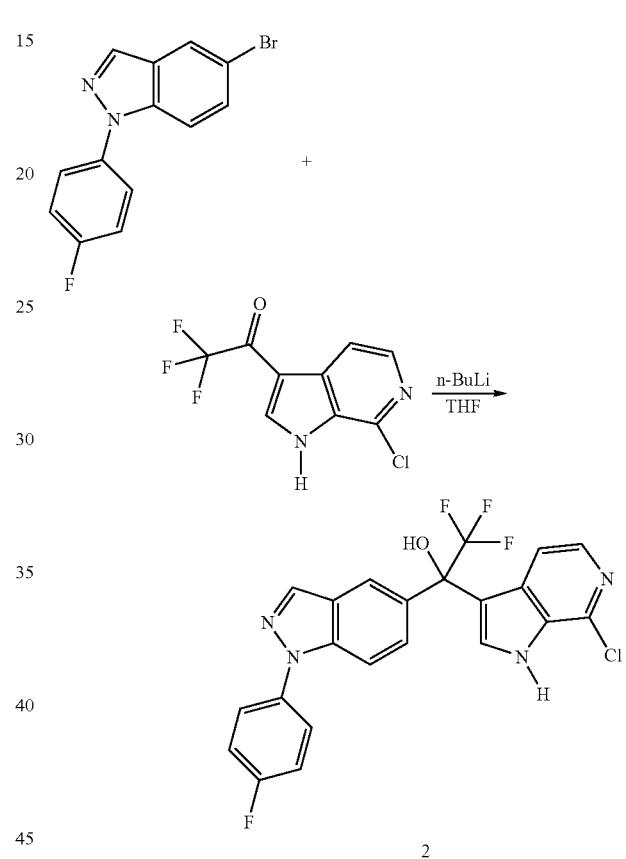

2

To a chilled (−78° C.) solution of 490 mg (1.68 mmol) of 5-bromo-1-(4-fluorophenyl)-1H-indazole in 5 mL of anhydrous THF was added 0.69 mL (1.73 mmol) of a 2.5 M solution of n-BuLi in hexanes. The mixture stirred for 5 minutes, and was then added to a chilled (dry ice-acetone) solution of the sodium salt of 1-(7-chloro-1H-pyrrolo[2,3-c]pyridin-3-yl)-2,2,2-trifluoroethanone prepared by adding at room temperature 83 mg (2.08 mmol) of 60% sodium hydride in mineral oil to 374 mg (1.50 mmol) of 1-(7-chloro-1H-pyrrolo[2,3-c]pyridin-3-yl)-2,2,2-trifluoroethanone (prepared as described in J. Org. Chem. 2002, 76, 6226) in 5 mL of THF. The mixture stirred for 30 minutes with the cold bath removed and was then diluted with 30 mL of saturated aqueous ammonium chloride and extracted with three 25 mL portions of ethyl acetate. The combined organic layers were washed with three 25 mL portions of brine, dried over magnesium sulfate, filtered, and concentrated in vacuo. The crude residue was chromatographed on silica gel using dichloromethane to load the sample and then eluting with dichloromethane-hexanes (50-100% gradient) and then ethyl acetate-dichloromethane (0-25%) to afford partially purified product. A second column eluting with ether-hexanes (5-50% gradient) followed by solidifying the material from the column from ether-hexanes gave 344 mg (49%) of the title compound. MS m/z 461.25 (MH+).

Example 3

2,2,2-Trifluoro-1-[1-(4-fluorophenyl)-1H-indazol-5-yl]-1-(1H-indazol-3-yl)ethanol

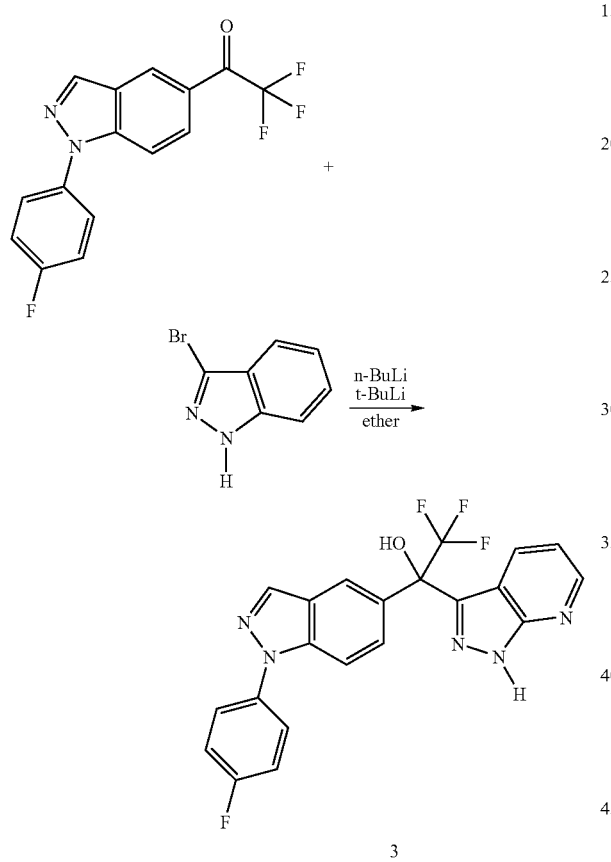

chromatographed on silica gel using dichloromethane-hexanes (1:1) to load the sample and then eluting with dichloromethane-hexanes (1:1, then 100:0) followed by ethyl acetate-hexanes (2:8). The material from the column was triturated with ether-hexanes to afford 41 mg (19%) of the title compound. MS m/z 427.20 (MH+).

Example 4

2-(3-{2,2,2-Trifluoro-1-[1-(4-fluorophenyl)-1H-indazol-5-yl]-1-hydroxyethyl}pyrrolo[2,3-b]pyridin-1-yl)acetamide

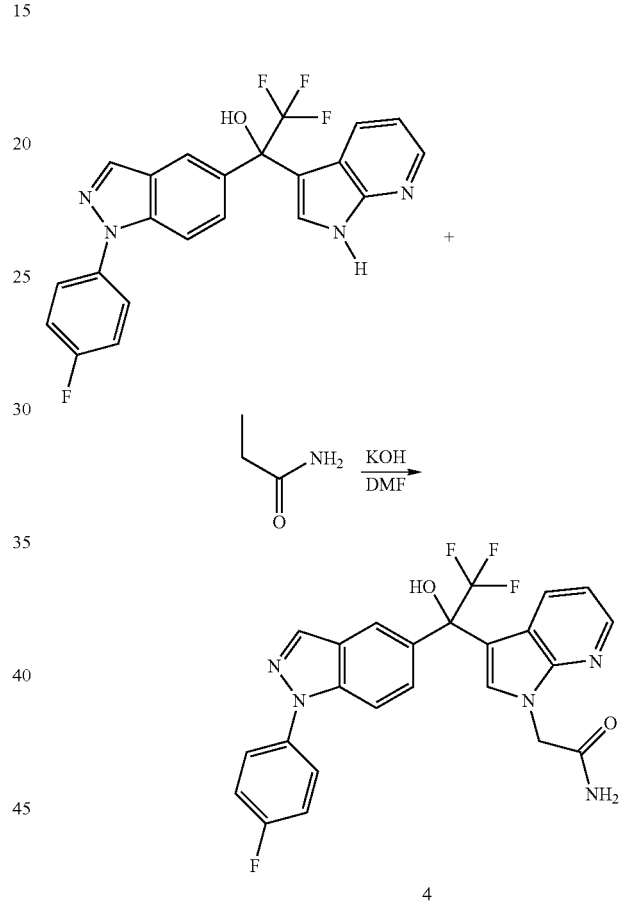

To a chilled (−78° C.) solution of 97 mg (0.49 mmol) of 3-bromo-1H-indazole in 5 mL of anhydrous ether was added 195 μL (0.49 mmol) of a 2.5 M solution of n-BuLi in hexanes dropwise. After 5 minutes, 590 μL (1.0 mmol) of a 1.7 M solution of tert-BuLi in pentane was added dropwise. The mixture stirred for 15 minutes and then a solution of 151 mg (0.49 mmol) of 2,2,2-trifluoro-1-[1-(4-fluorophenyl)-1H-indazol-5-yl]ethanone in 3 mL of ether was added dropwise. After 1 hour, the reaction was monitored by thin layer chromatography (30% ethyl acetate-hexanes) and LCMS. The mixture was diluted with 10 mL of saturated aqueous ammonium chloride and extracted with three 10 mL portions of ethyl acetate. The combined organic layers were washed with three 10 mL portions of brine, dried over magnesium sulfate, filtered, and concentrated in vacuo. The crude residue was To a solution of 60 mg (0.14 mmol) of 2,2,2-trifluoro-1-[1-(4-fluorophenyl)-1H-indazol-5-yl]-1-(1H-pyrrolo[2,3-b]pyridin-3-yl)ethanol in 2 mL of DMF was added 21 mg (0.27 mmol) of powdered KOH followed by 51 mg (0.28 mmol) of iodoacetamide. The mixture stirred for 30 minutes, and was then diluted with saturated aqueous ammonium chloride and extracted with three 7 mL portions of ethyl acetate. The combined organic layers were washed with two 7 mL portions of brine, dried over magnesium sulfate, filtered, and concentrated in vacuo. The residue was chromatographed on silica gel using dichloromethane to load the sample and then eluting with dichloromethane and then ethyl acetate. The material from the column was triturated with ether-hexanes and dried under house vacuum at 80° C. for 2 hours to afford 21 mg (30%) of the title compound. MS m/z 484.28 (MH+).

Example 5

1-(4-Chloro-1-phenyl-1H-pyrazolo[3,4-b]pyridin-5-yl)-2,2,2-trifluoro-1-(1H-pyrrolo[2,3-b]pyridin-3-yl)ethanol

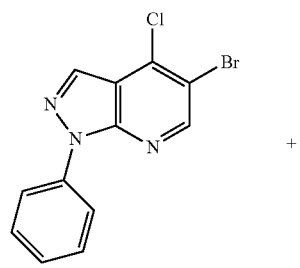

+

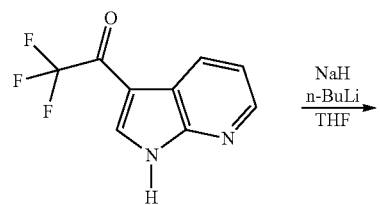

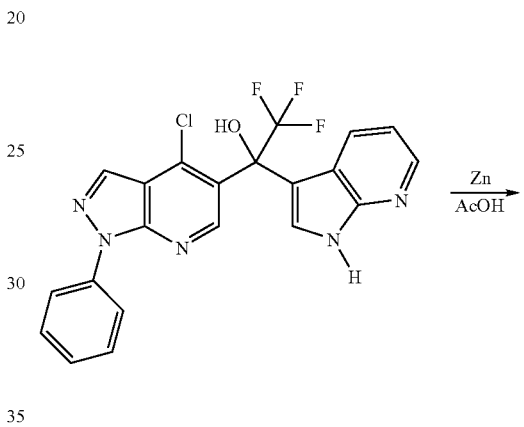

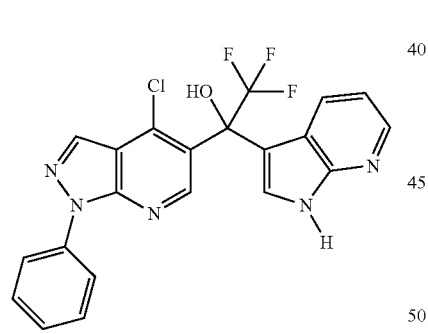

5

To a chilled (ice-bath) solution of 369 mg (1.72 mmol) of 2,2,2-trifluoro-1-(1H-pyrrolo[2,3-b]pyridin-3-yl)ethanone in 10 mL of THF was added 70 mg (1.75 mmol) of 60% sodium hydride in mineral oil and the mixture was then chilled to −78° C. In another flask, to a chilled (−78° C.) solution of 508 mg (1.65 mmol) of 5-bromo-4-chloro-1-phenyl-1H-pyrazolo[3,4-b]pyridine (prepared according to the procedures in Misra, *Bioorg. Med. Chem. Lett.* 2003, 13, 2405, and Nakai in *Chem. Pharm. Bull.* 2004, 52, 1098) in 10 mL of anhydrous THF was added 670 µL (1.68 mmol) of a 2.5 M solution of n-BuLi in hexanes. The mixture stirred for 5 minutes and was then added to the sodium salt of 2,2,2-trifluoro-1-(1H-pyrrolo[2,3-b]pyridin-3-yl)ethanone. The reaction was monitored by TLC [ethyl acetate-hexanes (6:4)] indicating a new more polar product than both starting materials. After 1 hour, the mixture was diluted with 30 mL of saturated aqueous ammonium chloride and extracted with three 30 mL portions of ethyl acetate. The combined organic layers were washed with three 30 mL portions of brine, dried over magnesium sulfate, filtered, and concentrated in vacuo. The crude residue was chromatographed on silica gel using dichloromethane to load the sample and then eluting with ethyl acetate-hexanes (10-50% gradient) to afford 337 mg (44%) of title compound. Trituration with ether afforded 85 mg of the title compound as a white solid. MS m/z 444.38 (MH+).

Example 6

2,2,2-Trifluoro-1-(1-phenyl-1H-pyrazolo[3,4-b]pyridin-5-yl)-1-(1H-pyrrolo[2,3-b]pyridin-3-yl)ethanol

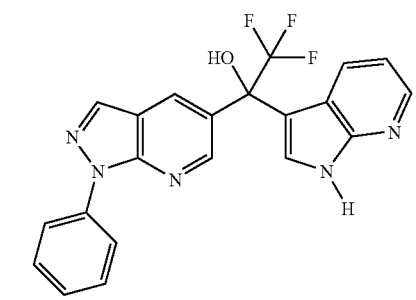

5

A mixture of 200 mg (0.45 mmol) of 1-(4-chloro-1-phenyl-1H-pyrazolo[3,4-b]pyridin-5-yl)-2,2,2-trifluoro-1-(1H-pyrrolo[2,3-b]pyridin-3-yl)ethanol and 185 mg (2.83 mmol) of zinc powder in acetic acid was warmed at reflux for 30 minutes. The mixture was then cooled and made basic with saturated aqueous sodium bicarbonate and extracted with three 30 mL portions of ethyl acetate. The combined organic layers were washed with two 15 mL portions of saturated aqueous sodium bicarbonate, three 15 mL portions of brine, dried over magnesium sulfate, filtered, and concentrated in vacuo to afford 145 mg (78%) of the title compound. The material from the column was triturated with ether-hexanes to afford 85 mg of the title compound as a white solid. The solid was dried under house vacuum at 90° C. and then 110° C. MS m/z 410.30 (MH+), m.p. 137° C.-141° C.

Example 7

2,2,2-Trifluoro-1-[1-(4-fluorophenyl)-1H-indazol-5-yl]-1-(7-oxy-1H-pyrrolo[2,3-b]pyridin-3-yl)ethanol

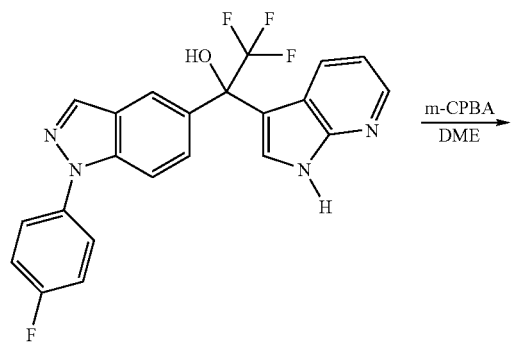

7

To a solution of 55 mg (0.13 mmol) of 2,2,2-trifluoro-1-[1-(4-fluorophenyl)-1H-indazol-5-yl]-1-(1H-pyrrolo[2,3-b]pyridin-3-yl)ethanol in dimethoxyethane was added 44 mg (0.20 mmol) of m-chloroperbenzoic acid. The mixture stirred for 2 hours and the resulting solid was collected by filtration and washed with ether. The solid was dissolved in water-methanol (4:1) and made basic with aqueous potassium carbonate, warmed on a hot plate, and concentrated to near dryness under a stream of nitrogen. The residue was diluted with additional water resulting in a cloudy solution. Ethyl acetate was added (solids were present in the organic phase), the organic layer was concentrated under a stream of nitrogen on a hot plate and the solid was collected from the aqueous, washing with water, and then ether to afford 37 mg (64%) of the title compound. MS m/z 443.21 (MH+).

Example 8

3-{2,2,2-Trifluoro-1-[1-(4-fluorophenyl)-1H-indazol-5-yl]-1-hydroxyethyl}pyrrolo[2,3-b]pyridine-1-sulfonic acid dimethylamide

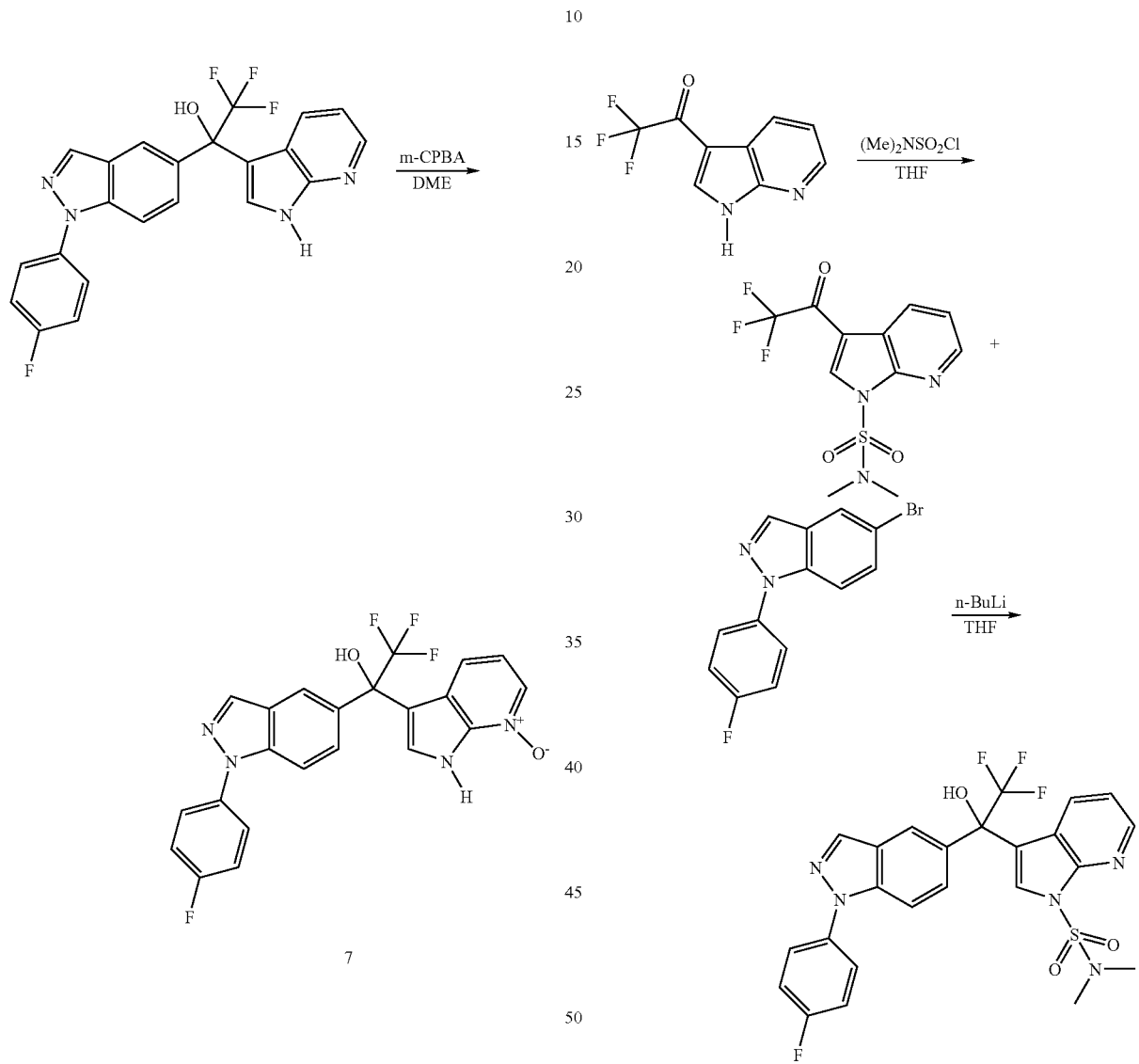

8

To a solution of 107 mg (0.5 mmol) of 2,2,2-trifluoro-1-(1H-pyrrolo[2,3-b]pyridin-3-yl)ethanone in 2 mL of DMF was added 60% sodium hydride in mineral oil followed by 80 mg (0.56 mmol) of N,N-dimethylsulfamoyl chloride. The mixture stirred for 30 minutes and was then diluted with 10 mL of saturated aqueous sodium bicarbonate and extracted with three 7 mL portions of ethyl acetate. The combined organic layers were washed with three 7 mL portions of brine, three 7 mL portions of saturated aqueous ammonium chloride, dried over magnesium sulfate, filtered and concentrated. The crude material was adsorbed onto silica gel and chromatographed on silica gel eluting with ethyl acetate-hexanes (10-100% gradient) to afford 88 mg (54%) of 3-(2,2,2-trifluoroacetyl)pyrrolo[2,3-b]pyridine-1-sulfonic acid dimethylamide as a white solid.

To a chilled (–78° C.) solution of 80 mg (0.27 mmol) of 5-bromo-1-(4-fluorophenyl)-1H-indazole in 1 mL of anhydrous THF was added 110 μL (0.28 mmol) of a solution of 2.5 M n-BuLi in hexane in one portion. This solution was then added to a chilled (–78° C.) solution of 88 mg (0.27 mmol) of 3-(2,2,2-trifluoro-acetyl)pyrrolo[2,3-b]pyridine-1-sulfonic acid dimethylamide in 3 mL of THF. The reaction was monitored by TLC (ethyl acetate-hexanes 4:6). After 30 minutes, the mixture was diluted with 7 mL of saturated aqueous ammonium chloride and extracted with three 10 mL portions of ethyl acetate. The combined organic layers were washed with three 10 mL portions of brine, dried over magnesium sulfate, filtered, and concentrated in vacuo. The crude residue was chromatographed on silica gel (prep. plate, 2×1 mm, ethyl acetate-hexanes 30:70). The material from the prep plate was washed from the silica gel with ethyl acetate and concentrated. The residue was triturated with ether-hexanes to afford 42 mg (28%) of the title compound. MS m/z 534.22 (MH+).

Example 9

N-[2-(3-{2,2,2-Trifluoro-1-[1-(4-fluorophenyl)-1H-indazol-5-yl]-1-hydroxyethyl}pyrrolo[2,3-b]pyridin-1-yl)acetyl]methanesulfonamide

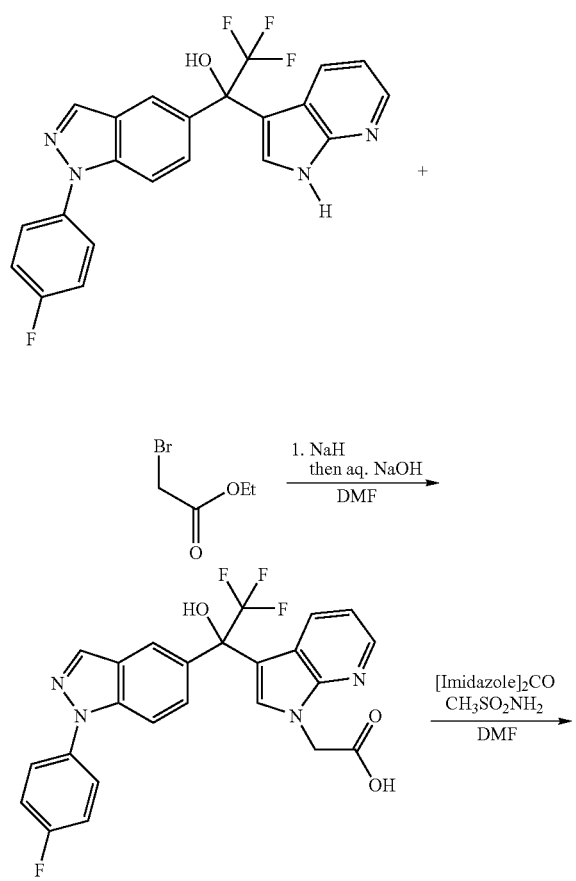

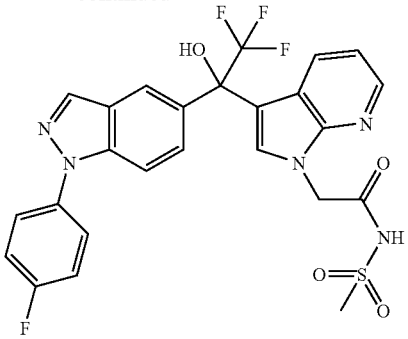

9

To a solution of 110.0 mg (0.26 mmol) of 2,2,2-trifluoro-1-[1-(4-fluorophenyl)-1H-indazol-5-yl]-1-(1H-pyrrolo[2,3-b]pyridin-3-yl)ethanol in 2 mL of DMF was added 16 mg (0.4 mmol) of 60% sodium hydride in mineral oil followed by 32 μL (0.29 mmol) of ethyl bromoacetate. The reaction was monitored by TLC (ethyl acetate) indicating a new polar product. The reaction was diluted with methanol and made basic with 2N aqueous sodium hydroxide. The mixture stirred for 1 hour and was then monitored by LCMS indicating a mass corresponding to the carboxylic acid (M+=485.30). The reaction was diluted with 7 mL of saturated aqueous ammonium chloride and extracted with three 7 mL portions of ethyl acetate. The combined organic layers were washed with three 7 mL portions of brine, dried over magnesium sulfate, filtered, and concentrated in vacuo to afford 110 mg (88%) of (3-{2,2,2-trifluoro-1-[1-(4-fluorophenyl)-1H-indazol-5-yl]-1-hydroxyethyl}pyrrolo[2,3-b]pyridin-1-yl)acetic acid which was used without further purification.

To a solution of 107 mg (0.22 mmol) of (3-{2,2,2-trifluoro-1-[1-(4-fluorophenyl)-1H-indazol-5-yl]-1-hydroxyethyl}pyrrolo[2,3-b]pyridin-1-yl)acetic acid in 3 mL of DMF was added 108 mg (0.66 mmol) of N,N-carbonyldiimidazole. The mixture stirred for 5 minutes and then 63 mg (0.66 mmol) of methanesulfonamide was added. After 30 minutes, the reaction was monitored by LCMS indicating only starting material [MS m/z 485.29 (MH+)]. To the mixture was added sodium hydride and the mixture stirred for 1.5 hours. The mixture was monitored by LCMS indicating desired product [MS m/z 562.37 (MH+)]. TLC (ethyl acetate or methanol-dichloromethane) indicated a new product. The mixture was diluted with saturated aqueous ammonium chloride and extracted with five 10 mL portions of ethyl acetate. The combined organic layers were washed with two 7 mL portions of saturated aqueous ammonium chloride, two 7 mL portions of brine, dried over magnesium sulfate, filtered, and concentrated in vacuo. The oily residue was chromatographed on silica gel using dichloromethane to load the sample and then methanol-dichloromethane (1-10%) to afford some mixed factions and clean fractions. Fractions containing product were chromatographed on four prep. plate (1 mm, methanol-dichloromethane 15:85). The most polar band was recovered eluting from the silica gel with 20% methanol-dichloromethane. The material was triturated with ether-hexanes to afford 42 mg (33%) of the title compound as a tan solid. MS m/z 562.39 (MH+).

Example 10

(2-Nitrophenyl)-{2,2,2-trifluoro-1-[1-(4-fluorophenyl)-1H-indazol-5-yl]ethyl}amine

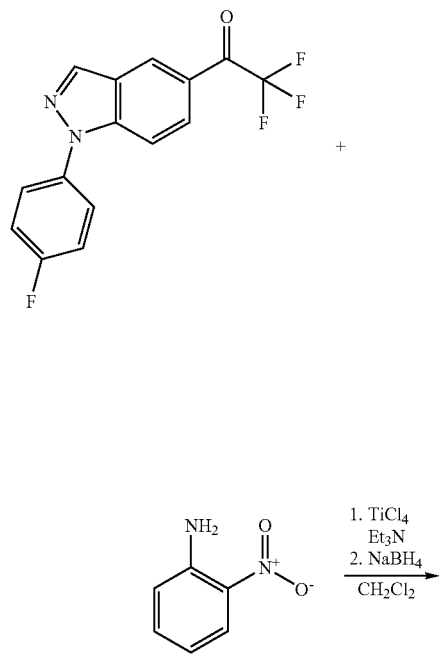

To a solution of 134 mg (0.97 mmol) of 2-nitroaniline in 5 mL of dichloromethane was added 300 mg (0.97 mmol) of 2,2,2-trifluoro-1-[1-(4-fluorophenyl)-1H-indazol-5-yl]ethanone, 210 µL (2.9 mmol) of triethylamine, followed by 500 µL 0.5 mmol) of TiCl4. The mixture stirred for 20 hours and was then diluted with methanol followed by 40 mg (1.0 mmol) of sodium borohydride. After 1 hour, the mixture was diluted with 50 mL of 1N aqueous NaOH and extracted with EtOAc. The combined organic layers were washed with brine, dried over sodium sulfate, and concentrated in vacuo. The crude product was purified by Combiflash chromatography using EtOAc-hexanes (0-70% gradient) to afford 220 mg (53%) of the title compound as a yellow foam. MS m/z 431 (MH+).

Example 11

N-{2,2,2-Trifluoro-1-[1-(4-fluorophenyl)-1H-indazol-5-yl]ethyl}benzene-1,2-diamine

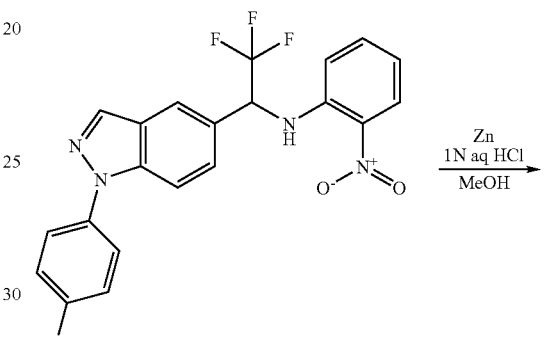

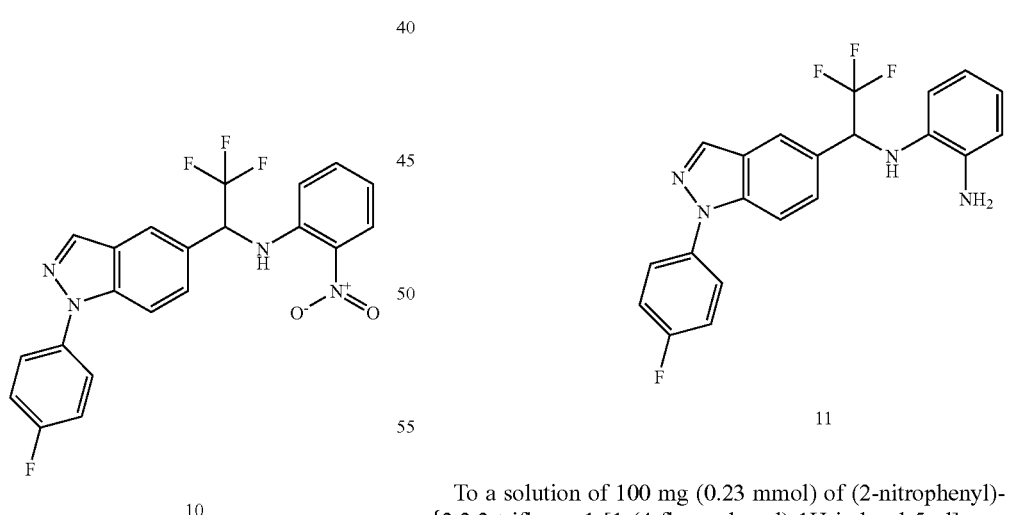

To a solution of 100 mg (0.23 mmol) of (2-nitrophenyl)-{2,2,2-trifluoro-1-[1-(4-fluorophenyl)-1H-indazol-5-yl]ethyl}amine in 10 mL of methanol was added 304 mg (4.65 mmol) of zinc powder followed by the addition of 4.65 mL (4.65 mmol) of 1 N aqueous HCl. After 1 hour, the mixture was made basic with saturated aqueous sodium bicarbonate and extracted with three 15 mL portions of ethyl acetate. The combined organic layers were washed with brine, dried over magnesium sulfate, filtered, and concentrated in vacuo. The residue was purified by prep-TLC using 10-20% EtOAc/ hexanes to provide 10 mg (14%) of the title compound as a white solid. MS m/z 401 (MH+).

Example 12

(1-Benzyl-2,2,2-trifluoroethyl)-[1-(4-fluorophenyl)-1H-indazol-5-yl]-amine

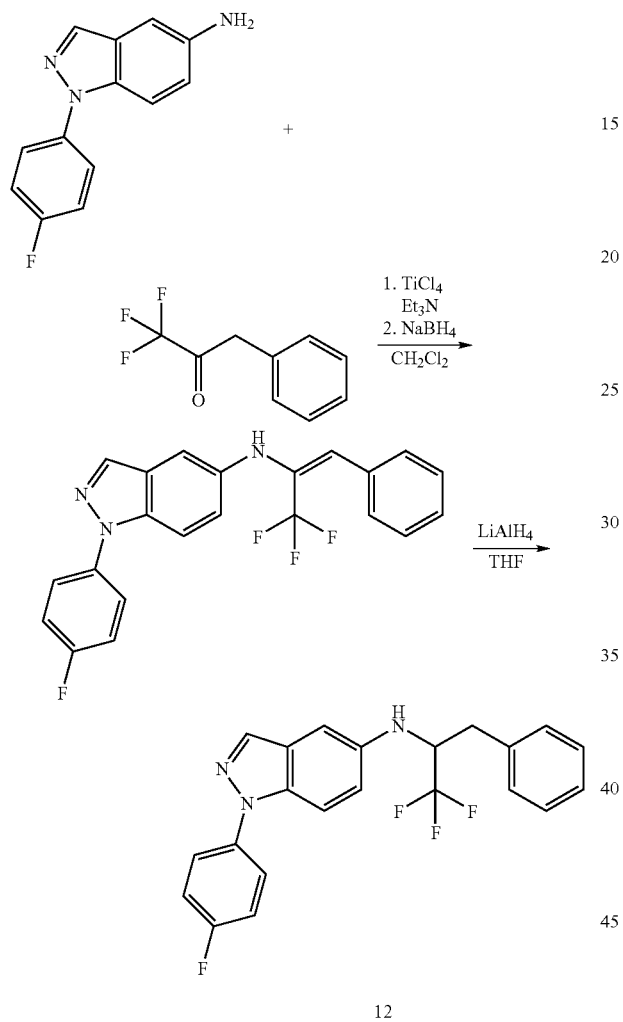

12

To a solution of 100 mg (0.44 mmol) of 1-(4-fluorophenyl)-1H-indazol-5-ylamine in 5 mL of dichloromethane was added 60 μL (1.04 mmol) of 1,1,1-trifluoro-3-phenylpropan-2-one, 70 μL (0.97 mmol) of triethylamine followed by 130 μL (1.02 mmol) of TiCl$_4$. The mixture was stirred for 20 hours and then MeOH was added followed by 200 mg (5.29 mmol) of sodium borohydride. After 1 hour, the mixture was diluted 50 mL of 1N aqueous NaOH and extracted with ethyl acetate. The combined organic layers were washed with brine, dried over sodium sulfate, and concentrated in vacuo. The crude material was purified by Combiflash chromatography using a EtOAc-hexanes (0-70% gradient) to provide 70 mg (37%) of [144-fluorophenyl)-1H-indazol-5-yl]-((E)-2-phenyl-1-trifluoromethylvinyl)amine as a yellow solid.

To a solution of 66 mg (0.17 mmol) of [1-(4-fluorophenyl)-1H-indazol-5-yl]-((E)-2-phenyl-1-trifluoromethylvinyl)amine in THF was added 10 mg (0.26 mmol) of lithium aluminum hydride. The mixture stirred for 2 hours at room temperature and was then quenched with saturated aqueous sodium sulfate and extracted with EtOAc. The organic layer was washed with brine, dried over sodium sulfate and concentrated. The crude was purified by prep. TLC using 100% dichloromethane to provide 10 mg (7%) of the title compound as a yellow solid. MS m/z 400 (MH+).

Example 13

2-Amino-4,6-dichloro-N-{2,2,2-trifluoro-1-[1-(4-fluorophenyl)-1H-indazol-5-yl]ethyl}benzenesulfonamide

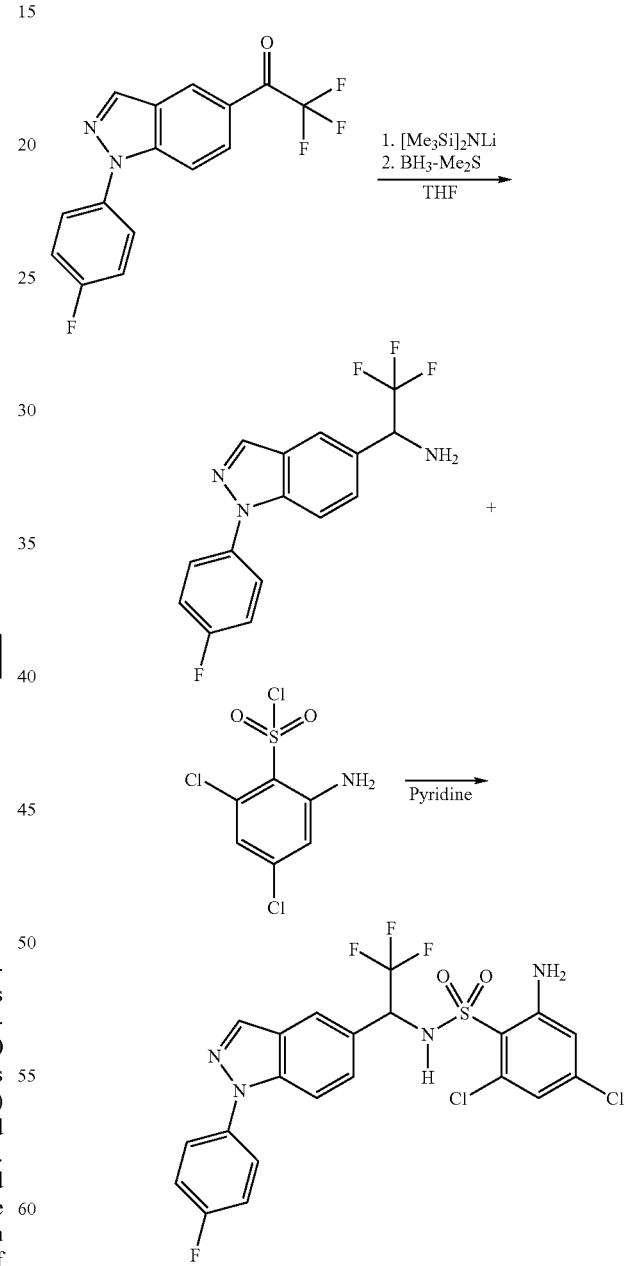

13

To a solution of 1.1 mL (1.1 mmol) of lithium bis(trimethylsilylamide) in THF was added a solution of 300 mg (0.97 mmol) of 2,2,2-trifluoro-1-[1-(4-fluorophenyl)-1H-indazol-5-yl]ethanone in 10 mL of toluene in several portions over a 10 minute period. The mixture stirred for 30 minutes at room temperature and then 1.0 mL (2.0 mmol) of a 2 M solution of $BH_3 \cdot SMe_2$ was added. After 1 hour, the mixture was cooled to 0° C. and 20 mL of 1N aqueous NaOH was added. After 20 minutes, the organic layer was separated and washed with two portions of 1N aqueous NaOH, brine, dried over sodium sulfate. and filtered. To the filtrate was added 2 mL of 4M solution of HCl in dioxane. The resulting solid was filtered, washed with ether, and dried in vacuo to provide 140 mg (41%) of 2,2,2-trifluoro-1-[1-(4-fluorophenyl)-1H-indazol-5-yl]ethylamine hydrochloride as a colorless powder.

A mixture of 60 mg (0.19 mmol) of 2,2,2-trifluoro-1-[1-(4-fluorophenyl)-1H-indazol-5-yl]ethylamine hydrochloride and 51 mg (0.19 mmol) of 2-amino-4,6-dichlorobenzenesulfonyl chloride in 8 mL of pyridine was stirred at room temperature for 1 hour and then warmed at 65° C. for 4 hours. The mixture was cooled to room temperature and diluted with 1N aqueous HCl and extracted with ethyl acetate. The combined organic layers were washed with saturated sodium bicarbonate, brine, dried over sodium sulfate, decanted, and concentrated in vacuo. The crude material was first purified by Combiflash chromatography using EtOAc-hexanes (0-60% gradient) and then by preparative TLC using EtOAc-hexanes (2:8) to provide 20 mg (17%) of the title compound as a colorless foam. MS m/z 534 (MH$^+$).

Example 14

2-(7-{2,2,2-Trifluoro-1-[1-(4-fluorophenyl)-1H-indazol-5-yl]ethylamino}indol-1-yl)acetamide

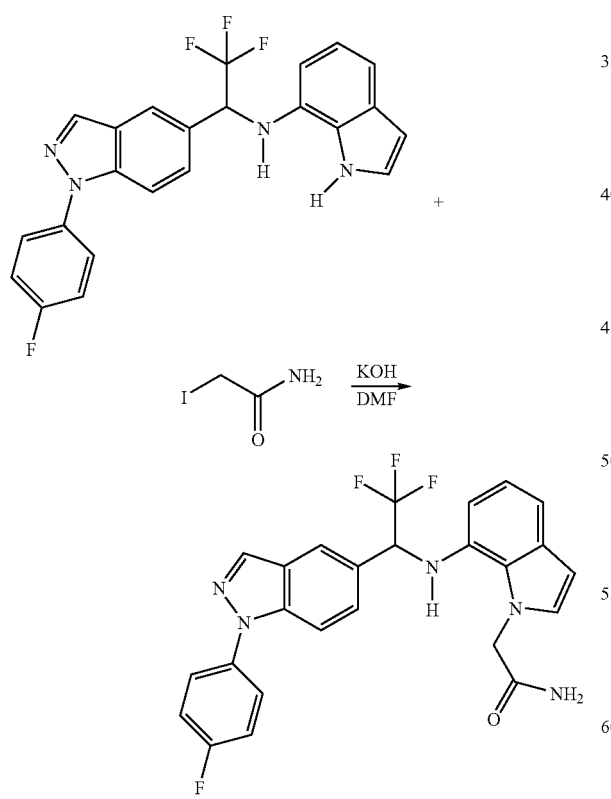

14

To a chilled (0° C.) solution of 78 mg (0.18 mmol) of (1H-Indol-7-yl)-{2,2,2-trifluoro-1-[1-(4-fluorophenyl)-1H-indazol-5-yl]ethyl}amine in 5 mL of DMF was added 15 mg (1.09 mmol) of powder KOH followed by 37 mg (1.09 mmol) of iodoacetamide. The mixture stirred overnight at room temperature. The mixture was then poured onto ice water and extracted with three 20 mL portions of ethyl acetate. The combined organic layers were washed with brine, saturated aqueous ammonium chloride, brine, and dried over sodium sulfate. The crude material was loaded onto a silica cartridge and purified by Combiflash chromatography using a 0-60% EtOAc-hexanes (0-60% gradient) to afford 30 mg (38%) of the title compound as a colorless foam, m.p. 105° C.

Example 15

2,2,2-Trifluoro-1-(1-methyl-1H-indol-3-yl)-1-(1-pyridin-3-yl-1H-indazol-5-yl)ethanol

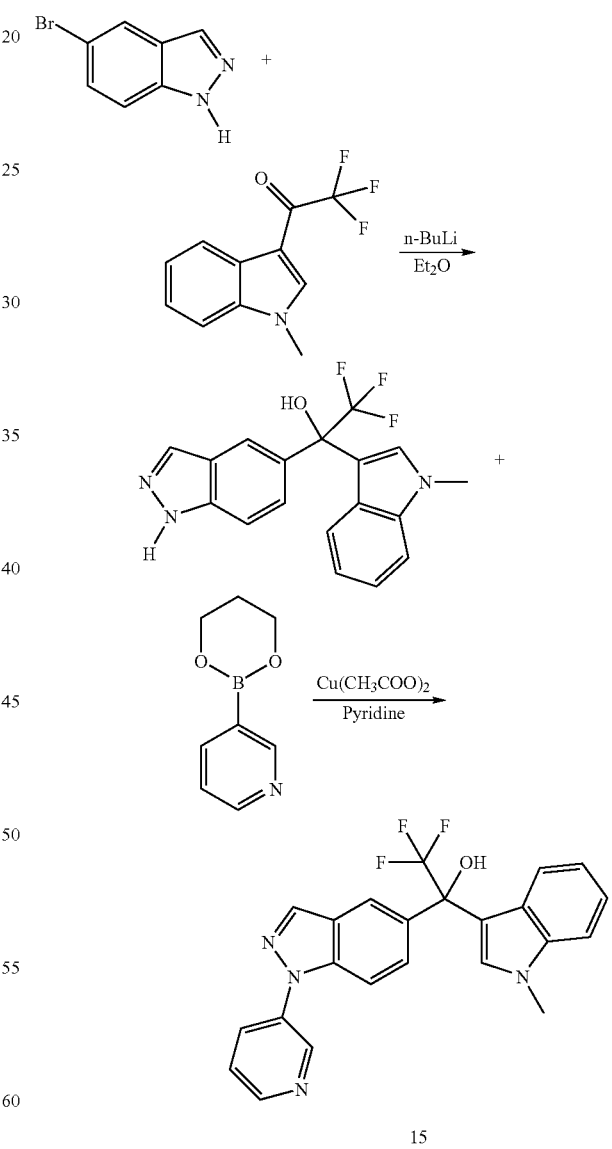

15

To a chilled (−78° C.) solution of 1.5 g (7.61 mmol) of 5-bromoindazole in 15 mL ether was added 9.2 mL (23.0 mmol) of a 2.5 M solution of n-butyllithium in hexanes. After 5 minutes, the cold bath was removed and the mixture stirred 6 hours at room temperature. The mixture was cooled to −78° C. and 3.5 g (15.4 mmol) of 2,2,2-trifluoro-1-(1-methyl-1H-indol-3-yl)ethanone in 4 mL of a 1:1 mixture of ether-THF was added. The mixture was stirred overnight while warming to room temperature and was then quenched with aqueous ammonium chloride and extracted with ether. The organic layer was washed with water, brine, and dried over magnesium sulfate. Removal of the volatiles in vacuo provided a residue which was purified by CombiFlash chromatography using 0-90% EtOAc-hexanes (product eluted at 35% EtOAc) to afford 700 mg (26%) of 2,2,2-trifluoro-1-(1H-indazol-5-yl)-1-(1-methyl-1H-indol-3-yl)ethanol as a pale yellow foam.

A mixture of 70 mg (0.20 mmol) of 2,2,2-trifluoro-1-(1H-indazol-5-yl)-1-(1-methyl-1H-indol-3-yl)ethanol, 65 mg (1.97 mmol) of 3-pyridyl boronic acid ester, 55 mg (0.3 mmol) of copper acetate and 50 μL (0.62 mmol) of pyridine in dry dichloromethane was stirred at room temperature. Oxygen gas was bubbled into the solution for 5 minutes and the mixture was stirred in a sealed tube. The reaction was monitored by LC-MS indicating partial conversion to product at 3 hours. The mixture was stirred overnight for 18 hours and then diluted with brine and extracted with EtOAc. The organic layer was washed with brine, dried over sodium sulfate, and absorbed onto silica gel and first purified by Combiflash chromatography using a 0-80% EtOAc-hexanes gradient and then by preparative TLC using 20% EtOAc-hexanes. Crystallization from ether-hexanes to gave 20 mg (26%) of the title compound as a colorless powder.

Example 16

2-{3-[2,2,2-Trifluoro-1-hydroxy-1-(1-pyridin-3-yl-1H-indazol-5-yl)ethyl]indol-1-yl}acetamide

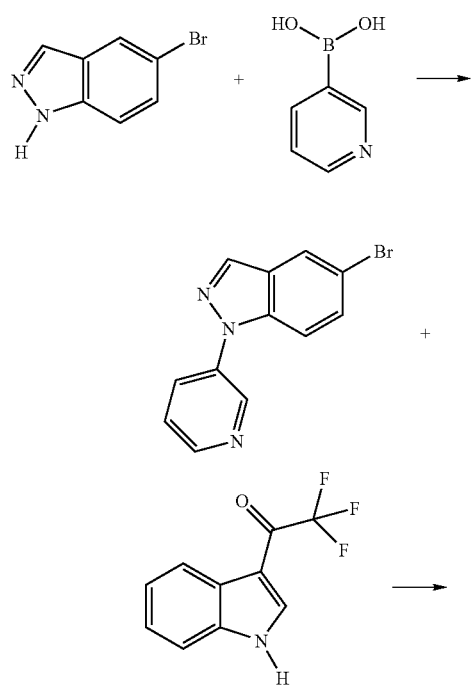

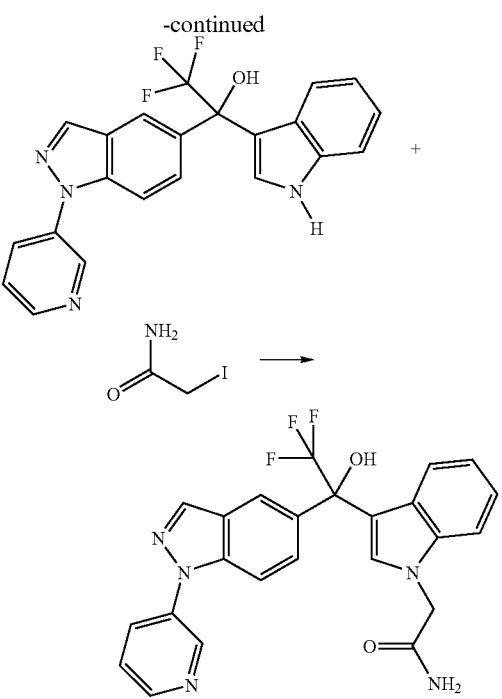

A mixture of 2.0 g (10.15 mmol) of 5-bromoindazole, 2.49 g (20.30 mmol) of 3-pyridyl boronic acid, 2.77 g (15.25 mmol) of copper acetate, and 2.4 mL of pyridine were dissolved in dry dichloromethane and stirred at room temperature. Oxygen gas was bubbled into the solution for 3 min and the mix was stirred in a screw top reaction vial in open atmosphere. After stirring overnight at room temperature, the reaction was monitored by LCMS which indicated ~10-15% conversion. The mixture was then warmed to 70° C. After 24 hours, the mixture was cooled to room temperature, diluted with brine and extracted with EtOAc. The organic was washed with brine, dried over sodium sulfate, and concentrated in vacuo onto silica gel. The crude was then purified by Combiflash chromatography using a 0-70% EtOAc/hexanes gradient (product eluted at 35% EtOAc). The product containing fractions were combined and concentrated in vacuo to afford 0.31 g (11%) of 5-bromo-1-pyridin-3-yl-1H-indazole.

To a chilled (−78° C.) solution of 241 mg (1.13 mmol) of 2,2,2-trifluoro-1-(1H-indol-3-yl)ethanone in 5 mL of anhydrous THF was added 45 mg (1.13 mmol) of 60% NaH in mineral oil. In another flask, 452 μL (1.13 mmol) of n-BuLi was then added to a chilled (−78° C.) solution of 310 mg (1.13 mmol) of 5-bromo-1-pyridin-3-yl-1H-indazole in 10 mL of THF. After 1 minute, the sodium salt of 2,2,2-trifluoro-1-(1H-indol-3-yl)ethanone was added to the indazole anion via a cannula. After 1 hour, the mixture was diluted with 25 mL of saturated aqueous ammonium chloride and extracted with three 15 mL portions of ethyl acetate. The combined organic layers were washed with three 10 mL portions of brine, dried over magnesium sulfate, filtered and concentrated. The crude material was purified using Combiflash chromatography using EtOAc-hexanes (0-70% gradient) to afford 45 mg (10%) of 2,2,2-trifluoro-1-(1H-indol-3-yl)-1-(1-pyridin-3-yl-1H-indazol-5-yl)ethanol as a colorless solid.

To a chilled (0° C.) solution of 45 mg (0.11 mmol) of 2,2,2-trifluoro-1-(1H-indol-3-yl)-1-(1-pyridin-3-yl-1H-indazol-5-yl)ethanol in 5 mL of DMF was added 13 mg (0.17 mmol) of powder KOH followed by 31 mg (0.17 mmol) of iodoacetamide. The mixture was stirred over night at room temperature, poured onto ice water and extracted with three 20 mL portions of ethyl acetate. The combined organic layers were dried over sodium sulfate, adsorbed on to silica gel and purified by Combiflash chromatography using EtOAc/hexanes (0-80% gradient, product eluted at 40% EtOAc) to provide a colorless film. The material from the column was crystallized from EtOAc-hexanes to afford 20 mg (39%) of the title compound as a colorless powder.

Example 17

2,2,2-Trifluoro-1-[1-(4-fluorophenyl)-1H-indazol-5-yl]-1-(5-methyl-6-methoxypyridin-3-yl)ethanol

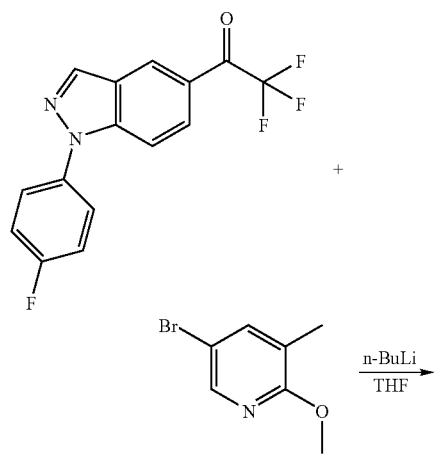

To a chilled (−78° C.) solution of 5-bromo-3-methyl-2-methoxypyridine (1.56 mmol) in 2 mL THF was added dropwise n-butyllithium (1.71 mmol from a 2.5 M solution in hexanes). The mixture was stirred for 30 minutes and then 2,2,2-trifluoro-1-[1-(4-fluorophenyl)-1H-indazol-5-yl]ethanone (1.39 mmol) in 3 mL THF was added. After 30 minutes, the mixture was diluted with ether and quenched with aqueous ammonium chloride. The organic layer was washed with brine and dried over magnesium sulfate. Removal of the volatiles in vacuo provided a residue which was purified by Combiflash chromatography using ethyl acetate-hexane. The product-rich fractions were concentrated in vacuo to provide the title compound.

Example 18

3-Methyl-5-{2,2,2-trifluoro-1-[1-(4-fluorophenyl)-1H-indazol-5-yl]-1-hydroxyethyl}-1H-pyridin-2-one

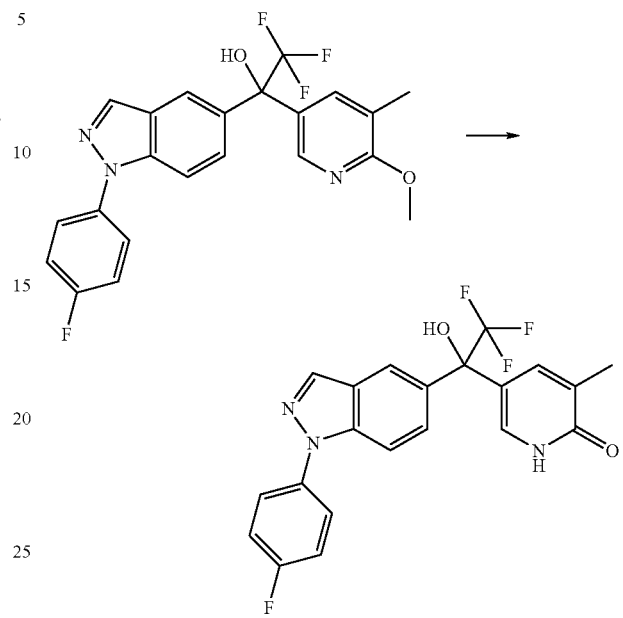

A mixture of 2,2,2-trifluoro-1-[1-(4-fluorophenyl)-1H-indazol-5-yl]-1-(5-methyl-6-methoxypyridin-3-yl)ethanol (0.679 mmol) and pyridinium hydrochloride (6.79 mmol) was warmed at 125° C. in a sealed tube for 20 minutes, cooled to room temperature and diluted with ether and water. The organic layer was washed with brine and dried over magnesium sulfate. The volatiles were removed in vacuo and the residue triturated with petroleum ether to provide the title compound.

Example 19

3-Methyl-2-oxo-5-{2,2,2-trifluoro-1-[1-(4-fluorophenyl)-1H-indazol-5-yl]-1-hydroxyethyl}-2H-pyridin-1-yl)acetamide

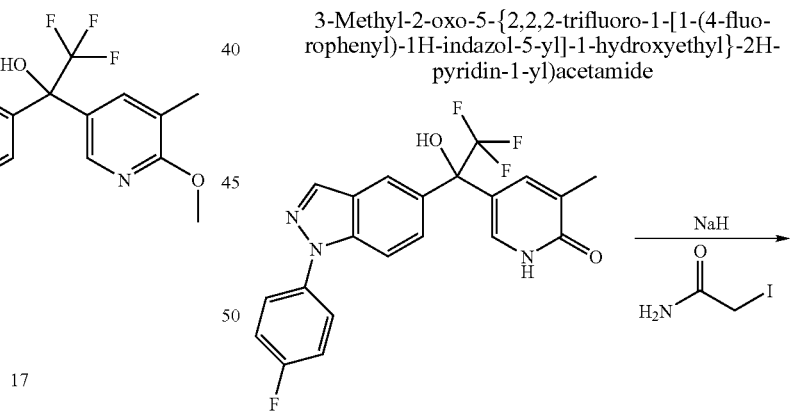

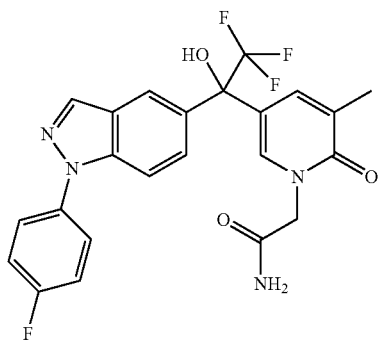

To a solution of 3-methyl-5-{2,2,2-trifluoro-1-[1-(4-fluorophenyl)-1H-indazol-5-yl]-1-hydroxyethyl}-1H-pyridin-2-one (0.17 mmol) in 1 mL DMF was added NaH (0.19 mmol; 60% suspension in oil) in several portions. After 1 hour, iodoacetamide (0.17 mmol) was added. The mixture was stirred overnight and diluted with ether and water. The organic layer was washed with water and brine and dried over magnesium sulfate. The volatiles were removed in vacuo and the residue purified by flash silica gel chromatography using 2% methanol in ethyl acetate. The product-rich fractions were concentrated in vacuo to provide 0.078 mmol of the title compound, m.p. 123° C.-125° C.

Example 20

1,3-Dimethyl-5-{2,2,2-trifluoro-1-[1-(4-fluorophenyl)-1H-indazol-5-yl]-1-hydroxyethyl}-1H-pyridin-2-one

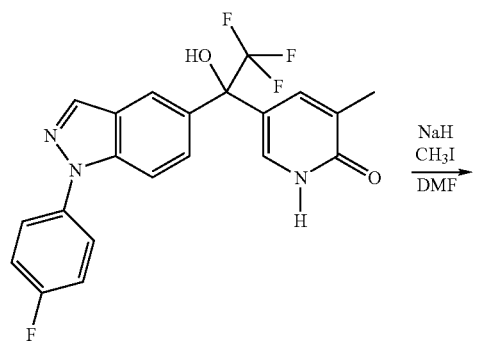

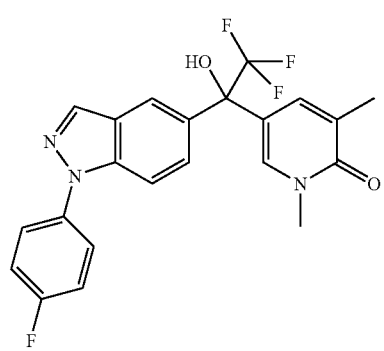

20

To a solution of 3-methyl-5-{2,2,2-trifluoro-1-[1-(4-fluorophenyl)-1H-indazol-5-yl]-1-hydroxyethyl}-1H-pyridin-2-one (0.184 mmol) in 1 mL DMF was added NaH (0.221 mmol; 60% suspension in oil) in several portions. After 1 hour, iodomethane (0.20 mmol) was added. After 1 hour, the mixture was diluted with water and the solid was collected by filtration, washed with water and dried. The residue was purified with flash silica gel chromatography using 25% hexanes in ethyl acetate. The product-rich fractions were concentrated in vacuo to provide the title compound (0.051 mmol), m.p.>200° C.

Example 21

Cyclobutyl-{5-[2,2,2-trifluoro-1-hydroxy-1-(1-methyl-1H-indol-3-yl)ethyl]indazol-1-yl}methanone

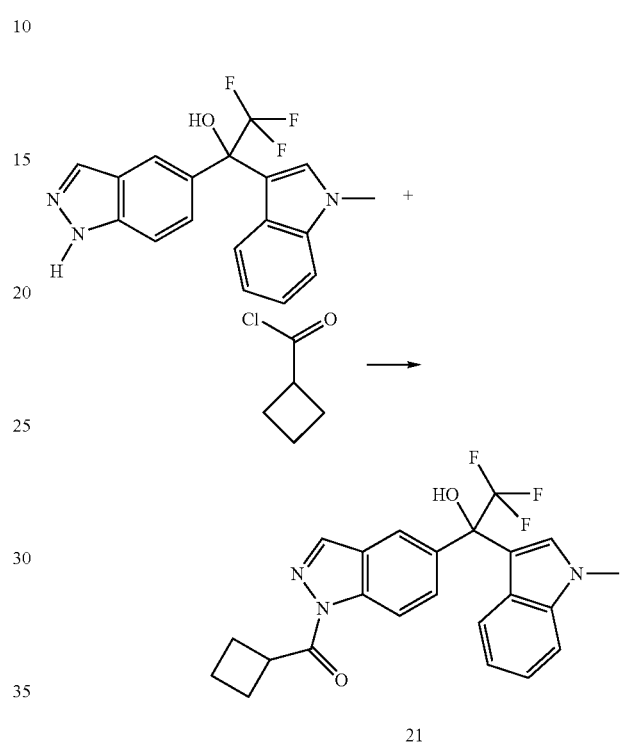

A mixture of 2,2,2-trifluoro-1-(1H-indazol-5-yl)-1-(1-methyl-1H-indol-3-yl)ethanol (0.122 mmol) and cyclobutanecarbonyl chloride (0.159 mmol) in 1 mL pyridine was heated at 100° C. for 1.5 hours, cooled to room temperature and diluted with ether and water. The organic layer was washed with water and brine and dried over magnesium sulfate. The volatiles were removed in vacuo and the residue purified by flash silica gel chromatography using 25% ethyl acetate in hexanes. The product-rich fractions were concentrated in vacuo to afford 0.091 mmol of the title compound, m.p. 79° C.-81° C.

Example 22

Phenyl-{5-[2,2,2-trifluoro-1-hydroxy-1-(1-methyl-1H-indol-3-yl)ethyl]indazol-1-yl}methanone

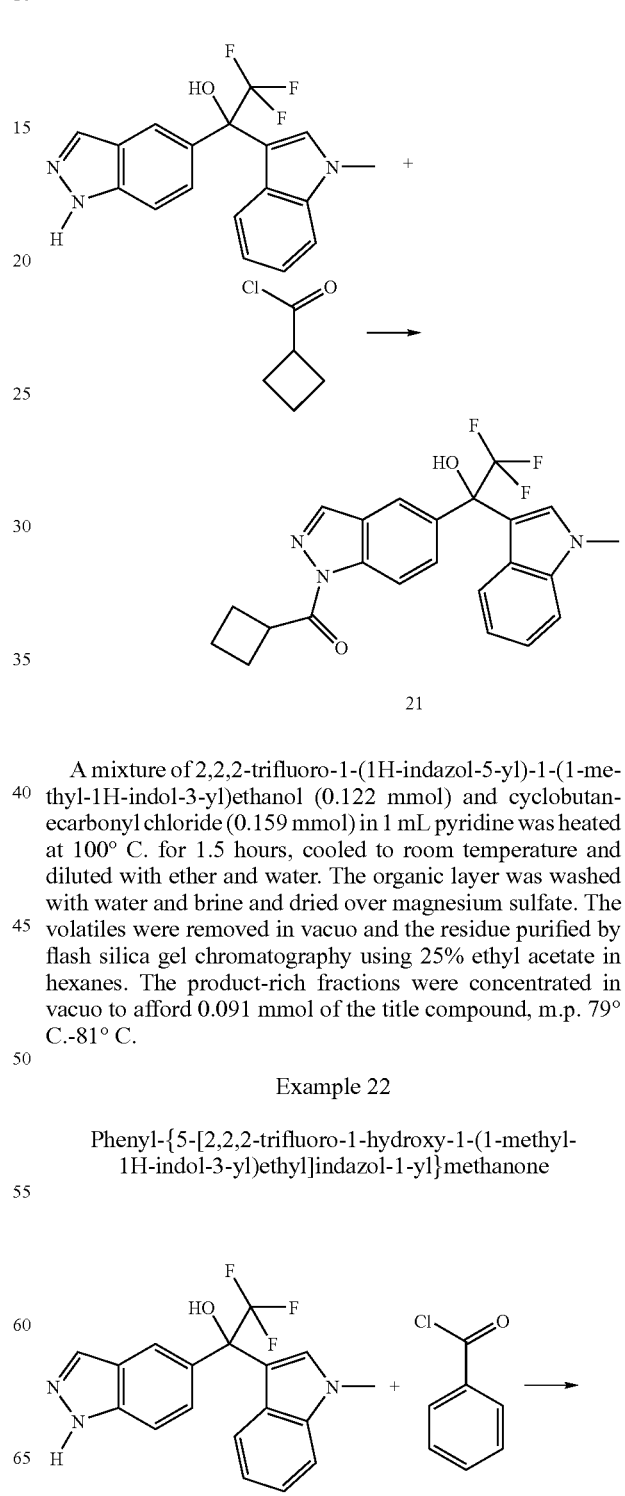

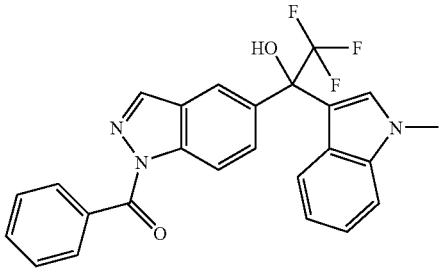

22

A mixture of 2,2,2-trifluoro-1-(1H-indazol-5-yl)-1-(1-methyl-1H-indol-3-yl)ethanol (0.162 mmol) and benzoyl chloride (0.324 mmol) in 1 mL pyridine was heated at 100° C. After 2 hours, the mixture was cooled to room temperature and diluted with ether and water. The organic layer was washed with aqueous HCl and brine and dried over magnesium sulfate. The volatiles were removed in vacuo and the residue purified by flash silica gel chromatography using 33% ethyl acetate in hexanes. The product-rich fractions were concentrated in vacuo to provide 0.093 mmol of the title compound, m.p. 102° C.-103° C.

Example 23

5-[1-(1-Allyl-1H-indol-3-yl)-2,2,2-trifluoro-1-hydroxyethyl]indazole-1-carboxylic acid ethylamide

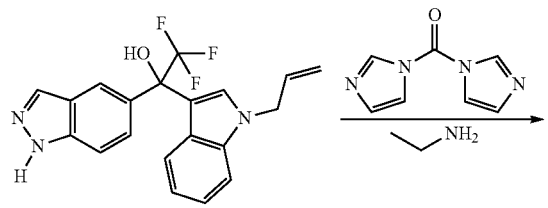

23

To a solution of carbonyldiimidazole (0.282 mmol) in 1 mL pyridine was added ethylamine (0.282 mmol; 2.0 M in THF) dropwise. The mixture was stirred 5 hours and then 2,2,2-trifluoro-1-(1H-indazol-5-yl)-1-(1-methyl-1H-indol-3-yl)ethanol (0.189 mmol) was added. The mixture was heated at 100° C. for 16 hours in a sealed tube. Removal of the volatiles provided a residue which was purified by flash silica gel chromatography using 33% ethyl acetate in hexanes. The product-rich fractions were concentrated in vacuo to afford the title compound (0.045 mmol), m.p. 162° C.-164° C.

Example 24

5-[2,2,2-Trifluoro-1-hydroxy-1-(1-methyl-1H-indol-3-yl)ethyl]indazole-1-carboxylic acid cyclopropylamide

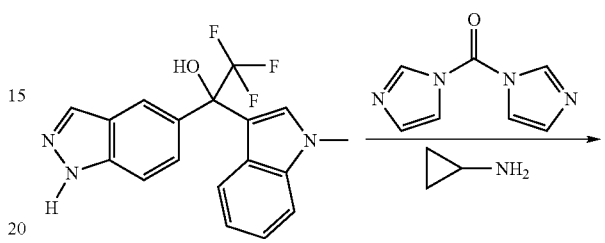

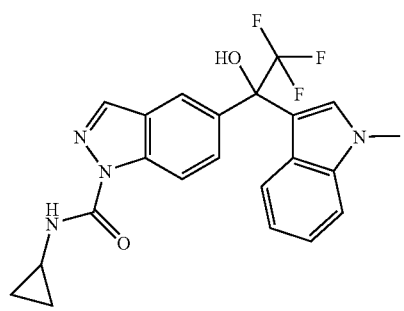

24

A mixture of 2,2,2-trifluoro-1-(1H-indazol-5-yl)-1-(1-methyl-1H-indol-3-yl)ethanol (0.437 mmol) and carbonyldiimidazole (0.546 mmol) in 3 mL of pyridine was heated at 85° C. for 10 hours and cooled to room temperature. The solution of imidazol-1-yl-{5-[2,2,2-trifluoro-1-hydroxy-1-(1-methyl-1H-indol-3-yl)ethyl]indazol-1-yl}methanone was taken forward without purification.

To a solution of imidazol-1-yl-{5-[2,2,2-trifluoro-1-hydroxy-1-(1-methyl-1H-indol-3-yl)ethyl]indazol-1-yl}-methanone (0.145 mmol) in 1 mL of pyridine was added cyclopropylamine (1.45 mmol). The mixture was stirred overnight, diluted with ether, washed with water and brine and dried over magnesium sulfate. The volatiles were removed in vacuo and the residue purified by flash silica gel chromatography using 33% ethyl acetate in hexanes. The product-rich fractions were concentrated in vacuo to provide the title compound, m.p. 116° C.-118° C.

Example 25

5-[1-(1-Methyl-1H-indol-3-yl)-2,2,2-trifluoro-1-hydroxyethyl]indazole-1-carboxylic acid isopropyl ester

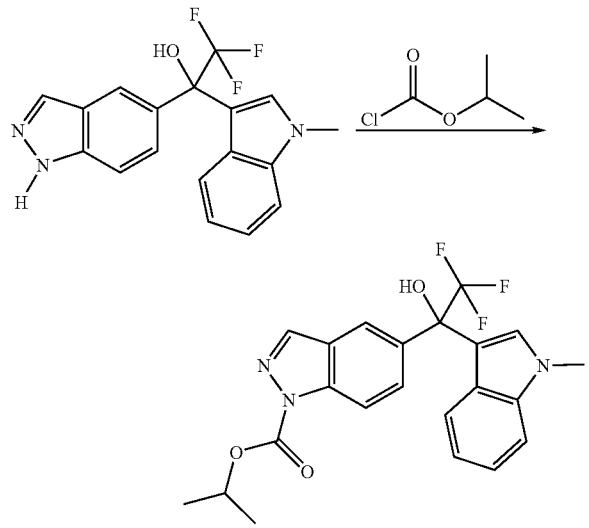

A mixture of 2,2,2-trifluoro-1-(1H-indazol-5-yl)-1-(1-methyl-1H-indol-3-yl)ethanol (0.165 mmol) and isopropyl chloroformate (0.49 mmol from a 1.0 M solution in toluene) in 1 mL of pyridine was heated at 85° C. for 10 hours, cooled to room temperature, and diluted with ether and water. The organic layer was washed with water and brine and dried over magnesium sulfate. The volatiles were concentrated in vacuo and the residue purified by flash silica gel chromatography using 33% ethyl acetate in hexanes. The product-rich fractions were concentrated in vacuo to afford 0.069 mmol of the desired compound, m.p. 105° C.-106° C.

Example 26

5-[1-(1-Methyl-1H-indol-3-yl)-2,2,2-trifluoro-1-hydroxyethyl]indazole-1-carboxylic acid cyclobutyl ester

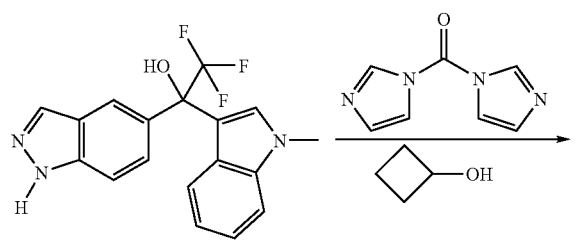

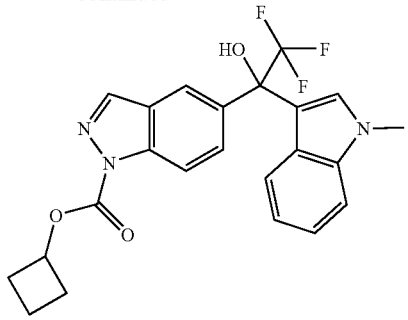

A mixture of 2,2,2-trifluoro-1-(1H-indazol-5-yl)-1-(1-methyl-1H-indol-3-yl)ethanol (0.142 mmol) and carbonyldiimidazole (0.185 mmol) in 1 mL of pyridine was heated at 80° C. for 10 hours, cooled to room temperature, and cyclobutanol (1.4 mmol) was added. The mixture was stirred overnight. The volatiles were removed and the residue purified by flash silica gel chromatography using 33% ethyl acetate in hexanes. The product-rich fractions were concentrated in vacuo to provide 0.076 mmol of the desired compound, m.p. 82° C.-84° C.

Example 27

(R)-1-(3-{2,2,2-Trifluoro-1-[1-(4-fluorophenyl)-1H-indazol-5-yl]-1-hydroxyethyl}indol-1-yl)propan-2-ol

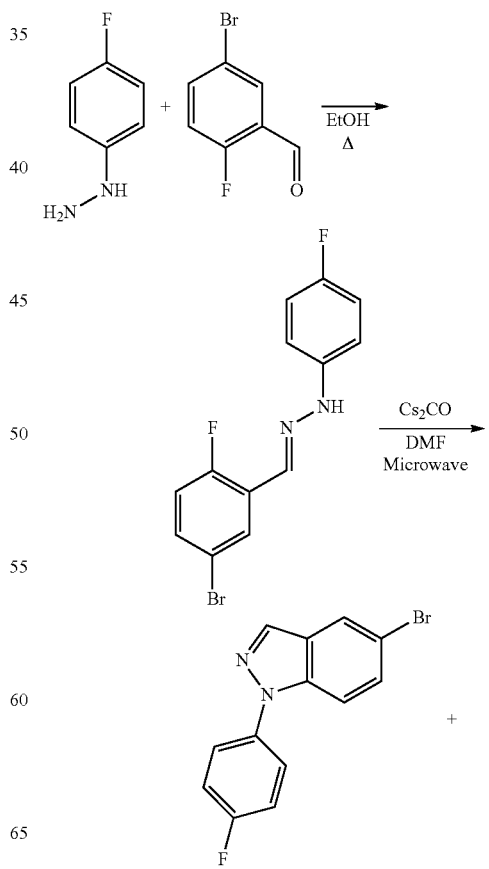

-continued

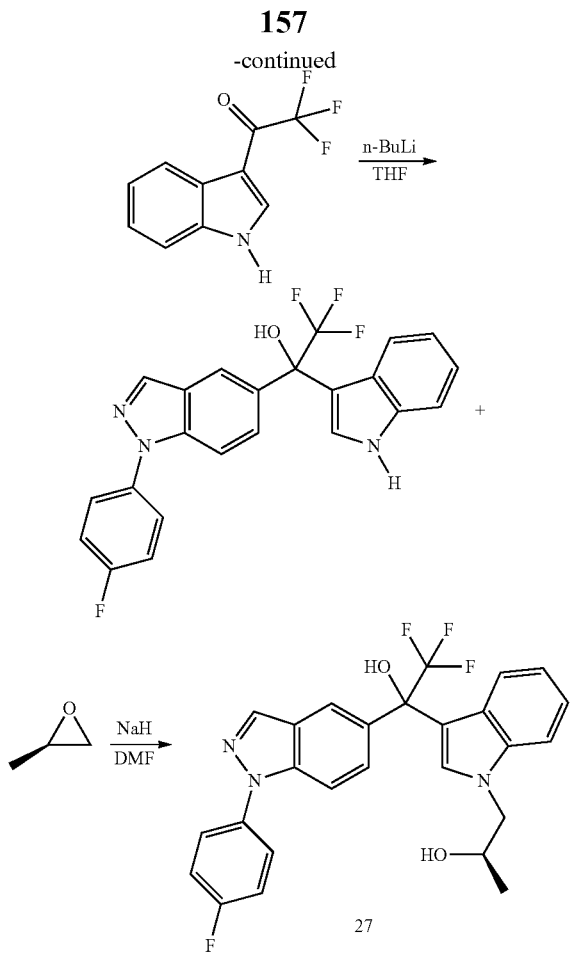

A 1000 mL round bottom flask was charged with 20.0 g (123 mmol) of 4-fluorophenylhydrazine and 28.4 g (140 mmol) of 5-bromo-2-fluorobenzaldehyde and 400 mL of EtOH and warmed at 90° C. After 2 hours, the mixture was cooled to room temperature and then diluted with 200 mL of water and filtered. The solid were then dissolved in EtOAc and washed with brine. The organic layer was dried over sodium sulfate, filtered and concentrated in vacuo. The residue was passed through a pad of silica gel to afford 37 g (97%) of N-[1-(5-bromo-2-fluorophenyl)meth-(E)-ylidene]-N'-(4-fluorophenyl)hydrazine. MS m/z 312.11 (MH+).

A 30 mL microwave vial was charged with 3.00 g (9.642 mmol) of N-[1-(5-bromo-2-fluorophenyl)meth-(E)-ylidene]-N'-(4-fluorophenyl)hydrazine and 3.14 g (9.64 mmol) of cesium carbonate and 10 mL of DMSO and sealed. The mixture was warmed at 220° C. in the microwave for 15 minutes cooled and opened at room temperature. The mixture was diluted with 10 mL of water and extracted with 20 mL of EtOAc. The organic layer was washed with brine, dried over sodium sulfate, filtered and concentrated in vacuo. The residue was absorbed onto silica gel and passed through a silica pad and eluted with 50% EtOAc-hexanes. The partially purified material from the pad was triturated with MeOH, collected by filtration, and dried to afford 2.8 g (99.7%) of 5-bromo-1-(4-fluorophenyl)-1H-indazole. MS m/z 279.11 (MH+).

To a chilled (−78° C.) solution of 2.67 g (9.20 mmol) 5-bromo-1-(4-fluorophenyl)-1H-indazole in 10 mL of anhydrous THF was added 7.36 mL (18.40 mmol) of a 2.5 M solution of n-butyllithium in hexane followed by a solution of 1.00 g (4.69 mmol) of 2,2,2-trifluoro-1-(1H-indol-3-yl)ethanone in 5 mL of THF in one portion. The reaction was then stirred at −78° C. for 30 minutes and quenched with 5 mL of water. The mixture was warmed to room temperature and extracted with ethyl acetate. The combined organic layer was washed with brine, dried over sodium sulfate and concentrated in vacuo. The residue was purified by flash chromatography (20%-40% ethyl acetate in hexanes). The major fractions were combined and concentrated to afford 978 mg of 2,2,2-trifluoro-1-[1-(4-fluorophenyl)-1H-indazol-5-yl]-1-(1H-indol-3-yl)ethanol. MS m/z 426.39 (MIT).

To a room temperature solution of 100 mg (0.23 mmol) of 2,2,2-trifluoro-1-[1-(4-fluorophenyl)-1H-indazol-5-yl]-1-(1H-indol-3-yl)ethanol in THF was added 20.0 mg (0.50 mmol) of 60% NaH in mineral oil. After hydrogen evolution ceased, 14.5 mg (0.25 mmol) of (R)-(+)-propylene oxide was added. The reaction was then warmed at 60° C. for 5 hours. The reaction was then cooled to room temperature and diluted with water and extracted with ether. The combined organic layers were washed with brine, dried over sodium sulfate, filtered, and concentrated in vacuo. The crude residue was purified by flash chromatography (20-40% ethyl acetate in hexanes). The major fractions were combined and concentrated to provide 53 mg (46.6%) of the title compound. MS m/z 484.47 (MH+).

The following additional compounds below were prepared by methods analogous to those described in Example 27:

(S)-1-(3-{2,2,2-Trifluoro-1-[1-(4-fluorophenyl)-1H-indazol-5-yl]-1-hydroxyethyl}indol-1-yl)propan-2-ol;

2,2,2-Trifluoro-1-[1-(4-fluorophenyl)-1H-indazol-5-yl]-1-[1-(tetrahydro-furan-2-ylmethyl)-1H-indol-3-yl]ethanol;

2,2,2-Trifluoro-1-[1-(4-fluorophenyl)-1H-indazol-5-yl]-1-[1-(2-morpholin-4-ylethyl)-1H-indol-3-yl]ethanol;

1-(1-Benzenesulfonyl-1H-indol-3-yl)-2,2,2-trifluoro-1-[1-(4-fluorophenyl)-1H-indazol-5-yl]ethanol; and 2,2,2-Trifluoro-1-[1-(4-fluorophenyl)-1H-indazol-5-yl]-1-[1-(propane-2-sulfonyl)-1H-indol-3-yl]ethanol.

Example 28

1-(5-Chlorothiophen-2-yl)-2,2,2-trifluoro-1-[1-(4-fluorophenyl)-1H-indazol-5-yl]ethanol

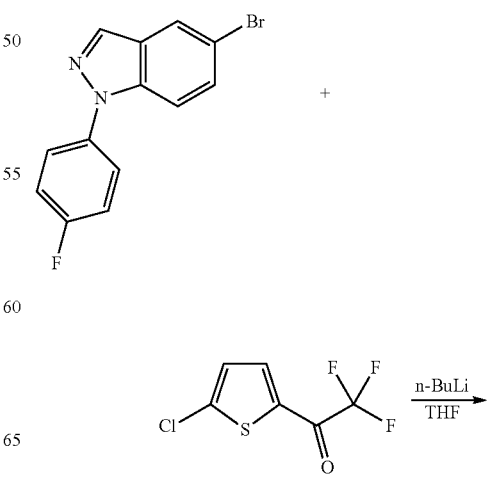

-continued

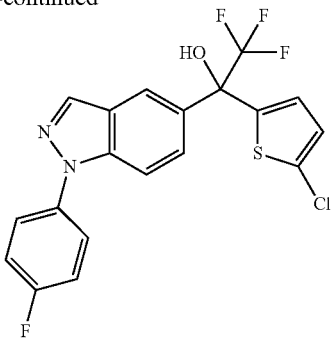

28

To a chilled (−78° C.) stirred solution of 1.5 g (5.0 mmol) of 5-bromo-1-(4-fluorophenyl)-1H-indazole in THF was added 2.0 mL (5.0 mmol) of n-butyllithium dropwise followed by 1.0 g (4.6 mmol) of 2-chloro-5-trifluoroacetylthiophene in one portion. After 30 minutes, the mixture was diluted with 10 mL of water, warmed to room temperature and extracted with ethyl acetate. The combined organic layers were washed with brine, dried over sodium sulfate, and concentrated in vacuo. The residue was purified by flash chromatography using ethyl acetate-hexanes (gradient 10-30%) to afford 300 mg (15.5%) of the title compound. MS m/z 427.82 (MH$^+$).

The following additional compounds below were prepared by methods analogous to those described in Example 28:
2,2,2-Trifluoro-1-[1-(4-fluorophenyl)-1H-indazol-5-yl]-1-(5-methylthiophen-2-yl)ethanol; and
1-(5-1,3-Dioxolan-2-ylthiophen-2-yl)-2,2,2-trifluoro-1-[1-(4-fluorophenyl)-1H-indazol-5-yl]ethanol.

Example 29

1-(5-Chloro-1,1-dioxo-1H-1λ$^6$-thiophen-2-yl)-2,2,2-trifluoro-1-[1-(4-fluorophenyl)-1H-indazol-5-yl]ethanol

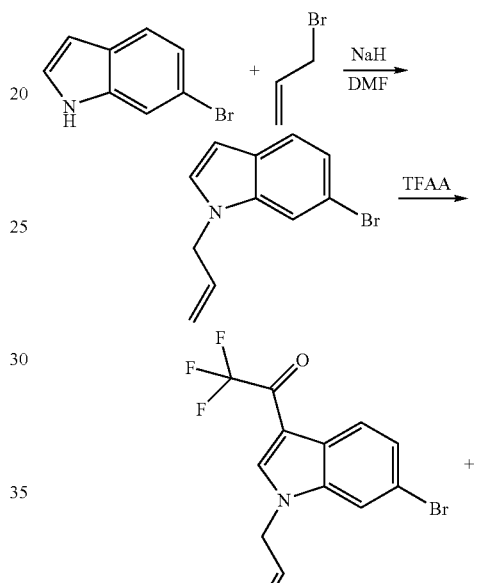

29

To a room temperature solution of 100 mg (0.2 mmol) of 1-(5-chlorothiophen-2-yl)-2,2,2-trifluoro-1-[1-(4-fluoro-rophenyl)-1H-indazol-5-yl]ethanol in 5 mL of CH$_2$Cl$_2$ was added 100 mg (0.5 mmol) of m-chloroperbenzoic acid. After 3 hours, the reaction was diluted with 5 mL of water and extracted with CH$_2$Cl$_2$. The combined organic layers were washed with brine, dried over sodium sulfate, and concentrated in vacuo. The residue was purified by flash chromatography using ethyl acetate in hexanes (10-30% gradient) to afford 14 mg (13%) of the title compound. MS m/z 459.82 (MH$^+$).

Example 30

1-(1-allyl-6-bromo-1H-indol-3-yl)-2,2,2-trifluoro-1-[1-(4-fluorophenyl)-1H-indazol-5-yl]ethanol

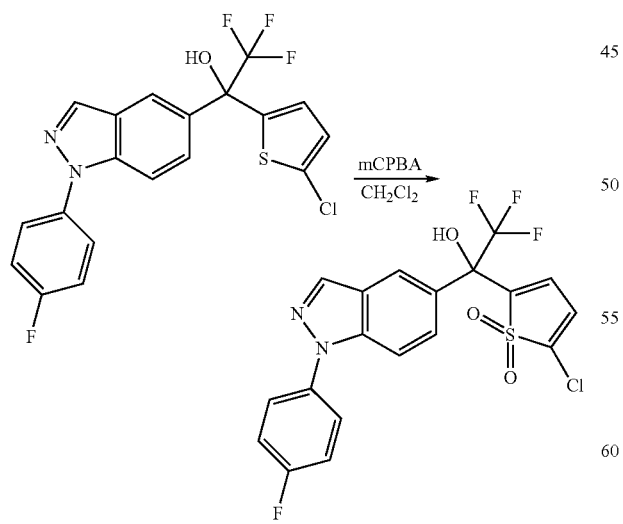

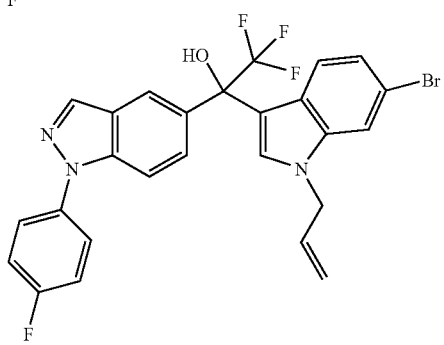

30

To a room temperature solution of 10.0 g (51.0 mmol) of 6-bromoindole in DMF was added 1.4 g (58.0 mmol) of 60%

NaH in mineral oil. Once evolution of hydrogen ceased, allyl bromide was added. After 2 hours, the reaction was quenched with water and was extracted with ethyl acetate. The combined organic layers were washed with brine, dried over sodium sulfate, and concentrated in vacuo to afford 11.8 g (98%) of 1-allyl-6-bromo-1H-indole. MS m/z 237.11 (MH⁺).

To a room temperature solution of 11.8 g (0.05 mol) of 1-allyl-6-bromo-1H-indole in THF was added 10 g of trifluoroacetic anhydride. After 4 hours, the reaction was diluted with and the resulting solid collected by filtration to afford 16.6 g (100%) of [1-(1-allyl-6-bromo-1H-indol-3-yl)-2,2,2-trifluoroethanone. MS m/z 333.11 (MH⁺).

To a chilled (−78° C.) solution of 0.9 g (3.1 mmol) of 1-allyl-6-bromo-1H-indole in anhydrous THF was added 1.3 mL (3.2 mmol) of a 2.5 M solution of n-butyllithium in one portion followed by a chilled (−78° C.) solution of 1.0 g (3.0 mmol) of 1-(1-allyl-6-bromo-1H-indol-3-yl)-2,2,2-trifluoroethanone in 5 mL THF in one portion. After 30 minutes, the mixture was quenched with 5 mL of water, warmed to room temperature, diluted with brine, and extracted with ethyl acetate. The combined organic layers were dried over sodium sulfate, filtered, and concentrated in vacuo. The residue was purified by flash chromatography using ethyl acetate-hexanes (0-30% gradient) to afford 0.5 g (32%) of the title compound. MS m/z 545.34 (MH⁺).

The following additional compounds below were prepared by methods analogous to those described in Example 30:

1-(6-Bromo-1-but-3-enyl-1H-indol-3-yl)-2,2,2-trifluoro-1-[1-(4-fluorophenyl)-1H-indazol-5-yl]ethanol; and 1-(1-But-3-enyl-1H-indol-3-yl)-2,2,2-trifluoro-1-[1-(4-fluorophenyl)-1H-indazol-5-yl]ethanol.

Example 31

1-[1-Allyl-6-(2H-pyrazol-3-yl)-1H-indol-3-yl]-2,2,2-trifluoro-1-[1-(4-fluorophenyl)-1H-indazol-5-yl]ethanol

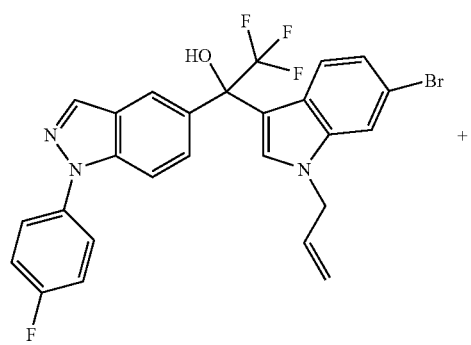

+

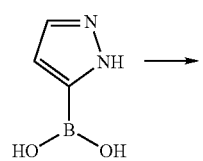

-continued

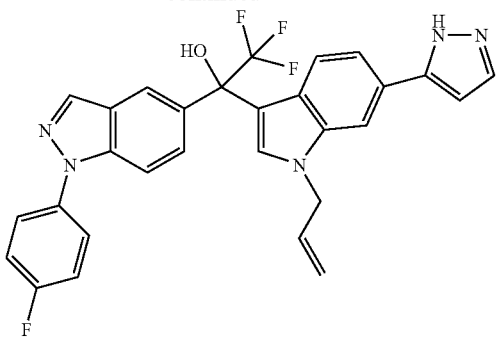

31

In a 10 mL microwave tube charged with 100.0 mg (0.18 mmol) of 1-(1-allyl-6-bromo-1H-indol-3-yl)-2,2,2-trifluoro-1-[1-(4-fluorophenyl)-1H-indazol-5-yl]ethanol, 40.3 mg (0.36 mmol) of 1H-pyrazole-5-boronic acid, 57.0 mg (0.53 mmol) of sodium carbonate, 23.1 mg (0.02 mmol) of tetrakis(triphenylphosphine)palladium, and 4 mL DMF was stirred in the microwave at 120° C. for 2.5 hours. The mixture was then cooled to room temperature, quenched with saturated ammonia chloride solution, and extracted with ethyl acetate. The combined organic layers were washed with brine, dried over sodium sulfate, filtered, and concentrated in vacuo. The residue was purified by flash chromatography using ethyl acetate-hexanes (30-80% gradient). The major fractions were combined and concentrated in vacuo to afford 35.0 mg (36%) of the title compound. MS m/z 532.5 (MH⁺).

Example 32

2,2,2-Trifluoro-1-[1-(4-fluorophenyl)-1H-indazol-5-yl]-1-[1-(4-methoxy-benzyl)-6-vinyl-1H-indol-3-yl]ethanol

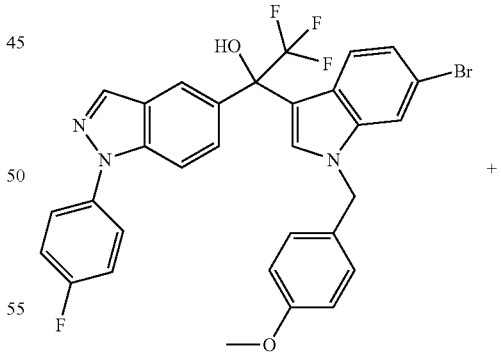

+

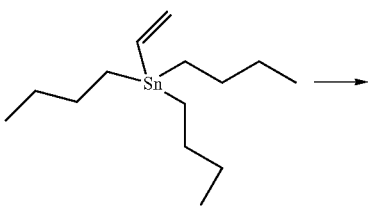

163

-continued

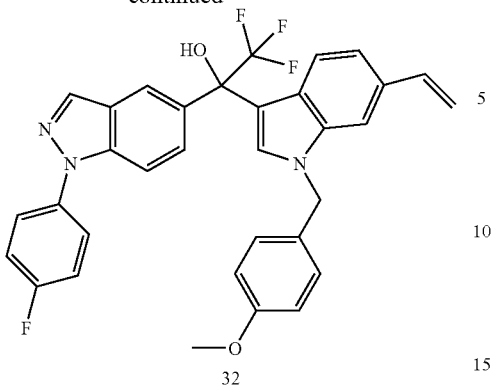

32

To a room temperature solution of 0.25 g (0.4 mmol) of 1-[6-bromo-1-(4-methoxybenzyl)-1H-indol-3-yl]-2,2,2-trifluoro-1-[1-(4-fluorophenyl)-1H-indazol-5-yl]ethanol in toluene was added 0.13 g (0.4 mmol) of tri-n-butyl(vinyl)tin. After 15 minutes, 3.0 mg of dichlorobis(triphenylphosphine) Pd (II) was added and the reaction was warmed to 100° C. and stirred overnight. The mixture was then cooled to room temperature, filtered through a pad of CELITE® filter aid, and concentrated in vacuo. The residue was purified by flash chromatography using ethyl acetate-hexanes (5-20% gradient) to afford 0.1 g (44%) of the title compound. MS m/z 572.6 (MH$^+$).

Example 33

1-(1-Allyl-6-pyrrolidin-1-yl-1H-indol-3-yl)-2,2,2-trifluoro-1-[1-(4-fluorophenyl)-1H-indazol-5-yl]ethanol

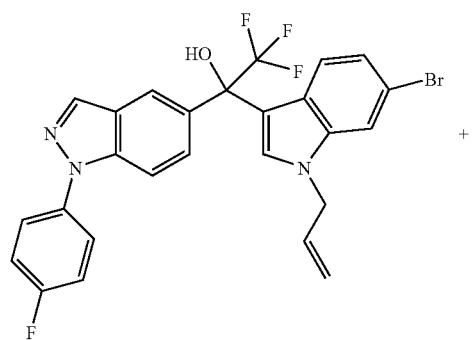

+

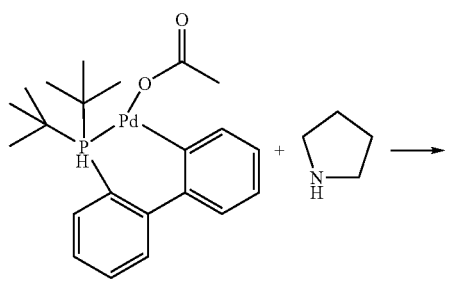

164

-continued

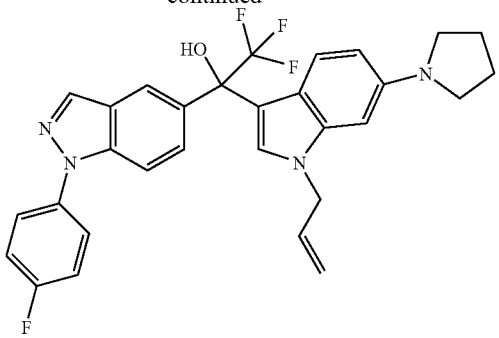

33

A mixture of 0.1 g (0.18 mmol) of 1-(1-allyl-6-bromo-1H-indol-3-yl)-2,2,2-trifluoro-1-[1-(4-fluorophenyl)-1H-indazol-5-yl]ethanol, 28.0 mg (0.4 mmol) of pyrrolidine, 5.0 mg of Pd catalyst (prepared according to a procedure described in *Org. Lett.* 2003 14 2413-2415), and 35.0 mg (0.36 mmol) of sodium tert-butoxide in 10 mL of dioxane was warmed at 90° C. After 2 hours, the mixture was cooled to room temperature, filtered through CELITE® filter aid, diluted with water, and extracted with ethyl acetate. The combined organic layers were washed with brine, dried over sodium sulfate, filtered and concentrated in vacuo. The residue was purified by flash chromatography using ethyl acetate in hexanes (30-80% gradient). The major fractions were combined and concentrated in vacuo to afford 21.0 mg 21.4%) of the title compound. MS m/z 534.5 (MH$^+$).

The following additional compound was prepared by methods analogous to those described in Example 33: 2,2,2-Trifluoro-1-[1-(4-fluorophenyl)-1H-indazol-5-yl]-1-[1-(4-methoxybenzyl)-6-pyrrolidin-1-yl-1H-indol-3-yl]ethanol.

Example 34

3-(6-bromo-3-{2,2,2-trifluoro-1-[1-(4-fluorophenyl)-1H-indazol-5-yl]-1-hydroxyethyl}indol-1-yl)propane-1,2-diol

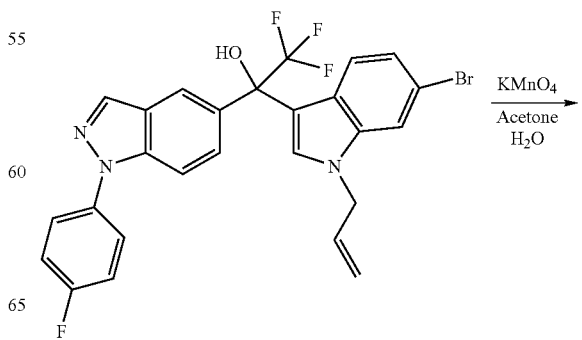

-continued

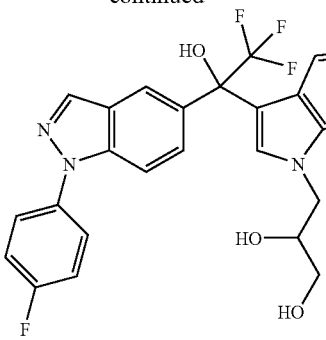

34

To a chilled (0° C.) solution of 0.3 g (0.5 mmol) 1-(1-allyl-6-bromo-1H-indol-3-yl)-2,2,2-trifluoro-1-[1-(4-fluorophenyl)-1H-indazol-5-yl]ethanol in acetone-H₂O (3:1) was added 93.2 mg (0.6 mmol) of KMnO₄ in 5 mL of a 3:1 mixture of acetone-H₂O dropwise. After 2 hours, the reaction was filtered and the solvent was concentrated in vacuo. The residue was diluted with water and extracted with ethyl acetate. The combined organic layers were dried over sodium sulfate, filtered and the solvent was concentrated in vacuo. The residue was purified by HPLC (5-100% CH₃CN-water buffered with TFA). The material from the column was concentrated, in vacuo to remove the acetonitrile. The aqueous layer was made basic and extracted with ethyl acetate. The combined organic layers were dried over sodium sulfate and concentrated in vacuo to afford 60 mg (23%) of the title compound. MS m/z 579.35 (MH⁺).

The following additional compounds below were prepared by methods analogous to those described in Example 34:
3-(6-Pyrrolidin-1-yl-3-{2,2,2-trifluoro-1-[1-(4-fluorophenyl)-1H-indazol-5-yl]-1-hydroxyethyl}indol-1-yl)propane-1,2-diol;
3-(6-(2H-Pyrazol-3-yl)-3-{2,2,2-trifluoro-1-[1-(4-fluorophenyl)-1H-indazol-5-yl]-1-hydroxyethyl}indol-1-yl)propane-1,2-diol;
3-(6-Bromo-3-{2,2,2-trifluoro-1-[1-(4-fluorophenyl)-1H-indazol-5-yl]-1-hydroxyethyl}indol-1-yl)propane-1,2-diol; and
4-(3-{2,2,2-Trifluoro-1-[1-(4-fluorophenyl)-1H-indazol-5-yl]-1-hydroxyethyl}indol-1-yl)-butane-1,2-diol.

Example 35

2-(6-Bromo-3-{2,2,2-trifluoro-1-[1-(4-fluorophenyl)-1H-indazol-5-yl]-1-hydroxyethyl}indol-1-yl)-N-methylacetamide

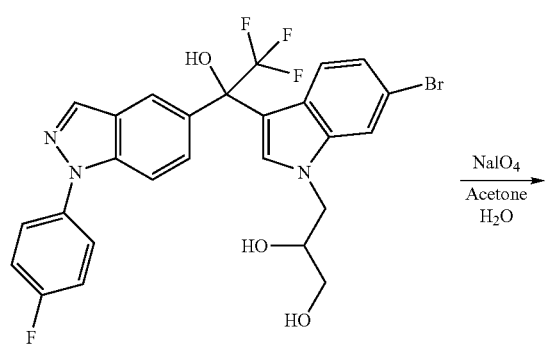

-continued

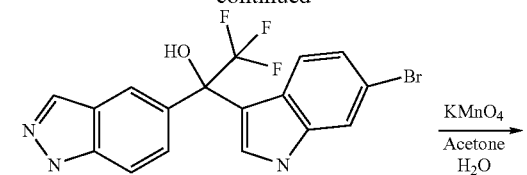

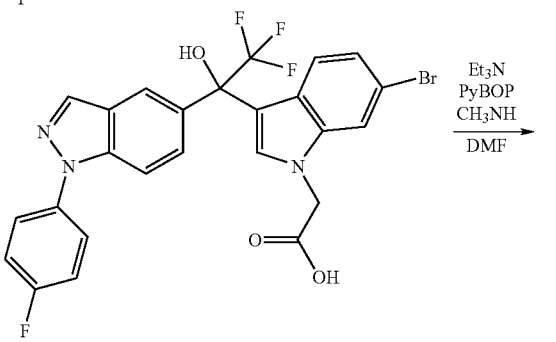

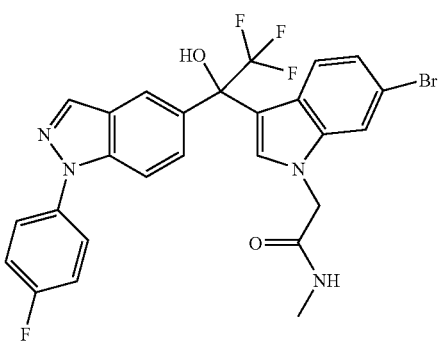

35

To a room temperature solution of 75 mg (0.13 mmol) of 3-(6-bromo-3-{2,2,2-trifluoro-1-[1-(4-fluorophenyl)-1H-indazol-5-yl]-1-hydroxyethyl}indol-1-yl)propane-1,2-diol in acetone-H₂O (3:1) was added 34.2 mg (0.16 mmol) of sodium periodate. After 2 hours, the mixture was concentrated in vacuo. The residue was basified and extracted with ethyl acetate. The combined organic layers were washed with brine, dried over sodium sulfate, filtered, and concentrated in vacuo to afford 60 mg (71%) of (6-bromo-3-{2,2,2-trifluoro-1-[1-(4-fluorophenyl)-1H-indazol-5-yl]-1-hydroxyethyl}indol-1-yl)acetaldehyde. MS m/z 547.31 (MH⁺).

To a room temperature solution of 60.0 mg (0.11 mmol) of 6-bromo-3-{2,2,2-trifluoro-1-[1-(4-fluorophenyl)-1H-indazol-5-yl]-1-hydroxyethyl}indol-1-yl)acetaldehyde in acetone-H₂O (3:1) was added 37.9 mg (0.24 mmol) of KMnO₄. After 2 hours, the mixture was filtered and the solid was washed with ethyl acetate and concentrated in vacuo. The residue was diluted with water, saturated aqueous ammonia chloride and extracted with ethyl acetate. The combined organic layers were dried over sodium sulfate, filtered and concentrated in vacuo to afford 61.0 mg (96%) of (6-bromo-3-{2,2,2-trifluoro-1-[1-(4-fluorophenyl)-1H-indazol-5-yl]-1-hydroxyethyl}indol-1-yl)acetic acid. MS m/z 563.31 (MH⁺).

To a room temperature solution of 135 mg (0.24 mmol) of (6-bromo-3-{2,2,2-trifluoro-1-[1-(4-fluorophenyl)-1H-indazol-5-yl]-1-hydroxyethyl}indol-1-yl)acetic acid in 1 mL of DMF was added 121 mg (1.2 mmol) of triethylamine followed by 210 mg (0.40 mmol) of benzotriazole-1-yloxytris (pyrrolidino)phosphonium hexafluorophosphate (PyBOP). After 5 minutes, 162 mg (2.4 mmol) of methyl amine was added. The mixture stirred overnight and was filtered and purified by HPLC using $CH_3CN$-water buffered with 0.1% TFA (5-90% gradient). The material from the column was concentrated to remove $CH_3CN$. The resulting aqueous portion was extracted with ethyl acetate. The combined organics were dried over sodium sulfate, filtered, and concentrated in vacuo to afford 20.0 mg (15%) of the title compound. LCMS [M+H]=576.35.

The following additional compounds below were prepared by methods analogous to those described in Example 35:
(3-{2,2,2-Trifluoro-1-[1-(4-fluorophenyl)-1H-indazol-5-yl]-1-hydroxyethyl}indol-1-yl)acetic acid;
3-(3-{2,2,2-Trifluoro-1-[1-(4-fluorophenyl)-1H-indazol-5-yl]-1-hydroxyethyl}indol-1-yl)propionamide; and
N-Methyl-3-(3-{2,2,2-trifluoro-1-[1-(4-fluorophenyl)-1H-indazol-5-yl]-1-hydroxyethyl}indol-1-yl)propionamide.

Example 36

2,2,2-Trifluoro-1-[1-(4-fluorophenyl)-1H-indazol-5-yl]-1-{1-[3-(4-hydroxymethylpiperidin-1-yl)propyl]-1H-indol-3-yl}ethanol To a chilled (0° C.) solution of 100 mg (0.21 mmol) of 3-(3-{2,2,2-trifluoro-1-[1-(4-fluorophenyl)-1H-indazol-5-yl]-1-hydroxyethyl}indol-1-yl)propionaldehyde (prepared according to methods described in Examples 34 and 35) in dichloroethane was added 160 mg (2.6 mmol) acetic acid and 300 mg (2.6 mmol) 4-piperidinemethanol. The solution was warmed to room temperature, stirred for 30 minutes, and 0.1 g (0.5 mmol) of sodium triacetoxyborohydride was added. The solution was stirred at room temperature overnight. The reaction was diluted with water and extracted with ethyl acetate, the aqueous layer was separated and the organic layers were combined and washed with saturated sodium bicarbonate, brine, dried over sodium sulfate, filtered, and concentrated in vacuo. The residue was purified by prep-HPLC to afford 42 mg (34.8%) of the title compound. MS m/z 581.6 (MH$^+$).

The following additional compounds below were prepared by methods analogous to those described in Example 36:
1-{1-[3-((S)-3-Dimethylaminopyrrolidin-1-yl)propyl]-1H-indol-3-yl}-2,2,2-trifluoro-1-[1-(4-fluorophenyl)-1H-indazol-5-yl]ethanol;
1-{1-[3-((R)-3-Dimethylaminopyrrolidin-1-yl)propyl]-1H-indol-3-yl}-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(3-pyrrolidin-1-ylpropyl)-1H-indol-3-yl]ethanol;
2,2,2-Trifluoro-1-[1-(4-fluorophenyl)-1H-indazol-5-yl]-1-[1-[3-(4-methylpiperazin-1-yl)propyl]-1H-indol-3-yl]ethanol;
2,2,2-Trifluoro-1-[1-(4-fluorophenyl)-1H-indazol-5-yl]-1-[1-(3-methylaminopropyl)-1H-indol-3-yl]ethanol;
2,2,2-Trifluoro-1-[1-(4-fluorophenyl)-1H-indazol-5-yl]-1-[1-(3-morpholin-4-ylpropyl)-1H-indol-3-yl]ethanol; and
1-[1-(3-Dimethylaminopropyl)-1H-indol-3-yl]-2,2,2-trifluoro-1-[1-(4-fluorophenyl)-1H-indazol-5-yl]ethanol.

Example 37

1-(1-Allyl-5-hydroxymethyl-1H-pyrrol-3-yl)-2,2,2-trifluoro-1-[1-(4-fluorophenyl)-1H-indazol-5-yl]ethanol

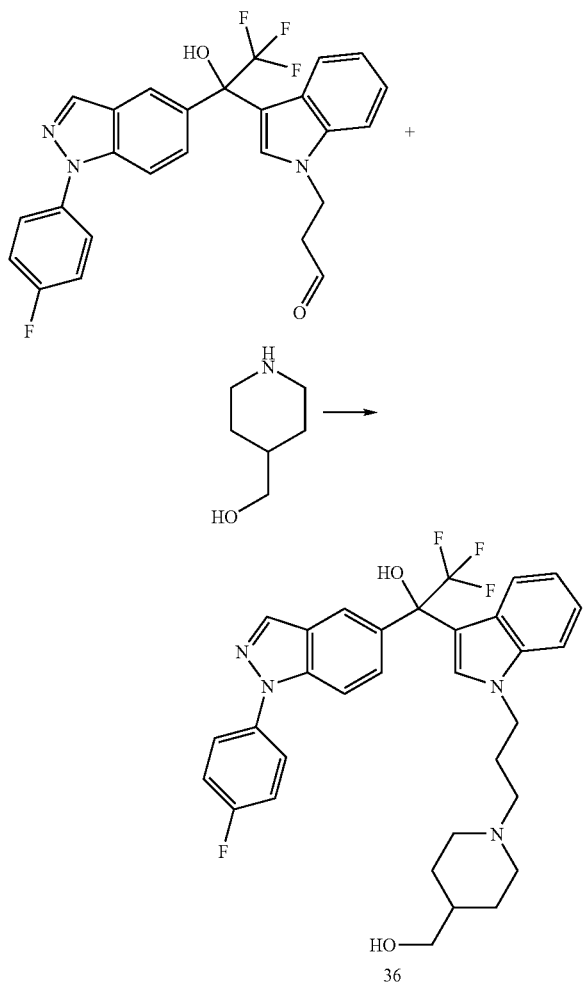

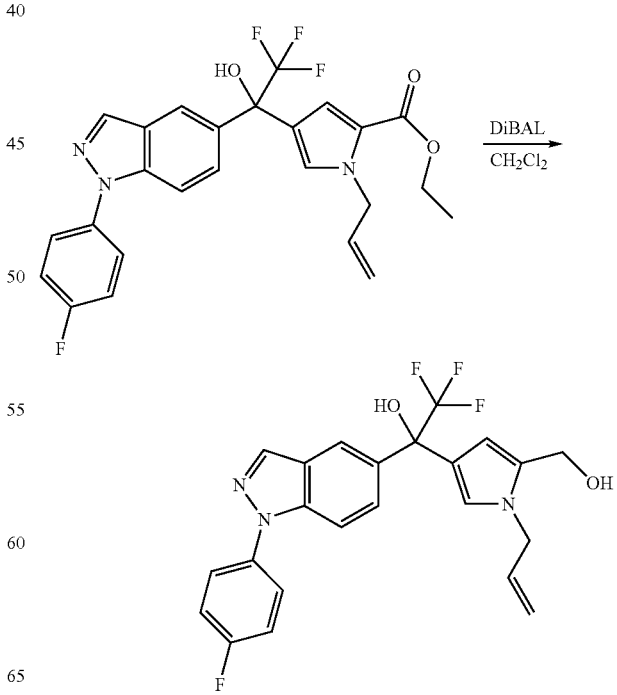

To a chilled (0° C.) solution of 250 mg (0.51 mmol) 1-allyl-4-{2,2,2-trifluoro-1-[1-(4-fluorophenyl)-1H-indazol-5-yl]-1-hydroxyethyl}-1H-pyrrole-2-carboxylic acid ethyl ester in anhydrous $CH_2Cl_2$ was added 1.5 mL (1.5 mmol) of a 1 M solution of diisobutylaluminum hydride (DIBAL) in $CH_2Cl_2$. The reaction was warmed to reflux and stirred overnight. The reaction was cooled to room temperature, poured into 100 mL of 1N aqueous HCl, then made basic with saturated aqueous sodium bicarbonate, and extracted with ethyl acetate. The combined organic layers were washed with brine, dried over sodium sulfate, and concentrated in vacuo. The residue was purified by HPLC using $CH_3CN$—$H_2O$ buffered with 0.1% TFA (5-90% gradient). The fractions from the column were concentrated in vacuo to remove $CH_3CN$ and then the resulting aqueous layer was extracted with ethyl acetate. The combined organic layers were washed with brine, dried over sodium sulfate. The solvent was concentrated in vacuo to afford 8.0 mg (4%) of the title compound. MS m/z 446.41 ($MH^+$).

Example 38

1-Allyl-4-{2,2,2-trifluoro-1-[1-(4-fluorophenyl)-1H-indazol-5-yl]-1-hydroxyethyl}-1H-pyrrole-2-carboxylic acid ethyl ester

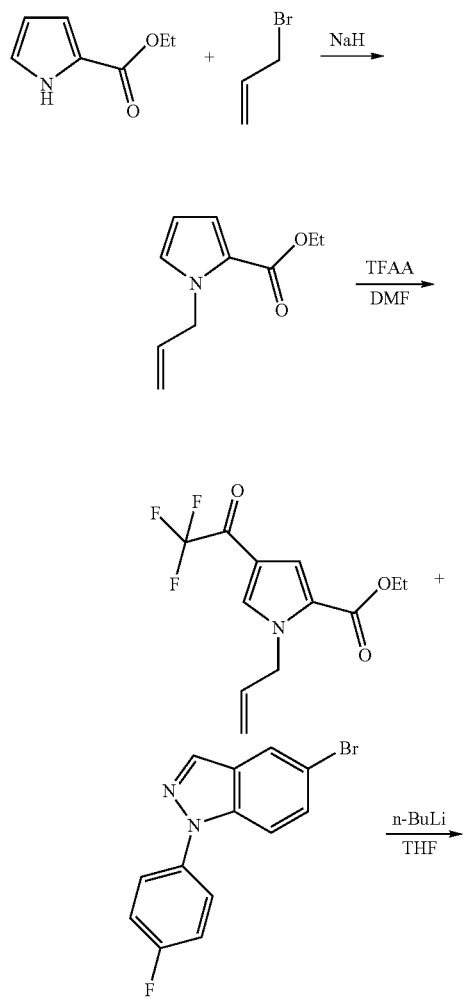

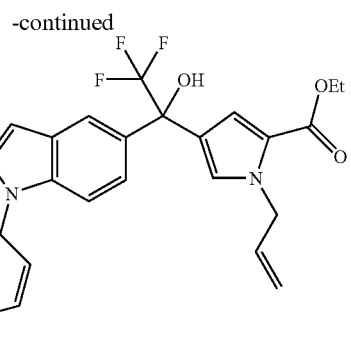

38

To a chilled (0° C.) solution of ethyl 2-pyrrolocarboxylate (10.0 g, 71.9 mmol) in 100 mL of DMF was added NaH (60% in mineral oil, 4.3 g, 107.8 mmol) in several portions. Once hydrogen evolution ceased, allyl bromide (7.3 ml, 121.0 mmol) was added and the reaction allowed warm to room temperature. After 2 hours, the mixture was poured into 400 mL of water and extracted with $Et_2O$. The combined organic layers were dried, filtered, and concentrated in vacuo. The residue was purified by flash chromatography (0-10% EtOAc-hexanes). The major fraction was combined and concentrated in vacuo to provide 12.5 g (97%) of 1-allyl-1H-pyrrole-2-carboxylic acid ethyl ester as a yellow oil.

Using the procedure described above, 1-allyl-1H-pyrrole-2-carbonitrile was prepared from 2-cyanopyrrole in quantitative yield.

In a 50 mL flask charged with 1-allyl-1H-pyrrole-2-carboxylic acid ethyl ester (2.0 g, 11.2 mmol) and 10 mL of DMF was added trifluoroacetic anhydride (2.3 mL, 16.7 mmol). The mixture was warmed at 70° C. After 48 hours, the reaction was poured into 300 mL of water and extracted with ethyl ether. The combined organics were dried, filtered, and evaporated. The residue was purified by flash chromatography (10% EtOAc/hex) to provide 1.74 g (57%) of the desired 1-allyl-4-(2,2,2-trifluoroacetyl)-1H-pyrrole-2-carboxylic acid ethyl ester as a yellow oil which was used without further purification.

To a chilled (−78° C.) solution of 5-bromo-1-(4-fluorophenyl)-1H-indazole (2.0 g, 6.8 mmol, 1.2 equiv.) in 20 mL of THF was added n-BuLi (2.5 mL, 6.2 mmol, 1.1 equiv.) followed by a chilled (−78° C.) solution of 1-allyl-4-(2,2,2-trifluoroacetyl)-1H-pyrrole-2-carboxylic acid ethyl ester (1.6 g, 5.7 mmol, 1.0 equiv.) in 3 mL of THF in one portion. After 30 minutes, the mixture was quenched with water, warmed to room temperature, diluted with brine, and extracted with EtOAc. The combined organics were dried, filtered, and concentrated in vacuo. The residue was purified by flash chromatography (5-30% EtOAc-hexanes) to provide 890 mg (32%) of the title compound as a pale orange solid. MS m/z 488.30 (MH+).

Example 39

1-Allyl-4-{2,2,2-trifluoro-1-[1-(4-fluorophenyl)-1H-indazol-5-yl]-1-hydroxyethyl}-1H-pyrrole-2-carboxylic acid

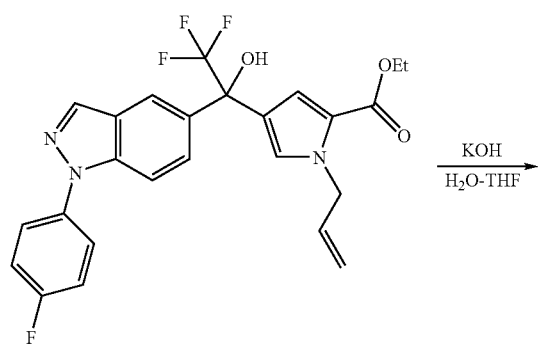

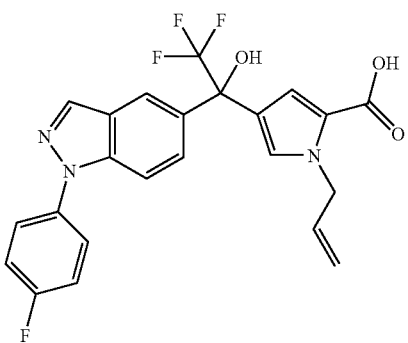

39

A mixture of 1-allyl-4-{2,2,2-trifluoro-1-[1-(4-fluorophenyl)-1H-indazol-5-yl]-1-hydroxyethyl}-1H-pyrrole-2-carboxylic acid ethyl ester (728 mg, 1.5 mmol) in 5 mL of EtOH and 30 mL of 3 M NaOH was stirred at room temperature. After 18 hours, the mixture was neutralized with saturated aqueous ammonium chloride, diluted with water, and extracted with EtOAc. The combined organic layers were dried, filtered, and concentrated in vacuo to provide 660 mg (96%) of the title compound as a beige solid. MS m/z 460.25 (MH+).

Example 40

1-Allyl-4-{2,2,2-trifluoro-1-[1-(4-fluorophenyl)-1H-indazol-5-yl]-1-hydroxyethyl}-1H-pyrrole-2-carboxylic acid dimethylamide

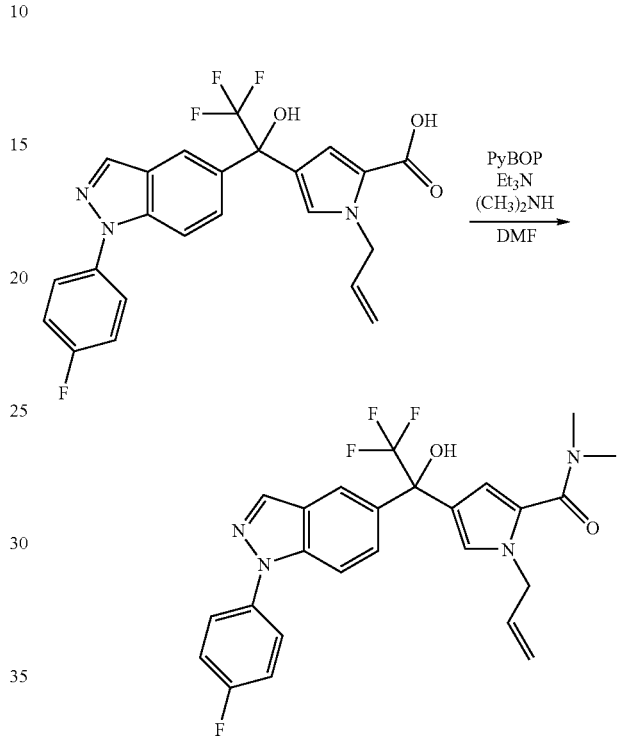

40

To a solution of 1-allyl-4-{2,2,2-trifluoro-1-[1-(4-fluorophenyl)-1H-indazol-5-yl]-1-hydroxyethyl}-1H-pyrrole-2-carboxylic acid (400 mg, 0.87 mmol, 1 equiv.) in 10 ml of DMF was added 0.22 mL of triethylamine (1.7 mmol, 2 equiv.) and PyBOP (500 mg, 0.96 mmol, 1.1 equiv.) followed by dimethylamine (2 M in THF, 1.3 mL, 2.6 mmol, 3 equiv.). After 18 hours, the mixture was diluted with 50 mL of brine and 50 mL of water and extracted with ethyl ether. The combined organic layers were dried, filtered, and concentrated in vacuo. The residue was purified by flash chromatography using EtOAc-hexanes (10-60% gradient) to afford 354 mg (84%) of the title compound as a white solid. MS m/z 487.29 (MH+).

The following additional compounds below were prepared by methods analogous to those described in Example 40:
1-Allyl-4-{2,2,2-trifluoro-1-[1-(4-fluorophenyl)-1H-indazol-5-yl]-1-hydroxyethyl}-1H-pyrrol-2-yl)morpholin-4-yl-methanone [MS m/z 529.04 (MH+)];
1-Allyl-4-{2,2,2-trifluoro-1-[1-(4-fluorophenyl)-1H-indazol-5-yl]-1-hydroxyethyl}-1H-pyrrole-2-carboxylic acid amide [(MS m/z 459.42 (MH+)];
1-Allyl-4-{2,2,2-trifluoro-1-[1-(4-fluorophenyl)-1H-indazol-5-yl]-1-hydroxyethyl}-1H-pyrrole-2-carboxylic acid cyanomethylamide [MS m/z 498.28 (MH+)];
1-Allyl-4-{2,2,2-trifluoro-1-[1-(4-fluorophenyl)-1H-indazol-5-yl]-1-hydroxyethyl}-1H-pyrrole-2-carboxylic acid carbamoylmethylamide [MS m/z 516.18 (MH+)]; and 1-Allyl-4-{2,2,2-trifluoro-1-[1-(4-fluorophenyl)-1H-indazol-5-yl]-1-hydroxyethyl}-1H-pyrrole-2-carboxylic acid methylamide [MS m/z 473.42 (MH$^+$)].

Example 41

1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid dimethylamide

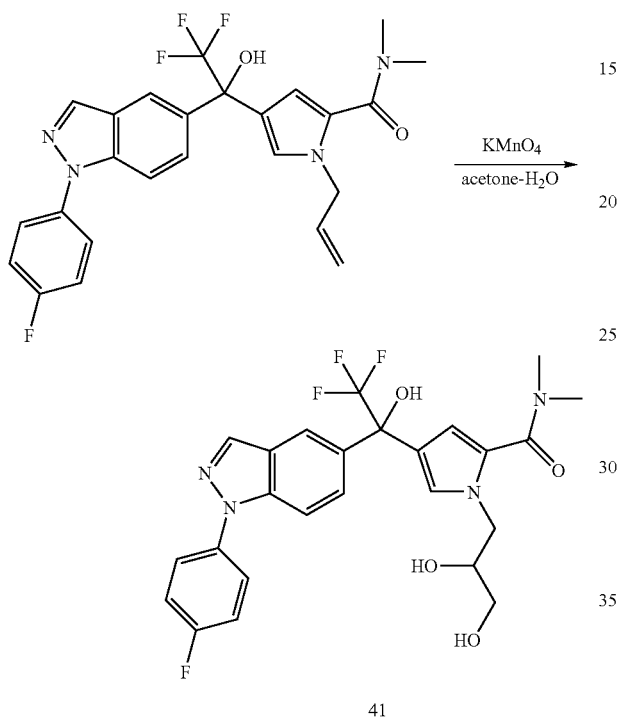

41

To a chilled (0° C.) solution of 1-allyl-4-{2,2,2-trifluoro-1-[1-(4-fluorophenyl)-1H-indazol-5-yl]-1-hydroxyethyl}-1H-pyrrole-2-carboxylic acid dimethylamide (352 mg, 0.72 mmol, 1 equiv.) in 9 mL of acetone and 3 mL of water was added a solution of KMnO$_4$ in 3 mL of acetone and 1 mL of water. The ice bath was removed and the reaction was warmed to room temperature. After 2 hours, the mixture was filtered through CELITE® filter aid and the filter cake washed with acetone. The volatiles were removed and the residue extracted with EtOAc. The combined organics were dried, filtered, and concentrated in vacuo. The residue was purified by flash chromatography (2-10% MeOH/CH$_2$Cl$_2$) to provide 217 mg (57%) of the title compound as a white solid. MS m/z 521.39 (MH$^+$).

The following additional compounds below were prepared by methods analogous to those described in Example 41:

(1-(2,3-Dihydroxypropyl)-4-{2,2,2-trifluoro-1-[1-(4-fluorophenyl)-1H-indazol-5-yl]-1-hydroxyethyl}-1H-pyrrol-2-yl)morpholin-4-yl-methanone [MS m/z 563.36 (MH$^+$)];

5-(2,3-Dihydroxypropyl)-7-{2,2,2-trifluoro-1-[1-(4-fluorophenyl)-1H-indazol-5-yl]-1-hydroxyethyl}-3,5-dihydropyrrolo[3,2-d]pyrimidin-4-one (53%) [MS m/z 518.38 (MH$^+$)];

1-(2,3-Dihydroxypropyl)-4-{2,2,2-trifluoro-1-[1-(4-fluorophenyl)-1H-indazol-5-yl]-1-hydroxyethyl}-1H-pyrrole-2-carbonitrile [MS m/z 475.24 (MH$^+$)];

4-{2,2,2-Trifluoro-1-[1-(4-fluorophenyl)-1H-indazol-5-yl]-1-hydroxyethyl}-1H-pyrrole-2-carbonitrile [MS m/z 410.17 (MH$^+$)];

1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester [MS m/z 522.19 (MH$^+$)]; and 3-Hydroxymethyl-7-{2,2,2-trifluoro-1-[1-(4-fluorophenyl)-1H-indazol-5-yl]-1-hydroxyethyl}-3,4-dihydropyrrolo[2,1-c][1,4]oxazin-1-one [MS m/z 476.16 (MH$^+$)].

Example 42

1-Allyl-4-{2,2,2-trifluoro-1-[1-(4-fluorophenyl)-1H-indazol-5-yl]-1-hydroxyethyl}-1H-pyrrole-2-carbonitrile

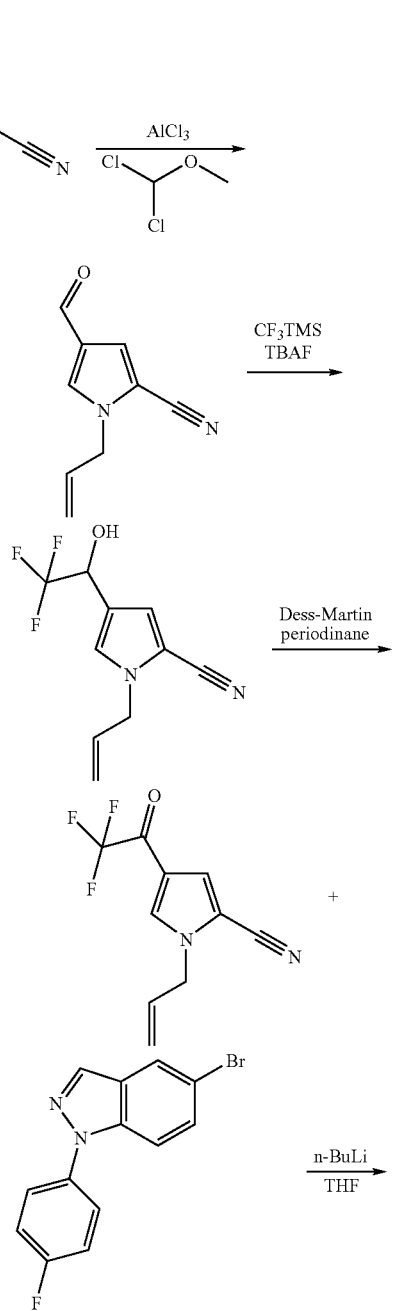

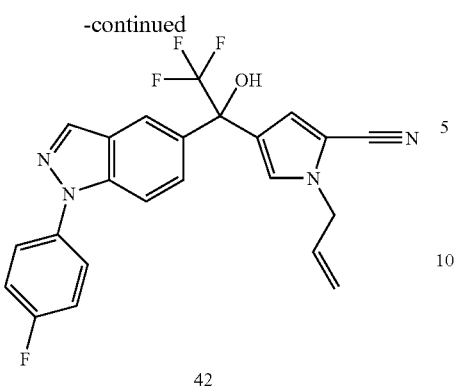

42

To a 100 mL flask charged with AlCl₃ (3.3 g, 25 mmol, 2.5 equiv.) and 35 mL of dry CH₂Cl₂ was added 2 mL of nitromethane. The mixture was cooled to 0° C. and a solution of 1-allyl-1H-pyrrole-2-carbonitrile (1.3 g, 10 mmol, 1 equiv.) in 5 mL of CH₂Cl₂ was added followed by a solution of dichloromethyl methyl ether in 10 mL of CH₂Cl₂ dropwise. After 30 minutes, the reaction was warmed to room temperature, stirred for 1.5 hours, poured over 100 mL of ice water, and the organic layer was separated. The organic layers were washed with 30 mL of 3M HCl, 30 mL of water, 18% aqueous sodium sulfite, filtered through CELITE® filter aid and concentrated in vacuo. The residue was purified by flash chromatography eluting with EtOAc-hexanes (5-40% gradient) to provide 1.25 g (78%) of 1-allyl-4-formyl-1H-pyrrole-2-carbonitrile as a yellow oil.

To a chilled (0° C.) solution of 1-allyl-4-formyl-1H-pyrrole-2-carbonitrile (1.25 g, 7.8 mmol, 1 equiv.) in 10 mL of THF was added CF₃TMS (1.5 ml, 9.5 mmol, 1.2 equiv.) dropwise followed by TBAF (1M in THF, 9.4 ml, 9.4 mmol, 1.2 equiv.) slowly dropwise. The cold bath was then removed and the mixture was stirred at room temperature. After 2 hours, the reaction was quenched with water and extracted with EtOAc. The organic was dried, filtered, and concentrated in vacuo. The residue was purified by flash chromatography eluting with EtOAc-hexanes (5-40% gradient) to afford 1-allyl-4-(2,2,2-trifluoro-1-hydroxyethyl)-1H-pyrrole-2-carbonitrile which was used without further purification.

To a room temperature solution of 1-allyl-4-(2,2,2-trifluoro-1-hydroxyethyl)-1H-pyrrole-2-carbonitrile (1.6 g, 7 mmol, 1 equiv.) in 50 mL of CH₂Cl₂ was added Dess-Martin periodinane (3.6 g, 8.3 mmol, 1.2 equiv). After 3 hours, the reaction was diluted with CH₂Cl₂ and made basic with saturated NaHCO₃. The organic layer was separated and the aqueous extracted with CH₂Cl₂. The combined organic layers were dried, filtered, and concentrated in vacuo. The residue was purified by flash chromatography using EtOAc-hexanes (0-15% gradient) to provide 1-allyl-4-(2,2,2-trifluoroacetyl)-1H-pyrrole-2-carbonitrile which was used without further purification.

To a chilled (−78° C.) solution of 5-bromo-1-(4-fluorophenyl)-1H-indazole (1.3 g, 4.3 mmol, 1.1 equiv.) in 20 mL of THF was added n-BuLi (2.5 M in hexanes, 1.7 ml, 4.3 mmol, 1.1 equiv.) followed by a chilled (−78° C.) solution of 1-allyl-4-(2,2,2-trifluoroacetyl)-1H-pyrrole-2-carbonitrile (0.9 g, 3.9 mmol, 1 equiv.) in 3 mL of THF. After 30 minutes, the mixture was warmed to 0° C., quenched with water, diluted with brine, and extracted with EtOAc. The combined organics were dried, filtered, and concentrated in vacuo. The residue was purified by flash chromatography using EtOAc-hexanes (5-30% gradient) to afford 1.15 g (66%) of the title compound as an off-white solid. MS m/z 441.26 (MH⁺).

Example 43

1-(2,3-Dihydroxypropyl)-4-{2,2,2-trifluoro-1-[1-(4-fluorophenyl)-1H-indazol-5-yl]-1-hydroxyethyl}-1H-pyrrole-2-carbonitrile and Example 44: 4-{2,2,2-Trifluoro-1-[1-(4-fluorophenyl)-1H-indazol-5-yl]-1-hydroxyethyl}-1H-pyrrole-2-carbonitrile

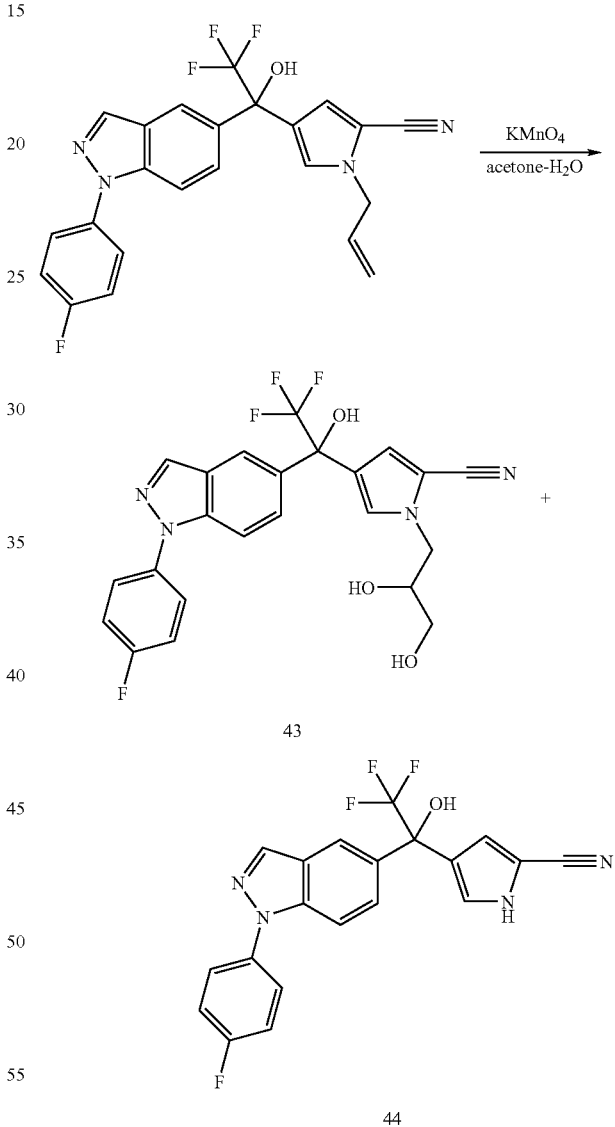

1-Allyl-4-{2,2,2-trifluoro-1-[1-(4-fluorophenyl)-1H-indazol-5-yl]-1-hydroxyethyl}-1H-pyrrole-2-carbonitrile was oxidized according to methods described in Example 34 to afford after purification using flash chromatography (15-75% EtOAc-hexanes) first 1-(2,3-dihydroxypropyl)-4-{2,2,2-trifluoro-1-[1-(4-fluorophenyl)-1H-indazol-5-yl]-1-hydroxyethyl}-1H-pyrrole-2-carbonitrile (45%), MS m/z 475.24 (MH⁺), and then 4-{2,2,2-trifluoro-1-[1-(4-fluorophenyl)-

1H-indazol-5-yl]-1-hydroxyethyl}-1H-pyrrole-2-carbonitrile (19%), MS m/z 401.17 (MH⁺).

Example 45

2-(2-Cyano-4-{2,2,2-trifluoro-1-[1-(4-fluorophenyl)-1H-indazol-5-yl]-1-hydroxyethyl}pyrrol-1-yl)acetamide

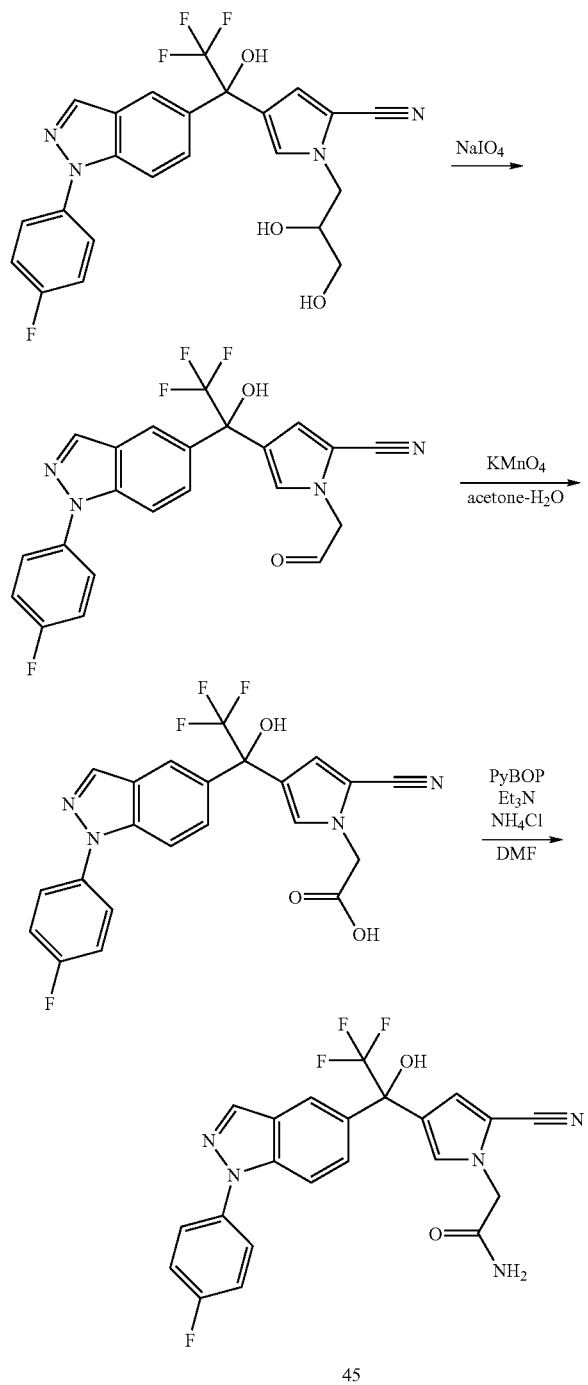

To a solution of 242 mg (0.51 mmol) of 1-(2,3-dihydroxypropyl)-4-{2,2,2-trifluoro-1-[1-(4-fluorophenyl)-1H-indazol-5-yl]-1-hydroxyethyl}-1H-pyrrole-2-carbonitrile in 6 mL of acetone and 3 mL of water was added 114 mg (0.53 mmol) of sodium periodate. After stirring overnight, the solids were filtered and rinsed with acetone. The acetone was then concentrated in vacuo and the residue was diluted with brine and extracted with EtOAc. The combined organic layers were dried, filtered, and concentrated in vacuo to afford 208 mg of 1-(2-oxoethyl)-4-{2,2,2-trifluoro-1-[1-(4-fluorophenyl)-1H-indazol-5-yl]-1-hydroxyethyl}-1H-pyrrole-2-carbonitrile which was used without further purification.

To a solution of 1-(2-oxoethyl)-4-{2,2,2-trifluoro-1-[1-(4-fluorophenyl)-1H-indazol-5-yl]-1-hydroxyethyl}-1H-pyrrole-2-carbonitrile (208 mg, 0.47 mmol, 1 equiv.) in 12 mL of 3:1 acetone-water was added KMnO₄ (78 mg, 0.49 mmol, 1.1 equiv.). After 18 hours, the mixture was filtered through CELITE® filter aid and the filter cake washed with acetone. The filtrate was evaporated and the aqueous was diluted with water and EtOAc. The mixture was diluted with saturated aqueous ammonium chloride and extracted with EtOAc. The combined organic layers were dried, filtered, and concentrated in vacuo to provide 197 mg (91%) of (2-cyano-4-{2,2,2-trifluoro-1-[1-(4-fluorophenyl)-1H-indazol-5-yl]-1-hydroxyethyl}pyrrol-1-yl)acetic acid which was used without further purification.

To a solution of (2-cyano-4-{2,2,2-trifluoro-1-[1-(4-fluorophenyl)-1H-indazol-5-yl]-1-hydroxyethyl}pyrrol-1-yl)acetic acid (95 mg, 0.2 mmol, 1 equiv.) and triethylamine (0.16 mL, 1.2 mmol, 6 equiv.) in 2 mL of DMF was added ammonium chloride (67 mg, 1.2 mmol, 6 equiv.) followed by PyBOP (113 mg, 0.22 mmol, 1.1 equiv.) After stirring overnight, the reaction was then filtered into an HPLC vial and purified by reverse phase HPLC (15-95% CH₃CN/water+ 0.1% TFA). The desired fractions were combined and the CH₃CN was removed. The aqueous was basified with saturated aqueous sodium bicarbonate and extracted with EtOAc. The combined organic layers were dried, filtered, and concentrated in vacuo to provide 50 mg (53%) of the title compound as a yellow foam. MS m/z 458.22 (MH⁺).

The following additional compound was prepared by methods analogous to those described in Example 45: 2-(2-cyano-4-{2,2,2-trifluoro-1-[1-(4-fluorophenyl)-1H-indazol-5-yl]-1-hydroxyethyl}pyrrol-1-yl)-N-methylacetamide was also prepared, MS m/z 472.37 (MH⁺).

Example 46

1-(5-Allyl-4-chloro-5H-pyrrolo[3,2-d]pyrimidin-7-yl)-2,2,2-trifluoro-1-[1-(4-fluorophenyl)-1H-indazol-5-yl]ethanol

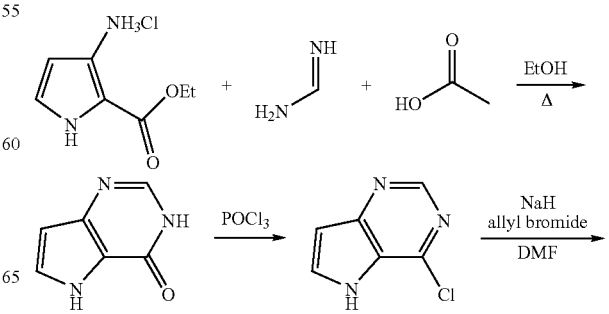

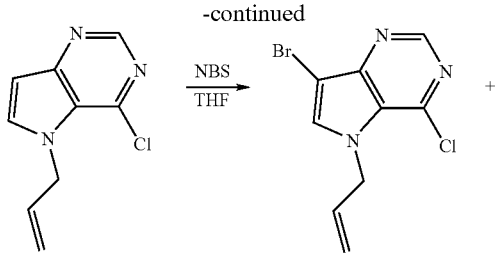

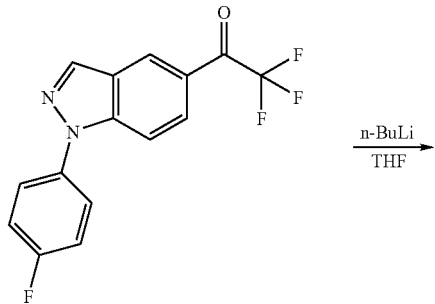

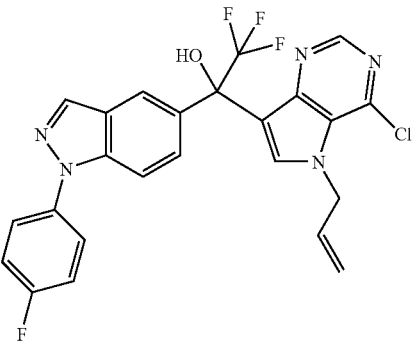

46

To a solution of 3-amino-1H-pyrrole-2-carboxylic acid ethyl ester hydrochloride (3.4 g, 17.7 mmol, 1 equiv.) in 40 mL of EtOH was added formamidine acetic acid salt (2.8 g, 26.6 mmol) and the mixture warmed at 110° C. After 18 hours, the reaction was cool to room temperature and the solids were filtered, rinsed with EtOH, and dried to provide 1.92 g (80%) of 3,5-dihydropyrrolo[3,2-d]pyrimidin-4-one as a beige solid.

A mixture of 3,5-dihydropyrrolo[3,2-d]pyrimidin-4-one, (1.8 g, 13.5 mmol, 1 equiv.) and 50 mL of POCl₃ was warmed at reflux for 2 hours, cooled to room temperature, and concentrated in vacuo. The residue was then diluted with 200 mL of water, made basic with solid potassium carbonate and extracted with EtOAc. The combined organic layers were dried, filtered, and concentrated in vacuo to provide 1.18 g (57%) of 4-chloro-5H-pyrrolo[3,2-d]pyrimidine as a yellow solid which was used without further purification.

To a room temperature solution of 4-chloro-5H-pyrrolo[3,2-d]pyrimidine (1.2 g, 7.8 mmol,) and allyl bromide in 40 mL of DMF was added 60% sodium hydride (625 mg, 15.6 mmol, 2 equiv.) in several portions. After 20 minutes, the reaction was quenched with water and extracted with EtOAc. The combined organics were dried, filtered, and concentrated in vacuo. The residue was purified by flash chromatography (20% EtOAc/hexanes) to provide 1.3 g (88%) of 5-allyl-4-chloro-5H-pyrrolo[3,2-d]pyrimidine as a yellow oil which was used without further purification.

To a room temperature solution of 5-allyl-4-chloro-5H-pyrrolo[3,2-d]pyrimidine (960 mg, 5 mmol, 1 equiv.) in 100 mL of THF was added N-bromosuccinimide (1.1 g, 6 mmol, 1.1 equiv.). After 1 hour, the THF was concentrated and the residue diluted with water and extracted with EtOAc. The combined organic layers were dried, filtered, and concentrated in vacuo. The solids were sonicated in water/saturated aqueous NaHCO₃/MeOH and filtered to provide 1.26 g (93%) of 5-allyl-7-bromo-4-chloro-5H-pyrrolo[3,2-d]pyrimidine as an off-white solid which was used without further purification.

To a chilled (−78° C.) solution of 5-allyl-7-bromo-4-chloro-5H-pyrrolo[3,2-d]pyrimidine (570 mg, 2.1 mmol) in 10 mL of THF was added n-BuLi (2.5 M in THF, 1.5 mL, 2.5 mmol) dropwise. After 5 minutes, a chilled (−78° C.) solution of 2,2,2-trifluoro-1-[1-(4-fluorophenyl)-1H-indazol-5-yl] ethanone (708 mg, 2.3 mmol) in 3 mL of THF was added in one portion. After 15 minutes, the mixture was diluted with water and warmed to room temperature, diluted with brine, and extracted with EtOAc. The combined organic layers were dried, filtered, and concentrated in vacuo. The residue was purified by flash chromatography using EtOAc-hexanes (15-60% gradient) to provide 245 mg (23%) of the title compound as a beige solid. MS m/z 502.23 (MH⁺).

Example 47

5-Allyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one

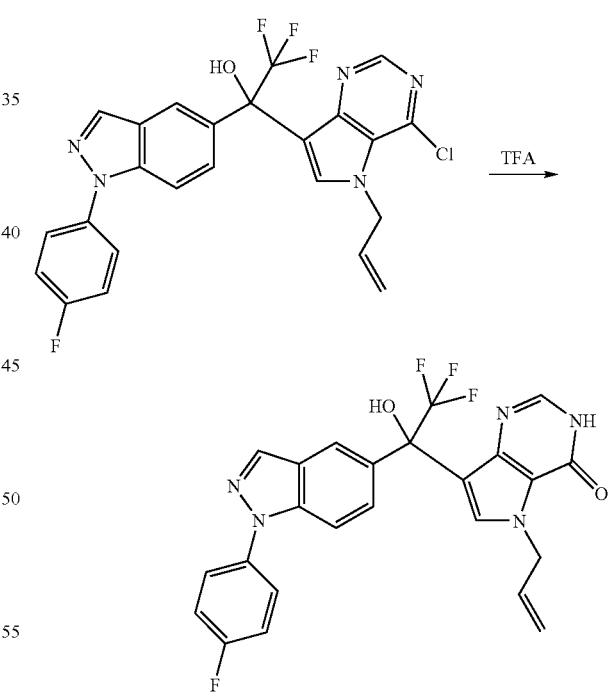

47

To a solution of 1-(5-allyl-4-chloro-5H-pyrrolo[3,2-d]pyrimidin-7-yl)-2,2,2-trifluoro-1-[1-(4-fluorophenyl)-1H-indazol-5-yl]ethanol (250 mg, 0.5 mmol) in 3 mL of dioxane was added 2 mL of water followed by 2 mL of trifluoroacetic acid. The mixture was warmed at 80° C. for 1.5 hours, cooled to room temperature and made basic with saturated sodium bicarbonate, diluted with water, and extracted with EtOAc.

The combined organic layers were dried, filtered, and evaporated. The residue was purified by flash chromatography eluting with MeOH—CH$_2$Cl$_2$ (0-2% gradient) to provide 129 mg (53%) of the title compound as a white solid. MS m/z 484.33 (MH$^+$).

Example 48

5-(2,3-Dihydroxypropyl)-7-{2,2,2-trifluoro-1-[1-(4-fluorophenyl)-1H-indazol-5-yl]-1-hydroxyethyl}-3,5-dihydropyrrolo[3,2-d]pyrimidin-4-one

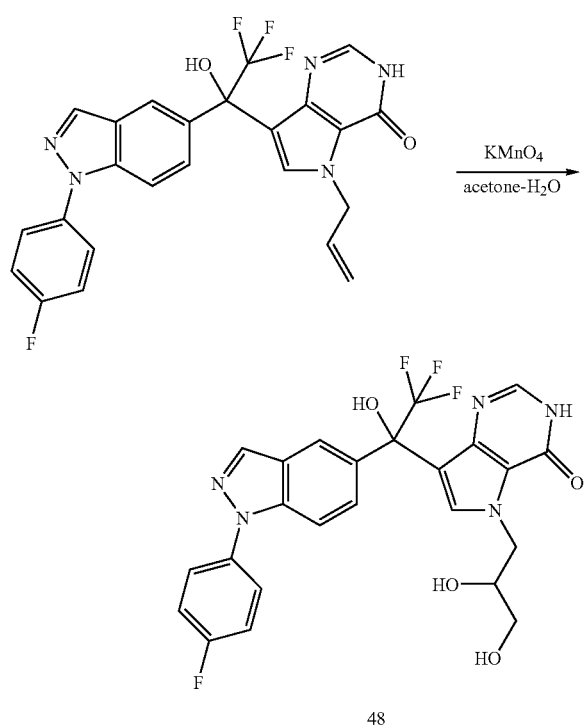 [SMILES: C=CCn1cc(C(O)(c2ccc3c(cnn3-c3ccc(F)cc3)c2)C(F)(F)F)c2nc[nH]c(=O)c21 ; "KMnO4" ; O=c1[nH]cnc2c(C(O)(c3ccc4c(cnn4-c4ccc(F)cc4)c3)C(F)(F)F)cn(CC(O)CO)c12]

48

Prepared from 5-allyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one (117 mg, 0.24 mmol) according to methods described in Example 34 to afford 67 mg (53%) of the title compound as a white solid. MS m/z 518.38 (MH$^+$).

Example 49

1-(4-Chloro-5H-pyrrolo[3,2-d]pyrimidin-7-yl)-2,2,2-trifluoro-1-[1-(4-fluorophenyl)-1H-indazol-5-yl]ethanol

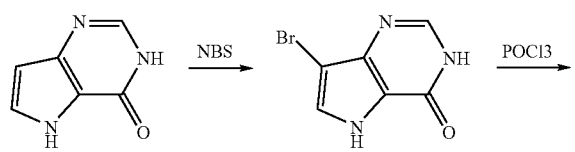

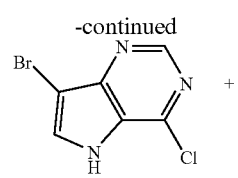

49

A mixture of 3,5-dihydropyrrolo[3,2-d]pyrimidin-4-one (200 mg, 1.5 mmol, 1 equiv.) and N-bromosuccinimide (320 mg, 1.8 mmol, 1.2 equiv.) in 10 mL of DMF was stirred for 18 hours at room temperature. The reaction was diluted with water and resulting solid was collected by filtration, dried, suspended in MeOH, and filtered. The filtrate was concentrated in vacuo to provide 7-bromo-3,5-dihydropyrrolo[3,2-d]pyrimidin-4-one as a beige solid which was used without further purification.

A mixture of 7-bromo-3,5-dihydropyrrolo[3,2-d]pyrimidin-4-one (100 mg, 0.5 mmol) and 6 mL of POCl$_3$ under argon was warmed at 115° C. After 3 hours, the mixture was cooled to room temperature and poured over 300 mL of ice, stirred, made basic with potassium carbonate and extracted with EtOAc. The combined organic layers were dried, filtered, and concentrated in vacuo to provide 101 mg (93%) of the desired 7-bromo-4-chloro-5H-pyrrolo[3,2-d]pyrimidine as beige solid which was used without further purification.

To a chilled (−78° C.) solution of 7-bromo-4-chloro-5H-pyrrolo[3,2-d]pyrimidine (80 mg, 0.34 mmol, 1 equiv.) in 5 mL of THF was added tert-BuLi (1.7 M in pentane, 0.43 mL, 0.73 mmol, 2.1 equiv.) dropwise. After 5 minutes, a chilled (−78° C.) solution of 2,2,2-trifluoro-1-[1-(4-fluorophenyl)-1H-indazol-5-yl]ethanone (106 mg, 0.34 mmol, 1 equiv.) in 1 mL of THF was added in one portion. After 15 minutes, the reaction was quenched with 15 mL of water, warmed to room temperature, diluted with 100 mL of saturated aqueous ammonium chloride, and then extracted with EtOAc. The combined organic layers were dried, filtered, and concentrated in vacuo. The residue was dissolved in DMF and purified by reverse phase HPLC (5-95% CH$_3$CN/water+0.1% TFA). The major fractions collected were made basic with saturated NaHCO$_3$ and the CH$_3$CN was concentrated in

Example 50

7-{2,2,2-Trifluoro-1-[1-(4-fluorophenyl)-1H-indazol-5-yl]-1-hydroxyethyl}-3,5-dihydropyrrolo[3,2-d]pyrimidin-4-one

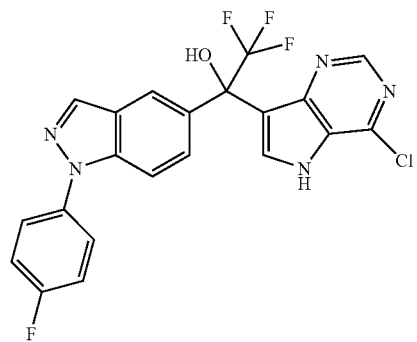

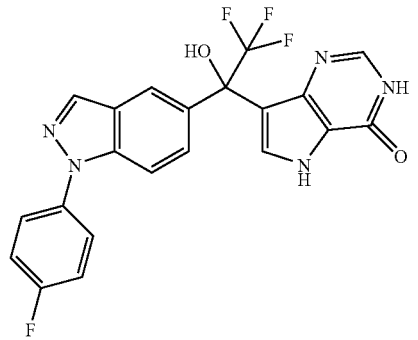

50

A mixture of 1-(4-chloro-5H-pyrrolo[3,2-d]pyrimidin-7-yl)-2,2,2-trifluoro-1-[1-(4-fluorophenyl)-1H-indazol-5-yl]ethanol (43 mg, 0.09 mmol) and 1 mL of trifluoroacetic acid in 1 mL of water and 2 mL of dioxane was warmed at 70° C. After 18 hours, the reaction was diluted with saturated NaHCO$_3$ and extracted with EtOAc. The combined organic layers were dried, filtered, and concentrated in vacuo. The residue was dissolved in 1 mL of DMF and purified by reverse phase HPLC (5-95% CH$_3$CN/water+0.1% TFA). The desired fractions were combined and the CH$_3$CN was removed in vacuo. The aqueous layer was made basic with saturated sodium bicarbonate and extracted with EtOAc. The combined organics were dried, filtered, and concentrated in vacuo to provide 18 mg (44%) of the title compound as a white solid. MS m/z 444.27 (MH$^+$).

Example 51

3-(4-Chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol

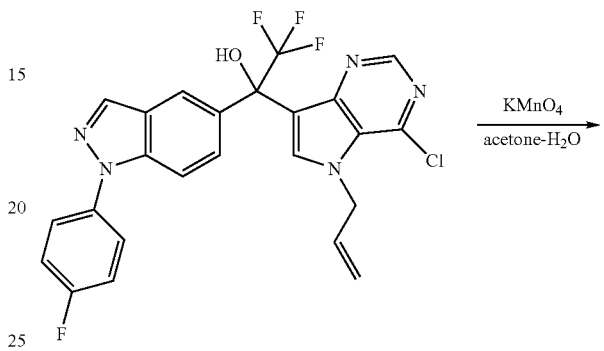

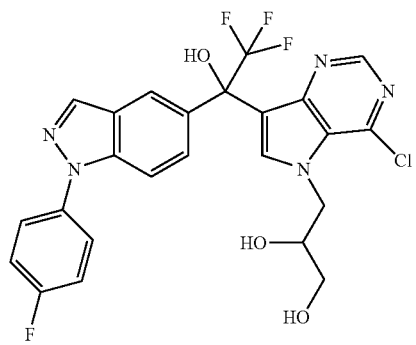

51

To a room temperature solution of 1-(5-allyl-4-chloro-5H-pyrrolo[3,2-d]pyrimidin-7-yl)-2,2,2-trifluoro-1-[1-(4-fluorophenyl)-1H-indazol-5-yl]ethanol (245 mg, 0.5 mmol, 1 equiv.) in 4 mL of acetone and 2 mL of water was added a solution of KMnO$_4$ in 1 mL of water and 2 mL of acetone. After 3 hours, the mixture was filtered and the filter cake washed with acetone. The filtrate was concentrated and the residue diluted with water and extracted with EtOAc. The combined organic layers were dried, filtered, and concentrated in vacuo. The residue was purified by HPLC (5-85% CH$_3$CN/water 0.1% TFA). The desired peaks were combined and made basic with saturated aqueous sodium bicarbonate. The CH$_3$CN was removed and the aqueous was extracted with EtOAc. The combined organic layers were dried, filtered, and concentrated in vacuo to provide 116 mg (44%) of the title compound as a white solid. MS m/z 536.10 (MH⁺).

Example 52

1-[4-Chloro-5-(2-hydroxyethyl)-5H-pyrrolo[3,2-d]pyrimidin-7-yl]-2,2,2-trifluoro-1-[1-(4-fluorophenyl)-1H-indazol-5-yl]ethanol

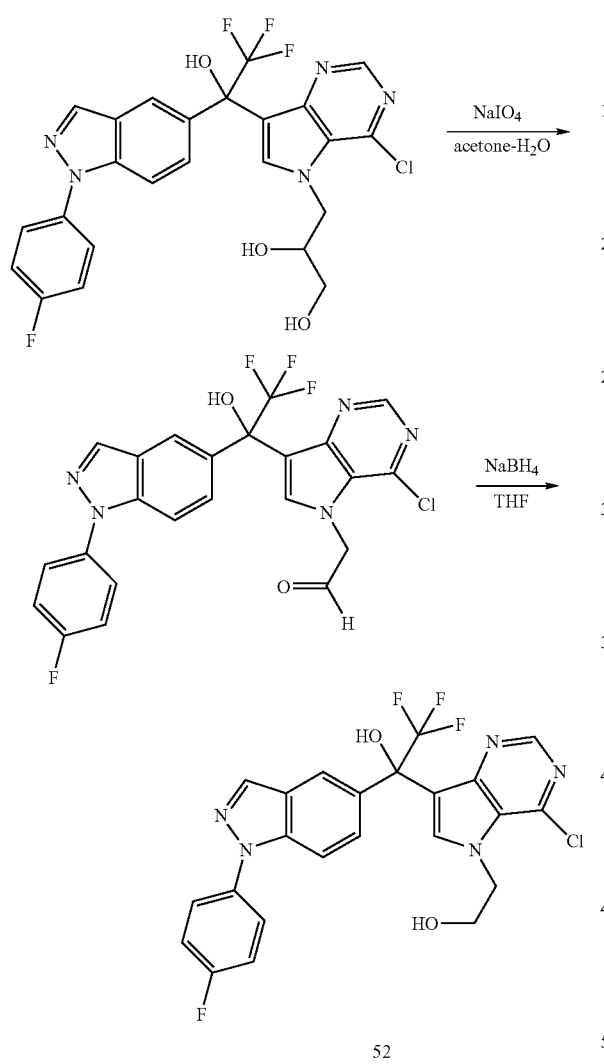

52

To a room temperature solution of 3-(4-chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol (95 mg, 0.18 mmol, 1 equiv.) in 3 mL of acetone and 1 mL of water was added NaIO₄ (120 mg, 0.56 mmol, 4 equiv.). After 3 days, the mixture was filtered and the filtrate concentrated to near dryness. The residue was diluted with water and extracted with EtOAc. The combined organic layers were dried, filtered and concentrated in vacuo to afford (4-chloro-7-{2,2,2-trifluoro-1-[1-(4-fluorophenyl)-1H-indazol-5-yl]-1-hydroxyethyl}pyrrolo[3,2-d]pyrimidin-5-yl)acetaldehyde which was used without further purification.

To a room temperature solution of (4-chloro-7-{2,2,2-trifluoro-1-[1-(4-fluorophenyl)-1H-indazol-5-yl]-1-hydroxyethyl}pyrrolo[3,2-d]pyrimidin-5-yl)acetaldehyde (91 mg, 0.18 mmol) in 3 mL of THF was added NaBH₄ (4 mg, 0.09 mmol, 0.5 equiv.). After 2 hours, the reaction was quenched with water and extracted with EtOAc. The organics were dried, filtered, and concentrated in vacuo. The residue was purified by HPLC (5-95% CH₃CN/water 0.1% TFA). The desired peaks were combined, made basic with saturated aqueous sodium bicarbonate, and concentrated to remove excess CH₃CN. The resulting aqueous layer was then extracted with EtOAc. The combined organic layers were dried, filtered, and concentrated in vacuo to provide 48 mg (53%) of the title compound as a white solid. MS m/z 506.34 (MH⁺).

Example 53

5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one

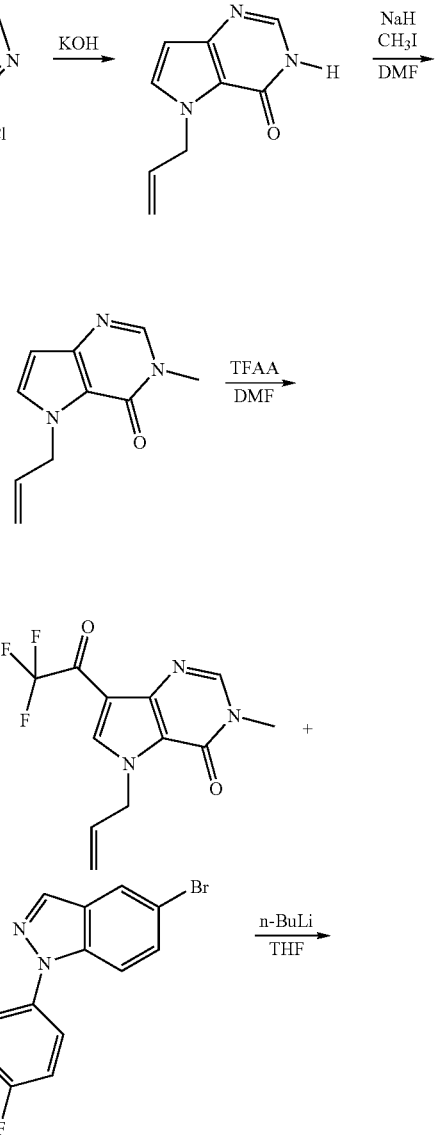

-continued

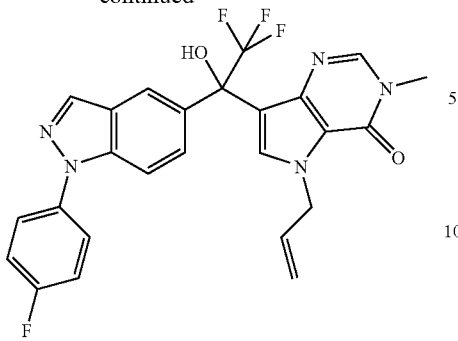

53

To a solution of 1.33 g (6.86 mmol) of 5-allyl-4-chloro-5H-pyrrolo[3,2-d]pyrimidine in 30 mL of dioxane was added 30 mL of 2 M aqueous NaOH and the mixture was warmed at reflux. After 2 hours, the mixture was concentrated in vacuo to remove dioxane. The aqueous residue was neutralized with saturated aqueous ammonium chloride and extracted with EtOAc. The combined organic layers were dried, filtered, and concentrated in vacuo to afford 1.05 g (87%) of 5-allyl-4-chloro-5H-pyrrolo[3,2-d]pyrimidine as a yellow solid which was used without further purification.

To a room temperature solution of 5-allyl-4-chloro-5H-pyrrolo[3,2-d]pyrimidine (220 mg, 1.3 mmol, 1 equiv.) in 3 mL of DMF was added 60% NaH (100 mg, 2.5 mmol, 2 equiv.) followed by MeI (0.18 ml, 1.8 mmol, 1.5 equiv.). After 30 minutes, the mixture was diluted with water and extracted with EtOAc. The combined organic layers were dried, filtered, and concentrated in vacuo. The residue was purified by reverse phase HPLC (5-90% CH$_3$CN/water+0.1% TFA). The desired fractions were combined and concentrated to remove CH$_3$CN. The remaining aqueous mixture was extracted with EtOAc, dried, filtered, and evaporated to provide 152 mg (64%) of 5-allyl-3-methyl-3,5-dihydropyrrolo[3,2-d]pyrimidin-4-one as a yellow oil which was used without further purification.

A mixture of 5-allyl-3-methyl-3,5-dihydropyrrolo[3,2-d]pyrimidin-4-one (500 mg, 2.6 mmol, 1 equiv.) and trifluoroacetic anhydride in 5 mL of DMF was warmed at 80° C. After 30 minutes, the reaction was poured into water, diluted with saturated sodium bicarbonate, and extracted with EtOAc. The combined organics were dried, filtered, and concentrated in vacuo. The residue was purified by flash chromatography eluting with EtOAc-hexanes (20-70% gradient) to provide 260 mg (37%) of 5-allyl-3-methyl-7-(2,2,2-trifluoroacetyl)-3,5-dihydropyrrolo[3,2-d]pyrimidin-4-one as a yellow solid which was used without further purification.

To a chilled (−78° C.) solution of 5-bromo-1-(4-fluorophenyl)-1H-indazole (94 mg, 0.32 mmol, 1.1 equiv.) in 1.5 mL of THF was added n-BuLi (2.5 M in hexanes, 0.13 ml, 0.32 mmol, 1.1 equiv.) followed by a chilled (−78° C.) solution of 5-allyl-3-methyl-7-(2,2,2-trifluoro-acetyl)-3,5-dihydropyrrolo[3,2-d]pyrimidin-4-one (83 mg, 0.29 mmol, 1 equiv.) in 1 mL of THF. After 15 minutes, the mixture was quenched with water, warmed to room temperature, diluted with brine, and extracted with EtOAc. The combined organic layers were dried, filtered, and concentrated in vacuo. The residue was purified by flash chromatography using EtOAc-hex (0-60% gradient) to provide 44 mg (30%) of the title compound as a yellow foam. MS m/z 498.31 (MH$^+$).

Example 54

5-(2,3-Dihydroxypropyl)-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one

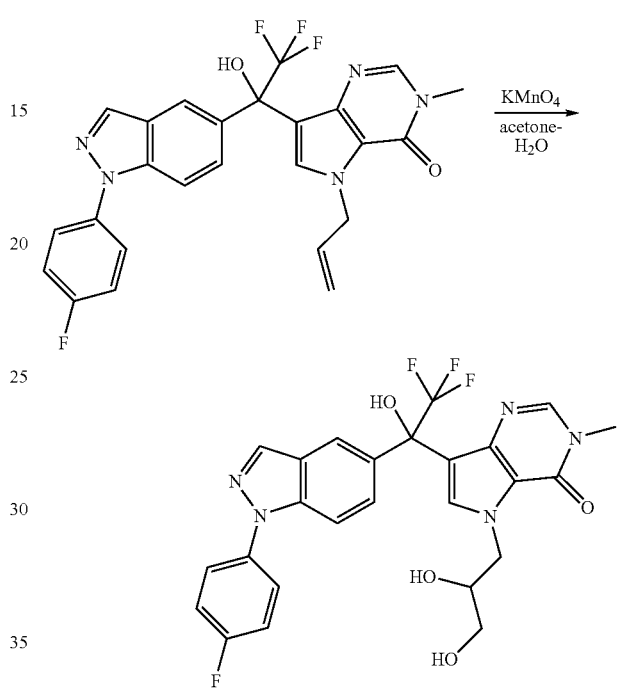

54

Prepared according to methods described in Example 34 from 5-allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one to afford the title compound. MS m/z 532.16 (MH$^+$).

Example 55

2-(3-Methyl-4-oxo-7-{2,2,2-trifluoro-1-[1-(4-fluorophenyl)-1H-indazol-5-yl]-1-hydroxyethyl}-3,4-dihydropyrrolo[3,2-d]pyrimidin-5-yl)acetamide

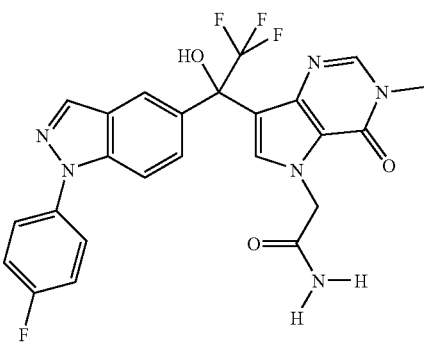

55

Prepared from Example 54 (dihydroxypropyl)-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one) according to methods described in Example 45 to afford the title compound. MS m/z 515.97 (MH⁺).

Example 56

3-Hydroxymethyl-7-{2,2,2-trifluoro-1-[1-(4-fluorophenyl)-1H-indazol-5-yl]-1-hydroxyethyl}-3,4-dihydropyrrolo[2,1-c][1,4]oxazin-1-one

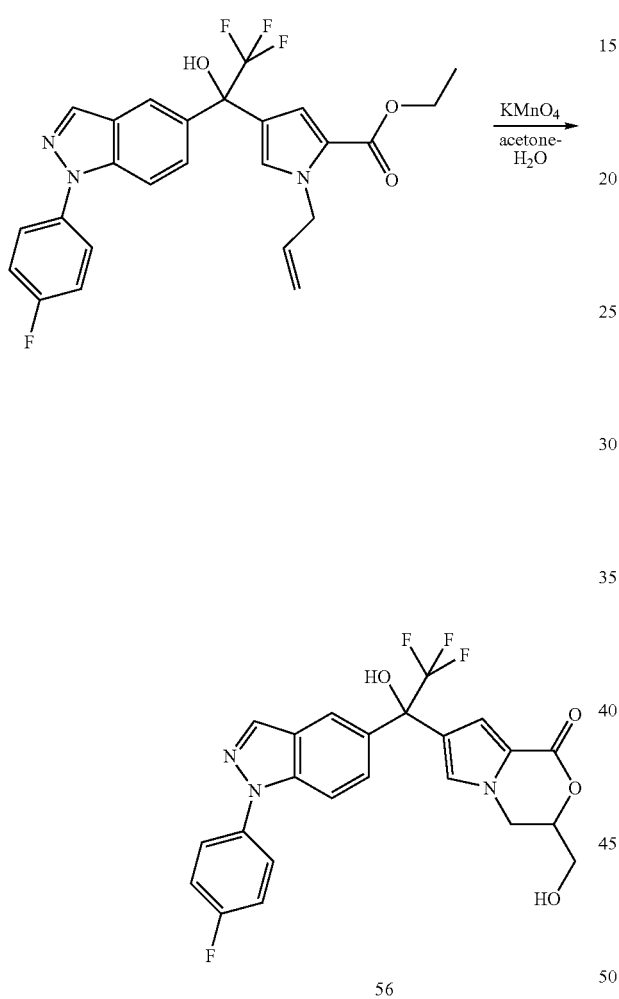

To a chilled (0° C.) solution of 1-allyl-4-{2,2,2-trifluoro-1-[1-(4-fluorophenyl)-1H-indazol-5-yl]-1-hydroxyethyl}-1H-pyrrole-2-carboxylic acid ethyl ester (100 mg, 0.2 mmol, 1 equiv.) in 3 mL of acetone and 1 mL of water was added a solution of KMnO₄ (39 mg, 0.25 mmol, 1.2 equiv.) in 3 mL of acetone and 1 mL of water. The ice bath was removed and the reaction was warmed to room temperature. After 2 hours, the reaction was filtered through CELITE® filter aid and the filter cake washed with acetone. The filtrate was concentrated in vacuo diluted with water and extracted with EtOAc. The combined organic layers were dried, filtered, and concentrated in vacuo. The residue was purified by reverse phase HPLC (5-95% CH₃CN/water 0.1% TFA). The fractions were combined and concentrated to remove CH₃CN. The aqueous residue was made basic with saturated aqueous sodium bicarbonate and extracted with EtOAc to provide 25 mg of the title compound as a white solid. MS m/z 476.16 (MH⁺).

Example 57

1-(4-Fluorophenyl)-5-[2,2,2-trifluoro-1-hydroxy-1-(1-methyl-1H-indol-3-yl)ethyl]-1,3-dihydrobenzimidazol-2-one

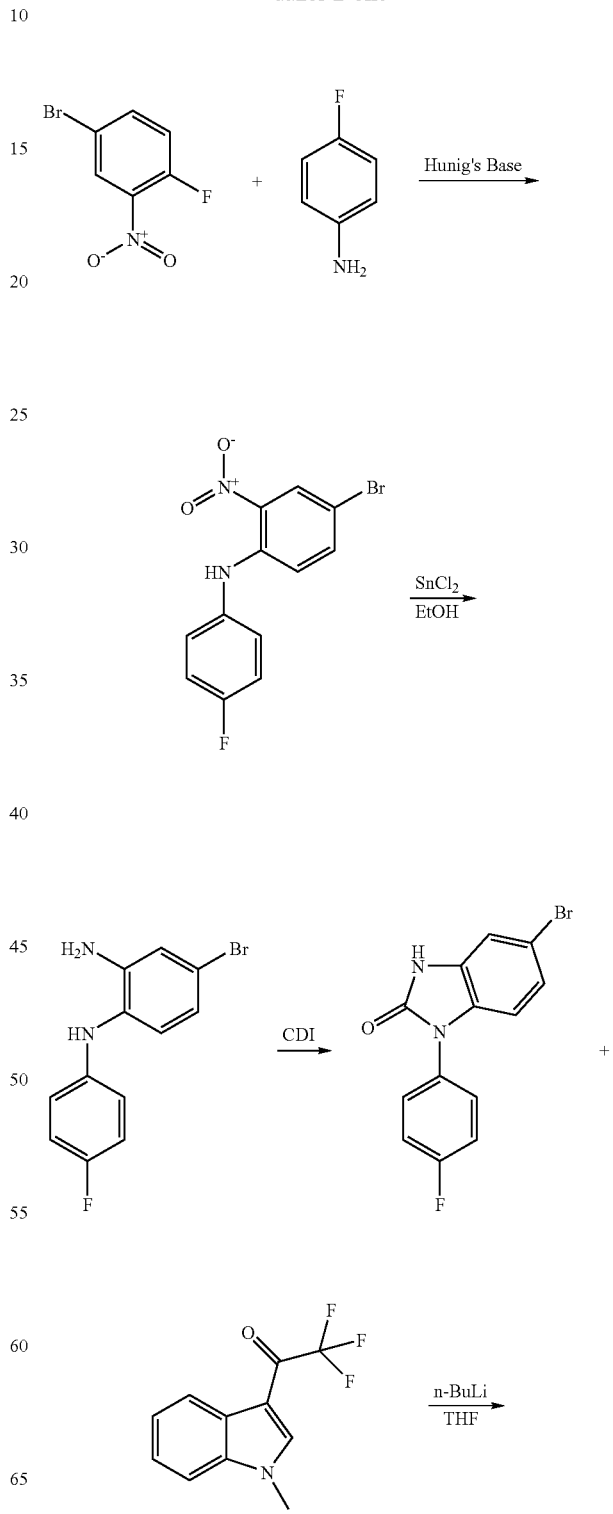

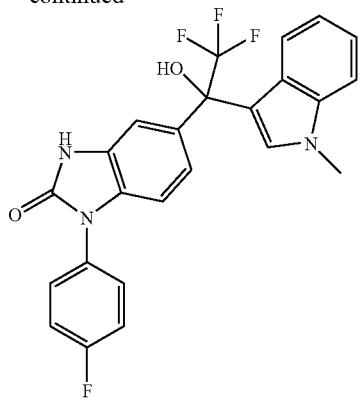

57

To a room temperature solution of 4-bromo-1-fluoro-2-nitrobenzene (3.3 g, 15 mmol) and 4-fluorophenylamine (1.42 mL, 15 mmol) in anhydrous acetonitrile (20 mL) was added N,N-diisopropylethylamine (2.9 mL, 16.5 mmol) and the mixture was warmed to 90° C. After 24 hours, the mixture was concentrated in vacuo and the crude material was purified by column chromatography over silica gel eluting with 0-20% ethyl acetate in hexanes to afford 4.7 g of (4-bromo-2-nitrophenyl)-(4-fluorophenyl)amine as an orange oil which solidified on standing. MS m/z 311/313 (MH$^+$).

To a stirred suspension of (4-bromo-2-nitrophenyl)-(4-fluorophenyl)amine (3.7 g, 11.9 mmol) in ethanol (125 mL) was added tin (II) chloride (6.8 g, 35.7 mmol) and the mixture was warmed at reflux. After 3 hours, LCMS showed only one peak [MS m/z 281/283 (MH$^+$)] corresponding to the desired product. The mixture was cooled, concentrated in vacuo, then diluted with cold water and made basic with 3 N sodium hydroxide (pH 11). The resulting precipitate was filtered, washed with water, and dried to afford 4-bromo-N$^1$-(4-fluorophenyl)benzene-1,2-diamine.

To a room temperature solution of 4-bromo-N$^1$-(4-fluorophenyl)benzene-1,2-diamine (843 mg, 3 mmol) in anhydrous THF (15 mL) was added 1,1-carbonyldiimidazole (650 mg, 4 mmol). After 2 hours, LCMS showed a peak [MS m/z 307/309 (MH$^+$)] corresponding to the desired product. The precipitate was filtered, washed with water, and dried to afford 890 mg of 5-bromo-1-(4-fluorophenyl)-1,3-dihydrobenzimidazol-2-one as an off-white solid.

To a chilled (−78° C.) solution of 5-bromo-1-(4-fluorophenyl)-1,3-dihydrobenzimidazol-2-one (152 mg, 0.5 mmol) in anhydrous bis(2-methoxyethyl)ether (10 mL) was added 0.5 mL (1.25 mmol) of a solution of 2.5 M n-butyllithium in hexanes. After 30 minutes, a solution of 2,2,2-trifluoro-1-(1-methyl-1H-indol-3-yl)ethanone (114 mg) in bis(2-methoxyethyl) in 1 mL of ether was added. The mixture stirred for 1 hour and was quenched with ammonium chloride solution. The resulting precipitate was filtered, washed with water, and dried to afford the title compound as an off-white solid. MS m/z 456 (MH$^+$).

Example 58

1-(4-Fluorophenyl)-3-methyl-5-[2,2,2-trifluoro-1-hydroxy-1-(1-methyl-1H-indol-3-yl)ethyl]-1,3-dihydro-benzimidazol-2-one

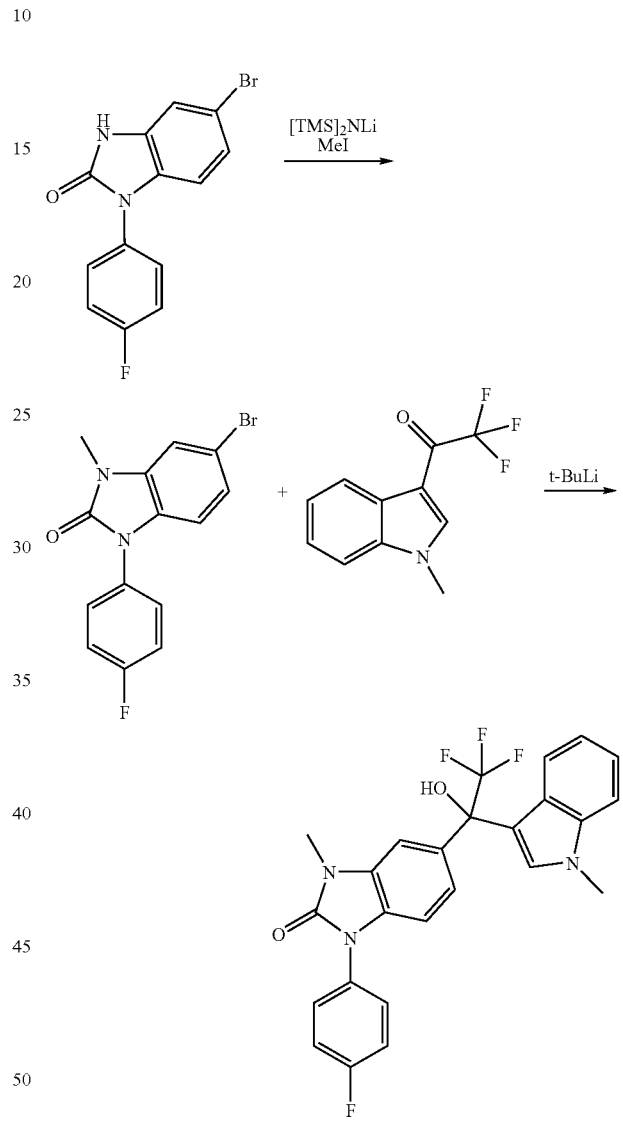

58

To a stirred room temperature suspension of 5-bromo-1-(4-fluorophenyl)-1,3-dihydro-benzimidazol-2-one (160 mg, 0.52 mmol) in anhydrous bis(2-methoxyethyl)ether (5 mL) was added lithium bis(trimethylsilyl)amide (0.55 mL of 1.06 M solution in THF, 0.58 mmol). After 30 minutes, methyl iodide (125 μL, 2 mmol) was added. After 2 hours, the mixture was poured into 1 N sulfuric acid containing ice. The resulting precipitate was filtered, washed with water, and dried to afford 160 mg of 5-bromo-1-(4-fluorophenyl)-3-methyl-1,3-dihydro-benzimidazol-2-one as an off-white solid. MS m/z 321/323 (MH$^+$).

To a chilled (−78° C.) solution of 5-bromo-1-(4-fluorophenyl)-3-methyl-1,3-dihydro-benzimidazol-2-one (80 mg, 0.25 mmol) in anhydrous THF (3 mL) was added tert-butyllithium (0.2 mL of 1.7 M solution in heptane, 0.34 mmol). After 1 minute, a chilled (−78° C.) solution of 2,2,2-trifluoro-1-(1-methyl-1H-indol-3-yl)ethanone (57 mg, 0.25 mmol) in anhydrous THF (1 mL) was added. After 10 minutes, the mixture was quenched with ammonium chloride solution and extracted with three 15 mL portions of methylene chloride. The combined organic layers were washed with water, dried over anhydrous sodium sulfate, and concentrated in vacuo to afford a brownish oil. The residue was purified by column chromatography over silica gel eluting with 0-10% ethyl acetate in methylene chloride to afford 15 mg of the title compound as a white powder. MS m/z 470 (MH+).

Example 59

2,2,2-Trifluoro-1-[1-(4-fluorophenyl)-2-methyl-1H-benzimidazol-5-yl]-1-(1-methyl-1H-indol-3-yl)ethanol

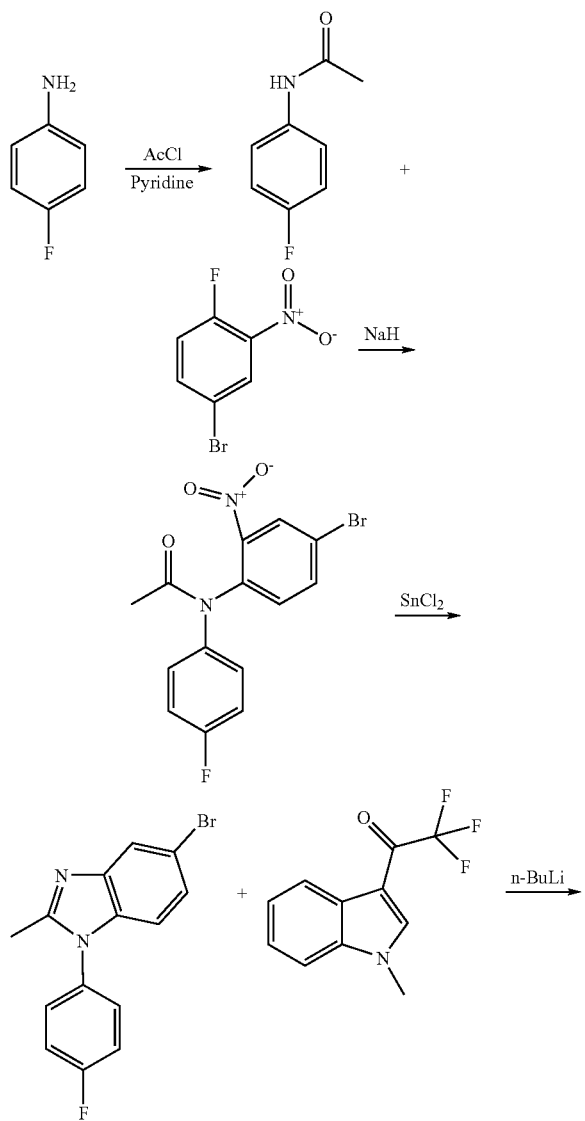

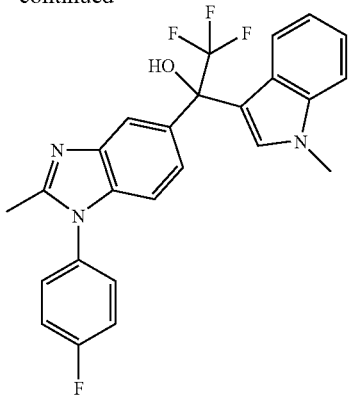

59

To a chilled (ice-bath) solution of 4-fluorophenylamine (2.9 mL, 30 mmol) and anhydrous pyridine (3.7 mL, 45 mmol) in methylene chloride (50 mL) was slowly added a solution of acetyl chloride (2.4 mL, 33 mmol) in methylene chloride (10 mL). After 15 minutes, the mixture was concentrated in vacuo and the residue was diluted with cold water. The resulting precipitate was filtered, washed with water and dried to afford 4.2 g of N-(4-fluorophenyl)acetamide as an off white solid. MS m/z 154 (MH+).

To a room temperature suspension of sodium hydride (33.4 mmol, 1.34 g of 60% in mineral oil) in 60 mL of THF was added a solution of the N-(4-fluorophenyl)acetamide (4.1 g, 26.8 mmol) in THF (30 mL) over a 5 minute period. After 30 minutes, a solution of 4-bromo-1-fluoro-2-nitrobenzene (3.2 mL, 26.8 mmol) in THF (10 mL) was added. After 15 hours, the reaction was concentrated in vacuo, the residue was diluted with 1 N sulfuric acid (300 mL) and extracted with three 100 mL portions of methylene chloride. The combined organic layers were washed with water, dried over anhydrous sodium sulfate, and concentrated in vacuo to afford a brownish oil. The residue was purified by column chromatography over silica gel eluting with 0-100% ethyl acetate in hexanes to afford 3.7 g of N-(4-bromo-2-nitrophenyl)-N-(4-fluorophenyl)acetamide as a thick yellow oil. MS m/z 353/355 (MH+).

To a stirred room temperature solution of N-(4-bromo-2-nitrophenyl)-N-(4-fluorophenyl)acetamide (3.7 g, 10.8 mmol) in ethanol (75 mL) was added tin (II) chloride (6 g, 31.4 mmol) and the mixture was warmed at 90° C. After 3 hours, the mixture was cooled, concentrated in vacuo, diluted with cold water, made basic with 2 N NaOH (pH 11), and extracted with three 75 mL portions of methylene chloride. The combined organic layers were washed with water, dried over anhydrous sodium sulfate, and concentrated in vacuo to afford a reddish brown oil. The residue was purified by column chromatography over silica gel eluting with 0-50% ethyl acetate in methylene chloride to afford 830 mg of 5-bromo-1-(4-fluorophenyl)-2-methyl-1H-benzimidazole as an off-white solid.

To a chilled (−78° C.) solution of 5-bromo-1-(4-fluorophenyl)-2-methyl-1H-benzimidazole (210 mg, 0.68 mmol) in anhydrous THF (3 mL) was added n-butyllithium (1 mmol, 400 µL of a 2.5 M solution in hexanes) over a 1 minute period followed by a chilled (−78° C.) solution of 2,2,2-trifluoro-1-(1-methyl-1H-indol-3-yl)ethanone (200 mg, 0.88 mmol) in 1 mL of anhydrous THF. After 30 minutes, the mixture was quenched with ammonium chloride solution and extracted with methylene chloride. The organic layer was concentrated to afford a yellow oil. The residue was purified by column chromatography over silica gel eluting with 0-50% ethyl acetate in hexanes. The product rich fractions were collected and concentrated in vacuo to afford a light yellow oil. A second purification by reverse phase HPLC (C-18 column) using a gradient of 20-100% acetonitrile (0.1% TFA) in water (0.1% TFA) over 15 minutes and fractions corresponding to an earlier eluting peak (M+H 455) were collected. The acetonitrile was concentrated in vacuo, the residue was made basic with aqueous sodium bicarbonate, and extracted with methylene chloride. The organic layer was concentrated to afford 55 mg of the title compound as an off-white solid. MS m/z 455 (MH$^+$).

Example 60

2,2,2-Trifluoro-1-[3-(4-fluorophenyl)imidazo[1,5-a]pyridin-7-yl]-1-(1-methyl-1H-indol-3-yl)ethanol

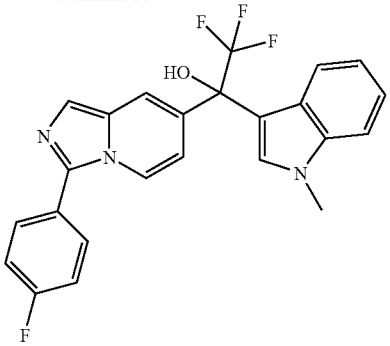

60

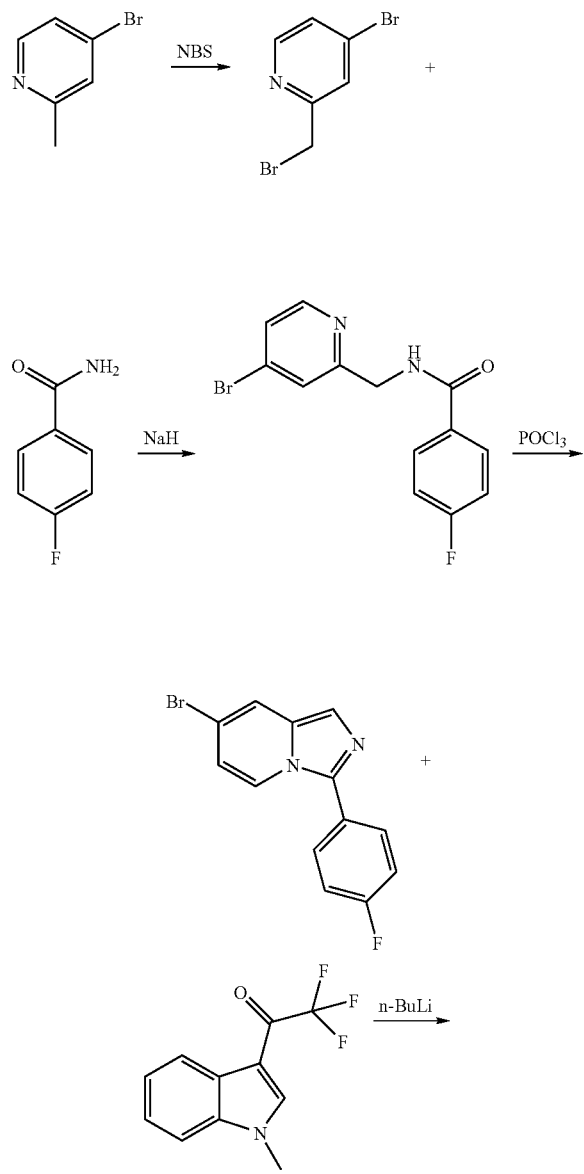

To a stirred room temperature solution of 4-bromo-2-methylpyridine (1.72 g, 10 mmol) in carbon tetrachloride at was added N-bromosuccinimide (1.9 g, 10.5 mmol). The mixture was warmed at 90° C. After 30 minutes, the mixture was cooled, and benzoyl peroxide (100 mg) was added and refluxing was continued. After 7 hours, the mixture was cooled to room temperature, washed with aqueous sodium bicarbonate, brine, dried over anhydrous sodium sulfate, and concentrated in vacuo to afford 4-bromo-2-bromomethylpyridine as a brown oil [MS m/z 250/252/254 (MH$^+$)] which was determined to be 75% pure and was used without further purification. The remaining material was determined to be 4-bromo-2-dibromomethylpyridine.

To a stirred room temperature solution of 4-fluorobenzamide (1.11 g, 8 mmol) in anhydrous THF (30 mL) was added sodium hydride (400 mg of 60% dispersion in mineral oil, 10 mmol). After 20 minutes, a solution of 4-bromo-2-bromomethylpyridine (~0.8 mmol) in 10 mL of THF was added and the mixture was warmed at reflux for 12 hours. The mixture was then concentrated in vacuo, diluted with brine (300 mL), and extracted with three 100 mL portions of methylene chloride. The combined organic layers were washed with water, dried over anhydrous sodium sulfate, and concentrated in vacuo to afford a brownish oil. The residue was purified by column chromatography over silica gel eluting with 0-100% ethyl acetate in methylene chloride to afford 1.1 g of N-(4-bromopyridin-2-ylmethyl)-4-fluorobenzamide as an off-white solid. MS m/z 309/311 (MH$^+$).

A mixture of N-(4-bromopyridin-2-ylmethyl)-4-fluorobenzamide (510 mg) in phosphorus oxychloride (5 mL) was warmed at 100° C. After 75 minutes, LC-MS showed two peaks (ratio 3:2) and the major peak showed M+H for the desired product. After cooling, the reaction was diluted with aqueous sodium bicarbonate and extracted with three 30 mL portions of methylene chloride. The combined organic layers were washed with water, dried over anhydrous sodium sulfate, and concentrated in vacuo to give brownish solid. The crude was purified by column chromatography over silica gel eluting with 0-50% ethyl acetate in hexanes to afford 7-bromo-3-(4-fluorophenyl)imidazo[1,5-a]pyridine as an off-white solid.

To a chilled (−78° C.) solution of 7-bromo-3-(4-fluorophenyl)imidazo[1,5-a]pyridine (58 mg, 0.2 mmol) in anhydrous THF (1 mL) was added n-butyllithium (0.1 mL of a 2.5 M solution in hexanes, 2.5 mmol). After 1 minute, a chilled (−78° C.) solution of 2,2,2-trifluoro-1-(1-methyl-1H-indol-3-yl)ethanone (68 mg, 0.3 mmol) in 1 mL of THF was added. After 5 minutes, the reaction mixture was quenched with 50 mL of brine solution and extracted with three 25 mL portions of methylene chloride. The combined organic extracts were washed with water, dried over anhydrous sodium sulfate, and concentrated in vacuo to afford a yellow oil. The residue was purified by column chromatography over silica gel eluting with 0-70% ethyl acetate to afford 30 mg of the title compound as a light yellow solid. MS m/z 440 (MH+).

Example 61

2,2,2-Trifluoro-1-[1-(4-fluorophenyl)-1H-benzotriazol-5-yl]-1-(1-methyl-1H-indol-3-yl)ethanol

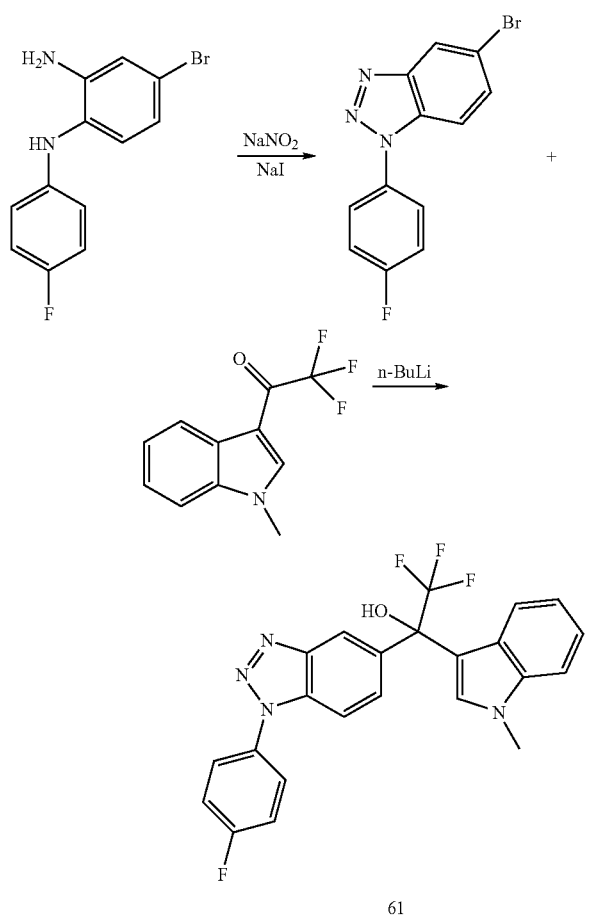

61

To a stirred room temperature solution of 4-bromo-N$^1$-(4-fluorophenyl)benzene-1,2-diamine (1.4 g, 5 mmol) in DMSO (12 mL), was added 30% sulfuric acid (12 mL). The mixture was then cooled (ice-bath) and a solution of sodium nitrite (380 mg, 5.5 mmol) in water (1 mL) was added dropwise. After 20 minutes, a solution of sodium iodide (2.4 g, 15.8 mmol) in water (2 mL) was added dropwise and the cold bath was removed. After 30 minutes, LCMS showed only a single product [MS m/z 292/294 (MH+)] consistent with the desired product. The mixture was poured into 150 mL of ice water and the resulting precipitate was filtered, washed with sodium thiosulfate solution, water and dried to afford 1.3 g of 5-bromo-1-(4-fluorophenyl)-1H-benzotriazole as a light purple solid. MS m/z 292/294 (MH+).

To a chilled (−78° C.) solution of 5-bromo-1-(4-fluorophenyl)-1H-benzotriazole (145 mg, 0.5 mmol) in anhydrous THF (3 mL) was added n-butyllithium (0.25 mL of a 2.5 M solution in hexanes, 0.625 mmol) over a 1 minute period followed by a chilled (−78° C.) solution of 2,2,2-trifluoro-1-(1-methyl-1H-indol-3-yl)ethanone (170 mg, 0.75 mmol) in 1 mL of THF. After 15 minutes, the mixture quenched with brine (50 mL) and extracted with three 50 mL portions of methylene chloride. The combined organic layers were washed with water, dried over anhydrous sodium sulfate and concentrated in vacuo to afford a yellow oil. The residue was purified by column chromatography over silica gel eluting with 0-50% ethyl acetate in hexanes to afford 40 mg of the title compound as a light yellow solid. MS m/z 441 (MH+).

Example 62

1-[1-(2,2-Dimethyl-1,3-dioxolan-4-ylmethyl)-1H-indol-3-yl]-2,2,2-trifluoro-1-[1-(4-fluorophenyl)-1H-benzotriazol-5-yl]ethanol

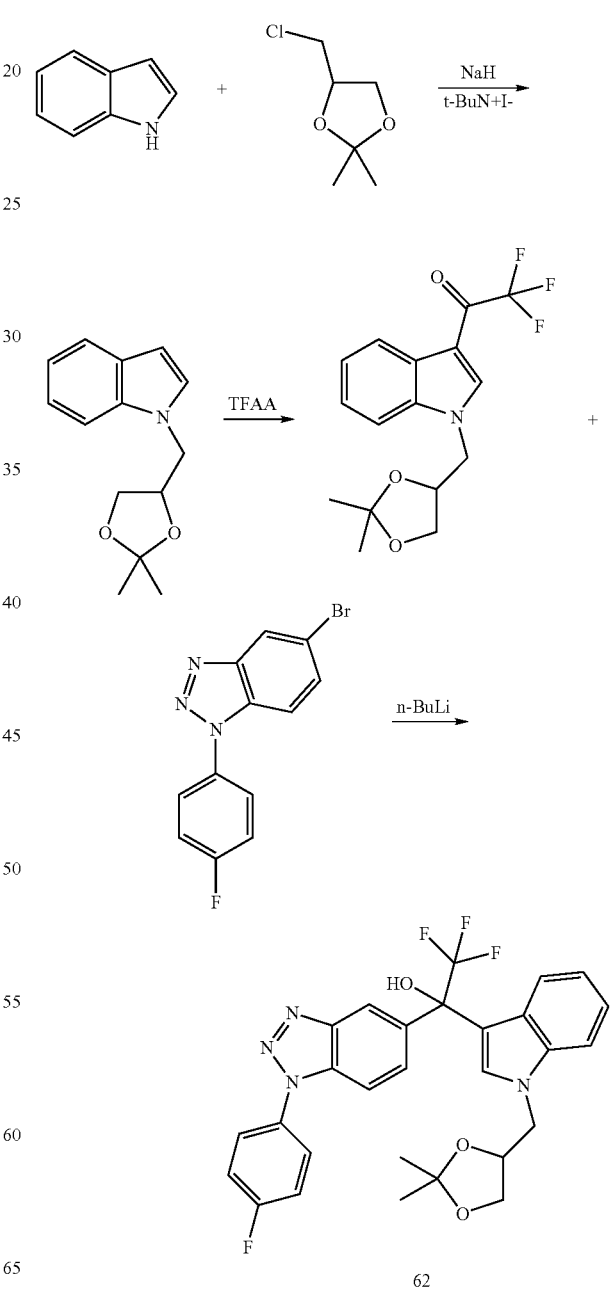

62

To a stirred room temperature solution of indole (5.9 g, 50 mmol) in THF (100 mL) was added sodium hydride (2.4 g of 60% in mineral oil, 60 mmol) in one portion. After 30 minutes, 4-chloromethyl-2,2-dimethyl-1,3-dioxolane (10.6 mL, 75 mmol) was added followed by tetra-n-butylammonium iodide (1.9 g, 5 mmol) and the mixture was warmed at reflux. After 24 hours, LCMS showed about 50% conversion [MS m/z 232 (MH⁺)]. Additional 4-chloromethyl-2,2-dimethyl-1,3-dioxolane (11.4 mL) was added and the refluxing continued. After 18 hours, the mixture was cooled, diluted with THF (300 mL), filtered, and concentrated in vacuo to afford a brown oil. The residue was purified by column chromatography over silica gel eluting with 0-100% methylene chloride in hexanes and the product-rich fractions were collected to afford 3.3 g of 1-(2,2-dimethyl-1,3-dioxolan-4-ylmethyl)-1H-indole as a brownish oil.

To a chilled (ice-bath), solution of 1-(2,2-dimethyl-1,3-dioxolan-4-ylmethyl)-1H-indole (3.3 g, 14.3 mmol) in DMF (20 mL) was added trifluoroacetic anhydride (2.15 mL, 15.2 mmol) dropwise. After 30 minutes, the cold bath was removed. After 3 hours, ~50% conversion to the product (M+H 328) was observed. Additional trifluoroacetic anhydride (3 mL) was added and LC-MS after 30 minutes showed a single product at M+H 328. The reaction mixture poured into aqueous sodium bicarbonate (300 mL) and extracted with three 100 mL portions of methylene chloride. The combined organic layers were washed with water, dried over anhydrous sodium sulfate, and concentrated in vacuo to afford 4.6 g of 1-[1-(2,2-dimethyl-1,3-dioxolan-4-ylmethyl)-1H-indol-3-yl]-2,2,2-trifluoroethanone as a brownish oil. MS m/z 328 (MH⁺).

To a chilled (-78° C.) solution of 5-bromo-1-(4-fluorophenyl)-1H-benzotriazole (145 mg, 0.5 mmol) in anhydrous THF (3 mL) was added n-butyllithium (0.22 mL of a 2.5 M solution in hexanes, 0.55 mmol). After 1 minute, a chilled (-78° C.) solution of 1-[1-(2,2-dimethyl-1,3-dioxolan-4-yl-methyl)-1H-indol-3-yl]-2,2,2-trifluoroethanone (185 mg, 0.57 mmol) in 1 mL of THF was added. After 30 minutes, the mixture was quenched with brine solution (50 mL) and extracted with ethyl acetate. The combined organic layers were washed with water, dried over anhydrous sodium sulfate, and solvent evaporated in vacuo to afford a yellow oil. The residue was purified by column chromatography over silica gel eluting with 0-60% ethyl acetate in hexanes and fractions corresponding to MS m/z 541 (MH⁺) peak were pooled and concentrated in vacuo to afford 150 mg of the title compound as a brownish solid.

Example 63

1-[1-(2,2-Dimethyl-1,3-dioxolan-4-ylmethyl)-1H-indol-3-yl]-2,2,2-trifluoro-1-[3-(4-fluorophenyl)imidazo[1,5-a]pyridin-7-yl]ethanol

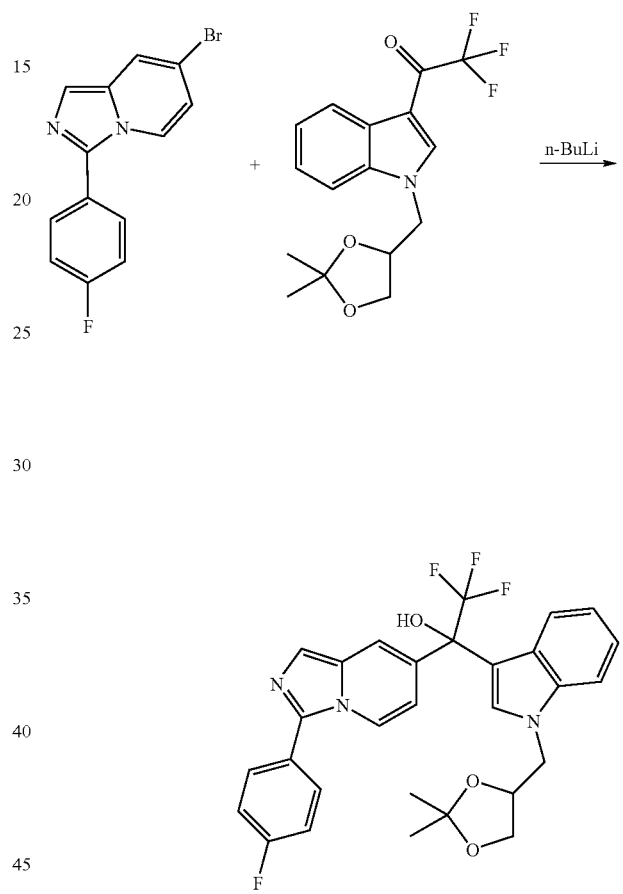

63

To a chilled (-78° C.) solution of 7-bromo-3-(4-fluorophenyl)imidazo[1,5-a]pyridine (160 mg, 0.55 mmol) in anhydrous THF (3 mL) was added n-butyllithium (275 μL of a 2.5 M solution in hexanes, 0.69 mmol). After 2 minutes, a chilled (-78° C.) solution of 1-[1-(2,2-dimethyl-1,3-dioxolan-4-yl-methyl)-1H-indol-3-yl]-2,2,2-trifluoroethanone (240 mg, 0.73 mmol) in 1 mL of THF was added. After 60 minutes, the mixture was quenched with brine (50 mL) and extracted with ethyl acetate. The combined organic layers were washed with water, dried over anhydrous sodium sulfate, and concentrated in vacuo to afford a yellow oil. The residue was purified by column chromatography over silica gel eluting with 0-75% ethyl acetate in hexanes and fractions corresponding to a MS

Example 64

3-(3-{2,2,2-Trifluoro-1-[1-(4-fluorophenyl)-1H-benzotriazol-5-yl]-1-hydroxyethyl}indol-1-yl)propane-1,2-diol

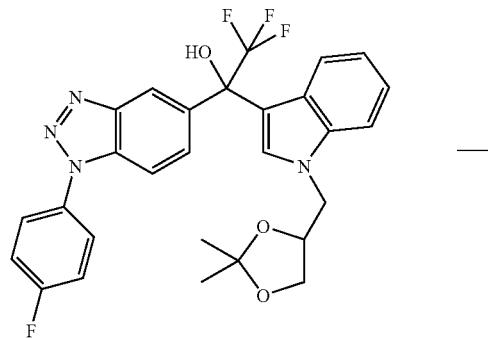

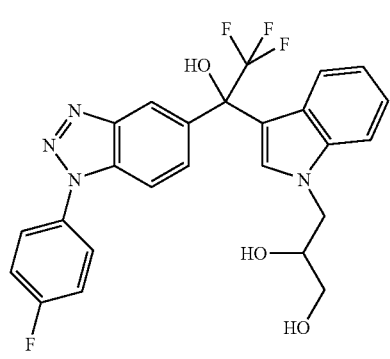

64

At room temperature, approximately 200 μL of concentrated HCl was added to 1-[1-(2,2-dimethyl-1,3-dioxolan-4-ylmethyl)-1H-indol-3-yl]-2,2,2-trifluoro-1-[1-(4-fluorophenyl)-1H-benzotriazol-5-yl]ethanol (100 mg) in aqueous acetonitrile. After 90 minutes, LCMS showed one peak MS m/z 501 (MH⁺) for the desired product. The mixture was then concentrated and the residue diluted with sodium bicarbonate and extracted with ethyl acetate. The combined organic extracts were washed with water, dried over anhydrous sodium sulfate, and concentrated in vacuo to afford 95 mg of the title compound as an off-white solid.

Example 65

3-(3-{2,2,2-Trifluoro-1-[3-(4-fluorophenyl)imidazo[1,5-a]pyridin-7-yl]-1-hydroxyethyl}indol-1-yl)propane-1,2-diol

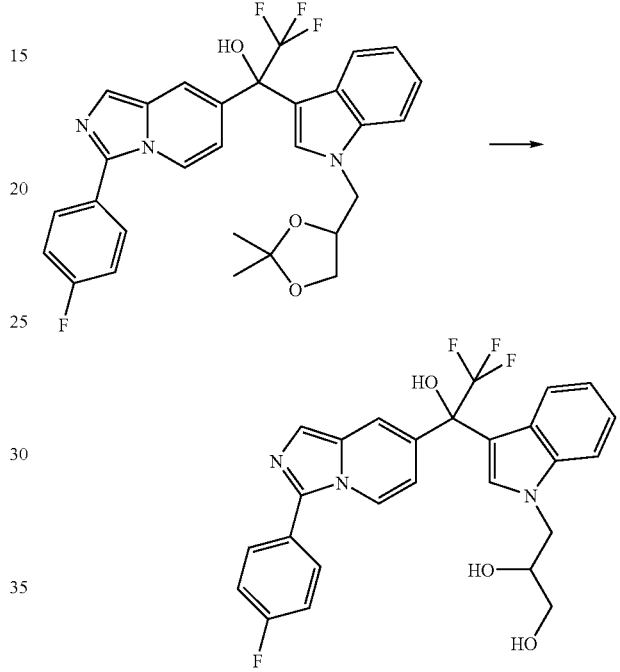

At room temperature, approximately 100 μL of concentrated HCl was added to 2,2,2-trifluoro-1-[3-(4-fluorophenyl)imidazo[1,5-a]pyridin-7-yl]-1-{1-[2-(1-methoxy-1-methylethoxy)propyl]-1H-indol-3-yl}ethanol (30 mg) in aqueous acetonitrile. After 90 minutes, LC-MS showed one peak M+H 500 for the desired product. The mixture was then concentrated in vacuo and diluted with sodium bicarbonate and extracted with ethyl acetate. The combined organic extracts were washed with water, dried over anhydrous sodium sulfate, and solvent evaporated in vacuo to afford 25 mg of the title compound as a light yellow solid.

Example 66

3-(2,2,2-Trifluoroacetyl)-1,6-dihydropyrrolo[2,3-c]pyridin-7-one

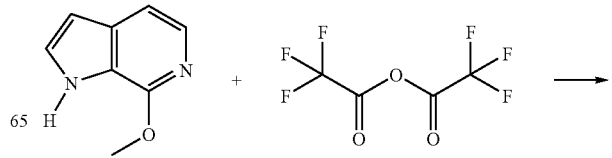

-continued

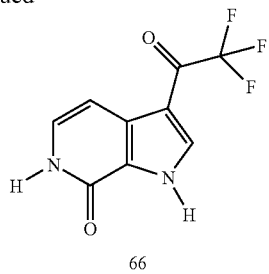

66

A room temperature solution of aluminum chloride (3.07 g, 23.1 mmol) in 100 mL of dichloromethane was added 7-methoxy-6-azaindole (684 mg, 4.62 mmol) (prepared according to a procedure described by Tyler et al., *J. Org. Chem.* 2001, 66, 5723-5730). After 1 hour, trifluoroacetic anhydride (3.35 mL, 23.7 mmol) was added. After 6 hours, the reaction mixture was poured into saturated aqueous sodium bicarbonate (250 mL), the organic layer was separated and the aqueous layer was extracted with four 50 mL portions of ethyl acetate. The combined organic layers were washed with three 30 mL portions of brine, dried over magnesium sulfate, filtered, and concentrated in vacuo. The residue was triturated with ether to afford 822 mg (77%) of the title compound.

Example 67

2,2,2-Trifluoro-1-(7-methoxy-1H-pyrrolo[2,3-c]pyridin-3-yl)ethanone

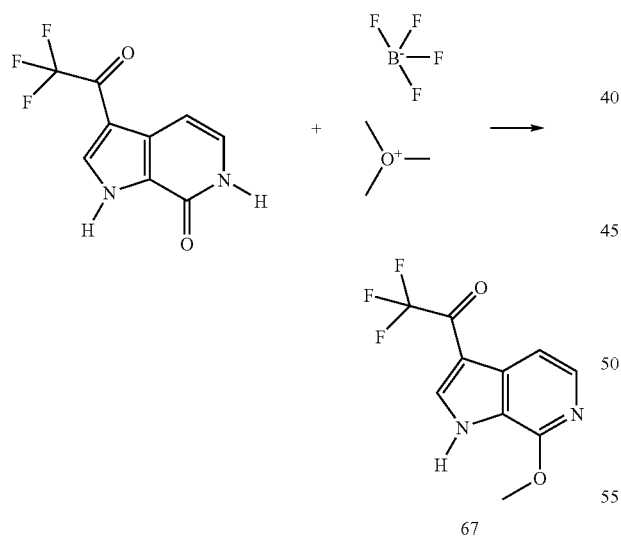

67

To a room temperature solution of the pyrrolo[2,3-c]pyridin-7-one (650 mg, 2.83 mmol) in CH$_2$Cl$_2$ (100 mL) was added trimethyloxonium tetrafluoroborate (627 mg, 4.24 mmol). After 18 hours, the mixture was diluted with 50 mL of saturated aqueous sodium bicarbonate and stirred for 8 hours. The aqueous layer was separated and extracted with three 100 mL portions of ethyl acetate. The combined organic layers were washed with 100 mL of brine, dried over magnesium sulfate, filtered, and concentrated in vacuo. The residue was chromatography on SiO$_2$ (0-50% ethyl acetate in hexanes, gradient) to afford 225 mg (33%) of the title compound. MS m/z 245.05 (MH$^+$).

Example 68

6-Methyl-3-(2,2,2-trifluoroacetyl)-1,6-dihydropyrrolo[2,3-c]pyridin-7-one

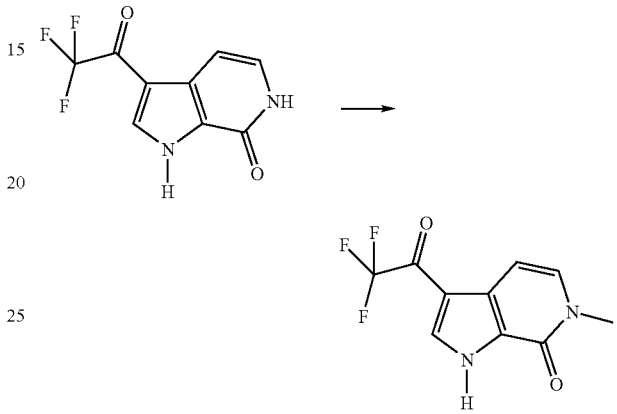

68

A solution of the pyrrolo[2,3-c]pyridin-7-one (240 mg, 1.04 mmol) in DMF (2 mL) was cooled to 0° C. and treated with NaH (91.8 mg, 2.29 mmol, 60% dispersion in oil). After the evolution of gas ceased, methyl iodide (98.0 µL, 1.57 mmol) was added and the mixture was stirred at room temperature for 1 hour. The reaction was poured into of water (2 mL) and extracted with ethyl acetate (2 mL). The combined organic layers were dried over magnesium sulfate, filtered, and concentrated. The crude mixture was purified on SiO$_2$ (Prep-TLC, 5% methanol in CH$_2$Cl$_2$, developed 4 times). The desired band was collected further purified on SiO$_2$ (0-10% methanol in CH$_2$Cl$_2$, gradient) to afford the title compound (74.0 mg, 29%).

Example 69

2,2,2-Trifluoro-1-[1-(4-fluorophenyl)-1H-indazol-5-yl]-1-(7-methoxy-1H-pyrrolo[2,3-c]pyridin-3-yl)ethanol

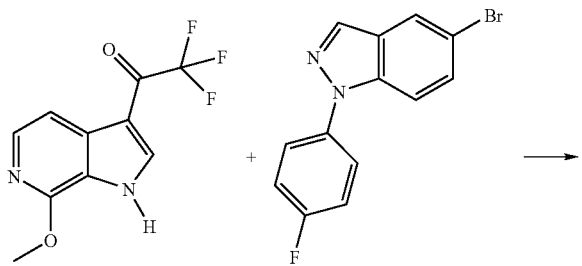

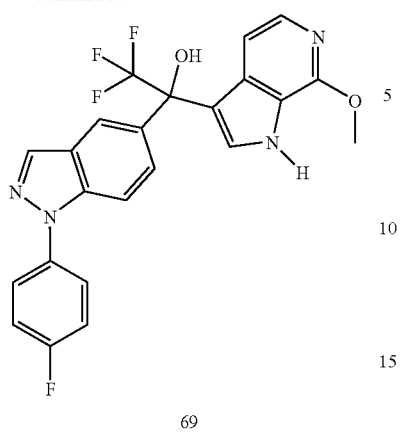

69

The title compound (76.8 mg, 75% yield) was prepared from 2,2,2-trifluoro-1-(7-methoxy-1H-pyrrolo[2,3-c]pyridin-3-yl)ethanone (55.0 mg, 0.225 mmol) according to methods described in Example 1. MS m/z 457.31 (MH+).

Example 70

6-Methyl-3-{2,2,2-trifluoro-1-[1-(4-fluorophenyl)-1H-indazol-5-yl]-1-hydroxyethyl}-1,6-dihydropyrrolo[2,3-c]pyridin-7-one The title compound (48.5 mg, 35% yield) was prepared from 6-methyl-3-(2,2,2-trifluoro-acetyl)-1,6-dihydropyrrolo[2,3-c]pyridin-7-one (74.0 mg, 0.303 mmol) according to methods described in Example 1.

Example 71

2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide

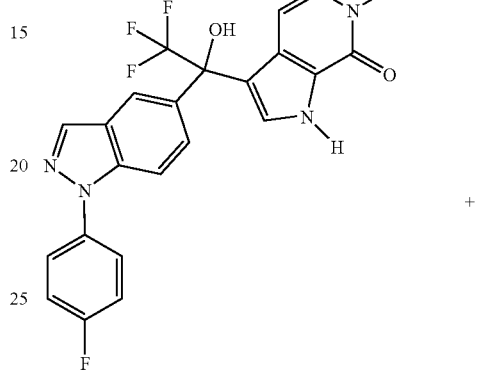

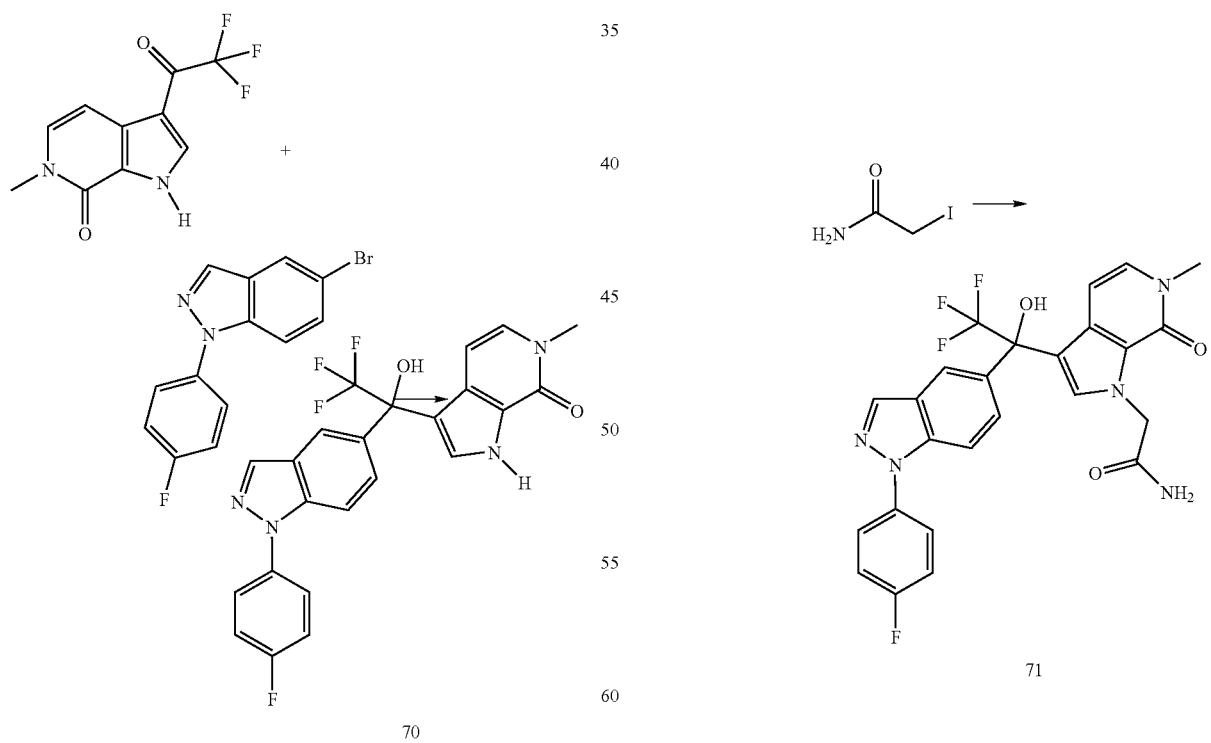

71

The title compound (29.5 mg, 66% yield) was prepared from 6-methyl-3-{2,2,2-trifluoro-1-[1-(4-fluorophenyl)-1H-indazol-5-yl]-1-hydroxyethyl}-1,6-dihydropyrrolo[2,3-c]

pyridin-7-one (40.0 mg, 0.088 mmol) according to methods described in Example 4. MS m/z 514.39 (MH+).

Example 72

1-(1-Allyl-7-methoxy-1H-pyrrolo[2,3-c]pyridin-3-yl)-2,2,2-trifluoro-1-[1-(4-fluorophenyl)-1H-indazol-5-yl]ethanol

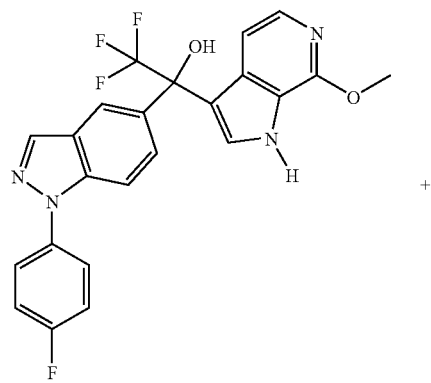

+

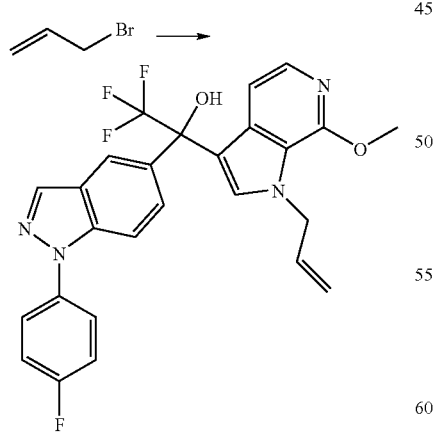

72

The title compound (46.2 mg, 79% yield) was prepared from 2,2,2-trifluoro-1-[1-(4-fluorophenyl)-1H-indazol-5-yl]-1-(7-methoxy-1H-pyrrolo[2,3-c]pyridin-3-yl)ethanol (54.0 mg, 0.118 mmol) according to methods described in Example 4. MS m/z 497.47 (MH+).

Example 73

3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol

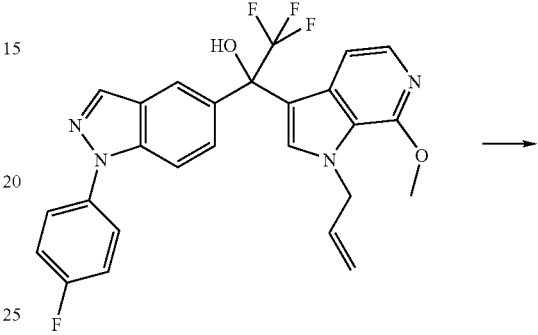

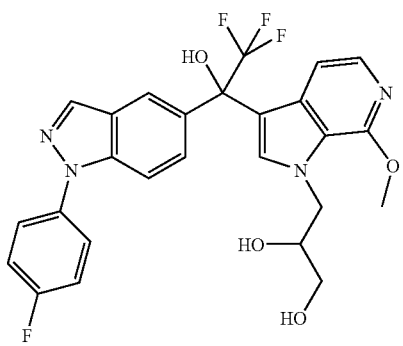

73

The title compound (19.4 mg, 40% yield) was prepared from 1-(1-allyl-7-methoxy-1H-pyrrolo[2,3-c]pyridin-3-yl)-2,2,2-trifluoro-1-[1-(4-fluorophenyl)-1H-indazol-5-yl]ethanol (46.0 mg, 0.093 mmol) according to methods described in Example 34. MS m/z 531.41 (MH+).

Example 74

1-Allyl-4-{2,2,2-trifluoro-1-[1-(4-fluorophenyl)-1H-indazol-5-yl]-1-hydroxyethyl}-1H-pyrrole-2-carboxylic acid (2,2-dimethoxyethyl)methylamide

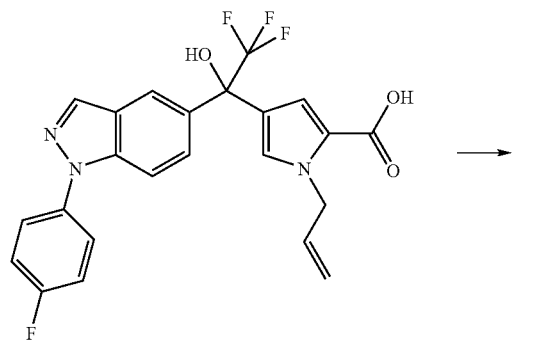

The title compound (268 mg, 99%) was prepared from 1-allyl-4-{2,2,2-trifluoro-1-[1-(4-fluorophenyl)-1H-indazol-5-yl]-1-hydroxyethyl}-1H-pyrrole-2-carboxylic acid (220.0 mg, 0.479 mmol) according to methods described in Example 40.

Example 75

1-Allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one

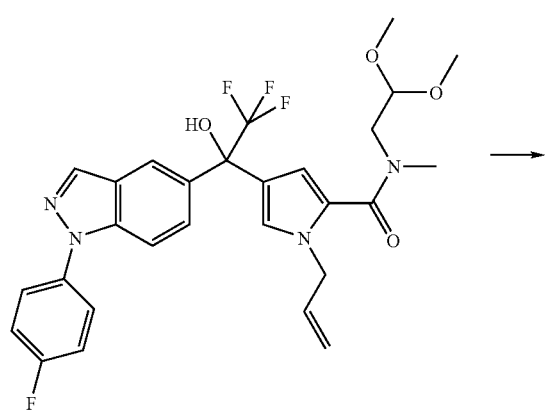

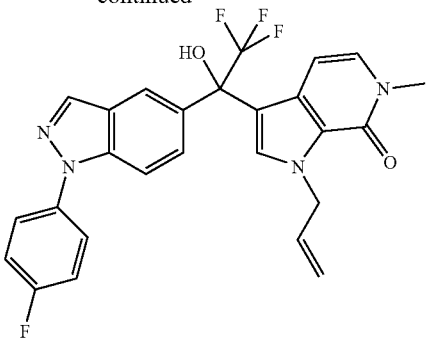

A room temperature solution of 1-allyl-4-{2,2,2-trifluoro-1-[1-(4-fluorophenyl)-1H-indazol-5-yl]-1-hydroxyethyl}-1H-pyrrole-2-carboxylic acid (2,2-dimethoxyethyl)methylamide (100 mg, 0.178 mmol) in ether (2 mL) was added H₂SO₄ (50 µL). After 13 hours, the mixture was carefully quenched with saturated aqueous sodium bicarbonate (3 mL) and extracted with three 10 mL portions of ethyl acetate. The combined organic layers were washed with brine (10 mL), dried over magnesium sulfate, filtered, and concentrated in vacuo. The residue was purified by chromatography on SiO₂ (0-80% ethyl acetate in hexanes, gradient) to give 84 mg (95%) of the title compound. MS m/z 497.36 (MH+), m.p. 91° C.-93° C.

Example 76

1-(2,3-Dihydroxypropyl)-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one and Example 77: 6-Methyl-3-{2,2,2-trifluoro-1-[1-(4-fluorophenyl)-1H-indazol-5-yl]-1-hydroxyethyl}-1,6-dihydropyrrolo[2,3-c]pyridin-7-one

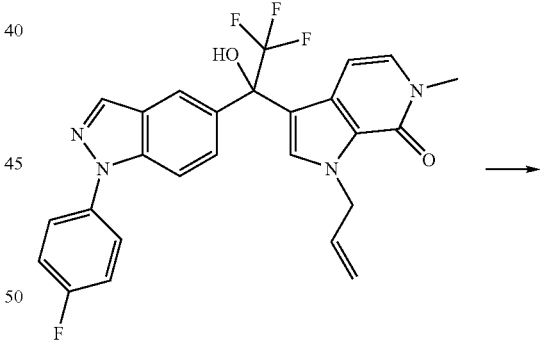

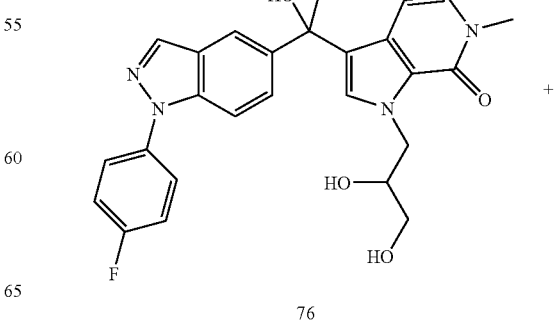

-continued

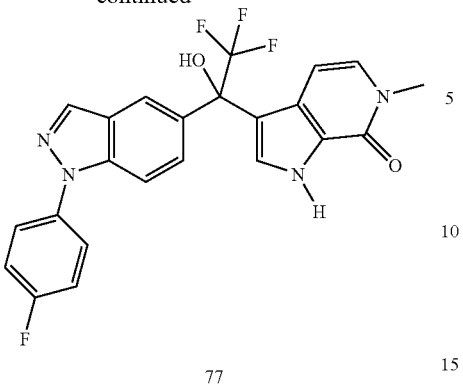

77

The title compounds (76: 32.2 mg, 36%; and 77: 4.7 mg, 6%) were prepared from 1-allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one (84.0 mg, 0.169 mmol) according to methods described in Example 34. MS m/z 531.45 (MH⁺) and m/z 457.33 (MH⁺), respectively.

Example 78

1-Allyl-4-bromo-1H-pyrazole-3-carbonitrile

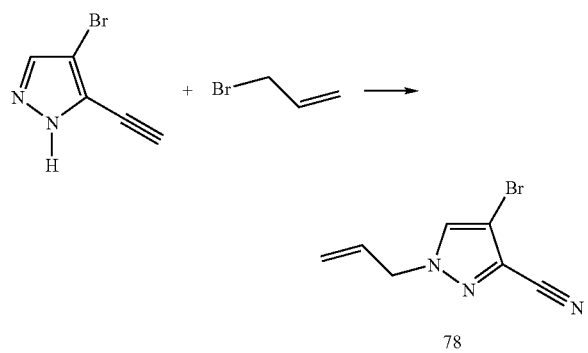

78

The title compound (564 mg, 46% yield) was prepared from 4-bromo-2H-pyrazole-3-carbonitrile (commercially available, 1.00 g, 0.581 mmol) according to methods described in Example 38. MS m/z 497.47 (MH⁺).

Example 79

1-Allyl-4-{2,2,2-trifluoro-1-[1-(4-fluorophenyl)-1H-indazol-5-yl]-1-hydroxyethyl}-1H-pyrazole-3-carbonitrile

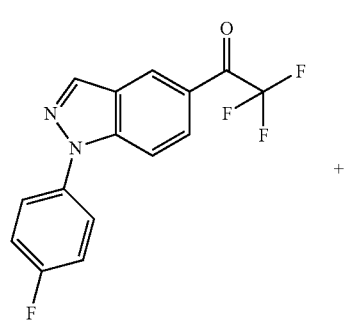

-continued

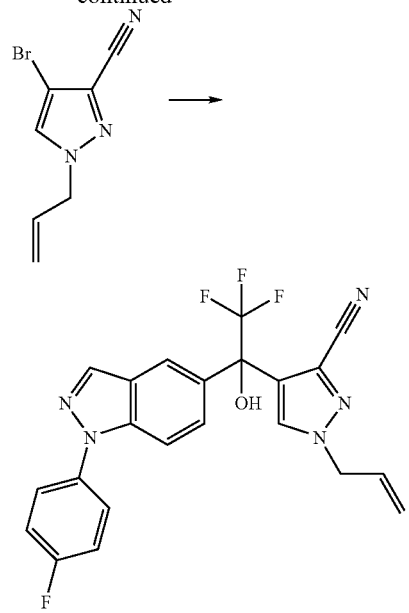

79

To a chilled (−78° C.) solution of 1-allyl-4-bromo-1H-pyrazole-3-carbonitrile (116.6 mg, 0.550 mmol) in dry ether (2 mL) was added n-BuLi (190 pt, 2.5 M in hexanes, 0.475 mmol). After 2 minutes a chilled (−78° C.) solution of 2,2,2-trifluoro-1-[1-(4-fluorophenyl)-1H-indazol-5-yl]ethanone (154 mg, 0.500 mmol) in THF (2 mL) was added. After 15 minutes, the mixture was warmed to room temperature, quenched with 10 mL of saturated aqueous sodium bicarbonate and extracted with three 10 mL portions of ethyl ether. The combined organic layers were washed with brine (10 mL), dried over magnesium sulfate, filtered, and concentrated in vacuo. The residue was purified by chromatography on SiO₂ (0-50% ethyl acetate in hexanes, gradient) to give 152 mg (69%) of the title compound. MS m/z 422.96 (MH⁺).

Example 80

1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile, and Example 81: 4-{2,2,2-Trifluoro-1-[1-(4-fluorophenyl)-1H-indazol-5-yl]-1-hydroxyethyl}-1H-pyrazole-3-carbonitrile

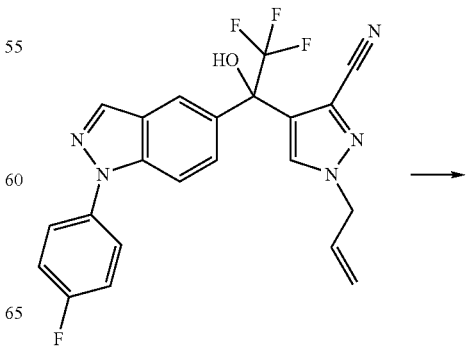

213
-continued

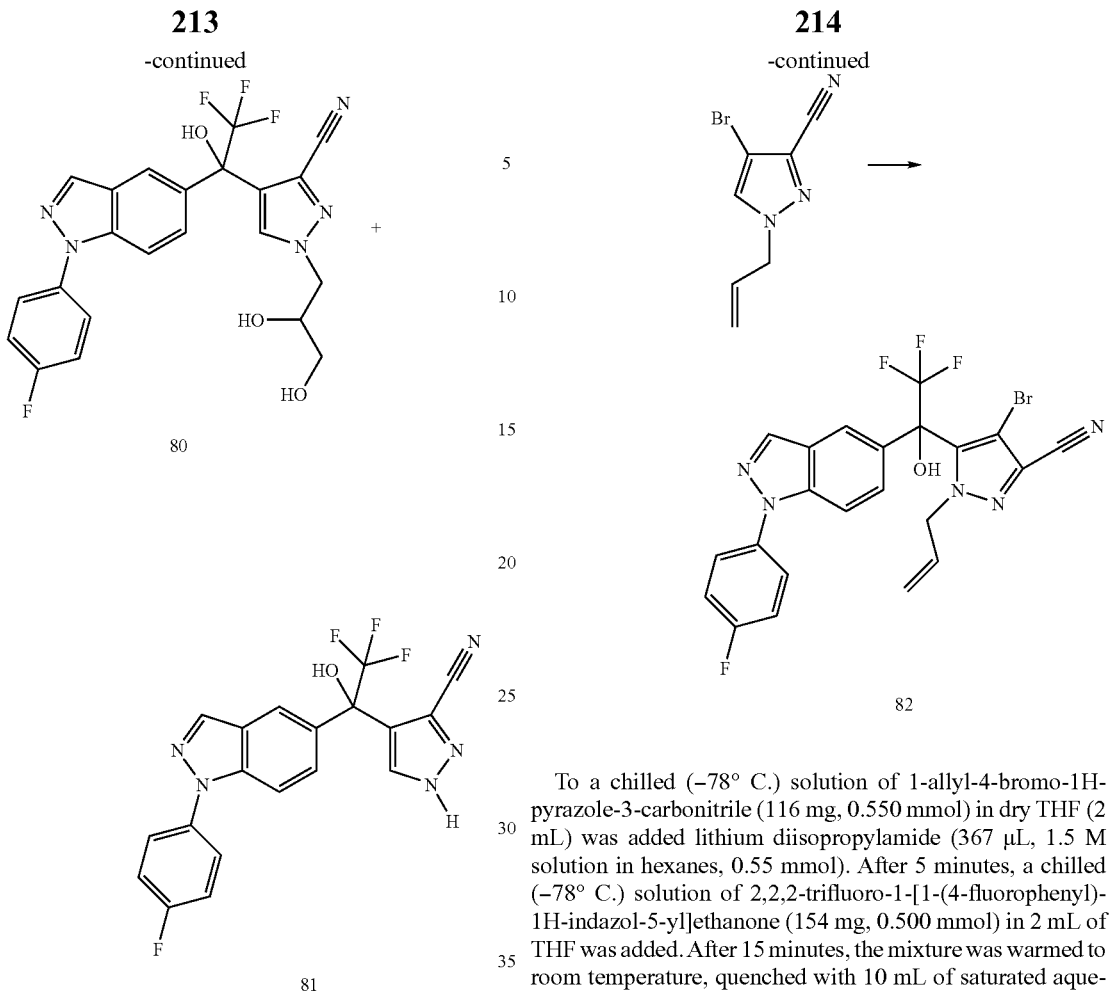

The title compounds (47.8 mg, 63% yield; 5.2 mg, 8% yield, respectively) were prepared from 1-allyl-4-{2,2,2-trifluoro-1-[1-(4-fluorophenyl)-1H-indazol-5-yl]-1-hydroxyethyl}-1H-pyrazole-3-carbonitrile (70.3 mg, 0.159 mmol) according to a procedure described in Example 34. MS m/z 476.30 (MH⁺), m/z 402.20 (MH⁺), respectively.

Example 82

1-Allyl-4-bromo-5-{2,2,2-trifluoro-1-[1-(4-fluorophenyl)-1H-indazol-5-yl]-1-hydroxyethyl}-1H-pyrazole-3-carbonitrile

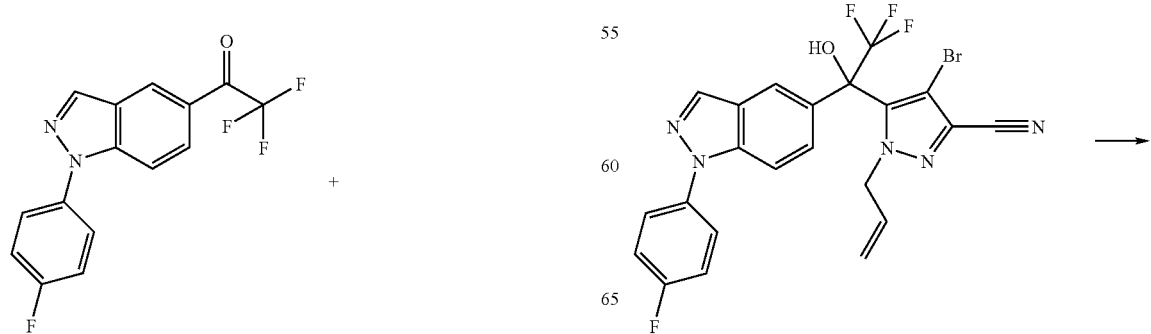

214
-continued

To a chilled (−78° C.) solution of 1-allyl-4-bromo-1H-pyrazole-3-carbonitrile (116 mg, 0.550 mmol) in dry THF (2 mL) was added lithium diisopropylamide (367 μL, 1.5 M solution in hexanes, 0.55 mmol). After 5 minutes, a chilled (−78° C.) solution of 2,2,2-trifluoro-1-[1-(4-fluorophenyl)-1H-indazol-5-yl]ethanone (154 mg, 0.500 mmol) in 2 mL of THF was added. After 15 minutes, the mixture was warmed to room temperature, quenched with 10 mL of saturated aqueous sodium bicarbonate and extracted with three 10 mL portions of ethyl ether. The combined organic layers were washed with 10 mL of brine, dried over sodium sulfate, filtered, and concentrated in vacuo. The residue was chromatographed on SiO₂ (0-50% ethyl acetate in hexanes, gradient) to afford 213 mg (82%) of the title product. MS m/z 520.19/ 522.20 (M⁺).

Example 83

4-Bromo-1-(2,3-dihydroxypropyl)-5-{2,2,2-trifluoro-1-[1-(4-fluorophenyl)-1H-indazol-5-yl]-1-hydroxyethyl}-1H-pyrazole-3-carbonitrile -continued

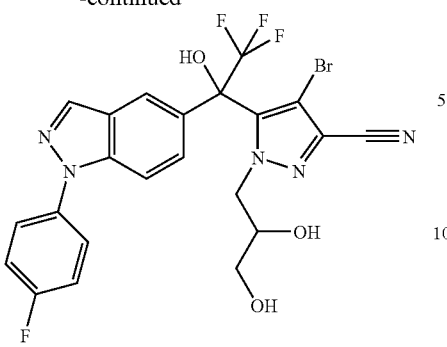

83

-continued

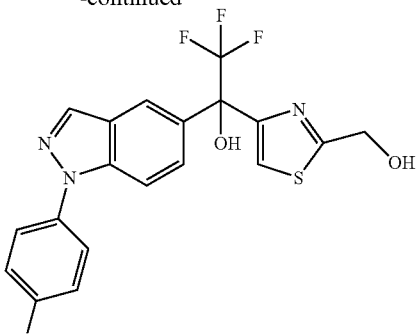

84

The title compound (29.3 mg, 55%) was prepared from 1-allyl-4-bromo-5-{2,2,2-trifluoro-1-[1-(4-fluorophenyl)-1H-indazol-5-yl]-1-hydroxyethyl}-1H-pyrazole-3-carbonitrile (50.3 mg, 0.097 mmol) according to methods described in Example 34. MS m/z 554.28/556.22 (M$^+$).

Example 84

2,2,2-Trifluoro-1-[1-(4-fluorophenyl)-1H-indazol-5-yl]-1-(2-hydroxymethylthiazol-4-yl)ethanol

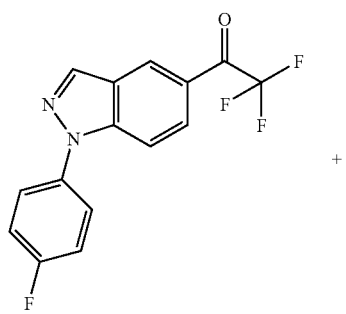

+

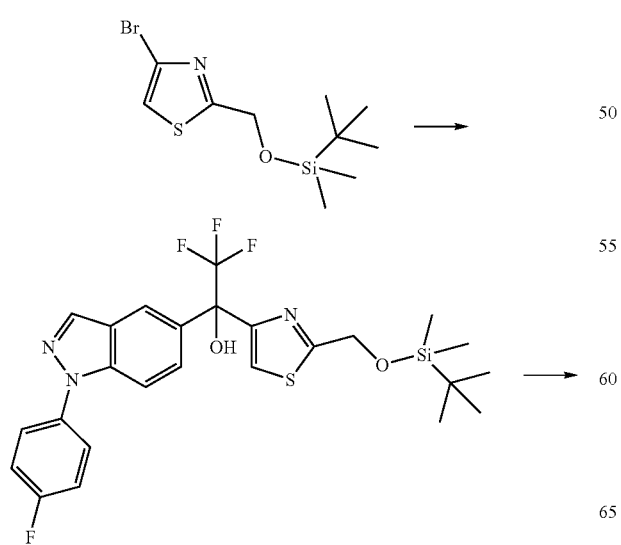

To a chilled (−78° C.) solution of 4-bromo-2-(tert-butyldimethylsilanyloxymethyl)thiazole (339 mg, 1.10 mmol) (prepared according to a procedure described by Nicolaou et al., *Bioorg. Med. Chem.* 1999, 7, 665-697) in dry ether (5 mL) was added n-BuLi (440 μL, 2.5 M in hexane, 1.10 mmol). After 2 minutes, a chilled (−78° C.) solution of 2,2,2-trifluoro-1-[1-(4-fluorophenyl)-1H-indazol-5-yl]ethanone (308 mg, 1.00 mmol) in 5 mL of dry ether added. After 15 minutes, the mixture was warmed to room temperature and quenched with 20 mL of saturated aqueous ammonium chloride and extracted with three 20 mL portions of diethyl ether. The combined organic layers were washed with 20 mL of brine, dried over magnesium sulfate, filtered, and concentrated in vacuo. The residue was chromatographed on SiO$_2$ (0-30% ethyl acetate in hexanes, gradient) to afford 358 mg (67%) of 1-[2-(tert-butyldimethylsilanyloxymethyl)thiazol-4-yl]-2,2,2-trifluoro-1-[1-(4-fluorophenyl)-1H-indazol-5-yl]ethanol. MS m/z 538.97 (MH$^+$).

To a chilled (0° C.) solution of 1-[2-(tert-butyldimethylsilanyloxymethyl)thiazol-4-yl]-2,2,2-trifluoro-1-[1-(4-fluorophenyl)-1H-indazol-5-yl]ethanol (300 mg, 0.558 mmol) in 15 mL of THF was added tetra-n-butylammonium fluoride (0.670 mL, 1 M solution in THF, 0.67 mmol). The mixture was warmed to room temperature. After 30 minutes, the mixture was quenched with 50 mL of saturated aqueous sodium bicarbonate and extracted with three 50 mL portions of diethyl ether. The combined organic layers were washed with 20 mL of brine, dried over magnesium sulfate, filtered, and concentrated in vacuo. The residue was chromatographed on SiO$_2$ (0-50% ethyl acetate in hexanes) to afford 230 mg (97%) of the title compound. MS m/z 424.71 (MH$^+$).

Example 85

2-(tert-Butyldimethylsilanyloxymethyl)thiazole

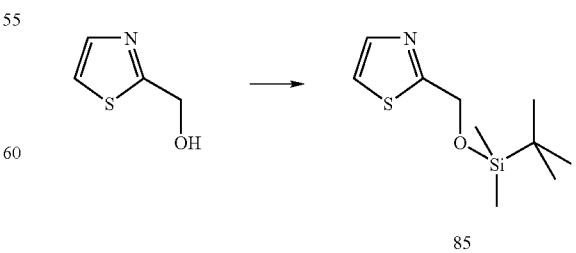

85

To a room temperature solution of thiazol-2-ylmethanol (1.00 g, 8.684 mmol) in CH$_2$Cl$_2$ was added imidazole (1.18 g, 17.4 mmol) followed by tert-butyldimethylsilyl chloride (1.70 g, 11.3 mmol). After 30 minutes, the mixture was quenched with 2 mL of MeOH and passed through a pad of silica gel eluting with $CH_2Cl_2$ (700 mL) and concentrated in vacuo to afford 2.01 g (100%) of the title compound.

Example 86

2,2,2-Trifluoro-1-[1-(4-fluorophenyl)-1H-indazol-5-yl]-1-(2-hydroxymethylthiazol-5-yl)ethanol

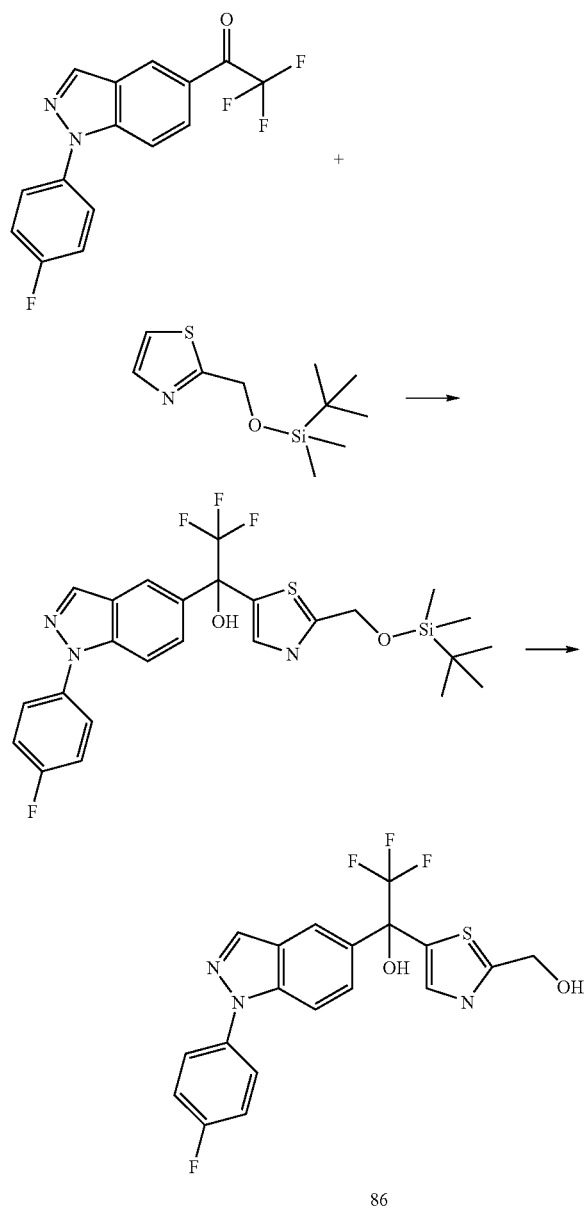

The title compound (73.1 mg, 17% overall yield) was prepared from 2-(tert-butyldimethylsilanyloxymethyl)thiazole (242 mg, 1.06 mmol) according to methods described for the synthesis of 2,2,2-trifluoro-1-[1-(4-fluorophenyl)-1H-indazol-5-yl]-1-(2-hydroxymethyl-thiazol-4-yl)ethanol (Example 84). MS m/z 424.48 (MH$^+$).

Example 87

2,2,2-Trifluoro-1-(2-morpholin-4-yl-thiazol-5-yl)ethanone

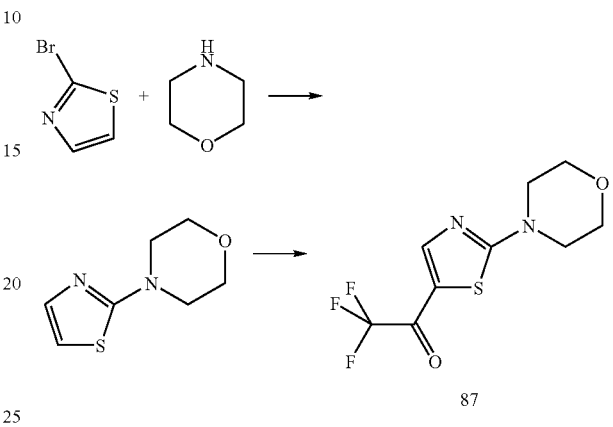

A solution of 2-bromothiazole (356 μL, 4.00 mmol) in morpholine (2.09 mL, 24.0 mmol) was warmed at 100° C. in a sealed tube. After 61 hours, the mixture was cooled to room temperature, diluted with 20 mL of water, and extracted with three 30 mL portions of diethyl ether. The combined organic layers were washed with five 30 mL portions of water, 30 mL of brine, dried over magnesium sulfate, filtered, and concentrated in vacuo. The residue was chromatographed over $SiO_2$ (20-100% ethyl acetate in hexanes, gradient) to afford 513 mg (75%) of 4-thiazol-2-yl-morpholine.

To a room temperature solution of 4-thiazol-2-yl-morpholine (340 mg, 2.00 mmol) in $CH_2Cl_2$ (1 mL) was added trifluoroacetic anhydride (565 μL, 4.0 mmol) dropwise. The mixture was warmed at 45° C. After 16 hours, the reaction was neutralized with 5 mL of saturated aqueous sodium bicarbonate. The organic phase was separated and the aqueous layer was extracted with three 15 mL portions of $CH_2Cl_2$. The combined organic layers were washed with brine, dried over magnesium sulfate, filtered, and concentrated in vacuo. The residue was purified on $SiO_2$ using ethyl acetate in hexanes (20-100% gradient) to afford 463 mg (87%) of the title compound. MS m/z 267.18 (MH$^+$).

Example 88

2,2,2-Trifluoro-1-[1-(4-fluorophenyl)-1H-indazol-5-yl]-1-(2-morpholin-4-yl-thiazol-5-yl)ethanol

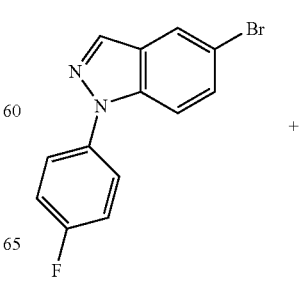

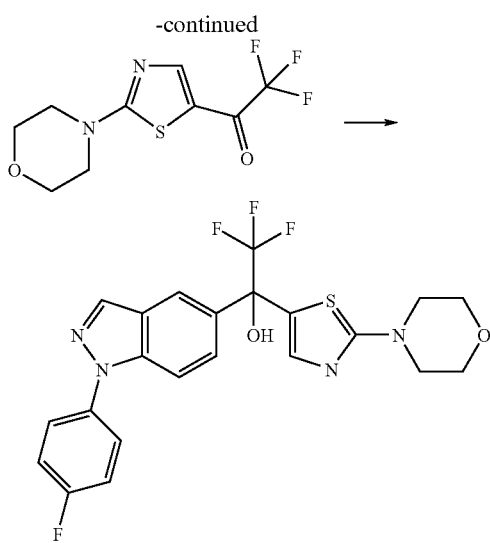

88

The title compound (59.3 mg, 17% overall yield) was prepared from 2,2,2-trifluoro-1-(2-morpholin-4-yl-thiazol-5-yl)ethanone (200 mg, 0.750 mmol) according to methods described in Example 1. MS m/z 479.36 (MH⁺).

Example 89

2,2,2-Trifluoro-1-(2-morpholin-4-yl-thiazol-4-yl)ethanone

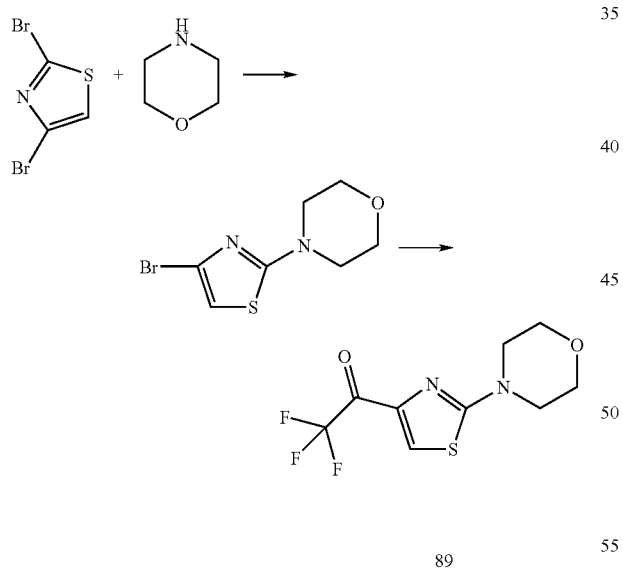

89

A solution of 2,4-dibromothiazole (500 mg, 2.06 mmol) in morpholine (4.0 mL, 22.3 mmol) was warmed at 50° C. in a sealed tube. After 16 hours, the mixture was cooled to room temperature, diluted with 20 mL of water and extracted with three 30 mL portions of diethyl ether. The combined organic layers was washed with five 30 mL portions of water, 30 mL of brine, dried over magnesium sulfate, filtered, and concentrated in vacuo. The residue was chromatographed over SiO₂ using ethyl acetate in hexanes (0-30% gradient) to afford 458 mg (89%) of 4-(4-bromothiazol-2-yl)morpholine.

To a chilled (−78° C.) solution of 4-(4-bromothiazol-2-yl)morpholine (249 mg, 1.00 mmol) in dry diethyl ether (10 mL) was added n-BuLi (480 μL, 2.5 M in hexanes, 1.20 mmol). After 20 minutes, a solution of 2,2,2-trifluoro-N-methoxy-N-methylacetamide (224 μL, 2 mmol) in THF (10 mL) was added over 10 minutes. After 30 minutes, the mixture was warmed to 0° C. After 30 minutes, the mixture was quenched with 10 mL of water, warmed to room temperature, and extracted with three 10 mL portions of ethyl acetate. The combined organic layers were dried over magnesium sulfate, filtered, and concentrated in vacuo. The residue was twice purified on SiO₂ using ethyl acetate-hexanes (20-100% gradient) to afford 125 mg (47%) of the title compound.

Example 90

2,2,2-Trifluoro-1-[1-(4-fluorophenyl)-1H-indazol-5-yl]-1-(2-morpholin-4-yl-thiazol-4-yl)ethanol

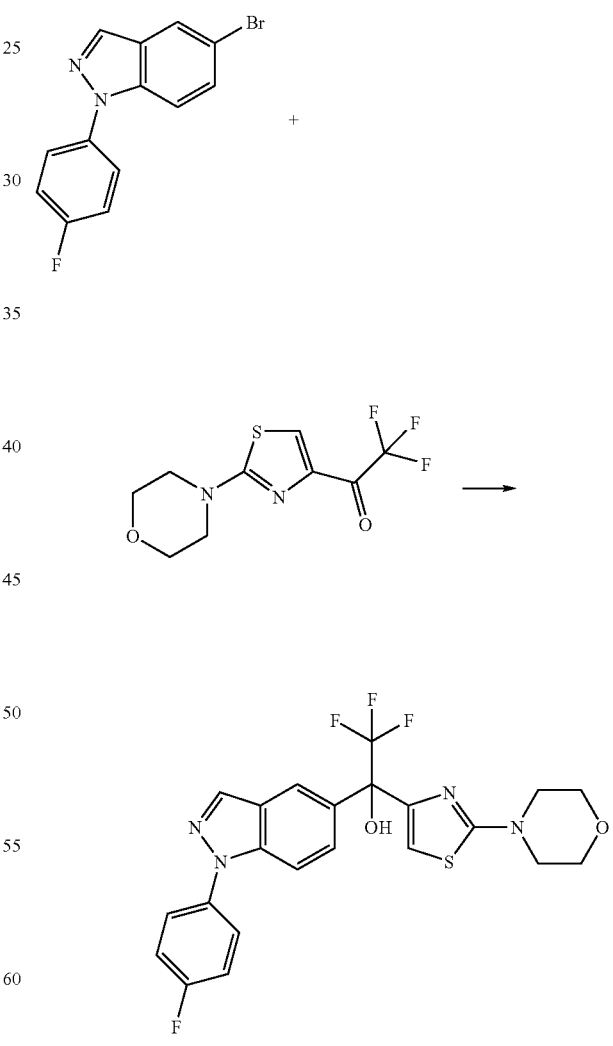

90

The title compound (66.5 mg, 30% overall yield) was prepared from 2,2,2-trifluoro-1-(2-morpholin-4-ylthiazol-4-yl)

ethanone (124 mg, 0.466 mmol) according to methods described in Example 1. MS m/z 479.29 (MH+).

Example 91

1-(2-Aminothiazol-5-yl)-2,2,2-trifluoro-1-[1-(4-fluorophenyl)-1H-indazol-5-yl]ethanol

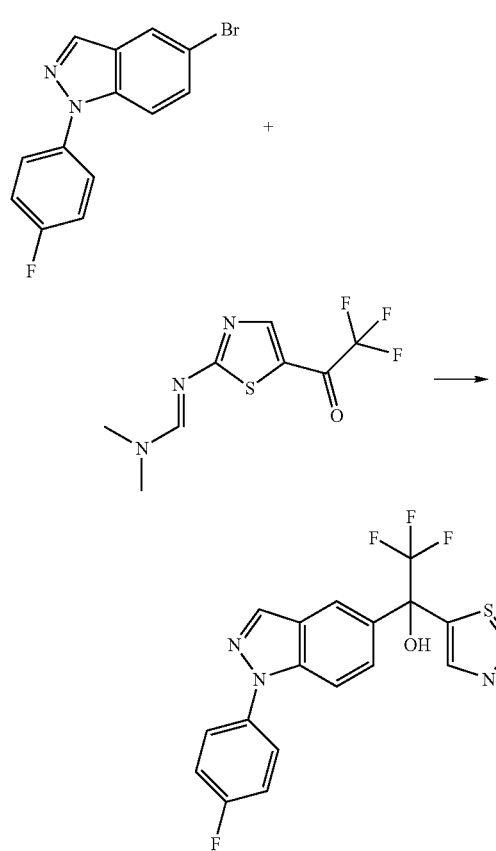

91

To a chilled (−78° C.) solution of bromophenylindazole (655 mg, 2.25 mmol) in dry THF (3 mL) was added n-BuLi (990 µL, 2.5 M in hexanes, 2.48 mmol). After 20 minutes, a chilled (−78° C.) solution of N,N-dimethyl-N'-[5-(2,2,2-trifluoro-acetyl)-thiazol-2-yl]-formamidine (565 mg, 2.25 mmol, commercially available) in 2 mL of THF was added over a 5 minute period. After 30 minutes, the mixture was quenched with 10 mL of water, warmed to room temperature and extracted with three 10 mL portions of ethyl acetate. The combined organic layers was dried over magnesium sulfate, filtered, and concentrated in vacuo. The residue was dissolved in a mixture of THF (2 mL) and water (2 mL) and 2 M HCl (1 mL) was added. After stirring for 18 hours, the mixture was quenched with 30 mL of saturated aqueous sodium bicarbonate and extracted with three 30 mL portions of ethyl acetate. The combined organic layers was dried over magnesium sulfate, filtered, and concentrated in vacuo. The residue was purified on SiO2 using ethyl acetate-hexanes (0-100% gradient). The fractions containing the desired product were pooled and further purified on SiO2 (0-100% ethyl acetate in hexane, slow gradient) to give the title compound as a yellow foam. MS m/z 409.25 (MIT).

Example 92

N-(5-{2,2-Difluoro-1-[1-(4-fluorophenyl)-1H-indazol-5-yl]-1-hydroxypropyl}thiazol-2-yl)acetamide

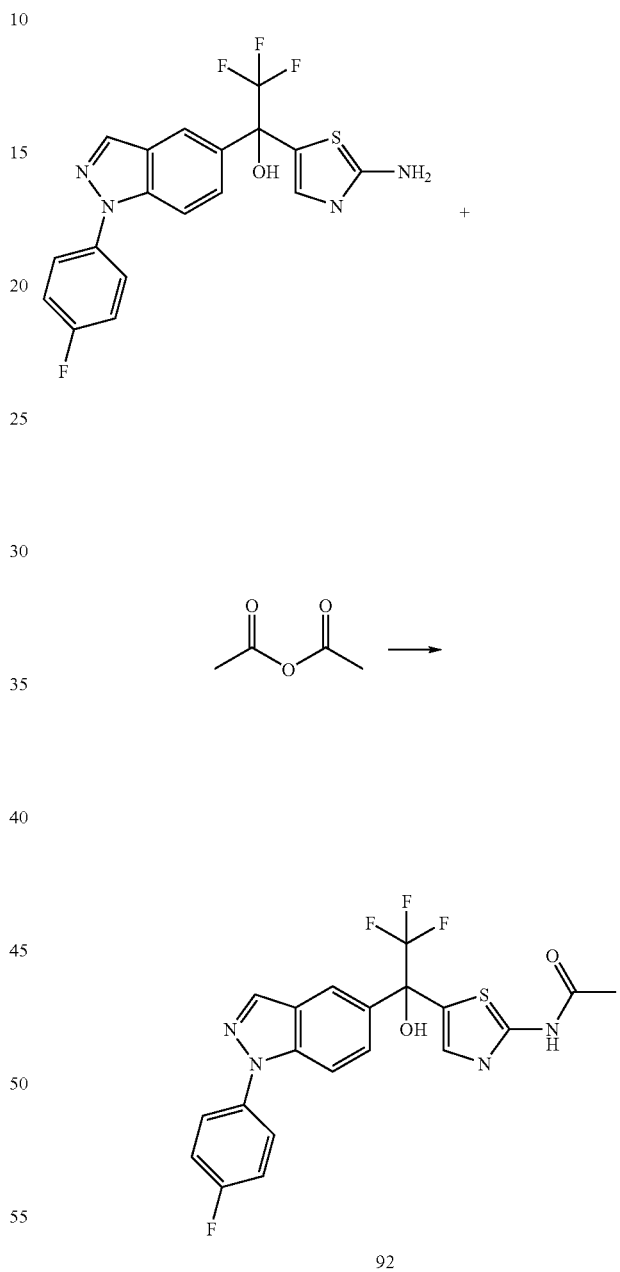

92

To a room temperature solution of the amine (45.0 mg, 0.11 mmol) in 2 mL of CH2Cl2 was added pyridine (44.5 µL, 0.550 mmol) followed by acetic anhydride (12.5 µL, 0.132 mmol). After 15 hours, the mixture was quenched with 1 N aqueous NaOH (3 mL) and extracted with three 5 mL portions of CH2Cl2. The aqueous layer was acidified with acetic acid (pH 7) and extracted with three 5 mL portions of ethyl acetate. The combined organic layers was dried over magnesium sulfate, filtered, and concentrated in vacuo. The residue was purified on $SiO_2$ (Prep TLC, 5% MeOH in $CH_2Cl_2$, developed 3 times) to afford 22 mg (44%) of the title compound. MS m/z 451.32 ($MH^+$).

Example 93

2,2,2-Trifluoro-1-[1-(4-fluorophenyl)-1H-indazol-5-yl]-1-thiazol-5-ylethanol

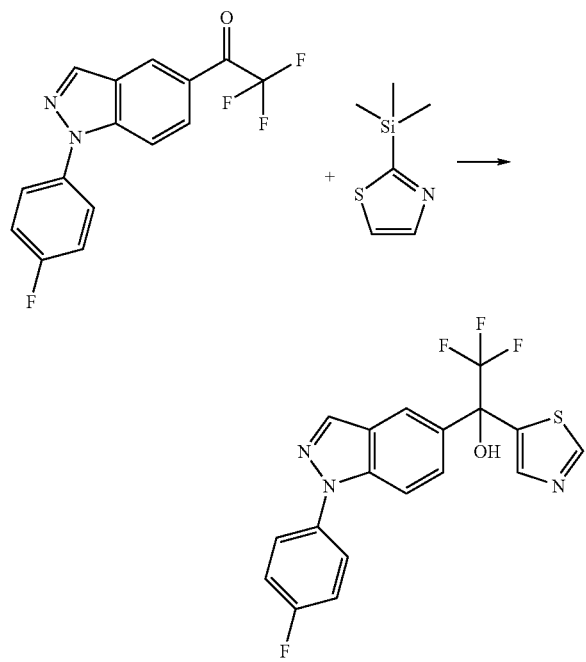

To a chilled (−78° C.) solution of 2-trimethylsilanyl-thiazole (157 mg, 1.00 mmol) in dry ether (2 mL) was added n-BuLi (440 µL, 2.5 M in hexanes, 1.10 mmol). After 30 minutes, a solution of 2,2,2-trifluoro-1-[1-(4-fluorophenyl)-1H-indazol-5-yl]ethanone (154 mg, 0.50 mmol) in dry ether (2 mL) was added. After 1 hour, the mixture was warmed to room temperature, quenched with 10 mL of saturated aqueous sodium bicarbonate and extracted with three 10 mL portions of ethyl ether. The combined organic layers was washed with 10 mL of brine, dried over sodium sulfate, filtered, and concentrated in vacuo to give 202 mg of the crude product. To a solution of crude product (100 mg) in THF (2 mL) was added 2 M HCl (1 mL) and the mixture was stirred overnight. The mixture was then quenched with 10 mL of saturated aqueous sodium bicarbonate and extracted with three 10 mL portions of ethyl acetate. The combined organic layers were washed with brine (10 mL), dried over magnesium sulfate, filtered, and concentrated in vacuo. The mixture was purified over $SiO_2$ using ethyl acetate-hexanes (0-100% gradient) to afford 38.4 mg (39% over two steps) of the title compound. MS m/z 394.26 ($MH^+$).

Assessment of Biological Properties

Compounds of the invention were evaluated for binding to the steroid receptor by a fluorescence polarization competitive binding assay. Detailed descriptions for preparation of recombinant glucocorticoid receptor (GR) complex used in the assay is described in U.S. Patent Application Publication No. US 2003/0017503, filed May 20, 2002, and incorporated herein by reference in its entirety. Preparation of the tetramethylrhodamine (TAMRA)-labeled dexamethasone probe was accomplished using a standard literature procedure (M. Pons et al., J. Steroid Biochem., 1985, 22, pp. 267-273).

A. Glucocorticoid Receptor Competitive Binding Assay

Step 1. Characterization of the Fluorescent Probe

The wavelengths for maximum excitation and emission of the fluorescent probe should first be measured. An example of such a probe is rhodamine (TAMRA)-labeled dexamethasone.

The affinity of the probe for the steroid receptor was then determined in a titration experiment. The fluorescence polarization value of the probe in assay buffer was measured on an SLM-8100 fluorometer using the excitation and emission maximum values described above. Aliquots of expression vector lysate were added and fluorescence polarization was measured after each addition until no further change in polarization value was observed. Non-linear least squares regression analysis was used to calculate the dissociation constant of the probe from the polarization values obtained for lysate binding to the probe.

Step 2. Screening for Inhibitors of Probe Binding

This assay uses fluorescence polarization (FP) to quantitate the ability of test compounds to compete with tetramethylrhodamine (TAMRA)-labeled dexamethasone for binding to a human glucocorticoid receptor (GR) complex prepared from an insect expression system. The assay buffer was: 10 mM TES, 50 mM KCl, 20 mM $Na_2MoO_4.2H_2O$, 1.5 mM EDTA, 0.04% w/v CHAPS, 10% v/v glycerol, 1 mM dithiothreitol, pH 7.4. Test compounds were dissolved to 1 mM in neat DMSO and then further diluted to 10× assay concentration in assay buffer supplemented with 10% v/v DMSO. Test compounds were serially diluted at 10× assay concentrations in 10% DMSO-containing buffer in 96-well polypropylene plates. Binding reaction mixtures were prepared in 96-well black Dynex microtiter plates by sequential addition of the following assay components to each well: 15 µL of 10× test compound solution, 85 µL of GR-containing baculovirus lysate diluted 1:170 in assay buffer, and 50 µL of 15 nM TAMRA-labeled dexamethasone. Positive controls were reaction mixtures containing no test compound; negative controls (blanks) were reaction mixtures containing 0.7 µM to 2 µM dexamethasone. The binding reactions were incubated for 1 hour at room temperature and then read for fluorescence polarization in the LJL Analyst set to 550 nm excitation and 580 nm emission, with the Rhodamine 561 dichroic mirror installed. $IC_{50}$ values were determined by iterative non-linear curve fitting of the FP signal data to a 4-parameter logistic equation.

Compounds found to bind to the glucocorticoid receptor may be evaluated for binding to the progesterone receptor (PR), estrogen receptor (ER), and mineralocorticoid receptors to evaluate the compound's selectivity for GR. The protocols for PR and MR are identical to the above GR method, with the following exceptions: PR insect cell lysate is diluted 1:7.1 and MR lysate diluted 1:9.4. PR probe is TAMRA-labeled mifepristone, used at a final concentration of 5 nM in the assay, and the negative controls (blanks) were reactions containing mifepristone at 0.7 µM to 2 µM.

The ER protocol is similar to the above protocols, but uses PanVera kit receptor, fluorescein-labeled probe. The assay components are made in the same volumes as above, to produce final assay concentrations for ER of 15 nM and ES2 probe of 1 nM. In addition, the component order of addition is modified from the above assays: probe is added to the plate first, followed by receptor and test compound. The plates are read in the LJL Analyst set to 485 nm excitation and 530 nm emission, with the Fluorescein 505 dichroic mirror installed.

Compounds found to bind to the glucocorticoid receptor may be evaluated for dissociation of transactivation and transrepression by assays cited in the Background of the Invention (C. M. Bamberger and H. M. Schulte, Eur. J. Clin. Invest., 2000, 30 (suppl. 3)$_{6-9}$) or by the assays described below.

B. Glucocorticoid Receptor Cell Assays

1. Induction of Aromatase in Fibroblasts (Cell Assay for Transactivation)

Dexamethasone, a synthetic ligand to the glucocorticoid receptor (GR), induces expression of aromatase in human foreskin fibroblast cells. The activity of aromatase is measured by the conversion of testosterone to estradiol in culture media. Compounds that exhibit binding to GR are evaluated for their ability to induce aromatase activity in human foreskin fibroblasts.

Human foreskin fibroblast cells (ATCC Cat. No. CRL-2429, designation CCD112SK) are plated on 96 well plates at 50,000 cells per well 5 days before use, in Iscove's Modified Dulbecco's Media (GibcoBRL Life Technologies Cat No. 12440-053) supplemented with 10% charcoal filtered FBS (Clonetech Cat No. SH30068) and Gentamycin (GibcoBRL Life Technologies Cat. No. 15710-064). On the day of the experiment, the media in the wells is replaced with fresh media. Cells are treated with test compounds to final concentrations of $10^{-5}$ M to $10^{-8}$ M, and testosterone to a final concentration of 300 ng/mL. Each well has a total volume of 100 µL. Samples are made in duplicates. Control wells include: (a) wells that receive testosterone only, and (b) wells that receive testosterone plus 2 µM of dexamethasone to provide maximum induction of aromatase. Plates are incubated at 37° C. overnight (15 to 18 hours), and supernatants are harvested at the end of incubation. Estradiol in the supernatant is measured using ELISA kits for estradiol (made by ALPCO, obtained from American Laboratory Products Cat. No. 020-DR-2693) according to the manufacture's instruction. The amount of estradiol is inversely proportional to the ELISA signals in each well. The extent of aromatase induction by test compounds is expressed as a relative percentage to dexamethasone. $EC_{50}$ values of test compounds are derived by non-linear curve fitting.

2. Inhibition of IL-6 Production in Fibroblasts (Cell Assay for Transrepression)

Human foreskin fibroblast cells produce IL-6 in response to stimulation by proinflammatory cytokine IL-1. This inflammatory response, as measured by the production of IL-6, can be effectively inhibited by dexamethasone, a synthetic ligand to the glucocorticoid receptor (GR). Compounds that exhibit binding to GR are evaluated for their ability to inhibit IL-6 production in human foreskin fibroblasts.

Human foreskin fibroblast cells (ATCC Cat. No. CRL-2429) are plated on 96 well plates at 5,000 cells per well the day before use, in Iscove's Modified Dulbecco's Media (GibcoBRL Life Technologies Cat. No. 12440-053) supplemented with 10% charcoal filtered FBS (Clonetech Cat. No. SH30068) and Gentamycin (GibcoBRL Life Technologies Cat. No. 15710-064). On the next day, media in the wells is replaced with fresh media. Cells are treated with IL-1 (rhIL-1α, R&D Systems Cat. No. 200-LA) to a final concentration of 1 ng/mL, and with test compounds to final concentrations of $10^{-5}$ M to $10^{-8}$ M, in a total volume of 200 µL per well. Samples are done in duplicates. Background control wells do not receive test compounds or IL-1. Positive control wells receive IL-1 only and represent maximum (or 100%) amount of IL-6 production. Plates are incubated at 37° C. overnight (15 to 18 hours), and supernatants are harvested at the end of incubation. IL-6 levels in the supernatants are determined by the ELISA kits for IL-6 (MedSystems Diagnostics GmbH, Vienna, Austria, Cat. No. BMS213TEN) according to manufacture's instructions. The extent of inhibition of IL-6 by test compounds is expressed in percentage relative to positive controls. $IC_{50}$ values of test compounds are derived by non-linear curve fitting.

Evaluation of agonist or antagonist activity of compounds binding to the glucocorticoid receptor may be determined by any of the assays.

3. Modulation of Tyrosine Aminotransferase (TAT) Induction in Rat Hepatoma Cells Testing of compounds for agonist or antagonist activity in induction of tyrosine aminotransferase (TAT) in rat hepatoma cells.

H4-II-E-C3 cells were incubated overnight in 96 well plates (20,000 cells/100 µL/well) in MEM medium containing 10% heat inactivated FBS and 1% nonessential amino acids. On the next day, cells were stimulated with the indicated concentrations of dexamethasone or test compound (dissolved in DMSO, final DMSO concentration 0.2%) for 18 hours. Control cells were treated with 0.2% DMSO. After 18 hours, the cells were lysed in a buffer containing 0.1% Triton X-100 and the TAT activity was measured in a photometric assay using tyrosine and alpha-ketoglutarate as substrates.

For measuring antagonist activity, the hepatoma cells were pre-stimulated by addition of dexamethasone (concentration ranges from $3\times10^{-9}$ M to $3\times10^{-8}$ M) shortly before the test compound was applied to the cells. The steroidal non-selective GR/PR antagonist mifepristone was used as control.

4. Modulation of MMTV-Luc Induction in HeLa Cells

Testing of compounds for agonist or antagonist activity in stimulation of MMTV-(mouse mammary tumor virus) promoter in HeLa cells.

HeLa cells were stably co-transfected with the pHHLuc-plasmid containing a fragment of the MMTV-LTR (−200 to +100 relative to the transcription start site) cloned in front of the luciferase gene (Norden, 1988) and the pcDNA3.1 plasmid (Invitrogen) constitutively expressing the resistance for the selective antibiotic GENETICIN®. Clones with best induction of the MMTV-promoter were selected and used for further experiments.

Cells were cultured overnight in DMEM medium without phenol red, supplemented with 3% CCS (charcoal treated calf serum) and then transferred to 96 well plates (15,000 cells/100 µL/well). On the next day, activation of the MMTV-promoter was stimulated by addition of test compound or dexamethasone dissolved in DMSO (final concentration 0.2%). Control cells were treated with DMSO only. After 18 hours, the cells were lysed with cell lysis reagent (Promega, Cat. No. E1531), luciferase assay reagent (Promega, Cat. No. E1501) was added and the glow luminescence was measured using a luminometer (BMG, Offenburg).

For measuring antagonist activity, the MMTV-promoter was pre-stimulated by adding dexamethasone ($3\times10^{-9}$ M to $3\times10^{-8}$ M) shortly before the test compound was applied to the cells. The steroidal non-selective GR/PR antagonist mifepristone was used as control.

5. Modulation of IL-8 Production in U937 Cells

Testing of compounds for agonist or antagonist activity in GR-mediated inhibition of LPS-induced IL-8 secretion in U-937 cells.

U-937 cells were incubated for 2 to 4 days in RPMI1640 medium containing 10% CCS (charcoal treated calf serum). The cells were transferred to 96 well plates (40,000 cells/100 µL/well) and stimulated with 1 µg/mL LPS (dissolved in PBS) in the presence or absence of dexamethasone or test compound (dissolved in DMSO, final concentration 0.2%).

Control cells were treated with 0.2% DMSO. After 18 hours, the IL-8 concentration in the cell supernatant was measured by ELISA, using the "OptEIA human IL-8 set" (Pharmingen, Cat. No. 2654KI).

For measuring antagonist activity, the LPS-induced IL-8 secretion was inhibited by adding dexamethasone ($3\times10^{-9}$ M to $3\times10^{-8}$ M) shortly before the test compound was applied to the cells. The steroidal non-selective GR/PR antagonist mifepristone was used as control.

6. Modulation of ICAM-Luc Expression in HeLa Cells

Testing of compounds for agonist or antagonist activity in inhibition of TNF-alpha-induced activation of the ICAM-promoter in HeLa cells.

HeLa cells were stably co-transfected with a plasmid containing a 1.3 kb fragment of the human ICAM-promoter (−1353 to −9 relative to the transcription start site, Ledebur and Parks, 1995) cloned in front of the luciferase gene and the pcDNA3.1 plasmid (Invitrogen) which constitutively expresses the resistance for the antibiotic GENETICIN®. Clones with best induction of the ICAM-promoter were selected and used for further experiments. Cells were transferred to 96 well plates (15,000 cells/100 µL/well) in DMEM medium supplemented with 3% CCS. On the following day the activation of the ICAM-promoter was induced by addition of 10 ng/mL recombinant TNF-alpha (R&D System, Cat. No. 210-TA). Simultaneously the cells were treated with the test compound or dexamethasone (dissolved in DMSO, final concentration 0.2%). Control cells were treated with DMSO only. After 18 hours, the cells were lysed with cell lysis reagent (Promega, Cat. No. E1531), luciferase assay reagent (Promega, Cat. No. E1501) was added and glow luminescence was measured using a luminometer (BMG, Offenburg).

For measuring antagonist activity, the TNF-alpha-induced activation of the ICAM-promoter was inhibited by adding dexamethasone ($3\times10^{-9}$ M to $3\times10^{-8}$ M) shortly before the test compound was applied to the cells. The steroidal non-selective GR/PR antagonist mifepristone was used as control.

In general, the preferred potency range in the above assays is between 0.1 nM and 10 µM, the more preferred potency range is 0.1 nM to 1 µM, and the most preferred potency range is 0.1 nM to 100 nM.

Representative compounds of the invention have been tested and have shown activity as modulators of the glucocorticoid receptor function in one or more of the above assays. For example, the following representative compounds of the invention have demonstrated potent activity (between 0.1 nM and 100 nM) in the GR binding assay:

(3-{2,2,2-Trifluoro-1-[1-(4-fluorophenyl)-1H-indazol-5-yl]-1-hydroxyethyl}pyrrolo[2,3-b]pyridin-1-yl)acetonitrile;
2-(7-Chloro-3-{2,2,2-trifluoro-1-[1-(4-fluorophenyl)-1H-indazol-5-yl]-1-hydroxyethyl}pyrrolo[2,3-c]pyridin-1-yl) acetamide;
1-(7-Chloro-1H-pyrrolo[2,3-c]pyridin-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-(7-oxy-1H-pyrrolo[2,3-b]pyridin-3-yl)ethanol;
2,2,2-Trifluoro-1-[1-(4-fluorophenyl)-1H-indazol-5-yl]-1-(1H-pyrrolo[3,2-b]pyridin-3-yl)ethanol;
2,2,2-Trifluoro-1-[1-(4-fluorophenyl)-1H-indazol-5-yl]-1-(1H-pyrrolo[2,3-c]pyridin-3-yl)ethanol;
3-{2,2,2-Trifluoro-1-[1-(4-fluorophenyl)-1H-indazol-5-yl]-1-hydroxyethyl}pyrrolo[2,3-b]pyridine-1-sulfonic acid dimethylamide;
2-(3-{2,2,2-Trifluoro-1-[1-(4-fluorophenyl)-1H-indazol-5-yl]-1-hydroxyethyl}pyrrolo[2,3-b]pyridin-1-yl)acetamide;
2,2,2-Trifluoro-1-[1-(4-fluorophenyl)-1H-indazol-5-yl]-1-(1H-pyrrolo[2,3-b]pyridin-3-yl)ethanol;
2,2,2-Trifluoro-1-[1-(4-fluorophenyl)-1H-indazol-5-yl]-1-(1H-indazol-3-yl)ethanol;
(1H-Indol-6-yl)-{2,2,2-trifluoro-1-[1-(4-fluorophenyl)-1H-indazol-5-yl]ethyl}amine;
(1H-Indol-7-yl)-{2,2,2-trifluoro-1-[1-(4-fluorophenyl)-1H-indazol-5-yl]ethyl}amine;
(1H-Indol-4-yl)-{2,2,2-trifluoro-1-[1-(4-fluorophenyl)-1H-indazol-5-yl]ethyl}amine;
N-{2,2,2-Trifluoro-1-[1-(4-fluorophenyl)-1H-indazol-5-yl]ethyl}-benzene-1,2-diamine;
2-Amino-4,6-dichloro-N-{2,2,2-trifluoro-1-[1-(4-fluorophenyl)-1H-indazol-5-yl]ethyl}-benzenesulfonamide;
2-(7-{2,2,2-Trifluoro-1-[1-(4-fluorophenyl)-1H-indazol-5-yl]ethylamino}indol-1-yl)acetamide;
2,2,2-Trifluoro-1-(1-methyl-1H-indol-3-yl)-1-(1-pyridin-3-yl-1H-indazol-5-yl)ethanol;
2,2,2-Trifluoro-1-(1-methyl-1H-indol-3-yl)-1-(1-pyridin-4-yl-1H-indazol-5-yl)ethanol
2,2,2-Trifluoro-1-(1-methyl-1H-indol-3-yl)-1-(1-thiophen-3-yl-1H-indazol-5-yl)ethanol;
2,2,2-Trifluoro-1-(1H-indol-3-yl)-1-(1-pyridin-3-yl-1H-indazol-5-yl)ethanol;
2-{3-[2,2,2-Trifluoro-1-hydroxy-1-(1-pyridin-3-yl-1H-indazol-5-yl)ethyl]indol-1-yl}acetamide;
2,2,2-Trifluoro-1-(1-methyl-1H-indol-3-yl)-1-[1-(5-methylthiophen-2-yl)-1H-indazol-5-yl]ethanol;
2,2,2-Trifluoro-1-(1-methyl-1H-indol-3-yl)-1-(1-pyridin-2-yl-1H-indazol-5-yl)ethanol;
2,2,2-Trifluoro-1-(1-methyl-1H-indol-3-yl)-1-[1-(1-methyl-1H-pyrazol-4-yl)-1H-indazol-5-yl]ethanol;
2,2,2-Trifluoro-1-[1-(6-fluoropyridin-3-yl)-1H-indazol-5-yl]-1-(1-methyl-1H-indol-3-yl)ethanol;
(R)-1-(3-{2,2,2-Trifluoro-1-[1-(4-fluorophenyl)-1H-indazol-5-yl]-1-hydroxyethyl}indol-1-yl)propan-2-ol;
(S)-1-(3-{2,2,2-Trifluoro-1-[1-(4-fluorophenyl)-1H-indazol-5-yl]-1-hydroxyethyl}indol-1-yl)propan-2-ol;
2,2,2-Trifluoro-1-[1-(4-fluorophenyl)-1H-indazol-5-yl]-1-[1-(tetrahydro-furan-2-ylmethyl)-1H-indol-3-yl]ethanol;
2,2,2-Trifluoro-1-[1-(4-fluorophenyl)-1H-indazol-5-yl]-1-[1-(2-morpholin-4-ylethyl)-1H-indol-3-yl]ethanol;
(3-{2,2,2-Trifluoro-1-[1-(4-fluorophenyl)-1H-indazol-5-yl]-1-hydroxyethyl}indol-1-yl)acetic acid;
1-(5-1,3-Dioxolan-2-ylthiophen-2-yl)-2,2,2-trifluoro-1-[1-(4-fluorophenyl)-1H-indazol-5-yl]ethanol;
(3-{2,2,2-Trifluoro-1-[1-(4-fluorophenyl)-1H-indazol-5-yl]-1-hydroxyethyl}indol-1-yl)acetic acid ethyl ester;
1-(5-Chlorothiophen-2-yl)-2,2,2-trifluoro-1-[1-(4-fluorophenyl)-1H-indazol-5-yl]ethanol;
1-{1-[3-((S)-3-Dimethylaminopyrrolidin-1-yl)propyl]-1H-indol-3-yl}-2,2,2-trifluoro-1-[1-(4-fluorophenyl)-1H-indazol-5-yl]ethanol;
1-{1-[3-((R)-3-Dimethylaminopyrrolidin-1-yl)propyl]-1H-indol-3-yl}-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(3-pyrrolidin-1-ylpropyl)-1H-indol-3-yl]ethanol;
2,2,2-Trifluoro-1-[1-(4-fluorophenyl)-1H-indazol-5-yl]-1-[1-(3-methylaminopropyl)-1H-indol-3-yl]ethanol;
2,2,2-Trifluoro-1-[1-(4-fluorophenyl)-1H-indazol-5-yl]-1-[1-(3-morpholin-4-ylpropyl)-1H-indol-3-yl]ethanol;
1-[1-(3-Dimethylaminopropyl)-1H-indol-3-yl]-2,2,2-trifluoro-1-[1-(4-fluorophenyl)-1H-indazol-5-yl]ethanol;

3-(6-(2H-Pyrazol-3-yl)-3-{2,2,2-trifluoro-1-[1-(4-fluorophenyl)-1H-indazol-5-yl]-1-hydroxyethyl}indol-1-yl)propane-1,2-diol;

1-[1-Allyl-6-(2H-pyrazol-3-yl)-1H-indol-3-yl]-2,2,2-trifluoro-1-[1-(4-fluorophenyl)-1H-indazol-5-yl]ethanol;

1-(6-Bromo-1-but-3-enyl-1H-indol-3-yl)-2,2,2-trifluoro-1-[1-(4-fluorophenyl)-1H-indazol-5-yl]ethanol;

2,2,2-Trifluoro-1-[1-(4-fluorophenyl)-1H-indazol-5-yl]-1-[1-(propane-2-sulfonyl)-1H-indol-3-yl]ethanol;

3-(3-{2,2,2-Trifluoro-1-[1-(4-fluorophenyl)-1H-indazol-5-yl]-1-hydroxyethyl}indol-1-yl)propionamide;

N-Methyl-3-(3-{2,2,2-trifluoro-1-[1-(4-fluorophenyl)-1H-indazol-5-yl]-1-hydroxyethyl}indol-1-yl)propionamide;

3-(6-Pyrrolidin-1-yl-3-{2,2,2-trifluoro-1-[1-(4-fluorophenyl)-1H-indazol-5-yl]-1-hydroxyethyl}indol-1-yl)propane-1,2-diol;

2-(6-Bromo-3-{2,2,2-trifluoro-1-[1-(4-fluorophenyl)-1H-indazol-5-yl]-1-hydroxyethyl}indol-1-yl)-N-methylacetamide;

4-(3-{2,2,2-Trifluoro-1-[1-(4-fluorophenyl)-1H-indazol-5-yl]-1-hydroxyethyl}indol-1-yl)-butane-1,2-diol;

1-(1-But-3-enyl-1H-indol-3-yl)-2,2,2-trifluoro-1-[1-(4-fluorophenyl)-1H-indazol-5-yl]ethanol;

1-(1-Allyl-6-bromo-1H-indol-3-yl)-2,2,2-trifluoro-1-[1-(4-fluorophenyl)-1H-indazol-5-yl]ethanol;

3-(6-Bromo-3-{2,2,2-trifluoro-1-[1-(4-fluorophenyl)-1H-indazol-5-yl]-1-hydroxyethyl}indol-1-yl)propane-1,2-diol;

2,2,2-Trifluoro-1-[1-(4-fluorophenyl)-1H-indazol-5-yl]-1-[1-(4-methoxy-benzyl)-6-vinyl-1H-indol-3-yl]ethanol;

2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide;

3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol;

2,2,2-Trifluoro-1-[1-(4-fluorophenyl)-1H-indazol-5-yl]-1-(7-methoxy-1H-pyrrolo[2,3-c]pyridin-3-yl)ethanol;

1-Allyl-6-methyl-3-{2,2,2-trifluoro-1-[1-(4-fluorophenyl)-1H-indazol-5-yl]-1-hydroxyethyl}1,6-dihydropyrrolo[2,3-c]pyridin-7-one;

4-{2,2,2-Trifluoro-1-[1-(4-fluorophenyl)-1H-indazol-5-yl]-1-hydroxyethyl}-1H-pyrazole-3-carbonitrile;

1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile;

1-Allyl-4-bromo-5-{2,2,2-trifluoro-1-[1-(4-fluorophenyl)-1H-indazol-5-yl]-1-hydroxyethyl}-1H-pyrazole-3-carbonitrile;

1-Allyl-4-{2,2,2-trifluoro-1-[1-(4-fluorophenyl)-1H-indazol-5-yl]-1-hydroxyethyl}-1H-pyrazole-3-carbonitrile;

2,2,2-Trifluoro-1-[1-(4-fluorophenyl)-1H-indazol-5-yl]-1-(2-morpholin-4-yl-thiazol-4-yl)ethanol;

1-[4-Chloro-5-(2-hydroxyethyl)-5H-pyrrolo[3,2-d]pyrimidin-7-yl]-2,2,2-trifluoro-1-[1-(4-fluorophenyl)-1H-indazol-5-yl]ethanol;

3-(4-Chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol;

1-(4-Chloro-5H-pyrrolo[3,2-d]pyrimidin-7-yl)-2,2,2-trifluoro-1-[1-(4-fluorophenyl)-1H-indazol-5-yl]ethanol;

5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

1-Allyl-4-{2,2,2-trifluoro-1-[1-(4-fluorophenyl)-1H-indazol-5-yl]-1-hydroxyethyl}-1H-pyrrole-2-carboxylic acid dimethylamide;

1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester;

1-Allyl-4-{2,2,2-trifluoro-1-[1-(4-fluorophenyl)-1H-indazol-5-yl]-1-hydroxyethyl}-1H-pyrrole-2-carboxylic acid ethyl ester;

4-{2,2,2-Trifluoro-1-[1-(4-fluorophenyl)-1H-indazol-5-yl]-1-hydroxyethyl}-1H-pyrrole-2-carbonitrile;

1-Allyl-4-{2,2,2-trifluoro-1-[1-(4-fluorophenyl)-1H-indazol-5-yl]-1-hydroxyethyl}-1H-pyrrole-2-carbonitrile;

2,2,2-Trifluoro-1-[3-(4-fluorophenyl)imidazo[1,5-a]pyridin-7-yl]-1-(1-methyl-1H-indol-3-yl)ethanol;

3-(3-{2,2,2-Trifluoro-1-[3-(4-fluorophenyl)imidazo[1,5-a]pyridin-7-yl]-1-hydroxyethyl}indol-1-yl)propane-1,2-diol;

1-[1-(2,2-Dimethyl-1,3-dioxolan-4-ylmethyl)-1H-indol-3-yl]-2,2,2-trifluoro-1-[3-(4-fluorophenyl)imidazo[1,5-a]pyridin-7-yl]ethanol;

(3-Methyl-2-oxo-5-{2,2,2-trifluoro-1-[1-(4-fluorophenyl)-1H-indazol-5-yl]-1-hydroxyethyl}-2H-pyridin-1-yl)acetamide;

1,3-Dimethyl-5-{2,2,2-trifluoro-1-[1-(4-fluorophenyl)-1H-indazol-5-yl]-1-hydroxyethyl}-1H-pyridin-2-one;

3-Methyl-5-{2,2,2-trifluoro-1-[1-(4-fluorophenyl)-1H-indazol-5-yl]-1-hydroxyethyl}-1H-pyridin-2-one;

2,2,2-Trifluoro-1-[1-(4-fluorophenyl)-1H-indazol-5-yl]-1-(6-methoxypyridin-3-yl)ethanol;

5-[1-(1-Allyl-1H-indol-3-yl)-2,2,2-trifluoro-1-hydroxyethyl]indazole-1-carboxylic acid ethylamide;

5-[1-(1-Allyl-1H-indol-3-yl)-2,2,2-trifluoro-1-hydroxyethyl]indazole-1-carboxylic acid (1-methylpropyl)amide 5-[1-(1-Allyl-1H-indol-3-yl)-2,2,2-trifluoro-1-hydroxyethyl]indazole-1-carboxylic acid propylamide;

5-[2,2,2-Trifluoro-1-hydroxy-1-(1-methyl-1H-indol-3-yl)ethyl]indazole-1-carboxylic acid cyclopropylmethylamide;

5-[2,2,2-Trifluoro-1-hydroxy-1-(1-methyl-1H-indol-3-yl)ethyl]indazole-1-carboxylic acid isopropylamide;

Phenyl-{5-[2,2,2-trifluoro-1-hydroxy-1-(1-methyl-1H-indol-3-yl)ethyl]indazol-1-yl}-methanone;

5-[1-(1-Methyl-1H-indol-3-yl)-2,2,2-trifluoro-1-hydroxyethyl]indazole-1-carboxylic acid isopropyl ester; and 1-(1-Allyl-6-dimethylamino-1H-indol-3-yl)-2,2,2-trifluoro-1-[1-(4-fluorophenyl)-1H-indazol-5-yl]ethanol, or a tautomer, prodrug, solvate, or salt thereof.

The following compounds of the invention have demonstrated agonistic activity ($EC_{50}$) equal to or below 1000 nM and greater than 50% efficacy by inhibiting IL-6 production in Fibroblasts (Cell Assay for Transrepression):

(3-{2,2,2-Trifluoro-1-[1-(4-fluorophenyl)-1H-indazol-5-yl]-1-hydroxyethyl}pyrrolo[2,3-b]pyridin-1-yl)acetonitrile;

2-(7-Chloro-3-{2,2,2-trifluoro-1-[1-(4-fluorophenyl)-1H-indazol-5-yl]-1-hydroxyethyl}pyrrolo[2,3-c]pyridin-1-yl)acetamide;

1-(7-Chloro-1H-pyrrolo[2,3-c]pyridin-3-yl)-2,2,2-trifluoro-1-[1-(4-fluorophenyl)-1H-indazol-5-yl]ethanol;

2,2,2-Trifluoro-1-[1-(4-fluorophenyl)-1H-indazol-5-yl]-1-(7-oxy-1H-pyrrolo[2,3-b]pyridin-3-yl)ethanol;

2-(3-{2,2,2-Trifluoro-1-[1-(4-fluorophenyl)-1H-indazol-5-yl]-1-hydroxyethyl}pyrrolo[2,3-b]pyridin-1-yl)acetamide;

2,2,2-Trifluoro-1-[1-(4-fluorophenyl)-1H-indazol-5-yl]-1-(1H-pyrrolo[2,3-b]pyridin-3-yl)ethanol;

2,2,2-Trifluoro-1-(1-methyl-1H-indol-3-yl)-1-(1-pyridin-3-yl-1H-indazol-5-yl)ethanol;

2,2,2-Trifluoro-1-(1-methyl-1H-indol-3-yl)-1-(1-thiophen-3-yl-1H-indazol-5-yl)ethanol;
2-{3-[2,2,2-Trifluoro-1-hydroxy-1-(1-pyridin-3-yl-1H-indazol-5-yl)ethyl]indol-1-yl}acetamide;
2,2,2-Trifluoro-1-(1-methyl-1H-indol-3-yl)-1-[1-(1-methyl-1H-pyrazol-4-yl)-1H-indazol-5-yl]ethanol;
2,2,2-Trifluoro-1-[1-(6-fluoropyridin-3-yl)-1H-indazol-5-yl]-1-(1-methyl-1H-indol-3-yl)ethanol;
(R)-1-(3-{2,2,2-Trifluoro-1-[1-(4-fluorophenyl)-1H-indazol-5-yl]-1-hydroxyethyl}indol-1-yl)propan-2-ol;
(S)-1-(3-{2,2,2-Trifluoro-1-[1-(4-fluorophenyl)-1H-indazol-5-yl]-1-hydroxyethyl}indol-1-yl)propan-2-ol;
2,2,2-Trifluoro-1-[1-(4-fluorophenyl)-1H-indazol-5-yl]-1-[1-(tetrahydro-furan-2-ylmethyl)-1H-indol-3-yl]ethanol;
2,2,2-Trifluoro-1-[1-(4-fluorophenyl)-1H-indazol-5-yl]-1-[1-(2-morpholin-4-ylethyl)-1H-indol-3-yl]ethanol;
(3-{2,2,2-Trifluoro-1-[1-(4-fluorophenyl)-1H-indazol-5-yl]-1-hydroxyethyl}indol-1-yl)acetic acid;
(3-{2,2,2-Trifluoro-1-[1-(4-fluorophenyl)-1H-indazol-5-yl]-1-hydroxyethyl}indol-1-yl)acetic acid ethyl ester;
1-(6-Bromo-1-but-3-enyl-1H-indol-3-yl)-2,2,2-trifluoro-1-[1-(4-fluorophenyl)-1H-indazol-5-yl]ethanol;
3-(3-{2,2,2-Trifluoro-1-[1-(4-fluorophenyl)-1H-indazol-5-yl]-1-hydroxyethyl}indol-1-yl)propionamide;
N-Methyl-3-(3-{2,2,2-trifluoro-1-[1-(4-fluorophenyl)-1H-indazol-5-yl]-1-hydroxyethyl}indol-1-yl)propionamide;
2-(6-Bromo-3-{2,2,2-trifluoro-1-[1-(4-fluorophenyl)-1H-indazol-5-yl]-1-hydroxyethyl}indol-1-yl)-N-methylacetamide;
4-(3-{2,2,2-Trifluoro-1-[1-(4-fluorophenyl)-1H-indazol-5-yl]-1-hydroxyethyl}indol-1-yl)-butane-1,2-diol;
1-(1-But-3-enyl-1H-indol-3-yl)-2,2,2-trifluoro-1-[1-(4-fluorophenyl)-1H-indazol-5-yl]ethanol;
1-(1-Allyl-6-bromo-1H-indol-3-yl)-2,2,2-trifluoro-1-[1-(4-fluorophenyl)-1H-indazol-5-yl]ethanol;
3-(6-Bromo-3-{2,2,2-trifluoro-1-[1-(4-fluorophenyl)-1H-indazol-5-yl]-1-hydroxyethyl}indol-1-yl)propane-1,2-diol;
2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide;
3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol;
2,2,2-Trifluoro-1-[1-(4-fluorophenyl)-1H-indazol-5-yl]-1-(7-methoxy-1H-pyrrolo[2,3-c]pyridin-3-yl)ethanol;
1-Allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one;
1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile;
1-Allyl-4-{2,2,2-trifluoro-1-[1-(4-fluorophenyl)-1H-indazol-5-yl]-1-hydroxyethyl}-1H-pyrazole-3-carbonitrile;
1-[4-Chloro-5-(2-hydroxyethyl)-5H-pyrrolo[3,2-d]pyrimidin-7-yl]-2,2,2-trifluoro-1-[1-(4-fluorophenyl)-1H-indazol-5-yl]ethanol;
5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;
1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester;
1-Allyl-4-{2,2,2-trifluoro-1-[1-(4-fluorophenyl)-1H-indazol-5-yl]-1-hydroxyethyl}-1H-pyrrole-2-carboxylic acid ethyl ester;
2,2,2-Trifluoro-1-[3-(4-fluorophenyl)imidazo[1,5-a]pyridin-7-yl]-1-(1-methyl-1H-indol-3-yl)ethanol;
3-(3-{2,2,2-Trifluoro-1-[3-(4-fluorophenyl)imidazo[1,5-a]pyridin-7-yl]-1-hydroxyethyl}indol-1-yl)propane-1,2-diol;
1-[1-(2,2-Dimethyl-1,3-dioxolan-4-ylmethyl)-1H-indol-3-yl]-2,2,2-trifluoro-1-[3-(4-fluorophenyl)imidazo[1,5-a]pyridin-7-yl]ethanol;
3-(3-{2,2,2-Trifluoro-1-[1-(4-fluorophenyl)-1H-benzotriazol-5-yl]-1-hydroxyethyl}indol-1-yl)propane-1,2-diol;
2,2,2-Trifluoro-1-[1-(4-fluorophenyl)-1H-benzotriazol-5-yl]-1-(1-methyl-1H-indol-3-yl)ethanol;
(3-Methyl-2-oxo-5-{2,2,2-trifluoro-1-[1-(4-fluorophenyl)-1H-indazol-5-yl]-1-hydroxyethyl}-2H-pyridin-1-yl)acetamide;
3-Methyl-5-{2,2,2-trifluoro-1-[1-(4-fluorophenyl)-1H-indazol-5-yl]-1-hydroxyethyl}-1H-pyridin-2-one; and
5-[2,2,2-Trifluoro-1-hydroxy-1-(1-methyl-1H-indol-3-yl)ethyl]indazole-1-carboxylic acid isopropylamide,
or a tautomer, prodrug, solvate, or salt thereof.

Methods of Therapeutic Use

As pointed out above, the compounds of the invention are useful in modulating the glucocorticoid receptor function. In doing so, these compounds have therapeutic use in treating disease-states and conditions mediated by the glucocorticoid receptor function or that would benefit from modulation of the glucocorticoid receptor function.

As the compounds of the invention modulate the glucocorticoid receptor function, they have very useful anti-inflammatory and antiallergic, immune-suppressive, and anti-proliferative activity and they can be used in patients as drugs, particularly in the form of pharmaceutical compositions as set forth below, for the treatment of disease-states and conditions.

The agonist compounds according to the invention can be used in patients as drugs for the treatment of the following disease-states or indications that are accompanied by inflammatory, allergic, and/or proliferative processes:

(i) Lung diseases: chronic, obstructive lung diseases of any genesis, particularly bronchial asthma and chronic obstructive pulmonary disease (COPD); adult respiratory distress syndrome (ARDS); bronchiectasis; bronchitis of various genesis; all forms of restrictive lung diseases, particularly allergic alveolitis; all forms of lung edema, particularly toxic lung edema; all forms of interstitial lung diseases of any genesis, e.g., radiation pneumonitis; and sarcoidosis and granulomatoses, particularly Boeck disease;

(ii) Rheumatic diseases or autoimmune diseases or joint diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); traumatic arthritis; collagenoses of any genesis, e.g., systemic lupus erythematosus, scleroderma, polymyositis, dermatomyositis, Sjögren syndrome, Still disease, and Felty syndrome;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vasculitis diseases: panarteritis nodosa, polyarteritis nodosa, arteritis temporalis, Wegner granulomatosis, giant cell arthritis, and erythema nodosum;

(v) Dermatological diseases: atopic dermatitis, particularly in children; psoriasis; pityriasis rubra pilaris; erythematous diseases triggered by various noxa, e.g., rays, chemicals, burns, etc.; bullous dermatoses; diseases of the lichenoid complex; pruritus (e.g., of allergic genesis); seborrheic dermatitis; rosacea; pemphigus vulgaris; erythema multiforme exudativum; balanitis; vulvitis; hair loss, such as occurs in alopecia greata; and cutaneous T cell lymphomas;

(vi) Renal diseases: nephrotic syndrome; and all types of nephritis, e.g., glomerulonephritis;

(vii) Hepatic diseases: acute liver cell disintegration; acute hepatitis of various genesis, e.g., viral, toxic, drug-induced; and chronically aggressive and/or chronically intermittent hepatitis;

(viii) Gastrointestinal diseases: inflammatory bowel diseases, e.g., regional enteritis (Crohn disease), colitis ulcerosa; gastritis; peptic esophagitis (refluxoesophagitis); and gastroenteritis of other genesis, e.g., nontropical sprue;

(ix) Proctological diseases: anal eczema; fissures; hemorrhoids; and idiopathic proctitis;

(x) Eye diseases: allergic keratitis, uveitis, or iritis; conjunctivitis; blepharitis; neuritis nervi optici; choroiditis; and sympathetic ophthalmia;

(xi) Diseases of the ear, nose, and throat (ENT) area: allergic rhinitis or hay fever; otitis externa, e.g., caused by contact eczema, infection, etc.; and otitis media;

(xii) Neurological diseases: brain edema, particularly tumor-related brain edema; multiple sclerosis; acute encephalomyelitis; meningitis; acute spinal cord injury; stroke; and various forms of seizures, e.g., nodding spasms;

(xiii) Blood diseases: acquired hemolytic anemia; and idiopathic thrombocytopenia;

(xiv) Tumor diseases: acute lymphatic leukemia; malignant lymphoma; lymphogranulomatoses; lymphosarcoma; extensive metastases, particularly in mammary, bronchial, and prostatic carcinoma;

(xv) Endocrine diseases: endocrine opthalmopathy; endocrine orbitopathia; thyrotoxic crisis; Thyroiditis de Quervain; Hashimoto thyroiditis; Morbus Basedow; granulomatous thyroiditis; struma lymphomatosa; and Grave disease;

(xvi) Organ and tissue transplantations and graft-versus-host diseases;

(xvii) Severe states of shock, e.g., septic shock, anaphylactic shock, and systemic inflammatory response syndrome (SIRS);

(xviii) Substitution therapy in: congenital primary adrenal insufficiency, e.g., adrenogenital syndrome; acquired primary adrenal insufficiency, e.g., Addison disease, autoimmune adrenalitis, post-infection, tumors, metastases, etc.; congenital secondary adrenal insufficiency, e.g., congenital hypopituitarism; and acquired secondary adrenal insufficiency, e.g., post-infection, tumors, metastases, etc.;

(xix) Pain of inflammatory genesis, e.g., lumbago; and (xx) various other disease-states or conditions including type I diabetes (insulin-dependent diabetes), osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis and syndromes associated with hemodialysis, leukopheresis, and granulocyte transfusion.

In addition, the compounds according to the invention can be used for the treatment of any other disease-states or conditions not mentioned above which have been treated, are treated, or will be treated with synthetic glucocorticoids (see, e.g., H. J. Hatz, *Glucocorticoide: Immunologische Grundlagen, Pharmakologie und Therapierichtlinien* [Glucocorticoids: Immunological Fundamentals, Pharmacology, and Therapeutic Guidelines], Stuttgart: Verlagsgesellschaft mbH, 1998, which is hereby incorporated by reference in its entirety). Most or all of the indications (i) through (xx) mentioned above are described in detail in H. J. Hatz, *Glucocorticoide: Immunologische Grundlagen, Pharmakologie und Therapierichtlinien*. Furthermore, the compounds of the invention can also be used to treat disorders other than those listed above or mentioned or discussed herein, including in the Background of the Invention.

The antagonist compounds according to the invention, whether full antagonists or partial antagonists, can be used in patients as drugs for the treatment of the following disease-states or indications, without limitation: type II diabetes (non-insulin-dependent diabetes); obesity; cardiovascular diseases; hypertension; arteriosclerosis; neurological diseases, such as psychosis and depression; adrenal and pituitary tumors; glaucoma; and Cushing syndrome based on an ACTH-secreting tumor like pituitary adenoma. In particular, the compounds of the invention are useful for treating obesity and all disease-states and indications related to a deregulated fatty acids metabolism such as hypertension, atherosclerosis, and other cardiovascular diseases. Using the compounds of the invention that are GR antagonists, it should be possible to antagonize both the carbohydrate metabolism and fatty acids metabolism. Thus, the antagonist compounds of the invention are useful in treating all disease-states and conditions that involve increased carbohydrate, protein, and lipid metabolism and would include disease-states and conditions leading to catabolism like muscle frailty (as an example of protein metabolism).

Methods of Diagnostic Use

The compounds of the invention may also be used in diagnostic applications and for commercial and other purposes as standards in competitive binding assays. In such uses, the compounds of the invention may be used in the form of the compounds themselves or they may be modified by attaching a radioisotope, luminescence, fluorescent label or the like in order to obtain a radioisotope, luminescence, or fluorescent probe, as would be known by one of skill in the art and as outlined in *Handbook of Fluorescent Probes and Research Chemicals*, 6th Edition, R. P. Haugland (ed.), Eugene: Molecular Probes, 1996; *Fluorescence and Luminescence Probes for Biological Activity*, W. T. Mason (ed.), San Diego: Academic Press, 1993; *Receptor-Ligand Interaction, A Practical Approach*, E. C. Hulme (ed.), Oxford: IRL Press, 1992, each of which is hereby incorporated by reference in their entireties.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

In particular, the compounds of the invention are useful in combination with glucocorticoids or corticosteroids. As pointed out above, standard therapy for a variety of immune and inflammatory disorders includes administration of corticosteroids, which have the ability to suppress immunologic and inflammatory responses. (A. P. Truhan et al., Annals of Allergy, 1989, 62, pp. 375-391; J. D. Baxter, Hospital Practice, 1992, 27, pp. 111-134; R. P. Kimberly, Curr. Opin. Rheumatol., 1992, 4, pp. 325-331; M. H. Weisman, Curr. Opin. Rheumatol., 1995, 7, pp. 183-190; W. Sterry, Arch. Dermatol. Res., 1992, 284 (Suppl.), pp. S27-S29). While therapeutically beneficial, however, the use of corticosteroids is associated with a number of side effects, ranging from mild to possibly life threatening, especially with prolonged and/or high dose steroid usage. Accordingly, methods and compositions that enable the use of a lower effective dosage of corticosteroids (referred to as the "steroid sparing effect") would be highly desirable to avoid unwanted side effects. The compounds of the invention provide such a steroid sparing effect by achieving the desired therapeutic effect while allowing the use of lower doses and less frequent administration of glucocorticoids or corticosteroids.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form by topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Generally, a therapeutically effective daily dose is from about 0.001 mg to about 15 mg/kg of body weight per day of a compound of the invention; preferably, from about 0.1 mg to about 10 mg/kg of body weight per day; and most preferably, from about 0.1 mg to about 1.5 mg/kg of body weight per day. For example, for administration to a 70 kg person, the dosage range would be from about 0.07 mg to about 1050 mg per day of a compound of the invention, preferably from about 7.0 mg to about 700 mg per day, and most preferably from about 7.0 mg to about 105 mg per day. Some degree of routine dose optimization may be required to determine an optimal dosing level and pattern. Pharmaceutically acceptable carriers and excipients encompass all the foregoing additives and the like.

Examples of Pharmaceutical Formulations

| A. TABLETS | |
|---|---|
| Component | Amount per tablet (mg) |
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B. TABLETS | |
|---|---|
| Component | Amount per tablet (mg) |
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C. COATED TABLETS | |
|---|---|
| Component | Amount per tablet (mg) |
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
|---|---|
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

E. AMPOULE SOLUTION

| Component | Amount per ampoule |
|---|---|
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

F. SUPPOSITORIES

| Component | Amount per suppository (mg) |
|---|---|
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

G. METERING AEROSOL

| Component | Amount |
|---|---|
| active substance | 0.005 |
| sorbitan trioleate | 0.1 |
| monofluorotrichloromethane and difluorodichloromethane (2:3) | to 100 |

The suspension is transferred into a conventional aerosol container with a metering valve. Preferably, 50 µL of suspension are delivered per spray. The active substance may also be metered in higher doses if desired (e.g., 0.02% by weight).

H. POWDER FOR INHALATION

| Component | Amount |
|---|---|
| active substance | 1.0 mg |
| lactose monohydrate | to 25 mg |

I. POWDER FOR INHALATION

| Component | Amount |
|---|---|
| active substance | 2.0 mg |
| lactose monohydrate | to 25 mg |

J. POWDER FOR INHALATION

| Component | Amount |
|---|---|
| active substance | 1.0 mg |
| lactose monohydrate | to 5 mg |

K. POWDER FOR INHALATION

| Component | Amount |
|---|---|
| active substance | 2.0 mg |
| lactose monohydrate | to 5 mg |

In Examples H, I, J, and K, the powder for inhalation is produced in the usual way by mixing the individual ingredients together.

We claim:
1. A compound selected from:
(3-{2,2,2-Trifluoro-1-[1-(4-fluorophenyl)-1H-indazol-5-yl]-1-hydroxyethyl}pyrrolo[2,3-b]pyridin-1-yl)acetonitrile;
2,2,2-Trifluoro-1-(1-phenyl-1H-pyrazolo[3,4-b]pyridin-5-yl)-1-(1H-pyrrolo[2,3-b]pyridin-3-yl)ethanol;
1-(4-Chloro-1-phenyl-1H-pyrazolo[3,4-b]pyridin-5-yl)-2,2,2-trifluoro-1-(1H-pyrrolo[2,3-b]pyridin-3-yl)ethanol;
2-(7-Chloro-3-{2,2,2-trifluoro-1-[1-(4-fluorophenyl)-1H-indazol-5-yl]-1-hydroxyethyl}pyrrolo[2,3-c]pyridin-1-yl)acetamide;
N-[2-(3-{2,2,2-Trifluoro-1-[1-(4-fluorophenyl)-1H-indazol-5-yl]-1-hydroxyethyl}pyrrolo[2,3-b]pyridin-1-yl)acetyl]methanesulfonamide;
1-(7-Chloro-1H-pyrrolo[2,3-c]pyridin-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-(7-oxy-1H-pyrrolo[2,3-b]pyridin-3-yl)ethanol;
2,2,2-Trifluoro-1-(1H-pyrrolo[2,3-b]pyridin-3-yl)-1-(1-p-tolyl-1H-indazol-5-yl)ethanol;
2,2,2-Trifluoro-1-[1-(4-fluorophenyl)-1H-indazol-5-yl]-1-(1H-pyrrolo[3,2-b]pyridin-3-yl)ethanol;
2,2,2-Trifluoro-1-[1-(4-fluorophenyl)-1H-indazol-5-yl]-1-(1H-pyrrolo[2,3-c]pyridin-3-yl)ethanol;
2,2,2-Trifluoro-1-[1-(4-fluorophenyl)-1H-indazol-5-yl]-1-(1H-pyrrolo[3,2-c]pyridin-3-yl)ethanol;

3-{2,2,2-Trifluoro-1-[1-(4-fluorophenyl)-1H-indazol-5-yl]-1-hydroxyethyl}pyrrolo[2,3-b]pyridine-1-sulfonic acid dimethylamide;
2-(3-{2,2,2-Trifluoro-1-[1-(4-fluorophenyl)-1H-indazol-5-yl]-1-hydroxyethyl}pyrrolo[2,3-b]pyridin-1-yl)acetamide;
2,2,2-Trifluoro-1-[1-(4-fluorophenyl)-1H-indazol-5-yl]-1-(1H-pyrrolo[2,3-b]pyridin-3-yl)ethanol;
2,2,2-Trifluoro-1-[1-(4-fluorophenyl)-1H-indazol-5-yl]-1-(1H-indazol-3-yl)ethanol;
Phenyl-{2,2,2-trifluoro-1-[1-(4-fluorophenyl)-1H-indazol-5-yl]ethyl}amine;
(1H-Indol-5-yl)-{2,2,2-trifluoro-1-[1-(4-fluorophenyl)-1H-indazol-5-yl]ethyl}amine;
(1H-Indol-6-yl)-{2,2,2-trifluoro-1-[1-(4-fluorophenyl)-1H-indazol-5-yl]ethyl}amine;
(1H-Indol-7-yl)-{2,2,2-trifluoro-1-[1-(4-fluorophenyl)-1H-indazol-5-yl]ethyl}amine;
(1H-Indol-4-yl)-{2,2,2-trifluoro-1-[1-(4-fluorophenyl)-1H-indazol-5-yl]ethyl}amine;
[1-(4-Fluorophenyl)-1H-indazol-5-yl]-(2,2,2-trifluoro-1-phenylethyl)amine;
(1-Benzyl-2,2,2-trifluoroethyl)-[1-(4-fluorophenyl)-1H-indazol-5-yl]amine;
Benzyl-{2,2,2-trifluoro-1-[1-(4-fluorophenyl)-1H-indazol-5-yl]ethyl}amine;
(2-Nitrophenyl)-{2,2,2-trifluoro-1-[1-(4-fluorophenyl)-1H-indazol-5-yl]ethyl}amine;
N-{2,2,2-Trifluoro-1-[1-(4-fluorophenyl)-1H-indazol-5-yl]ethyl}benzene-1,2-diamine;
2-Amino-4,6-dichloro-N-{2,2,2-trifluoro-1-[1-(4-fluorophenyl)-1H-indazol-5-yl]ethyl}benzenesulfonamide;
2-(7-{2,2,2-Trifluoro-1-[1-(4-fluorophenyl)-1H-indazol-5-yl]ethylamino}indol-1-yl)acetamide;
3-Methyl-$N^2$-{2,2,2-trifluoro-1-[1-(4-fluorophenyl)-1H-indazol-5-yl]ethyl}benzene-1,2-diamine;
2-{3-[2,2,2-Trifluoro-1-hydroxy-1-(1-methoxymethyl-1H-indazol-5-yl)ethyl]indol-1-yl}acetamide;
2-{3-[2,2,2-Trifluoro-1-hydroxy-1-(1H-indazol-5-yl)ethyl]indol-1-yl}acetamide;
2,2,2-Trifluoro-1-(1-methyl-1H-indol-3-yl)-1-(1-pyridin-3-yl-1H-indazol-5-yl)ethanol;
2,2,2-Trifluoro-1-(1-methyl-1H-indol-3-yl)-1-(1-pyridin-4-yl-1H-indazol-5-yl)ethanol;
2,2,2-Trifluoro-1-(1-methyl-1H-indol-3-yl)-1-(1-pyrimidin-5-yl-1H-indazol-5-yl)ethanol;
2,2,2-Trifluoro-1-(1-methyl-1H-indol-3-yl)-1-(1-thiophen-3-yl-1H-indazol-5-yl)ethanol;
2,2,2-Trifluoro-1-(1H-indol-3-yl)-1-(1-pyridin-3-yl-1H-indazol-5-yl)ethanol;
2-{3-[2,2,2-Trifluoro-1-hydroxy-1-(1-pyridin-3-yl-1H-indazol-5-yl)ethyl]indol-1-yl}acetamide;
2,2,2-Trifluoro-1-(1-methyl-1H-indol-3-yl)-1-[1-(6-methylpyridin-3-yl)-1H-indazol-5-yl]ethanol;
2,2,2-Trifluoro-1-(1-methyl-1H-indol-3-yl)-1-[1-(5-methylthiophen-2-yl)-1H-indazol-5-yl]ethanol;
2,2,2-Trifluoro-1-[1-(1-methyl-1H-imidazol-4-yl)-1H-indazol-5-yl]-1-(1-methyl-1H-indol-3-yl)ethanol;
2,2,2-Trifluoro-1-(1-methyl-1H-indol-3-yl)-1-(1-pyridin-2-yl-1H-indazol-5-yl)ethanol;
2,2,2-Trifluoro-1-(1-methyl-1H-indol-3-yl)-1-[1-(1-methyl-1H-pyrazol-4-yl)-1H-indazol-5-yl]ethanol;
2,2,2-Trifluoro-1-[1-(6-fluoropyridin-3-yl)-1H-indazol-5-yl]-1-(1-methyl-1H-indol-3-yl)ethanol;
(R)-1-(3-{2,2,2-Trifluoro-1-[1-(4-fluorophenyl)-1H-indazol-5-yl]-1-hydroxyethyl}indol-1-yl)propan-2-ol;
(S)-1-(3-{2,2,2-Trifluoro-1-[1-(4-fluorophenyl)-1H-indazol-5-yl]-1-hydroxyethyl}indol-1-yl)propan-2-ol;
1-(5-Chloro-1,1-dioxo-1H-1$\lambda^6$-thiophen-2-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-(5-methylthiophen-2-yl)ethanol;
2,2,2-Trifluoro-1-[1-(4-fluorophenyl)-1H-indazol-5-yl]-1-[1-(tetrahydrofuran-2-ylmethyl)-1H-indol-3-yl]ethanol;
2,2,2-Trifluoro-1-[1-(4-fluorophenyl)-1H-indazol-5-yl]-1-[1-(2-morpholin-4-ylethyl)-1H-indol-3-yl]ethanol;
(3-{2,2,2-Trifluoro-1-[1-(4-fluorophenyl)-1H-indazol-5-yl]-1-hydroxyethyl}indol-1-yl)acetic acid;
1-(1-Allyl-5-hydroxymethyl-1H-pyrrol-3-yl)-2,2,2-trifluoro-1-[1-(4-fluorophenyl)-1H-indazol-5-yl]ethanol;
1-(5-1,3-Dioxolan-2-ylthiophen-2-yl)-2,2,2-trifluoro-1-[1-(4-fluorophenyl)-1H-indazol-5-yl]ethanol;
(3-{2,2,2-Trifluoro-1-[1-(4-fluorophenyl)-1H-indazol-5-yl]-1-hydroxyethyl}indol-1-yl)acetic acid ethyl ester;
1-(5-Chlorothiophen-2-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-{1-[3-(4-hydroxymethylpiperidin-1-yl)propyl]-1H-indol-3-yl}ethanol;
1-{1-[3-((S)-3-Dimethylaminopyrrolidin-1-yl)propyl]-1H-indol-3-yl}-2,2,2-trifluoro-1-[1-(4-fluorophenyl)-1H-indazol-5-yl]ethanol;
1-{1-[3-((R)-3-Dimethylaminopyrrolidin-1-yl)propyl]-1H-indol-3-yl}-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(3-pyrrolidin-1-ylpropyl)-1H-indol-3-yl]ethanol;
2,2,2-Trifluoro-1-[1-(4-fluorophenyl)-1H-indazol-5-yl]-1-{1-[3-(4-methylpiperazin-1-yl)propyl]-1H-indol-3-yl}ethanol;
2,2,2-Trifluoro-1-[1-(4-fluorophenyl)-1H-indazol-5-yl]-1-[1-(3-methylaminopropyl)-1H-indol-3-yl]ethanol;
2,2,2-Trifluoro-1-[1-(4-fluorophenyl)-1H-indazol-5-yl]-1-[1-(3-morpholin-4-ylpropyl)-1H-indol-3-yl]ethanol;
1-[1-(3-Dimethylaminopropyl)-1H-indol-3-yl]-2,2,2-trifluoro-1-[1-(4-fluorophenyl)-1H-indazol-5-yl]ethanol;
3-(6-(2H-Pyrazol-3-yl)-3-{2,2,2-trifluoro-1-[1-(4-fluorophenyl)-1H-indazol-5-yl]-1-hydroxyethyl}indol-1-yl)propane-1,2-diol;
1-[1-Allyl-6-(2H-pyrazol-3-yl)-1H-indol-3-yl]-2,2,2-trifluoro-1-[1-(4-fluorophenyl)-1H-indazol-5-yl]ethanol;
1-(6-Bromo-1-but-3-enyl-1H-indol-3-yl)-2,2,2-trifluoro-1-[1-(4-fluorophenyl)-1H-indazol-5-yl]ethanol;
1-(1-Benzenesulfonyl-1H-indol-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(propane-2-sulfonyl)-1H-indol-3-yl]ethanol;
3-(3-{2,2,2-Trifluoro-1-[1-(4-fluorophenyl)-1H-indazol-5-yl]-1-hydroxyethyl}indol-1-yl)propionamide;
N-Methyl-3-(3-{2,2,2-trifluoro-1-[1-(4-fluorophenyl)-1H-indazol-5-yl]-1-hydroxyethyl}indol-1-yl)propionamide;
3-(6-Pyrrolidin-1-yl-3-{2,2,2-trifluoro-1-[1-(4-fluorophenyl)-1H-indazol-5-yl]-1-hydroxyethyl}indol-1-yl)propane-1,2-diol;
2-(6-Bromo-3-{2,2,2-trifluoro-1-[1-(4-fluorophenyl)-1H-indazol-5-yl]-1-hydroxyethyl}indol-1-yl)-N-methylacetamide;
4-(3-{2,2,2-Trifluoro-1-[1-(4-fluorophenyl)-1H-indazol-5-yl]-1-hydroxyethyl}indol-1-yl)-butane-1,2-diol;
1-(1-But-3-enyl-1H-indol-3-yl)-2,2,2-trifluoro-1-[1-(4-fluorophenyl)-1H-indazol-5-yl]ethanol;

1-(1-Allyl-6-pyrrolidin-1-yl-1H-indol-3-yl)-2,2,2-trifluoro-1-[1-(4-fluorophenyl)-1H-indazol-5-yl]ethanol;
1-(1-Allyl-6-bromo-1H-indol-3-yl)-2,2,2-trifluoro-1-[1-(4-fluorophenyl)-1H-indazol-5-yl]ethanol;
3-(6-Bromo-3-{2,2,2-trifluoro-1-[1-(4-fluorophenyl)-1H-indazol-5-yl]-1-hydroxyethyl}indol-1-yl)propane-1,2-diol;
2,2,2-Trifluoro-1-[1-(4-fluorophenyl)-1H-indazol-5-yl]-1-[1-(4-methoxybenzyl)-6-vinyl-1H-indol-3-yl]ethanol;
2,2,2-Trifluoro-1-[1-(4-fluorophenyl)-1H-indazol-5-yl]-1-[1-(4-methoxybenzyl)-6-pyrrolidin-1-yl-1H-indol-3-yl]ethanol;
1-[4-Chloro-5-(2-hydroxyethyl)-5H-pyrrolo[3,2-d]pyrimidin-7-yl]-2,2,2-trifluoro-1-[1-(4-fluorophenyl)-1H-indazol-5-yl]ethanol;
3-(4-Chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol;
5-Allyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;
5-Allyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;
7-{2,2,2-Trifluoro-1-[1-(4-fluorophenyl)-1H-indazol-5-yl]-1-hydroxyethyl}-3,5-dihydropyrrolo[3,2-d]pyrimidin-4-one;
1-(4-Chloro-5H-pyrrolo[3,2-d]pyrimidin-7-yl)-2,2,2-trifluoro-1-[1-(4-fluorophenyl)-1H-indazol-5-yl]ethanol;
2-(3-Methyl-4-oxo-7-{2,2,2-trifluoro-1-[1-(4-fluorophenyl)-1H-indazol-5-yl]-1-hydroxyethyl}-3,4-dihydropyrrolo[3,2-d]pyrimidin-5-yl)acetamide;
5-(2,3-Dihydroxypropyl)-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;
5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;
1-Methylcarbamoylmethyl-4-{2,2,2-trifluoro-1-[1-(4-fluorophenyl)-1H-indazol-5-yl]-1-hydroxyethyl}-1H-pyrrole-2-carboxylic acid dimethylamide;
1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid dimethylamide;
1-Allyl-4-{2,2,2-trifluoro-1-[1-(4-fluorophenyl)-1H-indazol-5-yl]-1-hydroxyethyl}-1H-pyrrole-2-carboxylic acid methylamide;
1-Allyl-4-{2,2,2-trifluoro-1-[1-(4-fluorophenyl)-1H-indazol-5-yl]-1-hydroxyethyl}-1H-pyrrole-2-carboxylic acid carbamoylmethylamide;
1-Allyl-4-{2,2,2-trifluoro-1-[1-(4-fluorophenyl)-1H-indazol-5-yl]-1-hydroxyethyl}-1H-pyrrole-2-carboxylic acid cyanomethylamide;
1-Allyl-4-{2,2,2-trifluoro-1-[1-(4-fluorophenyl)-1H-indazol-5-yl]-1-hydroxyethyl}-1H-pyrrole-2-carboxylic acid amide;
2-(2-Cyano-4-{2,2,2-trifluoro-1-[1-(4-fluorophenyl)-1H-indazol-5-yl]-1-hydroxyethyl}pyrrol-1-yl)acetamide;
2-(2-Cyano-4-{2,2,2-trifluoro-1-[1-(4-fluorophenyl)-1H-indazol-5-yl]-1-hydroxyethyl}pyrrol-1-yl)-N-methylacetamide;
1-Allyl-4-{2,2,2-trifluoro-1-[1-(4-fluorophenyl)-1H-indazol-5-yl]-1-hydroxyethyl}-1H-pyrrole-2-carboxylic acid dimethylamide;
1-Allyl-4-{2,2,2-trifluoro-1-[1-(4-fluorophenyl)-1H-indazol-5-yl]-1-hydroxyethyl}-1H-pyrrole-2-carboxylic acid;
1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester;
3-Hydroxymethyl-7-{2,2,2-trifluoro-1-[1-(4-fluorophenyl)-1H-indazol-5-yl]-1-hydroxyethyl}-3,4-dihydropyrrolo[2,1-c][1,4]oxazin-1-one;
1-Allyl-4-{2,2,2-trifluoro-1-[1-(4-fluorophenyl)-1H-indazol-5-yl]-1-hydroxyethyl}-1H-pyrrole-2-carboxylic acid ethyl ester;
4-{2,2,2-Trifluoro-1-[1-(4-fluorophenyl)-1H-indazol-5-yl]-1-hydroxyethyl}-1H-pyrrole-2-carbonitrile;
1-(2,3-Dihydroxypropyl)-4-{2,2,2-trifluoro-1-[1-(4-fluorophenyl)-1H-indazol-5-yl]-1-hydroxyethyl}-1H-pyrrole-2-carbonitrile;
1-Allyl-4-{2,2,2-trifluoro-1-[1-(4-fluorophenyl)-1H-indazol-5-yl]-1-hydroxyethyl}-1H-pyrrole-2-carbonitrile;
(1-(2,3-Dihydroxypropyl)-4-{2,2,2-trifluoro-1-[1-(4-fluorophenyl)-1H-indazol-5-yl]-1-hydroxyethyl}-1H-pyrrol-2-yl)morpholin-4-ylmethanone;
(1-Allyl-4-{2,2,2-trifluoro-1-[1-(4-fluorophenyl)-1H-indazol-5-yl]-1-hydroxyethyl}-1H-pyrrol-2-yl)-morpholin-4-ylmethanone;
2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide;
3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol;
2,2,2-Trifluoro-1-[1-(4-fluorophenyl)-1H-indazol-5-yl]-1-(7-methoxy-1H-pyrrolo[2,3-c]pyridin-3-yl)ethanol;
4-Bromo-1-(2,3-dihydroxypropyl)-5-{2,2,2-trifluoro-1-[1-(4-fluorophenyl)-1H-indazol-5-yl]-1-hydroxyethyl}-1H-pyrazole-3-carbonitrile;
1-Allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one;
4-{2,2,2-Trifluoro-1-[1-(4-fluorophenyl)-1H-indazol-5-yl]-1-hydroxyethyl}-1H-pyrazole-3-carbonitrile;
1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile;
2,2,2-Trifluoro-1-[1-(4-fluorophenyl)-1H-indazol-5-yl]-1-(2-hydroxymethylthiazol-5-yl)ethanol;
2,2,2-Trifluoro-1-[1-(4-fluorophenyl)-1H-indazol-5-yl]-1-(2-hydroxymethylthiazol-4-yl)ethanol;
1-Allyl-4-bromo-5-{2,2,2-trifluoro-1-[1-(4-fluorophenyl)-1H-indazol-5-yl]-1-hydroxyethyl}-1H-pyrazole-3-carbonitrile;
1-Allyl-4-{2,2,2-trifluoro-1-[1-(4-fluorophenyl)-1H-indazol-5-yl]-1-hydroxyethyl}-1H-pyrazole-3-c arbonitrile;
2,2,2-Trifluoro-1-[1-(4-fluorophenyl)-1H-indazol-5-yl]-1-(2-morpholin-4-yl-thiazol-4-yl)ethanol;
2,2,2-Trifluoro-1-[1-(4-fluorophenyl)-1H-indazol-5-yl]-1-thiazol-5-ylethanol;
N-(5-{2,2,2-Trifluoro-1-[1-(4-fluorophenyl)-1H-indazol-5-yl]-1-hydroxyethyl}thiazol-2-yl)acetamide;
1-(2-Aminothiazol-5-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-(2-morpholin-4-ylthiazol-5-yl)ethanol;

3-(3-{2,2,2-Trifluoro-1-[1-(4-fluorophenyl)-1H-benzotriazol-5-yl]-1-hydroxyethyl}indol-1-yl)propane-1,2-diol;
1-[1-(2,2-Dimethyl-1,3-dioxolan-4-ylmethyl)-1H-indol-3-yl]-2,2,2-trifluoro-1-[1-(4-fluorophenyl)-1H-benzotriazol-5-yl]ethanol;
2,2,2-Trifluoro-1-[1-(4-fluorophenyl)-1H-benzotriazol-5-yl]-1-(1-methyl-1H-indol-3-yl)ethanol;
2,2,2-Trifluoro-1-[1-(4-fluorophenyl)-2-methyl-1H-benzimidazol-5-yl]-1-(1-methyl-1H-indol-3-yl)ethanol;
1-(4-Fluorophenyl)-3-methyl-5-[2,2,2-trifluoro-1-hydroxy-1-(1-methyl-1H-indol-3-yl)ethyl]-1,3-dihydrobenzimidazol-2-one;
(3-Methyl-2-oxo-5-{2,2,2-trifluoro-1-[1-(4-fluorophenyl)-1H-indazol-5-yl]-1-hydroxyethyl}-2H-pyridin-1-yl)acetamide;
1,3-Dimethyl-5-{2,2,2-trifluoro-1-[1-(4-fluorophenyl)-1H-indazol-5-yl]-1-hydroxyethyl}-1H-pyridin-2-one;
(2-Oxo-5-{2,2,2-trifluoro-1-[1-(4-fluorophenyl)-1H-indazol-5-yl]-1-hydroxyethyl}-2H-pyridin-1-yl)acetamide;
3-Methyl-5-{2,2,2-trifluoro-1-[1-(4-fluorophenyl)-1H-indazol-5-yl]-1-hydroxyethyl}-1H-pyridin-2-one;
5-{2,2,2-trifluoro-1-[1-(4-fluorophenyl)-1H-indazol-5-yl]-1-hydroxyethyl}-1H-pyridin-2-one;
2,2,2-Trifluoro-1-[1-(4-fluorophenyl)-1H-indazol-5-yl]-1-(6-methoxypyridin-3-yl)ethanol;
5-[1-(1-Allyl-1H-indol-3-yl)-2,2,2-trifluoro-1-hydroxyethyl]indazole-1-carboxylic acid ethylamide;
5-[1-(1-Allyl-1H-indol-3-yl)-2,2,2-trifluoro-1-hydroxyethyl]indazole-1-carboxylic acid (1-ethylpropyl)amide;
5-[1-(1-Allyl-1H-indol-3-yl)-2,2,2-trifluoro-1-hydroxyethyl]indazole-1-carboxylic acid (1,2-dimethylpropyl)amide;
5-[1-(1-(1-Allyl-1H-indol-3-yl)-2,2,2-trifluoro-1-hydroxyethyl]indazole-1-carboxylic acid (1,1-dimethylethyl)amide;
5-[1-(1-Allyl-1H-indol-3-yl)-2,2,2-trifluoro-1-hydroxyethyl]indazole-1-carboxylic acid (1-methylpropyl)amide;
5-[1-(1-Allyl-1H-indol-3-yl)-2,2,2-trifluoro-1-hydroxyethyl]indazole-1-carboxylic acid propylamide;
5-[1-(1-Allyl-1H-indol-3-yl)-2,2,2-trifluoro-1-hydroxyethyl]indazole-1-carboxylic acid (1-methylethyl)amide;
5-[1-(1-Methyl-1H-indol-3-yl)-2,2,2-trifluoro-1-hydroxyethyl]indazole-1-carboxylic acid cyclobutyl ester;
Cyclopentyl-{5-[2,2,2-trifluoro-1-hydroxy-1-(1-methyl-1H-indol-3-yl)ethyl]indazol-1-yl}methanone;
Cyclobutyl-{5-[2,2,2-trifluoro-1-hydroxy-1-(1-methyl-1H-indol-3-yl)ethyl]indazol-1-yl}methanone;
Cyclopropyl-{5-[2,2,2-trifluoro-1-hydroxy-1-(1-methyl-1H-indol-3-yl)ethyl]indazol-1-yl}methanone;
5-[2,2,2-Trifluoro-1-hydroxy-1-(1-methyl-1H-indol-3-yl)ethyl]indazole-1-carboxylic acid cyclopentylmethylamide;
5-[2,2,2-Trifluoro-1-hydroxy-1-(1-methyl-1H-indol-3-yl)ethyl]indazole-1-carboxylic acid isopropylmethylamide;
5-[2,2,2-Trifluoro-1-hydroxy-1-(1-methyl-1H-indol-3-yl)ethyl]indazole-1-carboxylic acid cyclopropylamide;
5-[2,2,2-Trifluoro-1-hydroxy-1-(1-methyl-1H-indol-3-yl)ethyl]indazole-1-carboxylic acid cyclopentylamide;
5-[2,2,2-Trifluoro-1-hydroxy-1-(1-methyl-1H-indol-3-yl)ethyl]indazole-1-carboxylic acid cyclopropylmethylamide;
5-[2,2,2-Trifluoro-1-hydroxy-1-(1-methyl-1H-indol-3-yl)ethyl]indazole-1-carboxylic acid isopropylamide;
5-[1-(1-Methyl-1H-indol-3-yl)-2,2,2-trifluoro-1-hydroxyethyl]indazole-1-carboxylic acid cyclopentyl ester;
5-[1-(1-Methyl-1H-indol-3-yl)-2,2,2-trifluoro-1-hydroxyethyl]indazole-1-carboxylic acid ethyl ester;
5-[1-(1-Methyl-1H-indol-3-yl)-2,2,2-trifluoro-1-hydroxyethyl]indazole-1-carboxylic acid cyclopropylmethyl ester;
5-[2,2,2-Trifluoro-1-hydroxy-1-(1-methyl-1H-indol-3-yl)ethyl]indazole-1-carboxylic acid phenyl ester;
5-[1-(1-Methyl-1H-indol-3-yl)-2,2,2-trifluoro-1-hydroxyethyl]indazole-1-carboxylic acid isopropyl ester;
2,2,2-Trifluoro-1-(1-methyl-1H-indol-3-yl)-1-(1-phenylmethanesulfonyl-1H-indazol-5-yl)ethanol;
2-Phenyl-1-{5-[2,2,2-trifluoro-1-hydroxy-1-(1-methyl-1H-indol-3-yl)ethyl]indazol-1-yl}ethanone;
2-Thiophen-2-yl-1-{5-[2,2,2-trifluoro-1-hydroxy-1-(1-methyl-1H-indol-3-yl)ethyl]indazol-1-yl}ethanone;
Phenyl-{5-[2,2,2-trifluoro-1-hydroxy-1-(1-methyl-1H-indol-3-yl)ethyl]indazol-1-yl}-methanone;
3-Methyl-1-{5-[2,2,2-trifluoro-1-hydroxy-1-(1-methyl-1H-indol-3-yl)ethyl]indazol-1-yl}butan-1-one;
1-(1-Benzenesulfonyl-1H-indazol-5-yl)-2,2,2-trifluoro-1-(1-methyl-1H-indol-3-yl)ethanol;
2,2,2-Trifluoro-1-(1-methyl-1H-indol-3-yl)-1-[1-(propane-2-sulfonyl)-1H-indazol-5-yl]ethanol;
2,2,2-Trifluoro-1-(1-methanesulfonyl-1H-indazol-5-yl)-1-(1-methyl-1H-indol-3-yl)ethanol;
2,2,2-Trifluoro-1-(1H-indazol-5-yl)-1-(1-methyl-1H-indol-3-yl)ethanol;
2-Phenyl-1-[5-(2,2,2-trifluoro-1-hydroxy-1-phenylethyl)indazol-1-yl]ethanone; and
1-(1-Allyl-6-dimethylamino-1H-indol-3-yl)-2,2,2-trifluoro-1-[1-(4-fluorophenyl)-1H-indazol-5-yl]ethanol,
or a tautomer, ester, amide, or a pharmaceutically acceptable salt thereof.

2. A compound selected from:
(3-{2,2,2-Trifluoro-1-[1-(4-fluorophenyl)-1H-indazol-5-yl]-1-hydroxyethyl}pyrrolo[2,3-b]pyridin-1-yl)acetonitrile;
2,2,2-Trifluoro-1-(1-phenyl-1H-pyrazolo[3,4-b]pyridin-5-yl)-1-(1H-pyrrolo[2,3-b]pyridin-3-yl)ethanol;
1-(4-Chloro-1-phenyl-1H-pyrazolo[3,4-b]pyridin-5-yl)-2,2,2-trifluoro-1-(1H-pyrrolo[2,3-b]pyridin-3-yl)ethanol;
2-(7-Chloro-3-{2,2,2-trifluoro-1-[1-(4-fluorophenyl)-1H-indazol-5-yl]-1-hydroxyethyl}pyrrolo[2,3-c]pyridin-1-yl)acetamide;
N-[2-(3-{2,2,2-Trifluoro-1-[1-(4-fluorophenyl)-1H-indazol-5-yl]-1-hydroxyethyl}pyrrolo[2,3-b]pyridin-1-yl)acetyl]methanesulfonamide;
1-(7-Chloro-1H-pyrrolo[2,3-c]pyridin-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-(7-oxy-1H-pyrrolo[2,3-b]pyridin-3-yl)ethanol;
2,2,2-Trifluoro-1-(1H-pyrrolo[2,3-b]pyridin-3-yl)-1-(1-p-tolyl-1H-indazol-5-yl)ethanol;
2,2,2-Trifluoro-1-[1-(4-fluorophenyl)-1H-indazol-5-yl]-1-(1H-pyrrolo[3,2-b]pyridin-3-yl)ethanol;
2,2,2-Trifluoro-1-[1-(4-fluorophenyl)-1H-indazol-5-yl]-1-(1H-pyrrolo[2,3-c]pyridin-3-yl)ethanol;
2,2,2-Trifluoro-1-[1-(4-fluorophenyl)-1H-indazol-5-yl]-1-(1H-pyrrolo[3,2-c]pyridin-3-yl)ethanol;

3-{2,2,2-Trifluoro-1-[1-(4-fluorophenyl)-1H-indazol-5-yl]-1-hydroxyethyl}pyrrolo[2,3-b]pyridine-1-sulfonic acid dimethylamide;
2-(3-{2,2,2-Trifluoro-1-[1-(4-fluorophenyl)-1H-indazol-5-yl]-1-hydroxyethyl}pyrrolo[2,3-b]pyridin-1-yl)acetamide;
2,2,2-Trifluoro-1-[1-(4-fluorophenyl)-1H-indazol-5-yl]-1-(1H-pyrrolo[2,3-b]pyridin-3-yl)ethanol;
2,2,2-Trifluoro-1-[1-(4-fluorophenyl)-1H-indazol-5-yl]-1-(1H-indazol-3-yl)ethanol;
Phenyl-{2,2,2-trifluoro-1-[1-(4-fluorophenyl)-1H-indazol-5-yl]ethyl}amine;
(1H-Indol-5-yl)-{2,2,2-trifluoro-1-[1-(4-fluorophenyl)-1H-indazol-5-yl]ethyl}amine;
(1H-Indol-6-yl)-{2,2,2-trifluoro-1-[1-(4-fluorophenyl)-1H-indazol-5-yl]ethyl}amine;
(1H-Indol-7-yl)-{2,2,2-trifluoro-1-[1-(4-fluorophenyl)-1H-indazol-5-yl]ethyl}amine;
(1H-Indol-4-yl)-{2,2,2-trifluoro-1-[1-(4-fluorophenyl)-1H-indazol-5-yl]ethyl}amine;
(1-Benzyl-2,2,2-trifluoroethyl)-[1-(4-fluorophenyl)-1H-indazol-5-yl]amine;
Benzyl-{2,2,2-trifluoro-1-[1-(4-fluorophenyl)-1H-indazol-5-yl]ethyl}amine;
(2-Nitrophenyl)-{2,2,2-trifluoro-1-[1-(4-fluorophenyl)-1H-indazol-5-yl]ethyl}amine;
N-{2,2,2-Trifluoro-1-[1-(4-fluorophenyl)-1H-indazol-5-yl]ethyl}-benzene-1,2-diamine;
2-Amino-4,6-dichloro-N-{2,2,2-trifluoro-1-[1-(4-fluorophenyl)-1H-indazol-5-yl]ethyl}-benzenesulfonamide;
2-(7-{2,2,2-Trifluoro-1-[1-(4-fluorophenyl)-1H-indazol-5-yl]ethylamino}indol-1-yl)acetamide;
3-Methyl-N$^2$-{2,2,2-trifluoro-1-[1-(4-fluorophenyl)-1H-indazol-5-yl]ethyl}benzene-1,2-diamine;
2,2,2-Trifluoro-1-(1-methyl-1H-indol-3-yl)-1-(1-pyridin-3-yl-1H-indazol-5-yl)ethanol;
2,2,2-Trifluoro-1-(1-methyl-1H-indol-3-yl)-1-(1-pyridin-4-yl-1H-indazol-5-yl)ethanol;
2,2,2-Trifluoro-1-(1-methyl-1H-indol-3-yl)-1-(1-pyrimidin-5-yl-1H-indazol-5-yl)ethanol;
2,2,2-Trifluoro-1-(1-methyl-1H-indol-3-yl)-1-(1-thiophen-3-yl-1H-indazol-5-yl)ethanol;
2,2,2-Trifluoro-1-(1H-indol-3-yl)-1-(1-pyridin-3-yl-1H-indazol-5-yl)ethanol;
2-{3-[2,2,2-Trifluoro-1-hydroxy-1-(1-pyridin-3-yl-1H-indazol-5-yl)ethyl]indol-1-yl}acetamide;
2,2,2-Trifluoro-1-(1-methyl-1H-indol-3-yl)-1-[1-(6-methylpyridin-3-yl)-1H-indazol-5-yl]ethanol;
2,2,2-Trifluoro-1-(1-methyl-1H-indol-3-yl)-1-[1-(5-methylthiophen-2-yl)-1H-indazol-5-yl]ethanol;
2,2,2-Trifluoro-1-[1-(1-methyl-1H-imidazol-4-yl)-1H-indazol-5-yl]-1-(1-methyl-1H-indol-3-yl)ethanol;
2,2,2-Trifluoro-1-(1-methyl-1H-indol-3-yl)-1-(1-pyridin-2-yl-1H-indazol-5-yl)ethanol;
2,2,2-Trifluoro-1-(1-methyl-1H-indol-3-yl)-1-[1-(1-methyl-1H-pyrazol-4-yl)-1H-indazol-5-yl]ethanol;
2,2,2-Trifluoro-1-[1-(6-fluoropyridin-3-yl)-1H-indazol-5-yl]-1-(1-methyl-1H-indol-3-yl)ethanol;
(R)-1-(3-{2,2,2-Trifluoro-1-[1-(4-fluorophenyl)-1H-indazol-5-yl]-1-hydroxyethyl}indol-1-yl)propan-2-ol;
(S)-1-(3-{2,2,2-Trifluoro-1-[1-(4-fluorophenyl)-1H-indazol-5-yl]-1-hydroxyethyl}indol-1-yl)propan-2-ol;
1-(5-Chloro-1,1-dioxo-1H-1λ$^6$-thiophen-2-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(tetrahydro-furan-2-ylmethyl)-1H-indol-3-yl]ethanol;
2,2,2-Trifluoro-1-[1-(4-fluorophenyl)-1H-indazol-5-yl]-1-[1-(2-morpholin-4-ylethyl)-1H-indol-3-yl]ethanol;
(3-{2,2,2-Trifluoro-1-[1-(4-fluorophenyl)-1H-indazol-5-yl]-1-hydroxyethyl}indol-1-yl)acetic acid;
1-(1-Allyl-5-hydroxymethyl-1H-pyrrol-3-yl)-2,2,2-trifluoro-1-[1-(4-fluorophenyl)-1H-indazol-5-yl]ethanol;
1-(5-1,3-Dioxolan-2-ylthiophen-2-yl)-2,2,2-trifluoro-1-[1-(4-fluorophenyl)-1H-indazol-5-yl]ethanol;
(3-{2,2,2-Trifluoro-1-[1-(4-fluorophenyl)-1H-indazol-5-yl]-1-hydroxyethyl}indol-1-yl)acetic acid ethyl ester;
1-(5-Chlorothiophen-2-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-{1-[3-(4-hydroxymethylpiperidin-1-yl)propyl]-1H-indol-3-yl}ethanol;
1-{1-[3-((S)-3-Dimethylaminopyrrolidin-1-yl)propyl]-1H-indol-3-yl}-2,2,2-trifluoro-1-[1-(4-fluorophenyl)-1H-indazol-5-yl]ethanol;
1-{1-[3-((R)-3-Dimethylaminopyrrolidin-1-yl)propyl]-1H-indol-3-yl}-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(3-pyrrolidin-1-ylpropyl)-1H-indol-3-yl]ethanol;
2,2,2-Trifluoro-1-[1-(4-fluorophenyl)-1H-indazol-5-yl]-1-{1-[3-(4-methylpiperazin-1-yl)-propyl]-1H-indol-3-yl}ethanol;
2,2,2-Trifluoro-1-[1-(4-fluorophenyl)-1H-indazol-5-yl]-1-[1-(3-methylaminopropyl)-1H-indol-3-yl]ethanol;
2,2,2-Trifluoro-1-[1-(4-fluorophenyl)-1H-indazol-5-yl]-1-[1-(3-morpholin-4-ylpropyl)-1H-indol-3-yl]ethanol;
1-[1-(3-Dimethylaminopropyl)-1H-indol-3-yl]-2,2,2-trifluoro-1-[1-(4-fluorophenyl)-1H-indazol-5-yl]ethanol;
3-(6-(2H-Pyrazol-3-yl)-3-{2,2,2-trifluoro-1-[1-(4-fluorophenyl)-1H-indazol-5-yl]-1-hydroxyethyl}indol-1-yl)propane-1,2-diol;
1-[1-Allyl-6-(2H-pyrazol-3-yl)-1H-indol-3-yl]-2,2,2-trifluoro-1-[1-(4-fluorophenyl)-1H-indazol-5-yl]ethanol;
1-(6-Bromo-1-but-3-enyl-1H-indol-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(propane-2-sulfonyl)-1H-indol-3-yl]ethanol;
3-(3-{2,2,2-Trifluoro-1-[1-(4-fluorophenyl)-1H-indazol-5-yl]-1-hydroxyethyl}indol-1-yl)propionamide;
N-Methyl-3-(3-{2,2,2-trifluoro-1-[1-(4-fluorophenyl)-1H-indazol-5-yl]-1-hydroxyethyl}indol-1-yl)propionamide;
3-(6-Pyrrolidin-1-yl-3-{2,2,2-trifluoro-1-[1-(4-fluorophenyl)-1H-indazol-5-yl]-1-hydroxyethyl}indol-1-yl)propane-1,2-diol;
2-(6-Bromo-3-{2,2,2-trifluoro-1-[1-(4-fluorophenyl)-1H-indazol-5-yl]-1-hydroxyethyl}indol-1-yl)-N-methylacetamide;
4-(3-{2,2,2-Trifluoro-1-[1-(4-fluorophenyl)-1H-indazol-5-yl]-1-hydroxyethyl}indol-1-yl)-butane-1,2-diol;
1-(1-But-3-enyl-1H-indol-3-yl)-2,2,2-trifluoro-1-[1-(4-fluorophenyl)-1H-indazol-5-yl]ethanol;
1-(1-Allyl-6-pyrrolidin-1-yl-1H-indol-3-yl)-2,2,2-trifluoro-1-[1-(4-fluorophenyl)-1H-indazol-5-yl]ethanol;
1-(1-Allyl-6-bromo-1H-indol-3-yl)-2,2,2-trifluoro-1-[1-(4-fluorophenyl)-1H-indazol-5-yl]ethanol;
3-(6-Bromo-3-{2,2,2-trifluoro-1-[1-(4-fluorophenyl)-1H-indazol-5-yl]-1-hydroxyethyl}indol-1-yl)propane-1,2-diol;

2,2,2-Trifluoro-1-[1-(4-fluorophenyl)-1H-indazol-5-yl]-1-[1-(4-methoxybenzyl)-6-vinyl-1H-indol-3-yl]ethanol;

2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide;

3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol;

2,2,2-Trifluoro-1-[1-(4-fluorophenyl)-1H-indazol-5-yl]-1-(7-methoxy-1H-pyrrolo[2,3-c]pyridin-3-yl)ethanol;

4-Bromo-1-(2,3-dihydroxypropyl)-5-{2,2,2-trifluoro-1-[1-(4-fluorophenyl)-1H-indazol-5-yl]-1-hydroxyethyl}-1H-pyrazole-3-carbonitrile;

1-Allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one;

4-{2,2,2-Trifluoro-1-[1-(4-fluorophenyl)-1H-indazol-5-yl]-1-hydroxyethyl}-1H-pyrazole-3-carbonitrile;

1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile;

2,2,2-Trifluoro-1-[1-(4-fluorophenyl)-1H-indazol-5-yl]-1-(2-hydroxymethyl-thiazol-5-yl)ethanol;

2,2,2-Trifluoro-1-[1-(4-fluorophenyl)-1H-indazol-5-yl]-1-(2-hydroxymethyl-thiazol-4-yl)ethanol;

1-Allyl-4-bromo-5-{2,2,2-trifluoro-1-[1-(4-fluorophenyl)-1H-indazol-5-yl]-1-hydroxyethyl}-1H-pyrazole-3-carbonitrile;

1-Allyl-4-{2,2,2-trifluoro-1-[1-(4-fluorophenyl)-1H-indazol-5-yl]-1-hydroxyethyl}-1H-pyrazole-3-carbonitrile;

2,2,2-Trifluoro-1-[1-(4-fluorophenyl)-1H-indazol-5-yl]-1-(2-morpholin-4-yl-thiazol-4-yl)ethanol;

2,2,2-Trifluoro-1-[1-(4-fluorophenyl)-1H-indazol-5-yl]-1-thiazol-5-ylethanol;

N-(5-{2,2,2-Trifluoro-1-[1-(4-fluorophenyl)-1H-indazol-5-yl]-1-hydroxyethyl}thiazol-2-yl)acetamide;

2,2,2-Trifluoro-1-[1-(4-fluorophenyl)-1H-indazol-5-yl]-1-(2-morpholin-4-yl-thiazol-5-yl)ethanol;

1-[4-Chloro-5-(2-hydroxyethyl)-5H-pyrrolo[3,2-d]pyrimidin-7-yl]-2,2,2-trifluoro-1-[1-(4-fluorophenyl)-1H-indazol-5-yl]ethanol;

3-(4-Chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol;

5-(2,3-Dihydroxypropyl)-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

5-Allyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

7-{2,2,2-Trifluoro-1-[1-(4-fluorophenyl)-1H-indazol-5-yl]-1-hydroxyethyl}-3,5-dihydropyrrolo[3,2-d]pyrimidin-4-one;

1-(4-Chloro-5H-pyrrolo[3,2-d]pyrimidin-7-yl)-2,2,2-trifluoro-1-[1-(4-fluorophenyl)-1H-indazol-5-yl]ethanol;

2-(3-Methyl-4-oxo-7-{2,2,2-trifluoro-1-[1-(4-fluorophenyl)-1H-indazol-5-yl]-1-hydroxyethyl}-3,4-dihydropyrrolo[3,2-d]pyrimidin-5-yl)acetamide;

5-(2,3-Dihydroxypropyl)-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;

1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid dimethylamide;

1-Allyl-4-{2,2,2-trifluoro-1-[1-(4-fluorophenyl)-1H-indazol-5-yl]-1-hydroxyethyl}-1H-pyrrole-2-carboxylic acid methylamide;

1-Allyl-4-{2,2,2-trifluoro-1-[1-(4-fluorophenyl)-1H-indazol-5-yl]-1-hydroxyethyl}-1H-pyrrole-2-carboxylic acid carbamoylmethylamide;

1-Allyl-4-{2,2,2-trifluoro-1-[1-(4-fluorophenyl)-1H-indazol-5-yl]-1-hydroxyethyl}-1H-pyrrole-2-carboxylic acid cyanomethylamide;

1-Allyl-4-{2,2,2-trifluoro-1-[1-(4-fluorophenyl)-1H-indazol-5-yl]-1-hydroxyethyl}-1H-pyrrole-2-carboxylic acid amide;

2-(2-Cyano-4-{2,2,2-trifluoro-1-[1-(4-fluorophenyl)-1H-indazol-5-yl]-1-hydroxyethyl}pyrrol-1-yl)acetamide;

2-(2-Cyano-4-{2,2,2-trifluoro-1-[1-(4-fluorophenyl)-1H-indazol-5-yl]-1-hydroxyethyl}pyrrol-1-yl)-N-methylacetamide;

1-Allyl-4-{2,2,2-trifluoro-1-[1-(4-fluorophenyl)-1H-indazol-5-yl]-1-hydroxyethyl}-1H-pyrrole-2-carboxylic acid dimethylamide;

1-Allyl-4-{2,2,2-trifluoro-1-[1-(4-fluorophenyl)-1H-indazol-5-yl]-1-hydroxyethyl}-1H-pyrrole-2-carboxylic acid;

1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester;

3-Hydroxymethyl-7-{2,2,2-trifluoro-1-[1-(4-fluorophenyl)-1H-indazol-5-yl]-1-hydroxyethyl}-3,4-dihydropyrrolo[2,1-c][1,4]oxazin-1-one;

1-Allyl-4-{2,2,2-trifluoro-1-[1-(4-fluorophenyl)-1H-indazol-5-yl]-1-hydroxyethyl}-1H-pyrrole-2-carboxylic acid ethyl ester;

4-{2,2,2-Trifluoro-1-[1-(4-fluorophenyl)-1H-indazol-5-yl]-1-hydroxyethyl}-1H-pyrrole-2-carbonitrile;

1-(2,3-Dihydroxypropyl)-4-{2,2,2-trifluoro-1-[1-(4-fluorophenyl)-1H-indazol-5-yl]-1-hydroxyethyl}-1H-pyrrole-2-carbonitrile;

1-Allyl-4-{2,2,2-trifluoro-1-[1-(4-fluorophenyl)-1H-indazol-5-yl]-1-hydroxyethyl}-1H-pyrrole-2-carbonitrile;

(1-(2,3-Dihydroxypropyl)-4-{2,2,2-trifluoro-1-[1-(4-fluorophenyl)-1H-indazol-5-yl]-1-hydroxyethyl}-1H-pyrrol-2-yl)-morpholin-4-yl-methanone;

(1-Allyl-4-{2,2,2-trifluoro-1-[1-(4-fluorophenyl)-1H-indazol-5-yl]-1-hydroxyethyl}-1H-pyrrol-2-yl)-morpholin-4-yl-methanone;

3-(3-{2,2,2-Trifluoro-1-[1-(4-fluorophenyl)-1H-benzotriazol-5-yl]-1-hydroxyethyl}indol-1-yl)propane-1,2-diol;

2,2,2-Trifluoro-1-[1-(4-fluorophenyl)-1H-benzotriazol-5-yl]-1-(1-methyl-1H-indol-3-yl)ethanol;

1-[1-(2,2-Dimethyl-1,3-dioxolan-4-ylmethyl)-1H-indol-3-yl]-2,2,2-trifluoro-1-[1-(4-fluorophenyl)-1H-benzotriazol-5-yl]ethanol ;

(2-Oxo-5-{2,2,2-trifluoro-1-[1-(4-fluorophenyl)-1H-indazol-5-yl]-1-hydroxyethyl}-2H-pyridin-1-yl)acetamide;

5-[1-(1-Allyl-1H-indol-3-yl)-2,2,2-trifluoro-1-hydroxyethyl]indazole-1-carboxylic acid (1,1-dimethylethyl) amide;

5-[1-(1-Methyl-1H-indol-3-yl)-2,2,2-trifluoro-1-hydroxyethyl]indazole-1-carboxylic acid cyclobutyl ester;

Cyclopentyl-{5-[2,2,2-trifluoro-1-hydroxy-1-(1-methyl-1H-indol-3-yl)ethyl]indazol-1-yl}-methanone 5-[2,2,2-Trifluoro-1-hydroxy-1-(1-methyl-1H-indol-3-yl)ethyl]indazole-1-carboxylic acid cyclopentyl-methylamide 5-[2,2,2-Trifluoro-1-hydroxy-1-(1-methyl-1H-indol-3-yl)ethyl]indazole-1-carboxylic acid isopropyl-methylamide;

5-[1-(1-Methyl-1H-indol-3-yl)-2,2,2-trifluoro-1-hydroxyethyl]indazole-1-carboxylic acid ethyl ester;

2,2,2-Trifluoro-1-(1-methyl-1H-indol-3-yl)-1-(1-phenyl-methanesulfonyl-1H-indazol-5-yl)ethanol;

2-Phenyl-1-{5-[2,2,2-trifluoro-1-hydroxy-1-(1-methyl-1H-indol-3-yl)ethyl]indazol-1-yl}ethanone;

1-(1-Benzenesulfonyl-1H-indazol-5-yl)-2,2,2-trifluoro-1-(1-methyl-1H-indol-3-yl)ethanol;

2,2,2-Trifluoro-1-(1-methyl-1H-indol-3-yl)-1-[1-(propane-2-sulfonyl)-1H-indazol-5-yl]ethanol;

2,2,2-Trifluoro-1-(1-methanesulfonyl-1H-indazol-5-yl)-1-(1-methyl-1H-indol-3-yl)ethanol;

2-Phenyl-1-[5-(2,2,2-trifluoro-1-hydroxy-1-phenylethyl)indazol-1-yl]ethanone;

1-Methylcarbamoylmethyl-4-{2,2,2-trifluoro-1-[1-(4-fluorophenyl)-1H-indazol-5-yl]-1-hydroxyethyl}-1H-pyrrole-2-carboxylic acid dimethylamide;

1-(1-Allyl-6-dimethylamino-1H-indol-3-yl)-2,2,2-trifluoro-1-[1-(4-fluorophenyl)-1H-indazol-5-yl]ethanol or a tautomer, ester, amide, or a pharmaceutically acceptable salt thereof.

3. A compound selected from:

(3-{2,2,2-Trifluoro-1-[1-(4-fluorophenyl)-1H-indazol-5-yl]-1-hydroxyethyl}pyrrolo[2,3-b]pyridin-1-yl)acetonitrile;

2,2,2-Trifluoro-1-(1-phenyl-1H-pyrazolo[3,4-b]pyridin-5-yl)-1-(1H-pyrrolo[2,3-b]pyridin-3-yl)ethanol;

2-(7-Chloro-3-{2,2,2-trifluoro-1-[1-(4-fluorophenyl)-1H-indazol-5-yl]-1-hydroxyethyl}pyrrolo[2,3-c]pyridin-1-yl)acetamide;

N-[2-(3-{2,2,2-Trifluoro-1-[1-(4-fluorophenyl)-1H-indazol-5-yl]-1-hydroxyethyl}pyrrolo[2,3-b]pyridin-1-yl)acetyl]-methanesulfonamide;

1-(7-Chloro-1H-pyrrolo[2,3-c]pyridin-3-yl)-2,2,2-trifluoro-1-[1-(4-fluorophenyl)-1H-indazol-5-yl]ethanol;

2,2,2-Trifluoro-1-[1-(4-fluorophenyl)-1H-indazol-5-yl]-1-(7-oxy-1H-pyrrolo[2,3-b]pyridin-3-yl)ethanol;

2,2,2-Trifluoro-1-(1H-pyrrolo[2,3-b]pyridin-3-yl)-1-(1-p-tolyl-1H-indazol-5-yl)ethanol;

2,2,2-Trifluoro-1-[1-(4-fluorophenyl)-1H-indazol-5-yl]-1-(1H-pyrrolo[3,2-b]pyridin-3-yl)ethanol;

2,2,2-Trifluoro-1-[1-(4-fluorophenyl)-1H-indazol-5-yl]-1-(1H-pyrrolo[2,3-c]pyridin-3-yl)ethanol;

2,2,2-Trifluoro-1-[1-(4-fluorophenyl)-1H-indazol-5-yl]-1-(1H-pyrrolo[3,2-c]pyridin-3-yl)ethanol;

3-{2,2,2-Trifluoro-1-[1-(4-fluorophenyl)-1H-indazol-5-yl]-1-hydroxyethyl}pyrrolo[2,3-b]pyridine-1-sulfonic acid dimethylamide;

2-(3-{2,2,2-Trifluoro-1-[1-(4-fluorophenyl)-1H-indazol-5-yl]-1-hydroxyethyl}pyrrolo[2,3-b]pyridin-1-yl)acetamide;

2,2,2-Trifluoro-1-[1-(4-fluorophenyl)-1H-indazol-5-yl]-1-(1H-pyrrolo[2,3-b]pyridin-3-yl)ethanol;

2,2,2-Trifluoro-1-[1-(4-fluorophenyl)-1H-indazol-5-yl]-1-(1H-indazol-3-yl)ethanol;

Phenyl-{2,2,2-trifluoro-1-[1-(4-fluorophenyl)-1H-indazol-5-yl]ethyl}amine;

(1H-Indol-5-yl)-{2,2,2-trifluoro-1-[1-(4-fluorophenyl)-1H-indazol-5-yl]ethyl}amine;

(1H-Indol-6-yl)-{2,2,2-trifluoro-1-[1-(4-fluorophenyl)-1H-indazol-5-yl]ethyl}amine;

(1H-Indol-7-yl)-{2,2,2-trifluoro-1-[1-(4-fluorophenyl)-1H-indazol-5-yl]ethyl}amine;

(1H-Indol-4-yl)-{2,2,2-trifluoro-1-[1-(4-fluorophenyl)-1H-indazol-5-yl]ethyl}amine;

(1-Benzyl-2,2,2-trifluoroethyl)-[1-(4-fluorophenyl)-1H-indazol-5-yl]-amine;

Benzyl-{2,2,2-trifluoro-1-[1-(4-fluorophenyl)-1H-indazol-5-yl]ethyl}amine;

(2-Nitrophenyl)-{2,2,2-trifluoro-1-[1-(4-fluorophenyl)-1H-indazol-5-yl]ethyl}amine;

N-{2,2,2-Trifluoro-1-[1-(4-fluorophenyl)-1H-indazol-5-yl]ethyl}-benzene-1,2-diamine;

2-Amino-4,6-dichloro-N-{2,2,2-trifluoro-1-[1-(4-fluorophenyl)-1H-indazol-5-yl]ethyl}-benzenesulfonamide;

2-(7-{2,2,2-Trifluoro-1-[1-(4-fluorophenyl)-1H-indazol-5-yl]ethylamino}indol-1-yl)acetamide;

3-Methyl-$N^2$-{2,2,2-trifluoro-1-[1-(4-fluorophenyl)-1H-indazol-5-yl]ethyl}-benzene-1,2-diamine;

2,2,2-Trifluoro-1-(1-methyl-1H-indol-3-yl)-1-(1-pyridin-3-yl-1H-indazol-5-yl)ethanol;

2,2,2-Trifluoro-1-(1-methyl-1H-indol-3-yl)-1-(1-pyridin-4-yl-1H-indazol-5-yl)ethanol;

2,2,2-Trifluoro-1-(1-methyl-1H-indol-3-yl)-1-(1-pyrimidin-5-yl-1H-indazol-5-yl)ethanol;

2,2,2-Trifluoro-1-(1-methyl-1H-indol-3-yl)-1-(1-thiophen-3-yl-1H-indazol-5-yl)ethanol;

2,2,2-Trifluoro-1-(1H-indol-3-yl)-1-(1-pyridin-3-yl-1H-indazol-5-yl)ethanol;

2-{3-[2,2,2-Trifluoro-1-hydroxy-1-(1-pyridin-3-yl-1H-indazol-5-yl)ethyl]indol-1-yl}acetamide;

2,2,2-Trifluoro-1-(1-methyl-1H-indol-3-yl)-1-[1-(6-methylpyridin-3-yl)-1H-indazol-5-yl]ethanol;

2,2,2-Trifluoro-1-(1-methyl-1H-indol-3-yl)-1-[1-(5-methylthiophen-2-yl)-1H-indazol-5-yl]ethanol;

2,2,2-Trifluoro-1-[1-(1-methyl-1H-imidazol-4-yl)-1H-indazol-5-yl]-1-(1-methyl-1H-indol-3-yl)ethanol;

2,2,2-Trifluoro-1-(1-methyl-1H-indol-3-yl)-1-(1-pyridin-2-yl-1H-indazol-5-yl)ethanol;

2,2,2-Trifluoro-1-(1-methyl-1H-indol-3-yl)-1-[1-(1-methyl-1H-pyrazol-4-yl)-1H-indazol-5-yl]ethanol;

2,2,2-Trifluoro-1-[1-(6-fluoropyridin-3-yl)-1H-indazol-5-yl]-1-(1-methyl-1H-indol-3-yl)ethanol;

(R)-1-(3-{2,2,2-Trifluoro-1-[1-(4-fluorophenyl)-1H-indazol-5-yl]-1-hydroxyethyl}indol-1-yl)propan-2-ol;

(S)-1-(3-{2,2,2-Trifluoro-1-[1(4-fluorophenyl)-1H-indazol-5-yl]-1-hydroxyethyl}indol-1-yl)propan-2-ol;

2,2,2-Trifluoro-1-[1-(4-fluorophenyl)-1H-indazol-5-yl]-1-[1-(tetrahydro-furan-2-ylmethyl)-1H-indol-3-yl]ethanol;

2,2,2-Trifluoro-1-[1-(4-fluorophenyl)-1H-indazol-5-yl]-1-[1-(2-morpholin-4-ylethyl)-1H-indol-3-yl]ethanol;

(3-{2,2,2-Trifluoro-1-[1-(4-fluorophenyl)-1H-indazol-5-yl]-1-hydroxyethyl}indol-1-yl)acetic acid;

1-(1-Allyl-5-hydroxymethyl-1H-pyrrol-3-yl)-2,2,2-trifluoro-1-[1-(4-fluorophenyl)-1H-indazol-5-yl]ethanol;

1-(5-1,3-Dioxolan-2-ylthiophen-2-yl)-2,2,2-trifluoro-1-[1(4-fluorophenyl)-1H-indazol-5-yl]ethanol;

(3-{2,2,2-Trifluoro-1-[1(4-fluorophenyl)-1H-indazol-5-yl]-1-hydroxyethyl}indol-1-yl)acetic acid ethyl ester;

1-(5-Chlorothiophen-2-yl)-2,2,2-trifluoro-1-[1-(4-fluorophenyl)-1H-indazol-5-yl]ethanol;

2,2,2-Trifluoro-1-[1-(4-fluorophenyl)-1H-indazol-5-yl]-1-{1-[3-(4-hydroxymethylpiperidin-1-yl)propyl]-1H-indol-3-yl}ethanol;

1-{1-[3-((S)-3-Dimethylaminopyrrolidin-1-yl)propyl]-1H-indol-3-yl}-2,2,2-trifluoro-1-[1-(4-fluorophenyl)-1H-indazol-5-yl]ethanol;
1-{1-[3((R)-3-Dimethylaminopyrrolidin-1-yl)propyl]-1H-indol-3-yl}-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(3-pyrrolidin-1-ylpropyl)-1H-indol-3-yl]ethanol;
2,2,2-Trifluoro-1-[1-(4-fluorophenyl)-1H-indazol-5-yl]-1-{1-[3-(4-methylpiperazin-1-yl)-propyl]-1H-indol-3-yl}ethanol;
2,2,2-Trifluoro-1-[1-(4-fluorophenyl)-1H-indazol-5-yl]-1-[1-(3-methylaminopropyl)-1H-indol-3-yl]ethanol;
2,2,2-Trifluoro-1-[1-(4-fluorophenyl)-1H-indazol-5-yl]-1-[1-(3-morpholin-4-ylpropyl)-1H-indol-3-yl]ethanol;
1-[1-(3-Dimethylaminopropyl)-1H-indol-3-yl]-2,2,2-trifluoro-1-[1-(4-fluorophenyl)-1H-indazol-5-yl]ethanol;
3-(6-(2H-Pyrazol-3-yl)-3-{2,2,2-trifluoro-1-[1-(4-fluorophenyl)-1H-indazol-5-yl]-1-hydroxyethyl}indol-1-yl)propane-1,2-diol;
1-[1-Allyl-6-(2H-pyrazol-3-yl)-1H-indol-3-yl]-2,2,2-trifluoro-1-[1-(4-fluorophenyl)-1H-indazol-5-yl]ethanol;
1-(6-Bromo-1-but-3-enyl-1H-indol-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(propane-2-sulfonyl)-1H-indol-3-yl]ethanol;
3-(3-{2,2,2-Trifluoro-1-[1-(4-fluorophenyl)-1H-indazol-5-yl]-1-hydroxyethyl}indol-1-yl)propionamide;
N-Methyl-3-(3-{2,2,2-trifluoro-1-[1-(4-fluorophenyl)-1H-indazol-5-yl]-1-hydroxyethyl}indol-1-yl)propionamide;
3-(6-Pyrrolidin-1-yl-3-{2,2,2-trifluoro-1-[1-(4-fluorophenyl)-1H-indazol-5-yl]-1-hydroxyethyl}indol-1-yl)propane-1,2-diol;
2-(6-Bromo-3-{2,2,2-trifluoro-1-[1-(4-fluorophenyl)-1H-indazol-5-yl]-1-hydroxyethyl}indol-1-yl)-N-methylacetamide;
4-(3-{2,2,2-Trifluoro-1-[1-(4-fluorophenyl)-1H-indazol-5-yl]-1-hydroxyethyl}indol-1-yl)-butane-1,2-diol;
1-(1-But-3-enyl-1H-indol-3-yl)-2,2,2-trifluoro-1-[1-(4-fluorophenyl)-1H-indazol-5-yl]ethanol;
1-(1-Allyl-6-pyrrolidin-1-yl-1H-indol-3-yl)-2,2,2-trifluoro-1-[1-(4-fluorophenyl)-1H-indazol-5-yl]ethanol;
1-(1-Allyl-6-bromo-1H-indol-3-yl)-2,2,2-trifluoro-1-[1-(4-fluorophenyl)-1H-indazol-5-yl]ethanol;
3-(6-Bromo-3-{2,2,2-trifluoro-1-[1-(4-fluorophenyl)-1H-indazol-5-yl]-1-hydroxyethyl}indol-1-yl)propane-1,2-diol;
2,2,2-Trifluoro-1-[1-(4-fluorophenyl)-1H-indazol-5-yl]-1-[1-(4-methoxy-benzyl)-6-vinyl-1H-indol-3-yl]ethanol;
2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide;
3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol;
2,2,2-Trifluoro-1-[1-(4-fluorophenyl)-1H-indazol-5-yl]-1-(7-methoxy-1H-pyrrolo[2,3-c]pyridin-3-yl)ethanol;
1-Allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one;
4-{2,2,2-Trifluoro-1-[1-(4-fluorophenyl)-1H-indazol-5-yl]-1-hydroxyethyl}-1H-pyrazole-3-carbonitrile;
1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile;
2,2,2-Trifluoro-1-[1-(4-fluorophenyl)-1H-indazol-5-yl]-1-(2-hydroxymethyl-thiazol-5-yl)ethanol;
1-Allyl-4-bromo-5-{2,2,2-trifluoro-1-[1-(4-fluorophenyl)-1H-indazol-5-yl]-1-hydroxyethyl}-1H-pyrazole-3-carbonitrile;
1-Allyl-4-{2,2,2-trifluoro-1-[1-(4-fluorophenyl)-1H-indazol-5-yl]-1-hydroxyethyl}-1H-pyrazole-3-carbonitrile;
2,2,2-Trifluoro-1-[1-(4-fluorophenyl)-1H-indazol-5-yl]-1-(2-morpholin-4-yl-thiazol-4-yl)ethanol;
2,2,2-Trifluoro-1-[1-(4-fluorophenyl)-1H-indazol-5-yl]-1-thiazol-5-ylethanol;
2,2,2-Trifluoro-1-[1-(4-fluorophenyl)-1H-indazol-5-yl]-1-(2-morpholin-4-yl-thiazol-5-yl)ethanol;
1-[4-Chloro-5-(2-hydroxyethyl)-5H-pyrrolo[3,2-d]pyrimidin-7-yl)-2,2,2-trifluoro-1-[1-(4-fluorophenyl)-1H-indazol-5-yl]ethanol;
3-(4-Chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol;
5-Allyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;
7-{2,2,2-Trifluoro-1-[1-(4-fluorophenyl)-1H-indazol-5-yl]-1-hydroxyethyl}-3,5-dihydropyrrolo[3,2-d]pyrimidin-4-one;
1-(4-Chloro-5H-pyrrolo[3,2-d]pyrimidin-7-yl)-2,2,2-trifluoro-1-[1-(4-fluorophenyl)-1H-indazol-5-yl]ethanol;
2-(3-Methyl-4-oxo-7-{2,2,2-trifluoro-1-[1-(4-fluorophenyl)-1H-indazol-5-yl]-1-hydroxyethyl}-3,4-dihydropyrrolo[3,2-d]pyrimidin-5-yl)acetamide;
5-(2,3-Dihydroxypropyl)-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;
5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;
1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid dimethylamide;
1-Allyl-4-{2,2,2-trifluoro-1-[1-(4-fluorophenyl)-1H-indazol-5-yl]-1-hydroxyethyl}-1H-pyrrole-2-carboxylic acid methylamide;
1-Allyl-4-{2,2,2-trifluoro-1-[1-(4-fluorophenyl)-1H-indazol-5-yl]-1-hydroxyethyl}-1H-pyrrole-2-carboxylic acid cyanomethylamide;
1-Allyl-4-{2,2,2-trifluoro-1-[1-(4-fluorophenyl)-1H-indazol-5-yl]-1-hydroxyethyl}-1H-pyrrole-2-carboxylic acid amide;
2-(2-Cyano-4-{2,2,2-trifluoro-1-[1-(4-fluorophenyl)-1H-indazol-5-yl]-1-hydroxyethyl}pyrrol-1-yl)acetamide;
2-(2-Cyano-4-{2,2,2-trifluoro-1-[1-(4-fluorophenyl)-1H-indazol-5-yl]-1-hydroxyethyl}pyrrol-1-yl)-N-methylacetamide;
1-Allyl-4-{2,2,2-trifluoro-1-[1-(4-fluorophenyl)-1H-indazol-5-yl]-1-hydroxyethyl}-1H-pyrrole-2-carboxylic acid dimethylamide;
1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester;
1-Allyl-4-{2,2,2-trifluoro-1-[1-(4-fluorophenyl)-1H-indazol-5-yl]-1-hydroxyethyl}-1H-pyrrole-2-carboxylic acid ethyl ester;
4-{2,2,2-Trifluoro-1-[1-(4-fluorophenyl)-1H-indazol-5-yl]-1-hydroxyethyl}-1H-pyrrole-2-carbonitrile;

1-(2,3-Dihydroxypropyl)-4-{2,2,2-trifluoro-1-[1-(4-fluorophenyl)-1H-indazol-5-yl]-1-hydroxyethyl}-1H-pyrrole-2-carbonitrile;
1-Allyl-4-{2,2,2-trifluoro-1-[1-(4-fluorophenyl)-1H-indazol-5-yl]-1-hydroxyethyl}-1H-pyrrole-2-carbonitrile;
(1-Allyl-4-{2,2,2-trifluoro-1-[1-(4-fluorophenyl)-1H-indazol-5-yl]-1-hydroxyethyl}-1H-pyrrol-2-yl)-morpholin-4-yl-methanone;
3-(3-{2,2,2-Trifluoro-1-[1-(4-fluorophenyl)-1H-benzotriazol-5-yl]-1-hydroxyethyl}indol-1-yl)propane-1,2-diol;
2,2,2-Trifluoro-1-[1-(4-fluorophenyl)-1H-benzotriazol-5-yl]-1-(1-methyl-1H-indol-3-yl)ethanol;
5-{2,2,2-trifluoro-1-[1-(4-fluorophenyl)-1H-indazol-5-yl]-1-hydroxyethyl}-1H-pyridin-2-one;
5-[1-(1-Allyl-1H-indol-3-yl)-2,2,2-trifluoro-1-hydroxyethyl]indazole-1-carboxylic acid (1-ethylpropyl)amide;
5-[1-(1-Allyl-1H-indol-3-yl)-2,2,2-trifluoro-1-hydroxyethyl]indazole-1-carboxylic acid (1,2-dimethylpropyl)amide;
5-[1-(1-Allyl-1H-indol-3-yl)-2,2,2-trifluoro-1-hydroxyethyl]indazole-1-carboxylic acid (1-methylethyl)amide;
Cyclobutyl-{5-[2,2,2-trifluoro-1-hydroxy-1-(1-methyl-1H-indol-3-yl)ethyl]indazol-1-yl}-methanone;
Cyclopropyl-{5-[2,2,2-trifluoro-1-hydroxy-1-(1-methyl-1H-indol-3-yl)ethyl]indazol-1-yl}-methanone;
5-[2,2,2-Trifluoro-1-hydroxy-1-(1-methyl-1H-indol-3-yl)ethyl]indazole-1-carboxylic acid cyclopropylamide;
5-[2,2,2-Trifluoro-1-hydroxy-1-(1-methyl-1H-indol-3-yl)ethyl]indazole-1-carboxylic acid cyclopentylamide;
5-[1-(1-Methyl-1H-indol-3-yl)-2,2,2-trifluoro-1-hydroxyethyl]indazole-1-carboxylic acid cyclopentyl ester;
5-[1-(1-Methyl-1H-indol-3-yl)-2,2,2-trifluoro-1-hydroxyethyl]indazole-1-carboxylic acid cyclopropylmethyl ester;
5-[2,2,2-Trifluoro-1-hydroxy-1-(1-methyl-1H-indol-3-yl)ethyl]indazole-1-carboxylic acid phenyl ester;
2-Thiophen-2-yl-1-{5-[2,2,2-trifluoro-1-hydroxy-1-(1-methyl-1H-indol-3-yl)ethyl]indazol-1-yl}ethanone;
Phenyl-{5-[2,2,2-trifluoro-1-hydroxy-1-(1-methyl-1H-indol-3-yl)ethyl]indazol-1-yl}-methanone;
3-Methyl-1-{5-[2,2,2-trifluoro-1-hydroxy-1-(1-methyl-1H-indol-3-yl)ethyl]indazol-1-yl}-butan-1-one;
2,2,2-Trifluoro-1-(1H-indazol-5-yl)-1-(1-methyl-1H-indol-3-yl)ethanol;
1-Methylcarbamoylmethyl-4-{2,2,2-trifluoro-1-[1-(4-fluorophenyl)-1H-indazol-5-yl]-1-hydroxyethyl}-1H-pyrrole-2-carboxylic acid dimethylamide; and
1-(1-Allyl-6-dimethylamino-1H-indol-3-yl)-2,2,2-trifluoro-1-[1-(4-fluorophenyl)-1H-indazol-5-yl]ethanol,
or a tautomer, ester, amide, or a pharmaceutically acceptable salt thereof.

4. A compound selected from:
(3-{2,2,2-Trifluoro-1-[1-(4-fluorophenyl)-1H-indazol-5-yl]-1-hydroxyethyl}pyrrolo[2,3-b]pyridin-1-yl) acetonitrile;
2-(7-Chloro-3-{2,2,2-trifluoro-1-[1-(4-fluorophenyl)-1H-indazol-5-yl]-1-hydroxyethyl}pyrrolo[2,3-c]pyridin-1-yl)acetamide;
1-(7-Chloro-1H-pyrrolo[2,3-c]pyridin-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-(7-oxy-1H-pyrrolo[2,3-b]pyridin-3-yl)ethanol;
2,2,2-Trifluoro-1-[1-(4-fluorophenyl)-1H-indazol-5-yl]-1-(1H-pyrrolo[3,2-b]pyridin-3-yl)ethanol;
2,2,2-Trifluoro-1-[1-(4-fluorophenyl)-1H-indazol-5-yl]-1-(1H-pyrrolo[2,3-c]pyridin-3-yl)ethanol;
3-{2,2,2-Trifluoro-1-[1-(4-fluorophenyl)-1H-indazol-5-yl]-1-hydroxyethyl}pyrrolo[2,3-b]pyridine-1-sulfonic acid dimethylamide;
2-(3-{2,2,2-Trifluoro-1-[1-(4-fluorophenyl)-1H-indazol-5-yl]-1-hydroxyethyl}pyrrolo[2,3-b]pyridin-1-yl)acetamide;
2,2,2-Trifluoro-1-[1-(4-fluorophenyl)-1H-indazol-5-yl]-1-(1H-pyrrolo[2,3-b]pyridin-3-yl)ethanol;
2,2,2-Trifluoro-1-[1-(4-fluorophenyl)-1H-indazol-5-yl]-1-(1H-indazol-3-yl)ethanol;
(1H-Indol-6-yl)-{2,2,2-trifluoro-1-[1-(4-fluorophenyl)-1H-indazol-5-yl]ethyl}amine;
(1H-Indol-7-yl)-{2,2,2-trifluoro-1-[1-(4-fluorophenyl)-1H-indazol-5-yl]ethyl}amine;
(1H-Indol-4-yl)-{2,2,2-trifluoro-1-[1-(4-fluorophenyl)-1H-indazol-5-yl]ethyl}amine;
N-{2,2,2-Trifluoro-1-[1-(4-fluorophenyl)-1H-indazol-5-yl]ethyl}-benzene-1,2-diamine;
2-Amino-4,6-dichloro-N-{2,2,2-trifluoro-1-[1-(4-fluorophenyl)-1H-indazol-5-yl]ethyl}-benzenesulfonamide;
2-(7-{2,2,2-Trifluoro-1-[1-(4-fluorophenyl)-1H-indazol-5-yl]ethylamino}indol-1-yl)acetamide;
2,2,2-Trifluoro-1-(1-methyl-1H-indol-3-yl)-1-(1-pyridin-3-yl-1H-indazol-5-yl)ethanol;
2,2,2-Trifluoro-1-(1-methyl-1H-indol-3-yl)-1-(1-pyridin-4-yl-1H-indazol-5-yl)ethanol
2,2,2-Trifluoro-1-(1-methyl-1H-indol-3-yl)-1-(1-thiophen-3-yl-1H-indazol-5-yl)ethanol;
2,2,2-Trifluoro-1-(1H-indol-3-yl)-1-(1-pyridin-3-yl-1H-indazol-5-yl)ethanol;
2-{3-[2,2,2-Trifluoro-1-hydroxy-1-(1-pyridin-3-yl-1H-indazol-5-yl)ethyl]indol-1-yl}acetamide;
2,2,2-Trifluoro-1-(1-methyl-1H-indol-3-yl)-1-[1-(5-methylthiophen-2-yl)-1H-indazol-5-yl]ethanol;
2,2,2-Trifluoro-1-(1-methyl-1H-indol-3-yl)-1-(1-pyridin-2-yl-1H-indazol-5-yl)ethanol;
2,2,2-Trifluoro-1-(1-methyl-1H-indol-3-yl)-1-[1-(1-methyl-1H-pyrazol-4-yl)-1H-indazol-5-yl]ethanol;
2,2,2-Trifluoro-1-[1-(6-fluoropyridin-3-yl)-1H-indazol-5-yl]-1-(1-methyl-1H-indol-3-yl)ethanol;
(R)-1-(3-{2,2,2-Trifluoro-1-[1-(4-fluorophenyl)-1H-indazol-5-yl]-1-hydroxyethyl}indol-1-yl)propan-2-ol;
(S)-1-(3-{2,2,2-Trifluoro-1-[1-(4-fluorophenyl)-1H-indazol-5-yl]-1-hydroxyethyl}indol-1-yl)propan-2-ol;
2,2,2-Trifluoro-1-[1-(4-fluorophenyl)-1H-indazol-5-yl]-1-[1-(tetrahydro-furan-2-ylmethyl)-1H-indol-3-yl]ethanol;
2,2,2-Trifluoro-1-[1-(4-fluorophenyl)-1H-indazol-5-yl]-1-[1-(2-morpholin-4-ylethyl)-1H-indol-3-yl]ethanol;
(3-{2,2,2-Trifluoro-1-[1-(4-fluorophenyl)-1H-indazol-5-yl]-1-hydroxyethyl}indol-1-yl)acetic acid;
1-(5-1,3-Dioxolan-2-ylthiophen-2-yl)-2,2,2-trifluoro-1-[1-(4-fluorophenyl)-1H-indazol-5-yl]ethanol;
(3-{2,2,2-Trifluoro-1-[1-(4-fluorophenyl)-1H-indazol-5-yl]-1-hydroxyethyl}indol-1-yl)acetic acid ethyl ester;
1-(5-Chlorothiophen-2-yl)-2,2,2-trifluoro-1-[1-(4-fluorophenyl)-1H-indazol-5-yl]ethanol;
1-{1-[3-((S)-3-Dimethylaminopyrrolidin-1-yl)propyl]-1H-indol-3-yl}-2,2,2-trifluoro-1-[1-(4-fluorophenyl)-1H-indazol-5-yl]ethanol;

1-{1-[3-((R)-3-Dimethylaminopyrrolidin-1-yl)propyl]-1H-indol-3-yl}-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(3-pyrrolidin-1-ylpropyl)-1H-indol-3-yl]ethanol;
2,2,2-Trifluoro-1-[1-(4-fluorophenyl)-1H-indazol-5-yl]-1-[1-(3-methylaminopropyl)-1H-indol-3-yl]ethanol;
2,2,2-Trifluoro-1-[1-(4-fluorophenyl)-1H-indazol-5-yl]-1-[1-(3-morpholin-4-ylpropyl)-1H-indol-3-yl]ethanol;
1-[1-(3-Dimethylaminopropyl)-1H-indol-3-yl]-2,2,2-trifluoro-1-[1-(4-fluorophenyl)-1H-indazol-5-yl]ethanol;
3-(6-(2H-Pyrazol-3-yl)-3-{2,2,2-trifluoro-1-[1-(4-fluorophenyl)-1H-indazol-5-yl]-1-hydroxyethyl}indol-1-yl)propane-1,2-diol;
1-[1-Allyl-6-(2H-pyrazol-3-yl)-1H-indol-3-yl]-2,2,2-trifluoro-1-[1-(4-fluorophenyl)-1H-indazol-5-yl]ethanol;
1-(6-Bromo-1-but-3-enyl-1H-indol-3-yl)-2,2,2-trifluoro-1-[1-(4-fluorophenyl)-1H-indazol-5-yl]ethanol;
2,2,2-Trifluoro-1-[1-(4-fluorophenyl)-1H-indazol-5-yl]-1-[1-(propane-2-sulfonyl)-1H-indol-3-yl]ethanol;
3-(3-{2,2,2-Trifluoro-1-[1-(4-fluorophenyl)-1H-indazol-5-yl]-1-hydroxyethyl}indol-1-yl)propionamide;
N-Methyl-3-(3-{2,2,2-trifluoro-1-[1-(4-fluorophenyl)-1H-indazol-5-yl]-1-hydroxyethyl}indol-1-yl)propionamide;
3-(6-Pyrrolidin-1-yl-3-{2,2,2-trifluoro-1-[1-(4-fluorophenyl)-1H-indazol-5-yl]-1-hydroxyethyl}indol-1-yl)propane-1,2-diol;
2-(6-Bromo-3-{2,2,2-trifluoro-1-[1-(4-fluorophenyl)-1H-indazol-5-yl]-1-hydroxyethyl}indol-1-yl)-N-methylacetamide;
4-(3-{2,2,2-Trifluoro-1-[1-(4-fluorophenyl)-1H-indazol-5-yl]-1-hydroxyethyl}indol-1-yl)-butane-1,2-diol;
1-(1-But-3-enyl-1H-indol-3-yl)-2,2,2-trifluoro-1-[1-(4-fluorophenyl)-1H-indazol-5-yl]ethanol;
1-(1-Allyl-6-bromo-1H-indol-3-yl)-2,2,2-trifluoro-1-[1-(4-fluorophenyl)-1H-indazol-5-yl]ethanol;
3-(6-Bromo-3-{2,2,2-trifluoro-1-[1-(4-fluorophenyl)-1H-indazol-5-yl]-1-hydroxyethyl}indol-1-yl)propane-1,2-diol;
2,2,2-Trifluoro-1-[1-(4-fluorophenyl)-1H-indazol-5-yl]-1-[1-(4-methoxy-benzyl)-6-vinyl-1H-indol-3-yl]ethanol;
2-(6-Methyl-7-oxo-3-{2,2,2-trifluoro-1-[1-(4-fluorophenyl)-1H-indazol-5-yl]-1-hydroxyethyl}-6,7-dihydropyrrolo[2,3-c]pyridin-1-yl)acetamide;
3-(7-Methoxy-3-{2,2,2-trifluoro-1-[1-(4-fluorophenyl)-1H-indazol-5-yl]-1-hydroxyethyl}pyrrolo[2,3-c]pyridin-1-yl)propane-1,2-diol;
2,2,2-Trifluoro-1-[1-(4-fluorophenyl)-1H-indazol-5-yl]-1-(7-methoxy-1H-pyrrolo[2,3-c]pyridin-3-yl)ethanol;
1-Allyl-6-methyl-3-{2,2,2-trifluoro-1-[1-(4-fluorophenyl)-1H-indazol-5-yl]-1-hydroxyethyl}-1,6-dihydropyrrolo[2,3-c]pyridin-7-one;
4-{2,2,2-Trifluoro-1-[1-(4-fluorophenyl)-1H-indazol-5-yl]-1-hydroxyethyl}-1H-pyrazole-3-carbonitrile;
1-(2,3-Dihydroxypropyl)-4-{2,2,2-trifluoro-1-[1-(4-fluorophenyl)-1H-indazol-5-yl]-1-hydroxyethyl}-1H-pyrazole-3-carbonitrile;
1-Allyl-4-bromo-5-{2,2,2-trifluoro-1-[1-(4-fluorophenyl)-1H-indazol-5-yl]-1-hydroxyethyl}-1H-pyrazole-3-carbonitrile;
1-Allyl-4-{2,2,2-trifluoro-1-[1-(4-fluorophenyl)-1H-indazol-5-yl]-1-hydroxyethyl}-1H-pyrazole-3-carbonitrile;
2,2,2-Trifluoro-1-[1-(4-fluorophenyl)-1H-indazol-5-yl]-1-(2-morpholin-4-yl-thiazol-4-yl)ethanol;
1-[4-Chloro-5-(2-hydroxyethyl)-5H-pyrrolo[3,2-d]pyrimidin-7-yl]-2,2,2-trifluoro-1-[1-(4-fluorophenyl)-1H-indazol-5-yl]ethanol;
3-(4-Chloro-7-{2,2,2-trifluoro-1-[1-(4-fluorophenyl)-1H-indazol-5-yl]-1-hydroxyethyl}pyrrolo[3,2-d]pyrimidin-5-yl)propane-1,2-diol;
1-(4-Chloro-5H-pyrrolo[3,2-d]pyrimidin-7-yl)-2,2,2-trifluoro-1-[1-(4-fluorophenyl)-1H-indazol-5-yl]ethanol;
5-Allyl-3-methyl-7-{2,2,2-trifluoro-1-[1-(4-fluorophenyl)-1H-indazol-5-yl]-1-hydroxyethyl}-3,5-dihydropyrrolo[3,2-d]pyrimidin-4-one;
1-Allyl-4-{2,2,2-trifluoro-1-[1-(4-fluorophenyl)-1H-indazol-5-yl]-1-hydroxyethyl}-1H-pyrrole-2-carboxylic acid dimethylamide;
1-(2,3-Dihydroxypropyl)-4-{2,2,2-trifluoro-1-[1-(4-fluorophenyl)-1H-indazol-5-yl]-1-hydroxyethyl}-1H-pyrrole-2-carboxylic acid ethyl ester;
1-Allyl-4-{2,2,2-trifluoro-1-[1-(4-fluorophenyl)-1H-indazol-5-yl]-1-hydroxyethyl}-1H-pyrrole-2-carboxylic acid ethyl ester;
4-{2,2,2-Trifluoro-1-[1-(4-fluorophenyl)-1H-indazol-5-yl]-1-hydroxyethyl}-1H-pyrrole-2-carbonitrile;
1-Allyl-4-{2,2,2-trifluoro-1-[1-(4-fluorophenyl)-1H-indazol-5-yl]-1-hydroxyethyl}-1H-pyrrole-2-carbonitrile;
(3-Methyl-2-oxo-5-{2,2,2-trifluoro-1-[1-(4-fluorophenyl)-1H-indazol-5-yl]-1-hydroxyethyl}-2H-pyridin-1-yl)acetamide;
1,3-Dimethyl-5-{2,2,2-trifluoro-1-[1-(4-fluorophenyl)-1H-indazol-5-yl]-1-hydroxyethyl}-1H-pyridin-2-one;
3-Methyl-5-{2,2,2-trifluoro-1-[1-(4-fluorophenyl)-1H-indazol-5-yl]-1-hydroxyethyl}-1H-pyridin-2-one;
2,2,2-Trifluoro-1-[1-(4-fluorophenyl)-1H-indazol-5-yl]-1-(6-methoxypyridin-3-yl)ethanol;
5-[1-(1-Allyl-1H-indol-3-yl)-2,2,2-trifluoro-1-hydroxyethyl]indazole-1-carboxylic acid ethylamide;
5-[1-(1-Allyl-1H-indol-3-yl)-2,2,2-trifluoro-1-hydroxyethyl]indazole-1-carboxylic acid (1-methylpropyl)amide;
5-[1-(1-Allyl-1H-indol-3-yl)-2,2,2-trifluoro-1-hydroxyethyl]indazole-1-carboxylic acid propylamide;
5-[2,2,2-Trifluoro-1-hydroxy-1-(1-methyl-1H-indol-3-yl)ethyl]indazole-1-carboxylic acid cyclopropylmethylamide;
5-[2,2,2-Trifluoro-1-hydroxy-1-(1-methyl-1H-indol-3-yl)ethyl]indazole-1-carboxylic acid isopropylamide;
Phenyl-[5-{2,2,2-trifluoro-1-hydroxy-1-(1-methyl-1H-indol-3-yl)ethyl]indazol-1-yl]-methanone;
5-[1-(1-Methyl-1H-indol-3-yl)-2,2,2-trifluoro-1-hydroxyethyl]indazole-1-carboxylic acid isopropyl ester; and
1-(1-Allyl-6-dimethylamino-1H-indol-3-yl)-2,2,2-trifluoro-1-[1-(4-fluorophenyl)-1H-indazol-5-yl]ethanol,
or a tautomer, ester, amide, or a pharmaceutically acceptable salt thereof.

* * * * *